(12) United States Patent
Wang et al.

(10) Patent No.: US 11,945,810 B2
(45) Date of Patent: *Apr. 2, 2024

(54) AMINES FOR USE AS SIGMA RECEPTOR MODULATORS

(71) Applicant: Ecstasy LLC, Chapel Hill, NC (US)

(72) Inventors: Xiaodong Wang, Chapel Hill, NC (US); Baizhi Li, Jiangyin (CN)

(73) Assignee: Ecstasy LLC, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/092,348

(22) Filed: Jan. 2, 2023

(65) Prior Publication Data

US 2023/0159505 A1    May 25, 2023

Related U.S. Application Data

(62) Division of application No. 17/363,042, filed on Jun. 30, 2021, now Pat. No. 11,548,879.

(60) Provisional application No. 63/046,813, filed on Jul. 1, 2020.

(51) Int. Cl.
| | | |
|---|---|---|
| *C07D 409/14* | (2006.01) | |
| *C07D 401/06* | (2006.01) | |
| *C07D 401/12* | (2006.01) | |
| *C07D 401/14* | (2006.01) | |
| *C07D 405/14* | (2006.01) | |
| *C07D 413/14* | (2006.01) | |
| *C07D 417/14* | (2006.01) | |
| *C07D 471/04* | (2006.01) | |
| *C07D 491/052* | (2006.01) | |
| *C07D 495/04* | (2006.01) | |
| *C07D 498/04* | (2006.01) | |
| *C07D 513/04* | (2006.01) | |

(52) U.S. Cl.
CPC ......... *C07D 409/14* (2013.01); *C07D 401/06* (2013.01); *C07D 401/12* (2013.01); *C07D 401/14* (2013.01); *C07D 405/14* (2013.01); *C07D 413/14* (2013.01); *C07D 417/14* (2013.01); *C07D 471/04* (2013.01); *C07D 491/052* (2013.01); *C07D 495/04* (2013.01); *C07D 498/04* (2013.01); *C07D 513/04* (2013.01); *C07B 2200/07* (2013.01)

(58) Field of Classification Search
CPC .................................................. C07D 409/14
USPC ....................................................... 514/230.5
See application file for complete search history.

(56) References Cited

U.S. PATENT DOCUMENTS

| | | | |
|---|---|---|---|
| 7,915,274 B2 | 3/2011 | Ozaki et al. | |
| 10,676,456 B2 * | 6/2020 | Wang | ........... C07D 409/04 |
| 2004/0138220 A1 | 7/2004 | Liras | |
| 2004/0204453 A1 | 10/2004 | McHardy et al. | |
| 2005/0008007 A1 | 4/2005 | Aquila et al. | |
| 2010/0234427 A1 | 9/2010 | Peters et al. | |
| 2011/0021556 A1 | 1/2011 | Lucas et al. | |
| 2018/0258065 A1 | 9/2018 | Wang | |

FOREIGN PATENT DOCUMENTS

| | | |
|---|---|---|
| JP | 2008-179541 A | 7/2008 |
| WO | WO 02/22572 A1 | 3/2002 |

OTHER PUBLICATIONS

International Search Report PCT/US2021/039739 (2023).
Australian Examination report No. 1, dated Jul. 13, 2023.

* cited by examiner

*Primary Examiner* — Kahsay Habte
(74) *Attorney, Agent, or Firm* — Eric P. Mirabel

(57) ABSTRACT

The present invention discloses a number of polycyclic amines that are useful as opioid receptor modulators. The compounds of the invention are useful in both therapeutic and diagnostic methods, including for treating pain, neurological disorders, cardiac disorders, bowel disorders, drug and alcohol addiction, drug overdose, urinary disorders, respiratory disorders, sexual dysfunction, psoriasis, graft rejection or cancer.

4 Claims, No Drawings

AMINES FOR USE AS SIGMA RECEPTOR MODULATORS

BACKGROUND

There is a continuing need for new opioid receptors modulators for the management of pain with reduced or fewer side effects. There is also a continuing need for new opioid receptors modulators for the treatment migraine, depression, cognitive disorders, Parkinson's disease, locomotor disfunction, pruritus, diarrhea, irritable bowel syndrome and gastro-intestinal disorders, bladder dysfunctions, overactive bladder, urinary incontinence, neurogenic bladder, interstitial cystitis, drug addiction, alcohol addiction, drug overdose, premature ejaculation, cough, lung edema, cardiac disorders, cardioprotection, and respiratory depression, and as immunomodulatory and anti-tumor agents. A number of such opioid receptor modulators are disclosed in U.S. Pat. No. 10,676,456 (incorporated by reference). Some additional new compounds are shown below.

SUMMARY

The present invention provides polycyclic amines, prodrugs and pharmaceutically acceptable salts thereof ("compounds of the invention"), which are useful in the treatment of diseases through the modulation of opioid receptors; similar to the compounds and their uses disclosed in U.S. Pat. No. 10,676,456. The process of making the compounds listed below are disclosed in or similar to processes of making compounds disclosed in U.S. Pat. No. 10,676,456.

The compounds of the invention are useful for preventing or treating a disease or condition selected from the group consisting of cardioprotection, cardiac disorders, analgesia, functional pain, inflammatory pain, peripherally mediated and neuropathic pain, non-somatic pain, arthritis, mental illness, cognitive disorders, depression, Parkinson's disease, locomotor disfunction, urogenital tract disorders, bladder dysfunction, overactive bladder, urinary incontinence, neurogenic bladder, psoriasis, pruritus, emesis, acne, skin lesions, non-ulcerogenic dyspepisa, gastro-intestinal disorders, functional bowel disease, diarrhea, inflammatory bowel disease, irritable bowel syndrome, interstitial cystitis, sexual dysfunctions, drug addiction, alcohol addiction, drug overdose, premature ejaculation, asthma, cough, lung edema, disorders of respiratory function, respiratory depression, functional distension, and disorders of motility or secretion. These compounds are also useful for immunomodulation, inhibiting or preventing organ or skin graft rejection, or treating tumors or cancer. All such treatment involves administering, to a patient, an effective amount of one or more of the compounds of the invention.

The present invention also includes a pharmaceutical composition comprising a pharmaceutically acceptable carrier and one or more of the compounds of the invention.

These and other aspects and embodiments of the invention will be apparent from the detailed description that follows.

DETAILED DESCRIPTION

Certain compounds of the invention can exist in unsolvated forms as well as solvated forms, including hydrated forms. In general, the solvated forms are equivalent to unsolvated forms and are encompassed within the scope of the present invention. Certain compounds of the invention may exist in multiple crystalline or amorphous forms. In general, all physical forms are equivalent for the uses contemplated by the present invention and are intended to be within the scope of the present invention.

The compounds of the invention, or their pharmaceutically acceptable salts, may have asymmetric carbon atoms or double bonds in their structure. The compounds of the invention and their pharmaceutical acceptable salts may therefore exit as single stereoisomers, racemates, and as mixtures of enantiomers, diastereomers and geometric isomers. All such single stereoisomers, racemates and mixtures thereof are intended to be within the scope of the invention. Absolute configuration of certain carbon atoms within the compounds, if known, are indicated by the appropriate absolute descriptors R or S.

The compounds of the invention may be synthesized in the form of racemic mixtures of enantiomers which can be separated from one another following art-known resolution procedure. The racemic compounds of the invention may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of the invention involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are encompassed within the scope of the present invention.

"Therapeutic" as used herein, includes prevention, treatment and/or prophylaxis for humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired. The precise dosage will vary according to a variety of factors, including but not limited to the age and size of the subject, the disease and the treatment being effected.

A "host" or "patient" or "subject" is a living mammal, human or animal, for whom therapy is desired. The "host," "patient" or "subject" generally refers to the recipient of the therapy to be practiced according to the method of the invention. It should be noted that the invention described herein may be used for veterinary as well as human applications and that the term "host" should not be construed in a limiting manner. In the case of veterinary applications, the dosage ranges can be determined as described below, taking into account the body weight of the animal.

As used herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

Other examples of pharmaceutically acceptable salts of the invention include salts derived from an appropriate base, such as an alkali metal (for example, sodium, potassium), an alkaline earth metal (for example, calcium, magnesium), ammonium and $NR'_4$ (wherein R' is $C_1$-$C_4$ alkyl). Pharmaceutically acceptable salts of the invention having an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of the invention having a hydroxyl group consist of the anion of such compounds in combination with a suitable cation such as $Na^+$, $NH_4^+$, or $NR'_4^+$, (wherein R is for example a $C_1$-$C_4$ group).

The neutral forms of the compounds of the invention are preferably regenerated by contacting the salt with a base or acid and isolating the parent compound in the conventional manner. The parent form of the compound may differ from the various salt forms in certain physical properties, such as solubility in polar solvents.

In addition to salt forms, the invention provides compounds which are in a prodrug form. Prodrugs of the compounds described herein are those compounds that readily undergo chemical changes under physiological conditions to provide the compounds of the invention.

Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention. Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The compounds of the invention can combine with an exogenous receptor or be used as complexing compounds, and may be used for binding with an opioid receptor. Further, the compounds may be used as a conjugate in an agonist/antagonist pair that is employed for transductional assay of neurotransmitter function in appertaining cellular or differentiated tissue systems, as well as for receptor assay, differential binding, and specificity applications for cellular, histological, and corporeal monitoring and assessment purposes.

The compounds of the invention can be administered for therapeutic intervention in a pharmaceutical composition containing the compound and a pharmaceutically acceptable carrier. The invention contemplates the use of any means and/or of modality of administration of the compositions of the invention.

The compounds of the invention include their physiologically functional derivatives. "Physiologically functional derivative" includes a pharmaceutically acceptable salt, ether, ester or salt of an ether or ester of the compounds of the invention or any other compound which, upon administration to the recipient, is capable of providing (directly or indirectly) a compound of the invention or an active metabolite or residue thereof. Phenolic $C_1$-$C_6$ alkyl ethers are a sub-class of physiologically functional derivatives of the compounds of the invention.

The compounds of the invention when used in pharmaceutical or diagnostic applications preferably are prepared in a racemic mixture or an essentially pure enantiomer form, with an enantiopurity of at least 90% enantiomeric excess (EE), preferably at least 95% EE, more preferably at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

Subjects to be treated by administration of the compounds of the invention are preferably human subjects, but also include non-human mammals and other animals (e.g., bird, dog, cat, cow, horse).

Depending on the specific condition to be treated, subjects may be administered compounds of the invention at any suitable therapeutically effective and safe dosage, as may readily be determined within the skill of the art, and without undue experimentation, with extrapolation from the animal dosages set forth herein in the examples. In in vitro tests for agonist/antagonist activity, such as receptor binding affinity tests, and inhibition of electrically stimulated muscle twitch tests, compounds of the invention exhibit potency.

In general, while the effective dosage of compounds of the invention for therapeutic use may be widely varied in the broad practice of the invention, depending on the specific application, condition, or disease state involved, as readily determinable within the skill of the art, suitable therapeutic doses of the compounds of the invention, for each of the appertaining compositions described herein, and for achievement of therapeutic benefit in treatment of each of the conditions described herein, will be in the range of 10 micrograms (µg) to 100 milligrams (mg) per kilogram body weight of the recipient per day, preferably in the range of 50 µg to 75 mg per kilogram body weight per day, and most preferably in the range of 100 µg to 50 mg per kilogram body weight per day. The desired dose is preferably presented as one, two, three, four, five, six, or more sub-doses administered at appropriate intervals throughout the day. These sub-doses may be administered in unit dosage forms, for example, containing from 10 µg to 1000 mg, preferably from 50 µg to 500 mg, more preferably from 50 µg to 250 mg, and most preferably from 50 µg to 10 mg of active ingredient per unit dosage form. Alternatively, if the condition of the recipient so requires, the doses may be administered as a continuous infusion.

The mode of administration and dosage forms will affect the therapeutic amounts of the compounds which are desirable and efficacious for the given treatment application.

For example, orally administered dosages typically are at least twice, e.g., 2-10 times, the dosage levels used in parenteral administration methods, for the same active ingredient. In oral administration, dosage levels for delta receptor binding compounds of the invention may be on the order of 5-200 mg/70 kg body weight/day. In tablet dosage forms, typical active agent dose levels are on the order of 10-100 mg per tablet.

The compounds of the invention may be administered per se as well as in the form of pharmaceutically acceptable esters, salts, and ethers, as well as other physiologically functional derivatives of such compounds.

The present invention also contemplates pharmaceutical compositions, both for veterinary and for human medical use, which comprise as the active agent one or more compound(s) of the invention.

In such pharmaceutical compositions, the active agent preferably is utilized together with one or more pharmaceutically acceptable carrier(s) therefor and optionally any other therapeutic ingredients. The carrier(s) preferably are compatible with the other ingredients of the formulation and not unduly deleterious to the recipient thereof. The active agent is preferably in a pharmaceutically acceptable amount effective to achieve the desired pharmacological effect.

The formulations include those suitable for parenteral as well as non-parenteral administration, and specific administration modalities include oral, rectal, topical, sub-lingual, mucosal, transdermal, nasal, ophthalmic, subcutaneous, intramuscular, intravenous, transdermal, spinal, intrathecal, intra-articular, intra-arterial, sub-arachnoid, bronchial, lymphatic, and intra-uterine administration. Formulations suitable for oral administration are preferred.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may be advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the compounds of the invention may conveniently be presented in unit dosage forms and may be prepared by any of the methods well known in the art of pharmacy. Such methods generally include the step of bringing the compound(s) into association with a carrier that constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert compound, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The disease state or physiological condition involved in such therapeutic intervention may be of any type or kind noted above, e.g., centrally mediated disorders; pain, depression, drug addiction, and drug dependence, alcohol addiction; and peripherally mediated neuropathic pain, cough, lung edema, gastro-intestinal disorders, arthritis, psoriasis, asthma, inflammatory bowel disease, disorders of respiratory function, functional bowel disease, irritable bowel syndrome, diarrhea, functional distension, pain (e.g., functional pain, trauma pain, etc.), non-ulcerogenic dyspepsia, urogenital tract disorders, premature ejaculation, overactive bladder, urinary incontinence, organ transplant rejection, skin graft rejection, cardiac disorders, cardioprotection, emesis, acne and skin lesions.

The compounds of the present invention may be readily synthesized within the skill of the art and in view of the illustrative synthesis examples hereinafter set forth.

The invention is further illustrated by the following non-limiting preparation schemes and other examples.

Preparation of Opioid Receptor Modulators

The following exemplary schemes illustrate methods of preparing the compounds of the invention, wherein the compounds of the invention have a structure according to Formula I, and include pharmaceutically acceptable salts and other derivatives of this structure:

(Formula I)

wherein:

A includes substituted or unsubstituted: alkyl, heteroalkyl, cycloalkyl, heterocycloalkyl, aryl, heteroaryl, and arylalkyl;

Y includes substituted or unsubstituted: alkyl, heteroalkyl, cycloalkyl, and heterocycloalkyl;

Q includes: substituted or unsubstituted: aryl, heteroaryl, and null;

W includes substituted or unsubstituted, saturated or unsaturated: (i) 4- to 8-membered heterocyclic rings including an N-substituent as an atom of the ring; and (ii) bicyclic or heterobicyclic fused rings wherein each ring has 4- to 10-members, and wherein at least one of the rings includes an N-substituent as an atom of the ring;

G includes substituted or unsubstituted alkyl or an N atom;

Z includes substituted or unsubstituted aryl, substituted or unsubstituted heteroaryl, and null;

If Z is null then T is null, but if Z is not null, T is selected from: (i) the moieties H, OH, $NH_2$, $NO_2$, $-SO_2NH_2$, halogen, (ii) substituted or unsubstituted: alkyl, heteroalkyl, cycloalkyl, heterocycloalkyl, aryl, and heteroaryl;

n is an integer from 1-4 when G is alkyl and is 1 when G is an N atom;

$R^1$ and $R^3$ are members independently selected from H and substituted or unsubstituted: alkyl, heteroalkyl, 3- to 7-membered cycloalkyl, 3- to 7-membered heterocycloalkyl, aryl, and heteroaryl;

m is an integer from 0-8 and can be same or different for each of $R^2$, $R^4$, $R^5$ and $R^6$, and wherein $R^2$, $R^4$, $R^5$ and $R^6$ are each independently selected from H and substituted or unsubstituted: alkyl, heteroalkyl, 3- to 7-membered cycloalkyl, 3- to 7-membered heterocycloalkyl, and where m is greater than 1 for any of $R^2$, $R^4$, $R^5$ and $R^6$, each member in such a multi-member $R^2$, $R^4$, $R^5$ and $R^6$ chain can be the same or different; and further provided that the total number of $R^2$, $R^4$, $R^5$ and $R^6$ having an m value greater than 0 is always less than or equal to the number of W ring positions available for covalent bonding; and $R^1$ and $R^3$, or $R^1$ or $R^3$ and Z, or $R^2$ and A, or $R^2$ and Y together with groups to which they may be joined, optionally form a substituted or unsubstituted 3- to 7-membered ring.

Scheme 1

Compounds where "A" of Formula I is an alkyl or heteroalkyl moiety are synthesized as illustrated in Scheme 1. The synthesis of compounds 1-6 is exemplified.

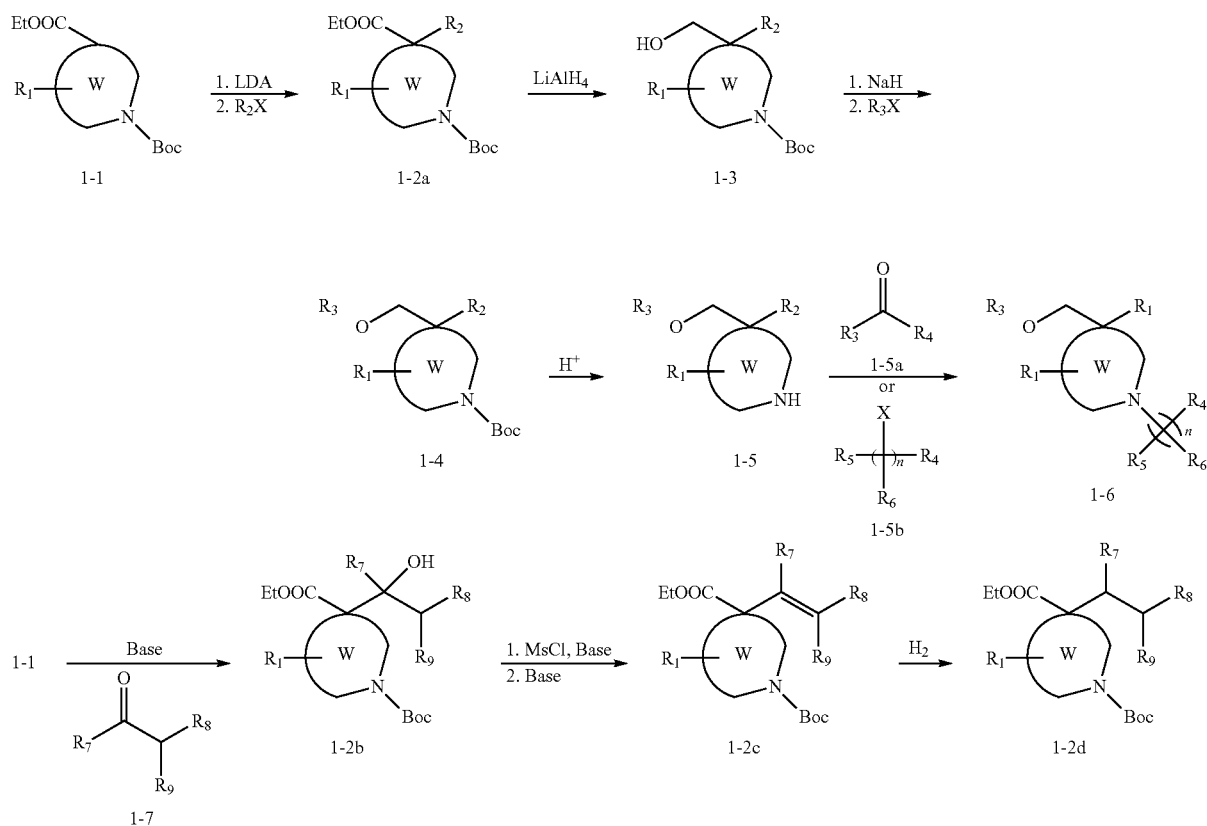

wherein for Scheme I above, X is selected from: Cl, Br, I, p-toluenesulfonyl (Tos), methanesulfonyl (Ms) and trifluoromethanesulfonyl (Tf).

In Scheme I, a substituted cyclic ester 1-1 is deprotonated in the presence of a strong base, such as LDA, LHMDS, or the like, followed by alkylation to produce 1-2a. Reduction of 1-2a followed by alkylation gives the ether 1-4. Deprotection of the Boc group of 1-4 is carried out in the presence of an acid, such as TFA, HCl or the like. Reductive amination of 1-5 with a suitable aldehyde or ketone 1-5a or alkylation of 1-5 with 1-5b under basic conditions gives 1-6. The compounds with different moieties from $R^1$ are exemplified by the synthesis of intermediates such as 1-2b, 1-2c, or 1-2d. Reaction of 1-1 with a suitable ketone or aldehyde 1-7 gives the intermediate 1-2b. Activation of the hydroxyl group of 1-2b using MsCl followed by the elimination in the presence of bases, such as DBU or the like, produces the unsaturated intermediates 1-2c. Hydrogenation of 1-2c gives the intermediate 1-2d.

Scheme 2

Compounds where "A" of Formula I is a cyclic alkyl or cyclic heteroalkyl moiety are synthesized as illustrated in Scheme 2. The synthesis of compounds 2-6 is used as an example.

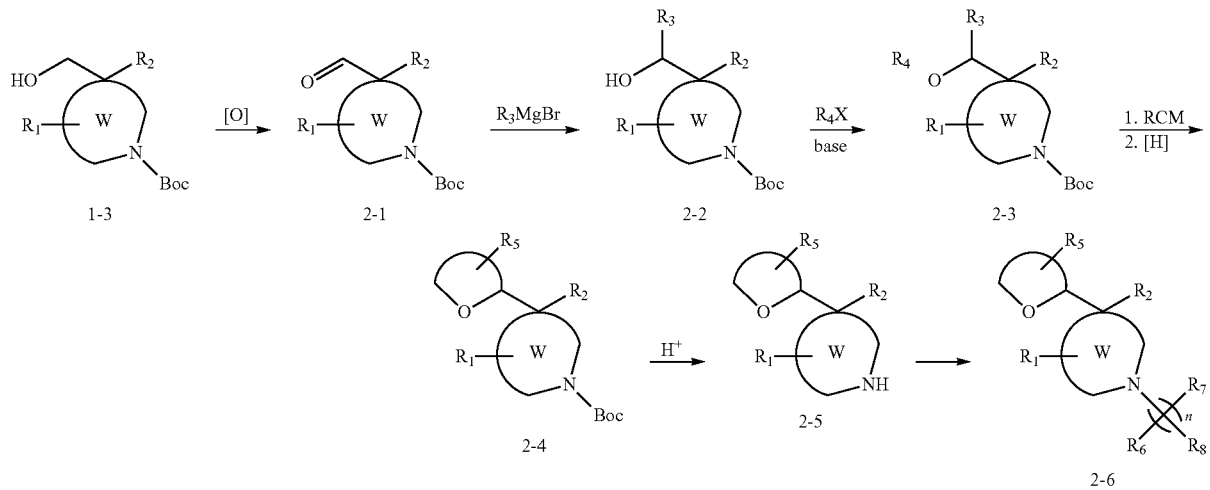

-continued

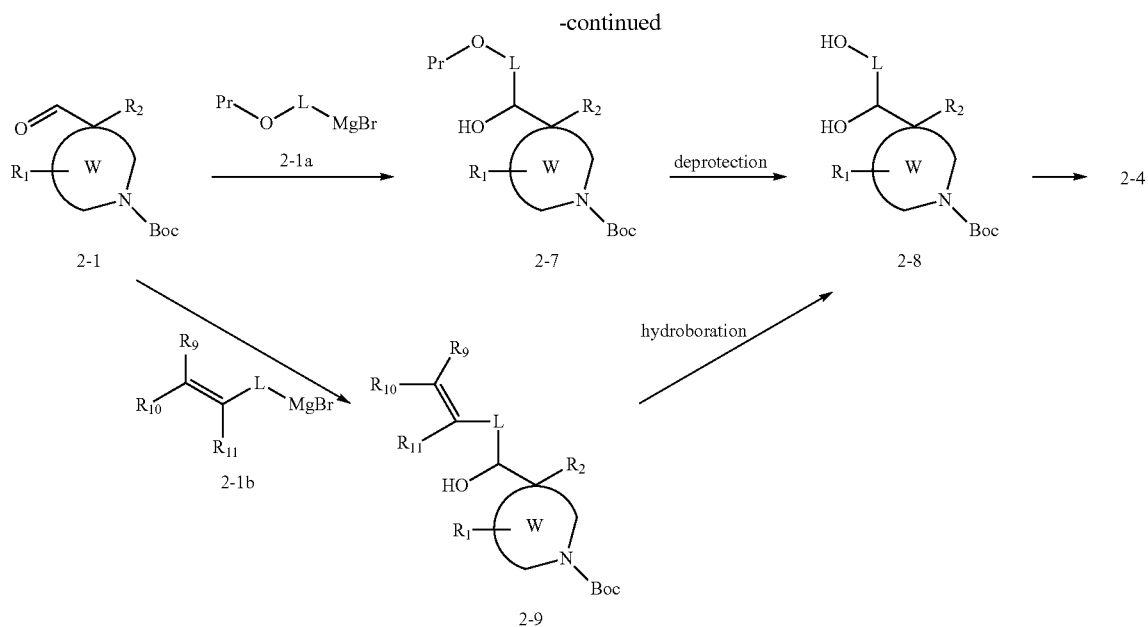

L: alkyl or heteroalkyl linkers; Pr: protection groups

Oxidation of 1-3 to 2-1 is carried out by Swern oxidation or other oxidants, such as Dess-Martin Periodiane or the like. Grignard reaction of aldehyde 2-1 with an unsaturated or a saturated Grignard reagent, followed by alkylation with an unsaturated or a saturated alkylating reagent under basic condition gives 2-3. Ring-closing metathesis (RCM) of 2-3 with a catalyst, such as Grubbs ruthenium-carbene complexes or the like, yields an unsaturated oxygen-containing heterocyclic 2-4 or a saturated oxygen-containing heterocyclic 2-4 after hydrogenation. Alternatively, the synthesis of 2-4 is achieved by a Grignard reaction of 2-1 with 2-1a or 2-1b, followed by either deprotection of the intermediate 2-7 or hydroboration of double bond of the intermediate 2-9 to give the corresponding diol 2-8. The diol 2-8 is converted to 2-4 by intramolecular cyclization under Mitsunobu reaction condition or displacement of the corresponding mesylates, tosylates, or the like.

Finally, the synthesis of 2-6 from 2-4 is achieved using the same methodology as the conversion of 1-4 to 1-6 in Scheme 1.

Scheme 3

Compounds where "A" of Formula I is a heteroaryl moiety are synthesized as illustrated in Scheme 3 and exemplified by the synthesis of 3-8.

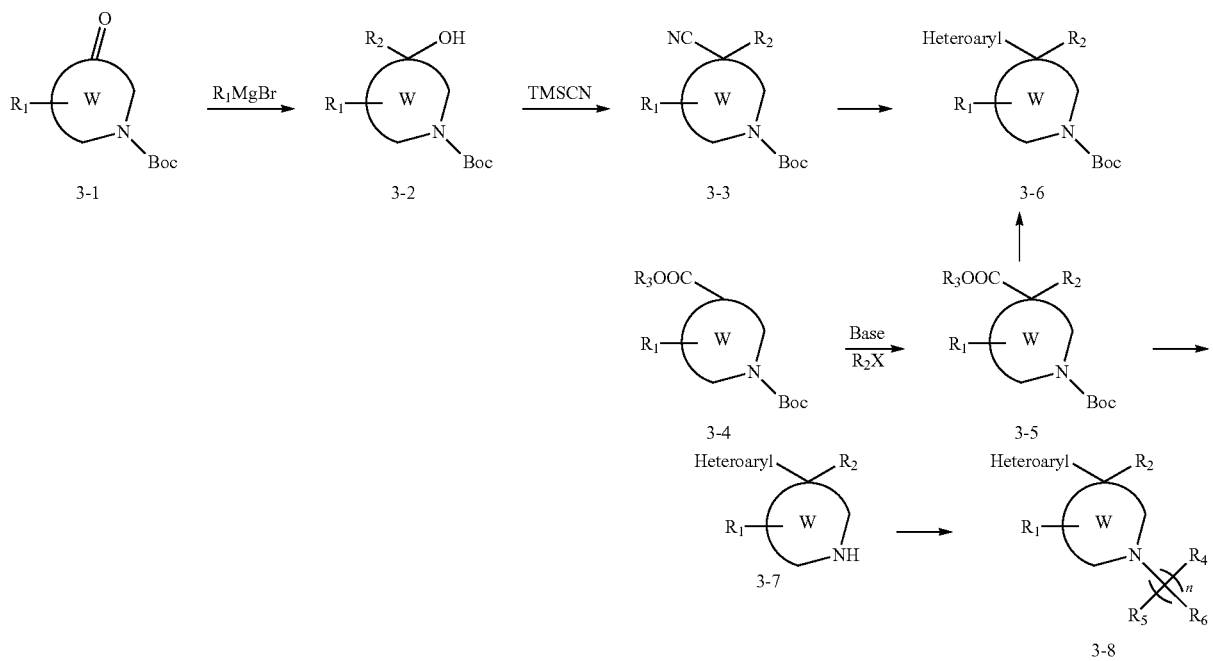

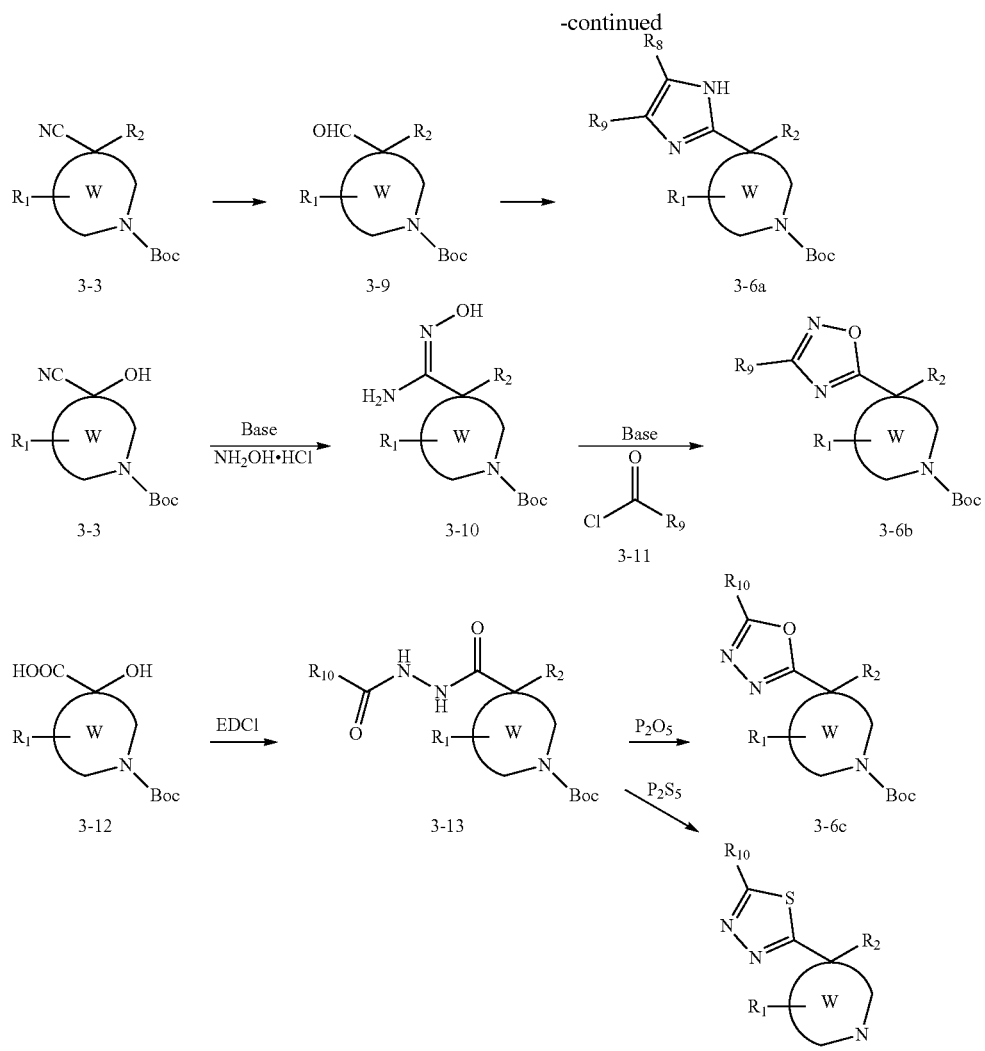

The cyano intermediate 3-3 and the ester intermediate 3-5 are prepared from substituted 3-2 by cynidation and 3-4 by alkylation as described in Scheme 1. The cyano group of 3-3 and the ester group of 3-5 are converted to heterocyclic rings such as imidazole, thiazole, thiadiazole, oxadiazole 3-6 (3-6a, 3-6b, 3-6c and 3-6d), etc. through the corresponding intermediates such as amide, thioamide, hydrazide, thiohydrazide or N-hydroxy-imidamide using the common methods exemplified in the scheme 3. The conversion of 3-6 to 3-8 is achieved using the methodology illustrated in Scheme 1.

Scheme 4

Compounds where "A" of Formula I is a heteroalkyl moiety are synthesized as illustrated in Scheme 4 and exemplified by the synthesis of 4-6.

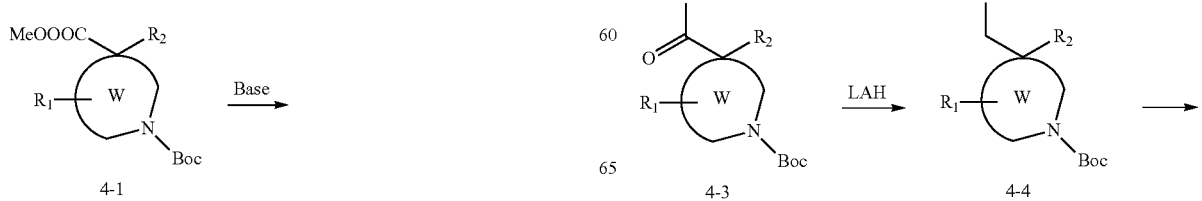

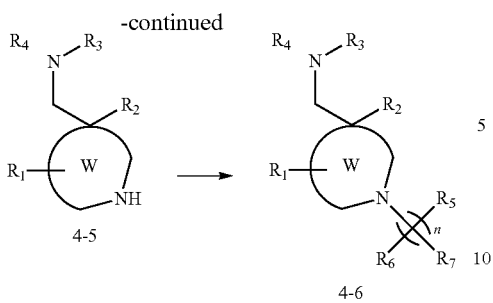

A suitable substituted cyclic amide 4-3 is prepared from the corresponding ester 4-1 by hydrolysis using bases, such as NaOH, LiOH, KOH, or the like, followed by coupling with an amine in the presence of coupling reagents, such as EDCl/HOBt, DCC, HATU, or the like. Reduction of 4-3 using $BH_3$ or $LiAlH_4$, followed by deprotection of Boc group of 4-4 and alkylation of 4-5 as described in Scheme 1 yields compound 4-6.

Scheme 5

As illustrated in Scheme 5, compounds where Y and Q of Formula I are certain moieties are synthesized.

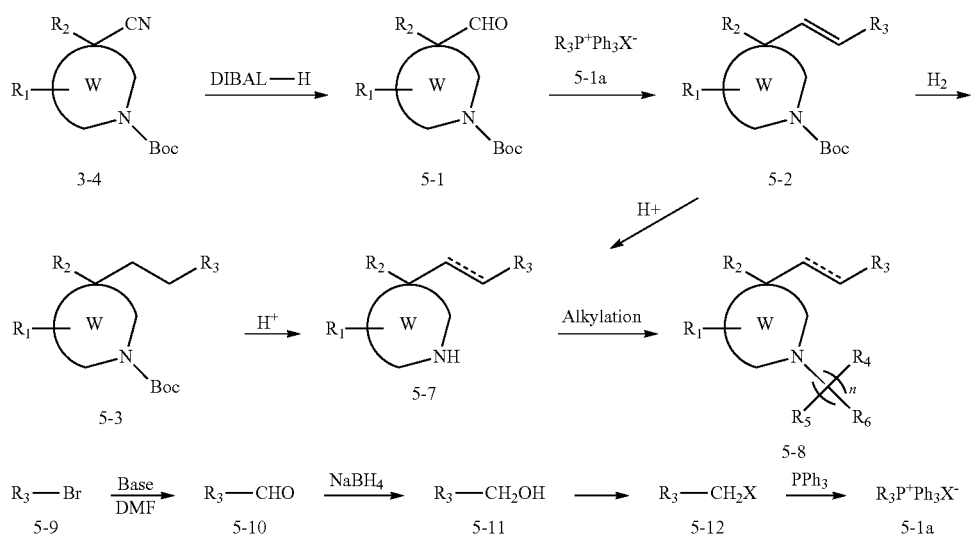

Reduction of CN group to aldehyde 5-1, followed by Wittig reaction with a quaternary phosphonium salt such as 5-1a produces compound 5-2. Hydrogenation of the double bond of 5-2 followed by deprotection or deprotection of 5-2 followed by the alkylation gives either an unsaturated or a saturated compound 5-8. The quaternary phosphonium salt 5-1a is prepared from a suitable bromide 5-9. Conversion of a suitable bromide 5-9 to the corresponding aldehyde 5-10, followed by reduction of the aldehyde with a suitable reducing agent, such as $NaBH_4$ or the like, gives alcohol 5-11. Halogenation of alcohol 5-11, followed by the treatment with $PPh_3$ gives a quaternary phosphonium salt 5-1a.

Scheme 6

As illustrated in Scheme 6, compounds where Y and Q of Formula I are other moieties than in Scheme 5 are synthesized.

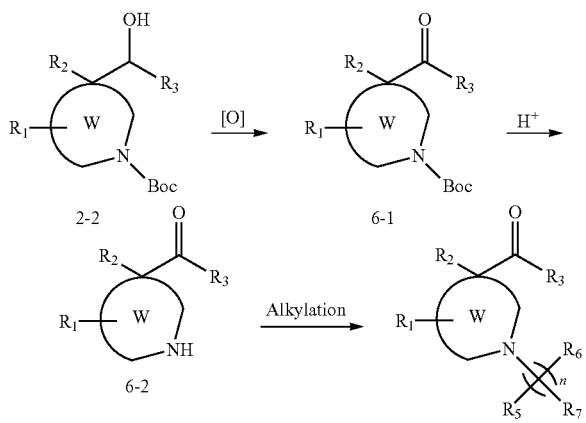

Alcohol 2-2 is oxidized with oxidants such as Dess-Martin Periodiane, PCC, or the like to form ketone 6-1. Deprotection of the Boc group of 6-1, followed by alkylation generates 6-3.

Scheme 7

As illustrated in Scheme 7, compounds where Z and T of Formula I are particular moieties are synthesized.

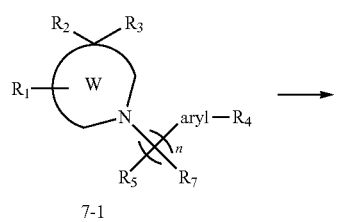

7-1

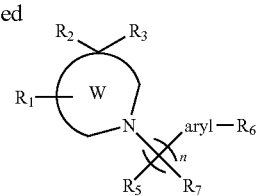

7-2

$R_4$ = Br, CN, $NO_2$, COOH, COOEt, pinacol boric ester, alkynyl
$R_6$ = alkynyl, aryl, heteroaryl The starting 7-1 is a group of intermediates which are prepared according to the schemes 1 to 6. The aryl group of 7-1 is a substituted or an unsubstituted aryl group, such as benzene, thiazolyl, thiophenyl, furanyl, imidazolyl, thiadiazolyl, oxadiazolyl, tetrazolyl. The $R_4$ is a functional group such as Br, I, CN, COOH, COOEt, boric acid. The conversion of $R_4$ to $R_6$ is achieved via Suzuki coupling of boric acid with Br or I, or the cyclization of hydrazide of ester with acid or the cyclization of N-hydroxy-imidamide with an acyl chloride.

Scheme 8

Scheme 8 illustrates one of the approaches for the synthesis of stereo isomers. In addition, the synthesis of the two enantiomerically pure isomers is also achieved by the chiral separation via chiral HPLC, chiral resolution, or column chromatography methods.

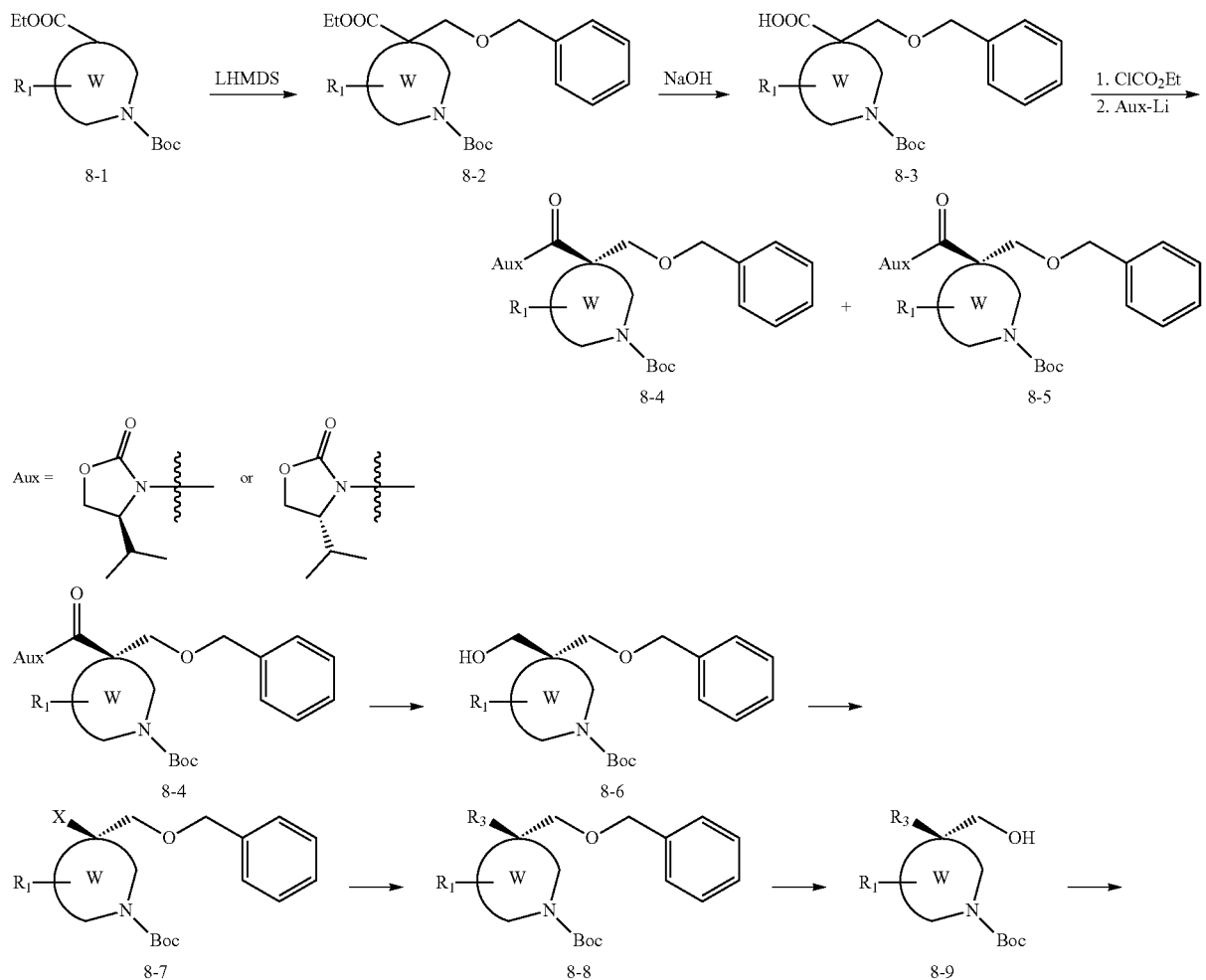

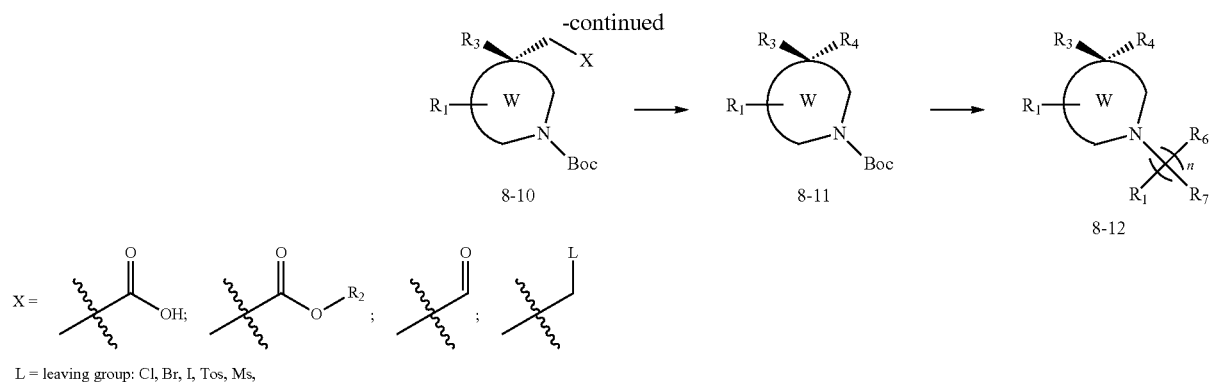

L = leaving group: Cl, Br, I, Tos, Ms,

In scheme 8, ester 8-2, prepared according to scheme 1, is hydrolyzed to acid 8-3 using inorganic bases, such as LiOH, NaOH, KOH, or the like. Acid 8-3 is activated to its corresponding acid chloride or mixed anhydride, followed by reaction with lithiated chiral auxiliary salt provides a mixture of diastereomers 8-4 and 8-5. The separation of diastereomeric mixture provides the single enantiomers 8-4 and 8-5.

The enantiomerically pure intermediates such as 8-4 and 8-5 are further transformed into a variety of the key intermediates, such as 8-8 and 8-10, in enantiomerically pure form, using the methodologies illustrated in the schemes 1-7. Some examples are illustrated in Scheme 9 and Scheme 10 below.

Scheme 9

Scheme 9 shows an example for the synthesis of enantiomerically pure compounds 9-8 starting from 8-4.

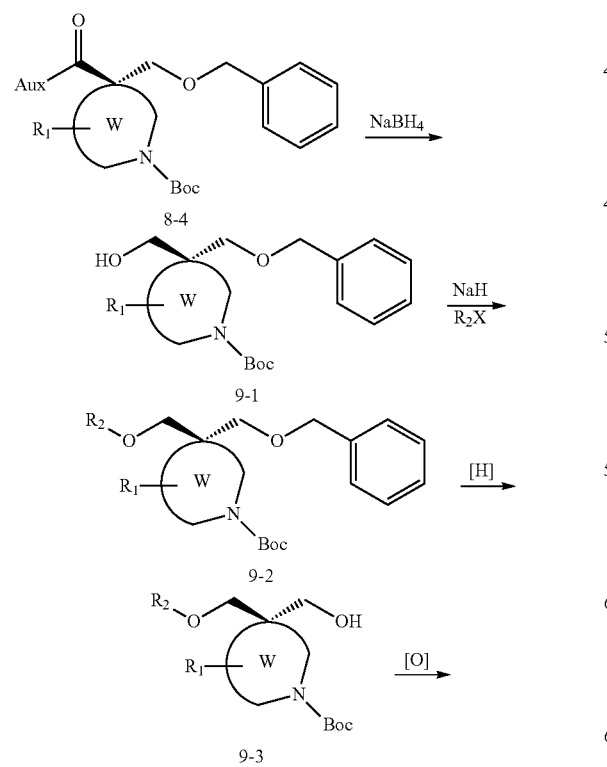

The enantiomerically pure intermediate 8-4 described in Scheme 8 is reduced using $NaBH_4$ to a chiral alcohol 9-1. The transformation of alcohol 9-1 to 9-8 is carried out according to the methodologies described in schemes 1 to 5. Using the same methodology as demonstrated in Scheme 9, the enantiomer of 9-8 is synthesized starting from the enantiomerically pure intermediate 8-5.

Scheme 10

Scheme 10 shows an example for the synthesis of enantiomerically pure compounds 10-8 starting from 8-5.

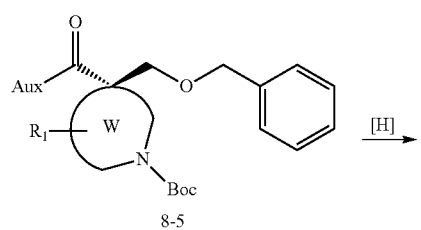

8-5

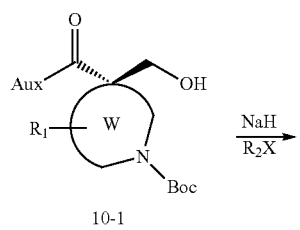

10-1

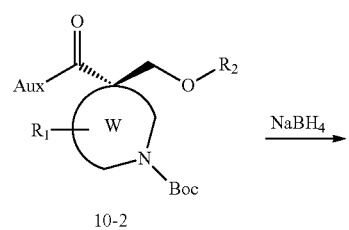

10-2

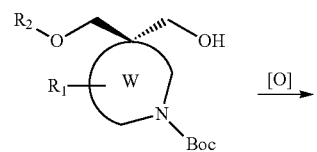

10-3

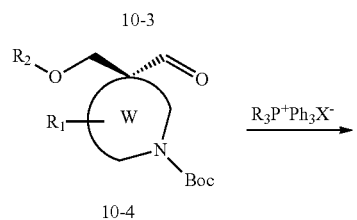

10-4

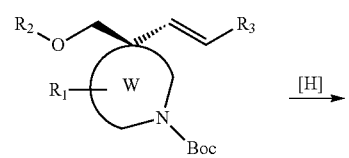

10-5

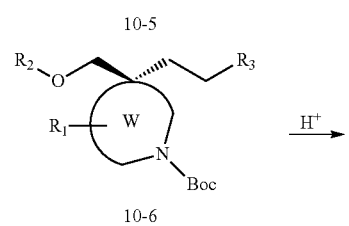

10-6

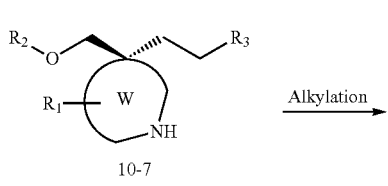

10-7

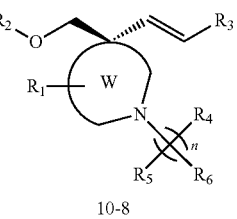

10-8

The enantiomerically pure compound 10-8 is synthesized starting from 8-5 according to the methodologies described in scheme 9. Using the same methodology as demonstrated in Scheme 10, the enantiomer of 10-8 is synthesized starting from the enantiomerically pure intermediate 8-4.

Scheme 11

Scheme 11 shows an example for the synthesis of enantiomerically intermediate 10-3 and 9-1 starting from 8-3 by chiral resolution.

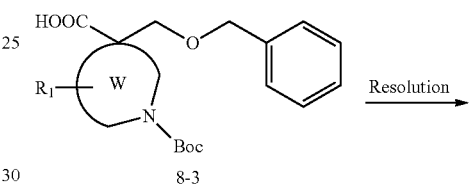

8-3

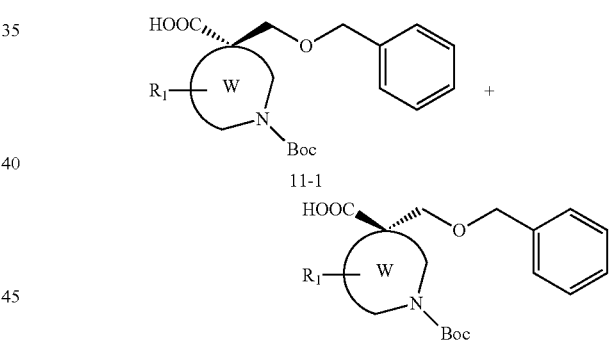

11-1

11-2

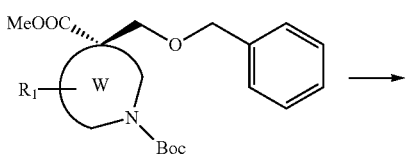

11-1

MeOOC 11-4

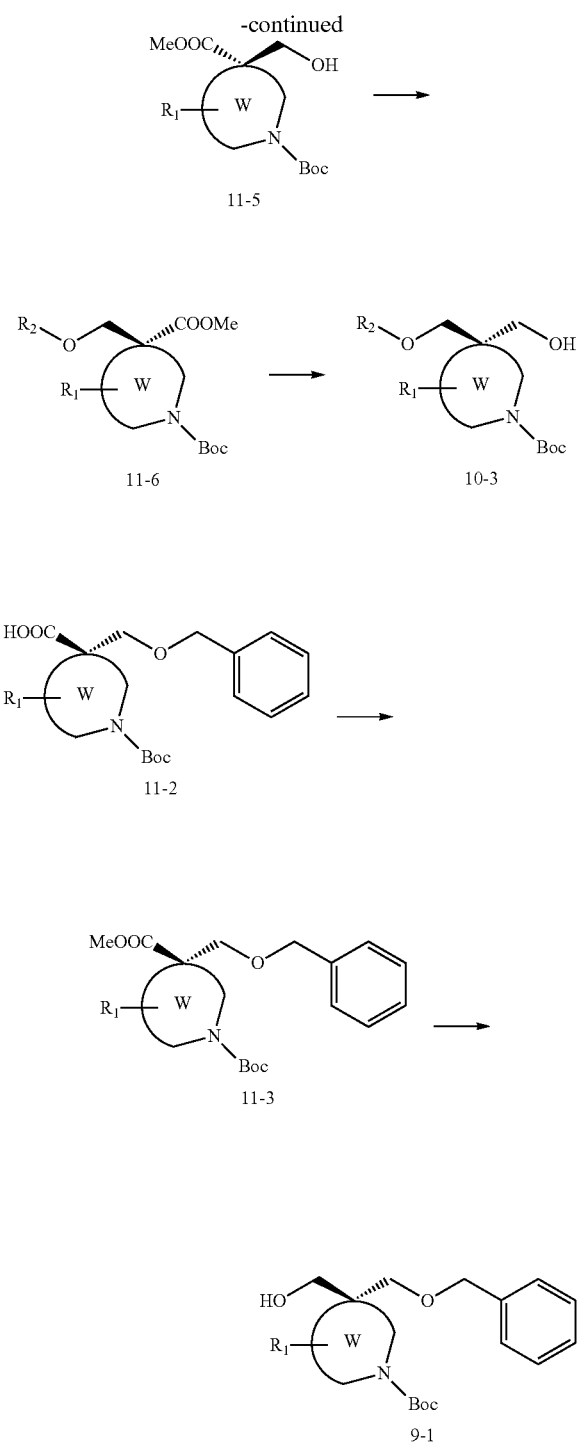

The enantiomerically intermediate 10-3 and 9-1 was synthesized starting from 8-3 according to the methodologies described in scheme 9 and 10. Using the same methodology as demonstrated in Scheme 11, the enantiomer of 10-3 and 9-1 is synthesized starting from the enantiomerically pure intermediate 11-2.

Formulation of the Compounds (Compositions)

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted to provide a pharmaceutically acceptable dosage of the active component.

The compounds of the invention and for some of them, their properties, are listed below in Tables I to VI.

TABLE I

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 1 | 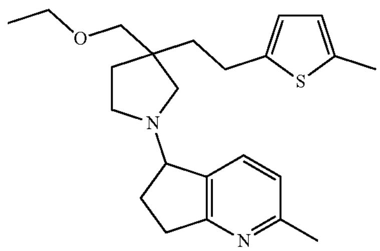 [SMILES: CCOCC1(CCc2ccc(C)s2)CCN(C2CCc3nc(C)ccc32)C1] | 5-((R or S)-3-(ethoxymethyl)-3-(2-(5-methylthiophen-2-yl)ethyl)pyrrolidin-1-yl)-2-methyl-6,7-dihydro-5H-cyclopenta[b]pyridine | 385 | $^1$H NMR (300 MHz, CDCl$_3$): δ 7.52 (d, J = 7.5 Hz, 1H), 6.95 (d, J = 7.8 Hz, 1H), 6.53-6.51 (m, 2H), 4.25-4.15 (m, 1H), 3.45 (q, J = 5.1 Hz, 2H), 3.31-3.23 (m, 2H), 3.15-3.03 (m, 1H), 2.95-2.81 (m, 1H), 2.79-2.60 (m, 3H), 2.60-2.55 (m, 1H), 2.52 (s, 3H), 2.42 (s, 3H), 2.39-2.35 (m, 1H), 2.18-2.10 (m, 2H), 2.10-1.98 (m, 1H), 1.90-1.75 (m, 2H), 1.65-1.59 (m, 2H), 1.17 (t, J = 7.2 Hz, 3H). |
| 2 | 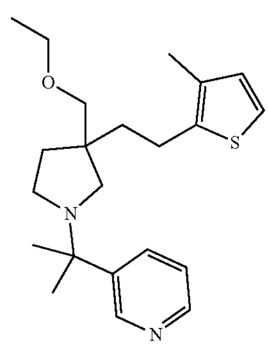 [SMILES: CCOCC1(CCc2sccc2C)CCN(C(C)(C)c2cccnc2)C1] | (S or R)-3-(2-(3-(ethoxymethyl)-3-(2-(3-methylthiophen-2-yl)ethyl)pyrrolidin-1-yl)propan-2-yl)pyridine | 373 | $^1$H NMR (300 MHz, MeOD): δ 8.70 (s, 1H), 8.38-8.36 (m, 1H), 8.00-7.97 (m, 1H), 7.41-7.37 (m, 1H), 7.01 (d, J = 5.1 Hz, 1H), 6.73 (d, J = 5.1 Hz, 1H), 3.48 (q, J = 6.9 Hz, 2H), 3.33-3.30 (m, 2H), 3.29-3.27 (m, 2H), 2.68-2.55 (m, 4H), 2.53 (d, J = 9.3 Hz, 1H), 2.32 (d, J = 9.3 Hz, 1H), 2.11 (s, 3H), 1.78-1.64 (m, 2H), 1.62-1.55 (m, 2H), 1.44 (s, 6H), 1.17 (t, J = 6.9 Hz, 3H) |
| 3 | 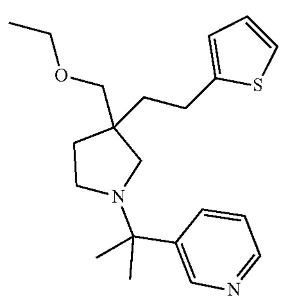 [SMILES: CCOCC1(CCc2cccs2)CCN(C(C)(C)c2cccnc2)C1] | (S or R)-3-(2-(3-(ethoxymethyl)-3-(2-(thiophen-2-yl)ethyl)pyrrolidin-1-yl)propan-2-yl)pyridine | 359 | $^1$H NMR (300 MHz, MeOD): δ 8.70 (s, 1H), 8.37 (d, J = 3.9 Hz, 1H), 7.98 (d, J = 8.1 Hz, 1H), 7.38 (m, 1H), 7.13 (dd, J = 5.1, 1.2 Hz, 1H), 6.87 (dd, J = 5.1, 3.3 Hz, 1H), 6.76 (d, J = 2.4 Hz, 1H), 3.47 (q, J = 6.9 Hz, 2H), 3.34-3.30 (m, 2H), 2.78 (t, J = 8.4 Hz, 2H), 2.64-2.60 (m, 2H), 2.52 (d, J = 9.3 Hz, 1H), 2.31 (d, J = 9.3 Hz, 1H), 1.82-1.77 (m, 2H), 1.59 (t, J = 6.9 Hz, 2H), 1.43 (s, 6H), 1.16 (t, J = 6.9 Hz, 3H) |
| 4 | 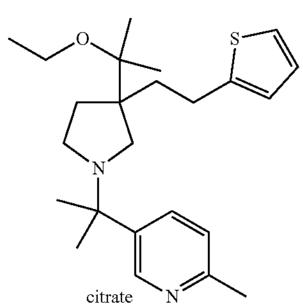 [SMILES: CCOC(C)(C)C1(CCc2cccs2)CCN(C(C)(C)c2ccc(C)nc2)C1] | (S or R)-5-(2-(3-(2-ethoxypropan-2-yl)-3-(2-(thiophen-2-yl)ethyl)pyrrolidin-1-yl)propan-2-yl)-2-methylpyridine citrate | 402 | $^1$H NMR (300 MHz, MeOD): δ 8.77 (s, 1H), 8.13 (dd, J = 8.4, 2.4 Hz, 1H), 7.46 (d, J = 8.4 Hz, 1H), 7.17-7.16 (m, 1H), 6.90-6.87 (m, 1H), 6.80-6.79 (m, 1H), 3.50-3.29 (m, 7H), 3.12-3.08 (m, 1H), 2.80 (q, J = 15.6 Hz, 4H), 2.56 (s, 3H), 2.37-2.25 (m, 1H), 1.92 (s, 6H), 1.87-1.78 (m, 3H), 1.13 (d, J = 8.7 Hz, 6H), 1.02 (t, J = 6.9 Hz, 3H) |

TABLE I-continued

Compounds with a pyrrolidine ring and a pyridine or pyridine-like molecule bonded to the pyrrolidine N-constituent

| Compound No. | Structure | Name | MS (ESI+): [M + H]$^+$ | H-NMR |
|---|---|---|---|---|
| 5 | 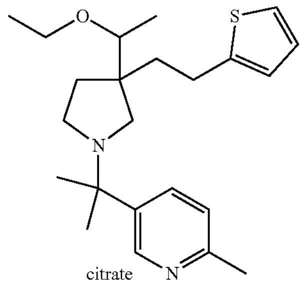 [SMILES: CCOC(C)C1(CCc2cccs2)CCN(C(C)(C)c2ccc(C)nc2)C1] | 5-(2-((S & R)-3-((S or R)-1-ethoxyethyl)-3-(2-(thiophen-2-yl)ethyl)pyrrolidin-1-yl)propan-2-yl)-2-methylpyridine citrate | 388 | $^1$H NMR (300 MHz, MeOD): δ 8.75-8.67 (m, 1H), 8.15-8.03 (m, 1H), 7.45 (t, J = 6.6 Hz, 1H), 7.18-7.17 (m, 1H), 6.90-6.88 (m, 1H), 6.81 (s, 1H), 3.56-3.50 (m, 2H), 3.40-3.31 (m, 2H), 3.25-3.15 (m, 3H), 2.87-2.75 (m, 6H), 2.58 (s, 3H), 2.33-2.08 (m, 2H), 1.90 (d, J = 7.8 Hz, 6H), 1.87-1.62 (m, 2H), 1.36-1.00 (m, 6H) |
| 6 | 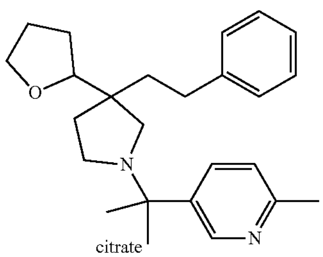 [SMILES: Cc1ccc(C(C)(C)N2CCC(CCc3ccccc3)(C3CCCO3)C2)cn1] | 2-methyl-5-(2-((3R or S)-3-phenethyl-3-(tetrahydrofuran-2-yl)pyrrolidin-1-yl)propan-2-yl)pyridine citrate | 379 | $^1$H NMR (300 MHz, MeOD): δ 8.73-8.71 (m, 1H), 8.07 (t, J = 8.4 Hz, 1H), 7.45 (dd, J = 8.4, 2.4 Hz, 1H), 7.27-7.12 (m, 5H), 3.92-3.80 (m, 2H), 3.65-3.26 (m, 2H), 3.47-3.38 (m, 2H), 3.31 (q, J = 1.5 Hz, 1H), 2.80 (q, J = 15.3 Hz, 4H), 2.61-2.50 (m, 5H), 2.20 (m, 1H), 2.15-1.95 (m, 3H), 1.87 (s, 3H), 1.85 (s, 3H), 1.77-1.72 (m, 3H), 1.28-1.15 (m, 1H) |
| 7 | 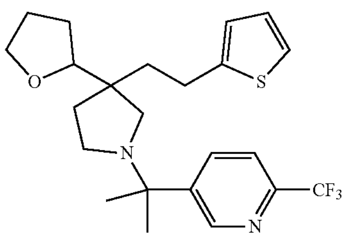 [SMILES: CC(C)(c1ccc(C(F)(F)F)nc1)N1CCC(CCc2cccs2)(C2CCCO2)C1] | 5-(2-((3R or S)-3-(tetrahydrofuran-2-yl)-3-(2-(thiophen-2-yl)ethyl)pyrrolidin-1-yl)propan-2-yl)-2-(trifluoromethyl)pyridine | 439 | $^1$H NMR (300 MHz, MeOD): δ 8.89 (s, 1H), 8.00 (d, J = 4.8 Hz, 1H), 7.62 (d, J = 8.1 Hz, 1H), 7.12-7.11 (m, 1H), 6.92-6.91 (m, 1H), 6.80 (s, 1H), 3.86-3.82 (m, 2H), 3.74-3.71 (m, 1H), 2.90-2.85 (m, 2H), 2.70-2.51 (m, 3H), 2.47-2.36 (m, 2H), 1.96-1.42 (m, 13H) |
| 8 | 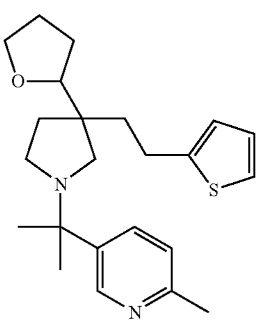 [SMILES: Cc1ccc(C(C)(C)N2CCC(CCc3cccs3)(C3CCCO3)C2)cn1] | 2-methyl-5-(2-((R or S)-3-((S or R)-tetrahydrofuran-2-yl)-3-(2-(thiophen-2-yl)ethyl)pyrrolidin-1-yl)propan-2-yl)pyridine | 387 | $^1$H NMR (300 MHz, CDCl$_3$): δ 8.60 (d, J = 1.5 Hz, 1H), 7.72 (dd, J = 6.0, 1.5 Hz, 1H), 7.11-7.08 (m, 2H), 6.91 (dd, J = 2.4, 3.9 Hz, 1H), 6.79 (d, J = 1.8 Hz, 1H), 3.87-3.83 (m, 2H), 3.73-3.71 (m, 1H), 3.00-2.88 (m, 1H), 2.87-2.78 (m, 1H), 2.59-2.53 (m, 3H), 2.51 (s, 3H), 2.43 (d, J = 6.9 Hz, 1H), 2.00-1.91 (m, 1H), 1.90-1.85 (m, 3H), 1.78-1.71 (m, 3H), 1.61-1.52 (m, 1H), 1.39 (d, J = 0.9 Hz, 6H) |
| 9 | 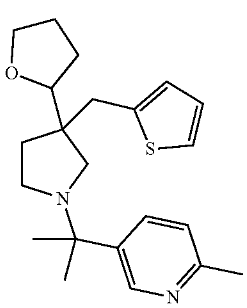 [SMILES: Cc1ccc(C(C)(C)N2CCC(Cc3cccs3)(C3CCCO3)C2)cn1] | 2-methyl-5-(2-((3S or R)-3-(tetrahydrofuran-2-yl)-3-(thiophen-2-ylmethyl)pyrrolidin-1-yl)propan-2-yl)pyridine | 371 | $^1$H NMR (300 MHz, CDCl$_3$): δ 8.57 (s, 1H), 7.63 (d, J = 7.5 Hz, 1H), 7.12 (s, 1H), 7.07 (d, J = 8.1 Hz, 1H), 6.93 (s, 1H), 6.81 (s, 1H), 3.88-3.78 (m, 1H), 3.76-3.69 (m, 3H), 3.15-3.10 (m, 1H), 2.95-2.83 (m, 1H), 2.52 (s, 3H), 2.48-2.36 (m, 3H), 1.76-1.60 (m, 6H), 1.36 (s, 3H), 1.35 (s, 3H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 10 | 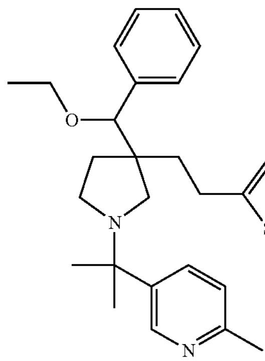 | 5-(2-((R or S)-3-((S or R)-ethoxy(phenyl)methyl)-3-(2-(thiophen-2-yl)ethyl)pyrrolidin-1-yl)propan-2-yl)-2-methylpyridine | 449 | $^1$H NMR (300 MHz, MeOD): δ 8.68 (d, J = 2.1 Hz, 1H), 8.02 (dd, J = 8.3, 2.1 Hz, 1H), 7.43-7.34 (m, 5H), 7.32-7.26 (m, 1H), 7.14 (d, J = 5.1 Hz, 1H), 6.88-6.85 (m, 1H), 6.74 (d, J = 2.4 Hz, 1H), 4.39 (s, 1H), 3.41-3.35 (m, 2H), 3.28-3.25 (m, 2H), 3.16-3.06 (m, 2H), 2.92-2.83 (m, 2H), 2.84-2.71 (m, 4H), 2.56 (s, 3H), 2.25-2.13 (m, 1H), 2.90-2.81 (m, 1H), 1.77-1.73 (m, 6H), 1.61-1.50 (m, 2H), 1.05 (t, J = 6.9 Hz, 3H) |
| 11 | 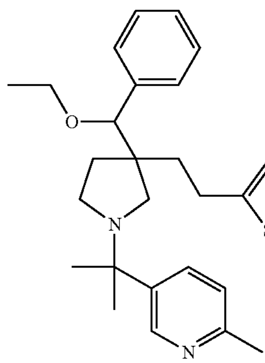 | 5-(2-((R or S)-3-((R or S)-ethoxy(phenyl)methyl)-3-(2-(thiophen-2-yl)ethyl)pyrrolidin-1-yl)propan-2-yl)-2-methylpyridine | 449 | $^1$H NMR (300 MHz, CDCl$_3$): δ 8.53 (d, J = 2.4 Hz, 1H), 7.60 (dd, J = 8.1, 2.4, Hz 1H), 7.32-7.28 (m, 5H), 7,10-7.04 (m, 2H), 6.90 (dd, J = 5.1, 3.6 Hz, 1H), 6.76 (d, J = 2.4 Hz, 1H), 4.20 (s, 1H), 3.41-3.30 (m, 1H), 3.27-3.12 (m, 1H), 3.05-2.92 (m, 1H), 2.91-2.82 (m, 1H), 2.74 (d, J = 9.2 Hz, 1H), 2.52 (s, 3H), 2.51-2.45 (m, 1H), 2.41-2.30 (m, 1H), 2.24 (d, J = 9.0 Hz, 1H), 2.02-1.88 (m, 2H), 1.71-1.65 (m, 2H), 1.37 (s, 3H), 1.34 (s, 3H), 1.15 (t, J = 6.9 Hz, 3H) |
| 12 | citrate | 5-(2-((R or S)-3-((R or S)-1-ethoxyethyl)-3-(2-(thiophen-2-yl)ethyl)pyrrolidin-1-yl)propan-2-yl)-2-methylpyridine citrate | 387 | $^1$H NMR (300 MHz, MeOD): δ 8.70 (d, J = 2.1 Hz, 1H), 8.05 (dd, J = 8.1, 2.4, Hz 1H), 7.41 (d, J = 8.1 Hz, 1H), 7.16 (dd, J = 5.1, 1.2 Hz, 1H), 6.88 (dd, J = 5.1, 3.3 Hz, 1H), 6.79 (d, J = 3.3 Hz, 1H), 3.61-3.58 (m, 1H), 3.50-3.34 (m, 1H), 3.32-3.30 (m, 2H), 3.25-3.22 (m, 2H), 3.21-3.19 (m, 1H), 2.92-2.82 (m, 2H), 2.80-2.70 (m, 4H), 2.56 (s, 3H), 2.09-1.95 (m, 1H), 1.94-1.85 (m, 3H), 1.82 (s, 6H), 1.10-1.03 (m, 6H) |
| 13 | citrate | 5-(2-((R or S)-3-((S or R)-1-ethoxyethyl)-3-(2-(thiophen-2-yl)ethyl)pyrrolidin-1-yl)propan-2-yl)-2-methylpyridine citrate | 387 | $^1$H NMR (300 MHz, MeOD): δ 8.69 (d, J = 2.1 Hz, 1H), 8.03 (d, J = 8.7 Hz, 1H), 7.42 (d, J = 7.2 Hz, 1H), 7.17 (dd, J = 4.8, 1.2, Hz, 1H), 6.88 (dd, J = 3.3, 5.1 Hz 1H), 6.79 (d, J = 3.0 Hz, 1H), 3.68-3.60 (m, 1H), 3.49-3.43 (m, 1H), 3.30-3.18 (m, 4H), 3.17-2.98 (m, 2H), 2.86-2.71 (m, 4H), 2.56 (s, 3H), 2.25-2.12 (m, 1H), 2.10-1.90 (m, 1H), 1.82 (s, 6H), 1.81-1.76 (m, 2H), 1.71-1.60 (m, 1H), 1.13-1.03 (m, 6H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 14 | 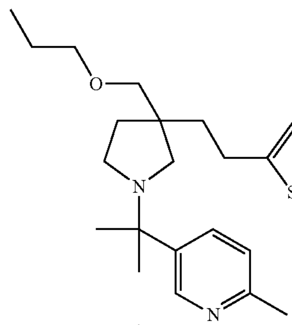 | (R or S)-2-methyl-5-(2-(3-(propoxymethyl)-3-(2-(thiophen-2-yl)ethyl)pyrrolidin-1-yl)propan-2-yl)pyridine citrate | 387 | $^1$H NMR (300 MHz, MeOD): δ 8.68 (d, J = 2.1 Hz, 1H), 8.03 (d, J = 6.3 Hz, 1H), 7.41 (d, J = 8.4 Hz, 1H), 7.15 (d, J = 5.1 Hz, 1H), 6.88 (dd, J = 5.1, 3.6 Hz, 1H), 6.78 (d, J = 3.3 Hz, 1H), 3.50-3.38 (m, 2H), 3.25-3.20 (m, 2H), 3.12-3.08 (m, 1H), 2.92-2.87 (m, 2H), 2.78-2.72 (m, 4H), 2.56 (s, 3H), 2.15-1.92 (m, 2H), 1.90-1.81 (m, 4H), 1.79 (s, 6H), 1.70-1.48 (m, 3H), 0.89 (t, J = 7.5 Hz, 3H) |
| 15 | 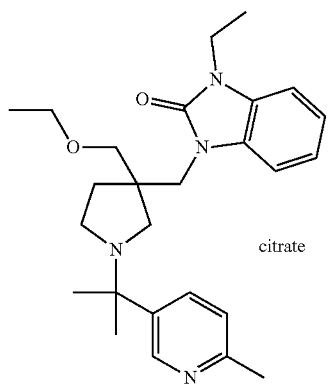 [SMILES: CCOCC1(Cn2c(=O)n(CC)c3ccccc32)CCN(C(C)(C)c2ccc(C)nc2)C1] | (R or S)-1-((3-(ethoxymethyl)-1-(2-(6-methylpyridin-3-yl)propan-2-yl)pyrrolidin-3-yl)methyl)-3-ethyl-1,3-dihydro-2H-benzo[d]imidazol-2-one citrate | 437 | $^1$H NMR (300 MHz, MeOD): δ 8.56 (d, J = 2.4 Hz, 1H), 7.91 (d, J = 8.3 Hz, 1H), 7.27 (d, J = 8.2 Hz, 1H), 7.13 (d, J = 6.8 Hz, 1H), 7.10-6.96 (m, 3H), 3.92-3.81 (m, 3H), 3.40-3.30 (m, 4H), 3.31 (m, 2H), 3.18 (s, 2H), 2.91 (d, J = 11.5 Hz, 1H), 2.78-2.61 (m, 4H), 2.45 (s, 3H), 1.96 (m, 1H), 1.83-1.72 (m, 1H), 1.65 (s, 3H), 1.64 (s, 3H), 1.20 (t, J = 7.2 Hz, 3H), 1.06 (t, J = 6.9 Hz, 3H) |
| 16 | 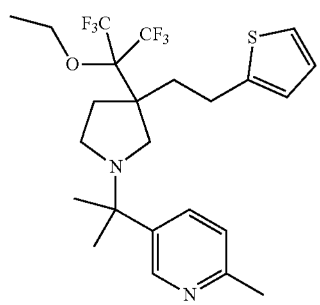 [SMILES: CCOC(C(F)(F)F)(C(F)(F)F)C1(CCc2cccs2)CCN(C(C)(C)c2ccc(C)nc2)C1] | (R or S)-5-(2-(3-(2-ethoxy-1,1,1,3,3,3-hexafluoro-propan-2-yl)-3-(2-(thiophen-2-yl)ethyl)pyrrolidin-1-yl)propan-2-yl)-2-methylpyridine | 509 | $^1$H NMR (300 MHz, CDCl$_3$): δ 8.51 (d, J = 2.1 Hz, 1H), 7.64 (dd, J = 8.1, 2.4 Hz, 1H), 7.07-7.02 (m, 2H), 6.86 (dd, J = 5.1, 3.3 Hz, 1H), 6.74-6.73 (m, 1H), 3.96-3.80 (m, 2H), 3.01 (t, J = 8.7 Hz, 2H), 2.89 (d, J = 9.6 Hz, 1H), 2.60-2.56 (m, 2H), 2.55 (s, 3H), 2.36-2.28 (m, 2H), 2.15-2.08 (m, 1H), 2.00-1.80 (m, 2H), 1.61 (s, 6H), 1.13 (t, J = 6.9 Hz, 3H) |
| 17 | 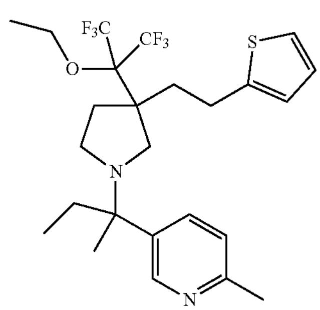 [SMILES: CCOC(C(F)(F)F)(C(F)(F)F)C1(CCc2cccs2)CCN(C(C)(CC)c2ccc(C)nc2)C1] | 5-(2-((R or S)-3-(2-ethoxy-1,1,1,3,3,3-hexafluoropropan-2-yl)-3-(2-(thiophen-2-yl)ethyl)pyrrolidin-1-yl)butan-2-yl)-2-methylpyridine citrate | 523 | $^1$H NMR (300 MHz, MeOD): δ 8.50 (d, J = 2.1 Hz, 1H), 7.92-7.87 (m, 1H), 7.35 (dd, J = 8.4, 2.7 Hz, 1H), 7.19-7.16 (m, 1H), 6.93-6.90 (m, 1H), 6.85-6.75 (m, 1H), 4.08-3.90 (m, 2H), 3.19-3.10 (m, 1H), 3.05-2.98 (m, 2H), 2.91-2.75 (m, 4H), 2.54 (s, 3H), 2.50-2.35 (m, 2H), 2.22-2.10 (m, 1H), 2.09-1.90 (m, 2H), 1.89-1.75 (m, 2H), 1.46 (s, 3H), 1.35-1.30 (m, 2H), 1.22-1.16 (m, 3H), 0.71-0.64 (m, 3H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 18 | 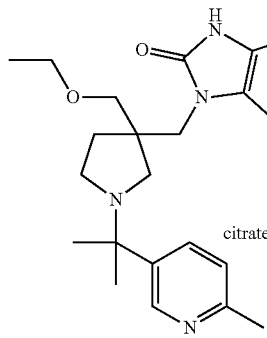 | (R or S)-1-((3-(ethoxymethyl)-1-(2-(6-methyl-pyridin-3-yl)propan-2-yl)pyrrolidin-3-yl)methyl)-1,3-dihydro-2H-benzo[d]imidazol-2-one citrate | 409 | $^1$H NMR (300 MHz, MeOD) δ 8.61 (s, 1H), 7.97 (d, J = 8.2 Hz, 1H), 7.31 (d, J = 8.1 Hz, 1H), 7.10-7.03 (m, 1H), 6.99-6.90 (m, 3H), 3.85 (s, 2H), 3.48-3.06 (m, 10H), 2.84-2.63 (q, J = 15.6 Hz, 4H), 2.46 (s, 3H), 1.94 (m, 2H), 1.76 (s, 6H), 1.04 (t, J = 6.9 Hz, 3H) |
| 19 | 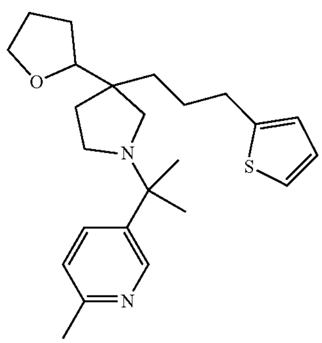 [SMILES: Cc1ccc(C(C)(C)N2CCC(CCCc3cccs3)(C3CCCO3)C2)cn1] | 2-methyl-5-(2-((3R or S)-3-(tetrahydrofuran-2-yl)-3-(3-(thiophen-2-yl)propyl)pyrrolidin-1-yl)propan-2-yl)pyridine | 399 | $^1$H NMR (300 MHz, CDCl$_3$): δ 8.58 (d, J = 2.1 Hz, 1H), 7.69 (dd, J = 8.1, 2.4 Hz, 1H), 7.12-7.05 (m, 2H), 6.93-6.90 (m, 1H), 6.78 (d, J = 3.3 Hz, 1H), 3.90-3.75 (m, 2H), 3.74-3.62 (m, 1H), 2.89-2.75 (m, 2H), 2.64-2.45 (m, 6H), 2.35-2.25 (m, 1H), 1.90-1.80 (m, 4H), 1.72-1.58 (m, 4H), 1.52-1.44 (m, 2H), 1.43-1.36 (m, 6H) |
| 20 | 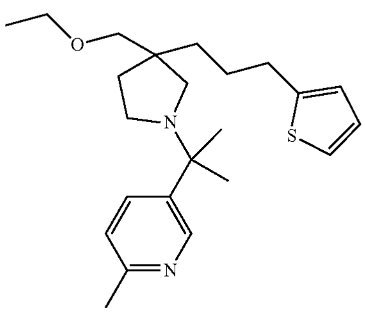 [SMILES: CCOCC1(CCCc2cccs2)CCN(C(C)(C)c2ccc(C)nc2)C1] | (R or S)-5-(2-(3-(ethoxymethyl)-3-(3-(thiophen-2-yl)propyl)pyrrolidin-1-yl)propan-2-yl)-2-methylpyridine | 387 | $^1$H NMR (300 MHz, CDCl$_3$): δ 8.58 (d, J = 2.4 Hz, 1H), 7.68 (dd, J = 8.4, 2.4 Hz, 1H), 7.11-7.05 (m, 2H), 6.90 (dd, J = 8.4, 3.3 Hz, 1H), 6.78-6.77 (m, 1H), 3.49 (s, 2H), 3.44 (dd, J = 14.1, 7.5 Hz, 2H), 3.24 (dd, J = 15.2, 8.7 Hz, 2H), 2.80 (t, J = 7.2 Hz, 2H), 2.60-2.55 (m, 1H), 2.54-2.50 (m, 4H), 2.43 (d, J = 9.0 Hz, 1H), 2.23 (d, J = 9.0 Hz, 1H), 1.55-1.48 (m, 4H), 1.36 (s, 6H), 1.15 (t, J = 6.9 Hz, 3H) |
| 21 | 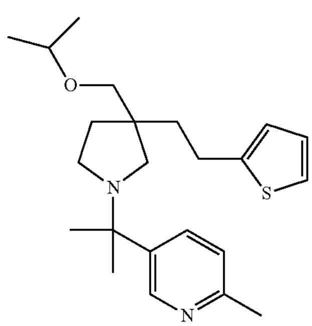 [SMILES: Cc1ccc(C(C)(C)N2CCC(CCc3cccs3)(COC(C)C)C2)cn1] | (R or S)-5-(2-(3-(isopropoxymethyl)-3-(2-(thiophen-2-yl)ethyl)pyrrolidin-1-yl)propan-2-yl)-2-methylpyridine | 387 | $^1$H NMR (300 MHz, CDCl$_3$): δ 8.59 (d, J = 2.1 Hz, 1H), 7.71 (dd, J = 8.1, 2.4 Hz, 1H), 7.10-7.06 (m,2H), 6.91 (dd, J = 5.1, 3.3 Hz, 1H), 6.77 (d, J = 2.4 Hz, 1H), 3.52-3.48 (m, 1H), 3.26 (q, J = 8.7 Hz, 2H), 2.79 (t, J = 8.4 Hz, 2H), 2.58-2.52 (m, 5H), 2.28 (d, J = 9.0 Hz, 1H), 2.95-2.75 (m, 2H), 2.55-2.50 (m, 2H), 1.37 (s, 6H), 1.30-1.26 (m, 1H), 1.14-1.12 (m, 6H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 22 | 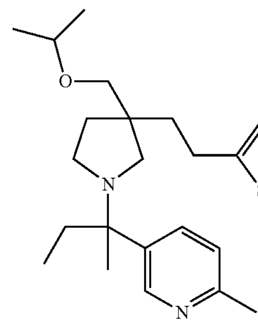 | 5-(2-((R or S)-3-(isopropoxymethyl)-3-(2-(thiophen-2-yl)ethyl)pyrrolidin-1-yl)butan-2-yl)-2-methylpyridine | 401 | $^1$H NMR (300 MHz, CDCl$_3$): δ 8.52 (s, 1H), 7.64 (dd, J = 8.1, 2.4 Hz, 1H), 7.10-7.07 (m, 2H), 6.91 (d, J = 2.1 Hz, 1H), 6.77 (d, J = 0.9 Hz, 1H), 3.55-3.45 (m, 1H), 3.35-3.20 (m, 2H), 2.85-2.72 (m, 2H), 2.70-2.60 (m, 1H), 2.53 (s, 3H), 2.50-2.40 (m, 2H), 2.35-2.18 (m, 1H), 1.90-1.73 (m, 3H), 1.68-1.62 (m, 1H), 1.57-1.52 (m, 2H), 1.34 (s, 3H), 1.15-1.11 (m, 6H), 0.62 (t, J = 7.2 Hz, 3H) |
| 23 | citrate | (R or S)-1-((3-(ethoxymethyl)-1-(2-(6-methylpyridin-3-yl)propan-2-yl)pyrrolidin-3-yl)methyl)-3-ethyl-5-fluoro-1,3-dihydro-2H-benzo[d]imidazol-2-one citrate | 455 | $^1$H NMR (300 MHz, MeOD): δ 8.68 (s, 1H), 8.04 (d, J = 8.1 Hz, 1H), 7.40 (d, J = 7.9 Hz, 1H), 7.20-7.16 (m, 1H), 7.06-7.02 (m, 1H), 6.85 (t, 9.6 Hz, 1H), 3.94-3.90 (m, 4H), 3.50-3.27 (m, 7H), 3.05 (d, J = 11.4 Hz, 1H), 2.81 (q, J = 15.6 Hz, 4H), 2.56 (s, 3H), 2.10-1.99 (m, 2H), 1.84-1.73 (m, 6H), 1.32-1.24 (m, 3H), 1.15 (t, J = 6.9 Hz, 3H) |
| 24 | citrate | (R or S)-2-methyl-5-(1-(2-(6-methylpyridin-3-yl)propan-2-yl)-3-(2-(thiophen-2-yl)ethyl)pyrrolidin-3-yl)-1,3,4-thiadiazole citrate | 413 | $^1$H NMR (300 MHz, MeOD): δ 8.55 (s, 1H), 7.95 (dd, J = 8.1, 2.4 Hz, 1H), 7.30 (d, J = 8.4 Hz, 1H), 7.07 (d, J = 4.8 Hz, 1H), 6.78 (t, J = 4.2 Hz, 1H), 6.67 (d, J = 2.7 Hz, 1H), 3.42 (d, J = 11.2 Hz, 1H), 3.05-2.96 (m, 1H), 2.94-2.83 (m, 1H), 2.70 (m, 6H), 2.52 (m, 2H), 2.47 (s, 3H), 2.30 (m, 1H), 2.11 (s, 3H), 2.03-1.93 (m, 1H), 1.85 (m, 1H), 1.61 (s, 6H) |
| 25 | citrate | (R or S)-5-(2-(3-(ethoxymethyl)-3-(2-(5-fluorobenzo[b]thiophen-2-yl)ethyl)pyrrolidin-1-yl)propan-2-yl)-2-methylpyridine citrate | 450 | $^1$HNMR (300 MHz, MeOD): δ 8.68 (s, 1H), 8.02 (d, J = 8.1 Hz, 1H), 7.73 (dd, J = 9.0, 4.8 Hz, 1H), 7.39 (s, 1H), 7.36 (s, 1H), 7.07-7.00 (m, 2H), 3.50-3.45 (m, 2H), 3.38-3.43 (m, 2H), 3.27-3.20 (m, 2H), 3.15-3.08 (m, 1H), 2.92-2.85 (m, 3H), 2.79 (q, J = 15.6 Hz, 4H), 2.54 (s, 3H), 1.98-1.82 (m, 4H), 1.77 (s, 6H), 1.14 (t, J = 6.9 Hz, 3H). |

TABLE I-continued

Compounds with a pyrrolidine ring and a pyridine or pyridine-like molecule bonded to the pyrrolidine N-constituent

| Compound No. | Structure | Name | MS (ESI+): [M + H]$^+$ | H-NMR |
|---|---|---|---|---|
| 26 | 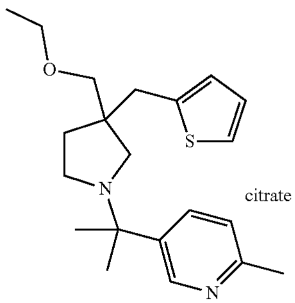 [SMILES: CCOCC1(Cc2cccs2)CCN(C(C)(C)c2ccc(C)nc2)C1] | (S or R)-5-(2-(3-(ethoxymethyl)-3-(thiophen-2-ylmethyl)pyrrolidin-1-yl)propan-2-yl)-2-methylpyridine citrate | 359 | $^1$H NMR (300 MHz, MeOD): δ 8.70 (s, 1H), 8.04 (d, J = 6.0 Hz, 1H), 7.44 (d, J = 8.2 Hz, 1H), 7.24 (d, J = 5.3 Hz, 1H), 6.95-6.90 (m, 1H), 6.82 (s, 1H), 3.47-3.40 (m, 2H), 3.20-3.19 (m, 3H), 3.10-3.07 (m, 3H), 3.05-2.98 (m, 2H), 2.82 (q, J = 15.6 Hz, 4H), 2.59 (s, 3H), 2.06-1.96 (m, 1H), 1.93-1.86 (m, 1H), 1.83 (s, 6H), 1.15 (t, J = 7.0 Hz, 3H). |
| 27 | 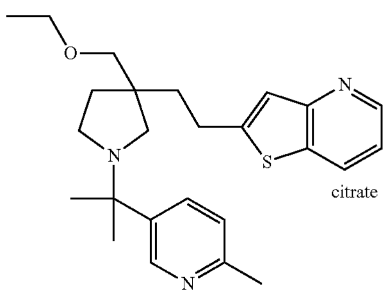 [SMILES: CCOCC1(CCc2cc3ncccc3s2)CCN(C(C)(C)c2ccc(C)nc2)C1] | (R or S)-2-(2-(3-(ethoxymethyl)-1-(2-(6-methylpyridin-3-yl)propan-2-yl)pyrrolidin-3-yl)ethyl)thieno[3,2-b]pyridine citrate | 424 | $^1$H NMR (300 MHz, MeOD): δ 8.66 (d, J = 2.1 Hz, 1H), 8.53 (dd, J = 4.8, 1.2 Hz, 1H), 8.27 (d, J = 8.1 Hz, 1H), 8.01 (dd, J = 4.8, 1.2 Hz, 1H), 7.36 (d, J = 8.4 Hz, 1H), 7.30 (dd, J = 7.8, 3.6 Hz, 1H), 7.23 (s, 1H), 3.52-3.44 (m, 2H), 3.38-3.35 (m, 2H), 3.18-3.10 (m, 2H), 3.08-3.02 (m, 1H), 2.96 (t, J = 8.4 Hz, 2H), 2.92-2.87 (m, 1H), 2.80 (q, J = 15.6 Hz, 4H), 2.53 (s, 3H), 2.00-1.83 (m, 4H), 1.74 (s, 6H), 1.14 (t, J = 6.9 Hz, 3H) |
| 28 | 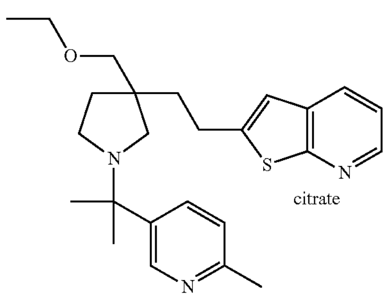 [SMILES: CCOCC1(CCc2cc3cccnc3s2)CCN(C(C)(C)c2ccc(C)nc2)C1] | (R or S)-2-(2-(3-(ethoxymethyl)-1-(2-(6-methylpyridin-3-yl)propan-2-yl)pyrrolidin-3-yl)ethyl)thieno[2,3-b]pyridine citrate | 424 | $^1$H NMR (300 MHz, MeOD): δ 8.68 (d, J = 1.8 Hz, 1H), 8.40 (d, J = 3.3 Hz, 1H), 8.10-8.02 (m, 2H), 7.39-7.34 (m, 2H), 7.08 (s, 1H), 3.50-3.42 (m, 2H), 3.38-3.36 (m, 1H), 3.25-3.18 (m, 2H), 3.15-3.10 (m, 1H), 3.09-3.00 (m, 1H), 2.99-2.88 (m, 3H), 2.81 (q, J = 15.6 Hz, 4H), 2.54 (s, 3H), 2.02-1.88 (m, 4H), 1.77 (s, 6H), 1.14 (t, J = 7.2 Hz, 3H) |
| 29 | 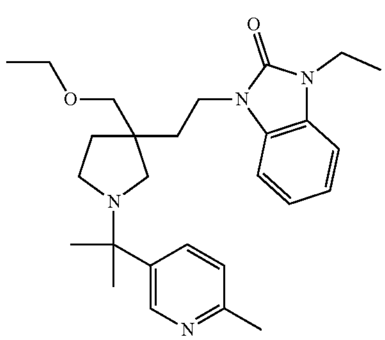 [SMILES: CCOCC1(CCn2c(=O)n(CC)c3ccccc32)CCN(C(C)(C)c2ccc(C)nc2)C1] | (S & R)-1-(2-(3-(ethoxymethyl)-1-(2-(6-methylpyridin-3-yl)propan-2-yl)pyrrolidin-3-yl)ethyl)-3-ethyl-1,3-dihydro-2H-benzo[d]imidazol-2-one | 451 | $^1$H NMR (300 MHz, MeOD): δ 8.67 (d, J = 1.9 Hz, 1H), 8.03 (dd, J = 8.2, 2.4 Hz, 1H), 7.39 (d, J = 8.3 Hz, 1H), 7.18-7.14 (m, 4H), 4.01-3.87 (m, 4H), 3.49-3.41 (m, 2H), 3.38-3.34 (m, 2H), 3.23-3.18 (m, 2H), 3.10 (d, J = 11.5 Hz, 1H), 2.94 (d, J = 11.7 Hz, 1H), 2.80 (q, J = 15.5 Hz, 4H), 2.55 (s, 3H), 2.01-1.82 (m, 4H), 1.77 (s, 6H), 1.29 (t, J = 7.2 Hz, 3H), 1.13 (t, J = 7.0 Hz, 3H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 30 | citrate | (R or S)-5-(2-(3-(ethoxymethyl)-3-(2-(5-(trifluoromethyl)thiophen-2-yl)ethyl)pyrrolidin-1-yl)propan-2-yl)-2-methylpyridine citrate | 425 | $^1$H NMR (300 MHz, MeOD): δ 8.70 (d, J = 2.5 Hz, 1H), 8.06 (dd, J = 8.3, 2.6 Hz, 1H), 7.42 (d, J = 8.3 Hz, 1H), 7.33 (d, J = 3.8 Hz, 1H), 6.87 (d, J = 3.5 Hz, 1H), 3.52-3.43 (m, 2H), 3.37-3.33 (m, 1H), 3.28-3.22 (m, 2H), 3.17 (d, J = 11.7 Hz, 1H), 2.98 (d, J = 11.7 Hz, 1H), 2.80 (m, 7H), 2.56 (s, 3H), 2.05-1.84 (m, 4H), 1.81 (s, 6H), 1.13 (t, J = 7.0 Hz, 3H). |
| 31 | citrate | (R or S)-5-(2-(3-(2-(4-chloro-5-fluorothiophen-2-yl)ethyl)-3-(ethoxymethyl)pyrrolidin-1-yl)propan-2-yl)-2-methylpyridine citrate | 425 | $^1$H NMR (300 MHz, MeOD): δ 8.68 (d, J = 2.4 Hz, 1H), 8.04 (dd, J = 8.3, 2.5 Hz, 1H), 7.41 (d, J = 8.3 Hz, 1H), 6.48 (d, J = 3.4 Hz, 1H), 3.49-3.41 (m, 2H), 3.40-3.37 (m, 2H), 3.35-3.32 (m, 2H), 3.30-3.22 (m, 2H), 3.09 (d, J = 11.5 Hz, 1H), 2.80 (q, J = 15.5 Hz, 4H), 2.69-2.59 (m, 2H), 2.56 (s, 3H), 2.09-1.82 (m, 3H), 1.78 (s, 6H), 1.13 (t, J = 7.0 Hz, 3H). |
| 32 | 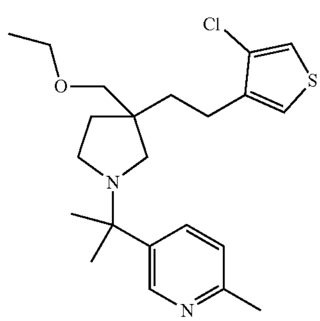 [SMILES: CCOCC1(CCc2cscc2Cl)CCN(C(C)(C)c2ccc(C)nc2)C1] | (R or S)-5-(2-(3-(2-(4-chlorothiophen-3-yl)ethyl)-3-(ethoxymethyl)pyrrolidin-1-yl)propan-2-yl)-2-methylpyridine | 407 | $^1$H NMR (500 MHz, MeOD): δ 8.54 (d, J = 2.1 Hz, 1H), 7.87 (dd, J = 8.2, 2.3 Hz, 1H), 7.28-7.22 (m, 2H), 7.12 (d, J = 3.4 Hz, 1H), 3.47 (q, J = 7.0 Hz, 2H), 3.34-3.32 (m, 1H), 3.30-3.29 (m, 1H), 2.69-2.62 (m, 2H), 2.56-2.52 (m, 3H), 2.50 (s, 3H), 2.37 (d, J = 9.2 Hz, 1H), 1.74-1.66 (m, 2H), 1.63 (t, J = 6.9 Hz, 2H), 1.45 (s, 6H), 1.16 (t, J = 7.0 Hz, 3H). |
| 33 | 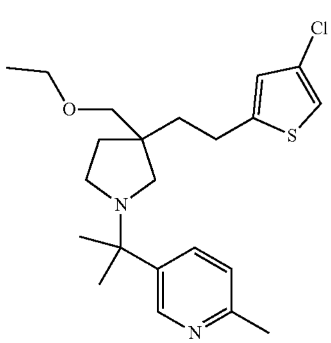 [SMILES: CCOCC1(CCc2cc(Cl)cs2)CCN(C(C)(C)c2ccc(C)nc2)C1] | (R or S)-5-(2-(3-(2-(4-chlorothiophen-2-yl)ethyl)-3-(ethoxymethyl)pyrrolidin-1-yl)propan-2-yl)-2-methylpyridine | 407 | $^1$H NMR (300 MHz, CDCl$_3$): δ 8.66 (s, 1H), 7.74 (t, J = 6.3 Hz, 1H), 7.21 (d, J = 8.0 Hz, 1H), 6.89 (d, J = 6.2 Hz, 1H), 6.66 (m, 1H), 3.73 (t, J = 7.3 Hz, 1H), 3.68-3.21 (m, 7H), 2.87-2.69 (m, 2H), 2.60 (s, 3H), 2.05-1.89 (m, 2H), 1.86-1.71 (m, 2H), 1.63 (s, 6H), 1.17-1.12 (m, 3H). |

TABLE I-continued

Compounds with a pyrrolidine ring and a pyridine or pyridine-like molecule bonded to the pyrrolidine N-constituent

| Compound No. | Structure | Name | MS (ESI+): [M + H]⁺ | H-NMR |
|---|---|---|---|---|
| 34 | 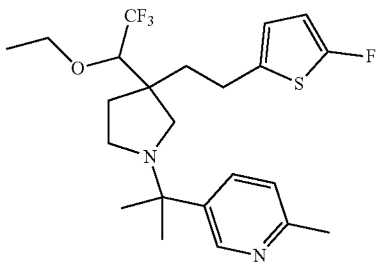 [SMILES: CCOC(C(F)(F)F)C1(CCc2ccc(F)s2)CCN(C(C)(C)c2ccc(C)nc2)C1] | 5-(2-((R & S)-3-((S or R)-1-ethoxy-2,2,2-trifluoroethyl)-3-(2-(5-fluorothiophen-2-yl)ethyl)pyrrolidin-1-yl)propan-2-yl)-2-methylpyridine | 459 | $^1$H NMR (300 MHz, MeOD): δ 8.59 (dd, J = 9.0, 2.1 Hz, 1H), 7.69 (d, J = 8.1 Hz, 1H), 7.09 (d, J = 8.1 Hz, 1H), 6.33 (t, J = 3.0 Hz, 1H), 6.23 (dd, J = 2.1, 1.2 Hz, 1H), 3.95-3.82 (m, 1H), 3.55-3.45 (m, 2H), 2.91-2.80 (m, 1H), 2.69-2.60 (m, 2H), 2.53 (s, 3H), 2.48-2.39 (m, 1H), 2.10-1.85 (m, 2H), 1.84-1.55 (m, 4H), 1.39 (s, 6H), 1.15 (t, J = 6.9 Hz, 3H) |
| 35 | 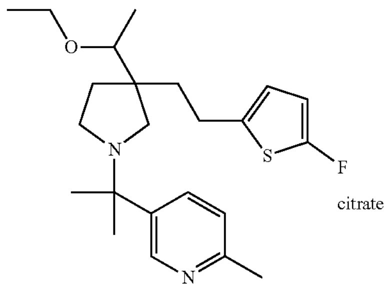 [SMILES: CCOC(C)C1(CCc2ccc(F)s2)CCN(C(C)(C)c2ccc(C)nc2)C1] | 5-(2-((R or S)-3-((S or R)-1-ethoxyethyl)-3-(2-(5-fluorothiophen-2-yl)ethyl)pyrrolidin-1-yl)propan-2-yl)-2-methylpyridine citrate | 405 | $^1$H NMR (300 MHz, MeOD): δ 8.69 (s, 1H), 8.04 (d, J = 8.1 Hz, 1H), 7.41 (d, J = 8.1 Hz, 1H), 6.41 (m, 1H), 6.30 (d, J = 2.1 Hz, 1H), 3.65-3.57 (m, 1H), 3.48-3.39 (m, 1H), 3.28-3.14 (m, 4H), 3.12-2.95 (m, 2H), 2.75 (q, J = 15.5 Hz, 4H), 2.68-2.63 (m, 2H), 2.56 (s, 3H), 2.24-2.08 (m, 1H), 2.06-1.94 (m, 1H), 1.69 (s, 6H), 1.68-1.59 (m, 1H), 1.12-1.02 (m, 6H) |
| 36 | 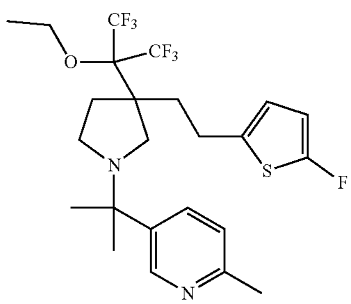 [SMILES: CCOC(C(F)(F)F)(C(F)(F)F)C1(CCc2ccc(F)s2)CCN(C(C)(C)c2ccc(C)nc2)C1] | (R or S)-5-(2-(3-(2-ethoxy-1,1,1,3,3,3-hexafluoropropan-2-yl)-3-(2-(5-fluorothiophen-2-yl)ethyl)pyrrolidin-1-yl)propan-2-yl)-2-methylpyridine | 527 | $^1$HNMR (300 MHz, MeOD): δ 8.58 (d, J = 1.8 Hz, 1H), 7.68 (dd, J = 8.1, 1.8 Hz, 1H), 7.10 (d, J = 8.1 Hz, 1H), 6.36 (d, J = 3.3 Hz, 1H), 6.25 (dd, J = 3.6, 1.8 Hz, 1H), 3.97-3.88 (m, 2H), 2.95-2.89 (m, 3H), 2.71-2.56 (m, 2H), 2.53 (s, 3H), 2.45-2.30 (m, 2H), 2.18-2.02 (m, 1H), 1.92-1.80 (m, 1H), 1.72-1.65 (m, 1H), 1.40 (s, 6H), 1.20 (t, J = 6.9 Hz, 3H). |
| 37 | 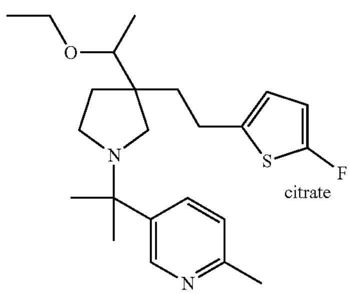 [SMILES: CCOC(C)C1(CCc2ccc(F)s2)CCN(C(C)(C)c2ccc(C)nc2)C1] | 5-(2-((R or S)-3-((R or S)-1-ethoxyethyl)-3-(2-(5-fluorothiophen-2-yl)ethyl)pyrrolidin-1-yl)propan-2-yl)-2-methylpyridine citrate | 405 | $^1$H NMR (300 MHz, MeOD): δ 8.70 (d, J = 1.8 Hz, 1H), 8.06 (dd, J = 8.4, 2.4 Hz, 1H), 7.42 (d, J = 8.4 Hz, 1H), 6.41 (d, J = 3.6 Hz, 1H), 6.30 (m, 1H), 3.63-3.55 (m, 1H), 3.50-3.44 (m, 1H), 3.38-3.32 (m, 2H), 3.26-3.18 (m, 2H), 2.96-2.88 (m, 1H), 2.76 (q, J = 15.5 Hz, 4H), 2.69-2.61 (m, 2H), 2.56 (s, 3H), 2.05-1.97 (m, 1H), 1.95-1.89 (m, 1H), 1.83 (s, 6H), 1.80-1.74 (m, 2H), 1.11-1.00 (m, 6H) |
| 38 | 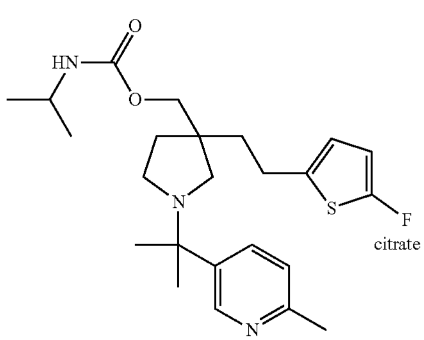 [SMILES: Cc1ccc(C(C)(C)N2CCC(CCc3ccc(F)s3)(COC(=O)NC(C)C)C2)cn1] | (R or S)-(3-(2-(5-fluorothiophen-2-yl)ethyl)-1-(2-(6-methylpyridin-3-yl)propan-2-yl)pyrrolidin-3-yl)methylisopropylcarbamate citrate | 448 | $^1$H NMR (300 MHz, MeOD): δ 8.66 (s, 1H), 8.04 (d, J = 8.2 Hz, 1H), 7.40 (d, J = 8.2 Hz, 1H), 6.42 (m, 1H), 6.35-6.25 (m, 1H), 4.08-3.91 (m, 2H), 3.83-3.73 (m, 2H), 3.18 (m, 2H), 2.97 (d, J = 10.9 Hz, 1H), 2.90-2.73 (m, 6H), 2.71-2.64 (m, 2H), 2.56 (s, 3H), 1.85-1.78 (m, 2H), 1.73 (s, 6H), 1.10 (d, J = 6.5 Hz, 6H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 39 | 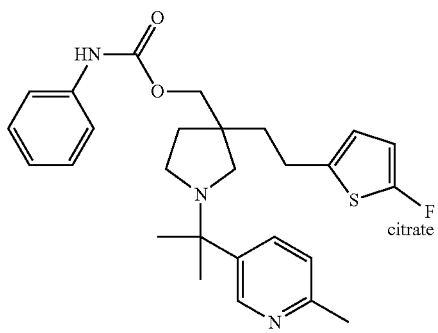 [SMILES: Cc1ccc(C(C)(C)N2CCC(CCc3ccc(F)s3)(COC(=O)Nc3ccccc3)C2)cn1] | (R or S)-(3-(2-(5-fluoro-thiophen-2-yl)ethyl)-1-(2-(6-methylpyridin-3-yl)propan-2-yl)pyrrolidin-3-yl)methyl-phenylcarbamate citrate | 482 | $^{1}$H NMR (300 MHz, MeOD): δ 8.66 (s, 1H), 8.05(d, J = 8.2 Hz, 1H), 7.42 (d, J = 7.8 Hz, 2H), 7.36 (d, J = 8.3 Hz, 1H), 7.28 (t, J = 7.9 Hz, 2H), 7.03 (t, J = 7.3 Hz, 1H), 6.43 (m, 1H), 6.28 (m, 1H), 4.09 (q, J = 11.1 Hz, 2H), 3.18 (m, 2H), 2.99 (m, 1H), 2.90-2.68 (m, 5H), 2.49 (s, 3H), 1.96-1.79 (m, 4H), 1.73 (s, 6H). |
| 40 | 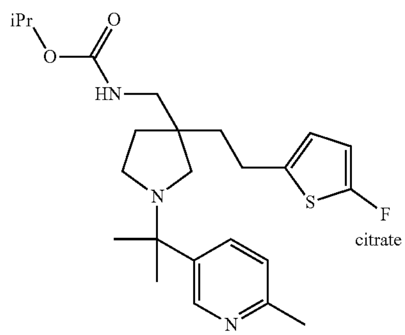 [SMILES: Cc1ccc(C(C)(C)N2CCC(CCc3ccc(F)s3)(CNC(=O)OC(C)C)C2)cn1] | isopropyl (S or R)-((3-(2-(5-fluoro-thiophen-2-yl)ethyl)-1-(2-(6-methylpyridin-3-yl)propan-2-yl)pyrrolidin-3-yl)methyl)carbamate citrate | 448 | $^{1}$HNMR (300 MHz, MeOD): δ 8.66 (s, 1H), 8.03 (d, J = 7.2 Hz, 1H), 7.39 (d, J = 8.1 Hz, 1H), 6.42 (t, J = 3.3 Hz, 1H), 6.28 (dd, J = 2.4, 1.2 Hz, 1H), 4.88-4.68 (m, 2H), 3.25-3.13 (m, 4H), 3.05-2.93 (m, 1H), 2.73 (q, J = 15.6 Hz, 4H), 2.71-2.62 (m, 2H), 2.55 (s, 3H), 1.92-1.80 (m, 2H), 1.75 (s, 6H), 1.68-1.63 (m, 2H), 1.26 (m, 6H) |
| 41 | 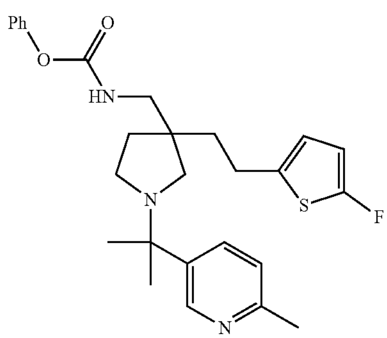 | phenyl (S or R)-((3-(2-(5-fluoro-thiophen-2-yl)ethyl)-1-(2-(6-methylpyridin-3-yl)propan-2-yl)pyrrolidin-3-yl)methyl)carbamate | 482 | $^{1}$HNMR (300 MHz, MeOD): δ 8.53 (d, J = 1.2 Hz, 1H), 7.89 (dd, J = 6.0, 2.4 Hz, 1H), 7.36 (t, J = 7.8 Hz, 2H), 7.23 (d, J = 8.1 Hz, 1H), 7.20 (m, 1H), 7.08 (d, J = 7.8 Hz, 2H), 6.42 (t, J = 3.3 Hz, 1H), 6.28 (dd, J = 3.3, 2.1 Hz, 1H), 2.85-2.70 (m, 7H), 2.55 (m, 1H), 2.49 (s, 3H), 1.80-1.60 (m, 4H), 1.45 (s, 6H) |
| 42 | 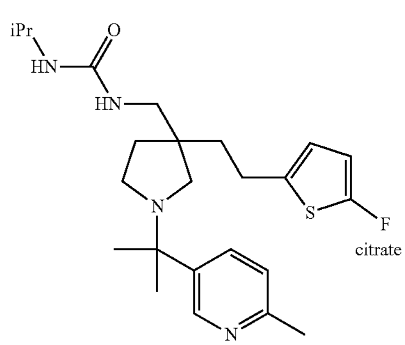 [SMILES: Cc1ccc(C(C)(C)N2CCC(CCc3ccc(F)s3)(CNC(=O)NC(C)C)C2)cn1] | (S or R)-1-((3-(2-(5-fluoro-thiophen-2-yl)ethyl)-1-(2-(6-methylpyridin-3-yl)propan-2-yl)pyrrolidin-3-yl)methyl)-3-isopropylurea citrate | 447 | $^{1}$H NMR (300 MHz, MeOD): δ 8.72 (s, 1H), 8.08 (d, J = 8.3 Hz, 1H), 7.43 (d, J = 8.2 Hz, 1H), 6.50-6.40 (m, 1H), 6.35-6.25 (m, 1H), 3.91-3.73 (m, 1H), 3.22-3.09 (m, 3H), 2.90 (d, J = 4.8 Hz, 1H), 2.88-2.65 (m, 8H), 2.57 (s, 3H), 1.88-1.68 (m, 10H), 1.12 (m, 6H). |

TABLE I-continued

Compounds with a pyrrolidine ring and a pyridine or pyridine-like molecule bonded to the pyrrolidine N-constituent

| Compound No. | Structure | Name | MS (ESI+): [M + H]⁺ | H-NMR |
|---|---|---|---|---|
| 43 | 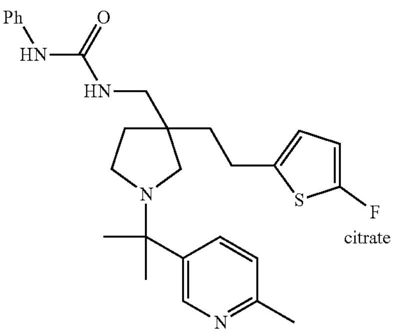 [SMILES: Cc1ccc(C(C)(C)N2CCC(CCc3ccc(F)s3)(CNC(=O)Nc3ccccc3)C2)cn1] | (S or R)-1-((3-(2-(5-fluoro-thiophen-2-yl)ethyl)-1-(2-(6-methylpyridin-3-yl)propan-2-yl)pyrrolidin-3-yl)methyl)-3-phenylurea citrate | 481 | ¹H NMR (300 MHz, MeOD): δ 8.71 (s, 1H), 8.09 (d, J = 8.4 Hz, 1H), 7.41-7.33 (m, 3H), 7.27 (t, J = 7.8 Hz, 2H), 7.00 (t, J = 7.2 Hz, 1H), 6.48-6.44 (m, 1H), 6.34-6.26 (m, 1H), 3.44-3.34 (m, 3H), 3.18 (m, 1H), 2.95 (m, 1H), 2.91-2.68 (m, 7H), 2.50 (s, 3H), 2.00-1.87 (m, 2H), 1.84 (m, 6H), 1.81-1.71 (m, 2H). |
| 44 | 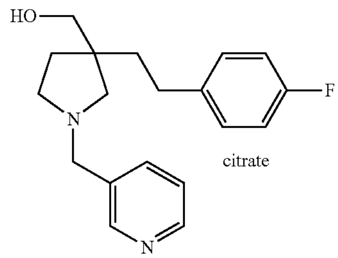 [SMILES: OCC1(CCc2ccc(F)cc2)CCN(Cc2cccnc2)C1] | (R or S)-3-(4-fluoro-phenethyl)-1-(pyridin-3-ylmethyl)pyrrolidin-3-yl)methanol citrate | 315 | ¹H NMR (300 MHz, MeOD): δ 8.69 (s, 1H), 8.63 (d, J = 4.8 Hz, 1H), 8.03 (s, 1H), 7.54 (s, 1H), 7.21 (dd, J = 8.4, 5.4 Hz, 2H), 6.98 (t, J = 8.6 Hz, 2H), 4.45-4.26 (m, 2H), 3.57 (s, 4H), 3.06 (d, J = 10.5 Hz, 1H), 2.87-2.71 (m, 5H), 2.59 (t, J = 8.6 Hz, 2H), 2.04 (s, 2H), 1.81 (d, J = 9.2 Hz, 2H). |
| 45 | 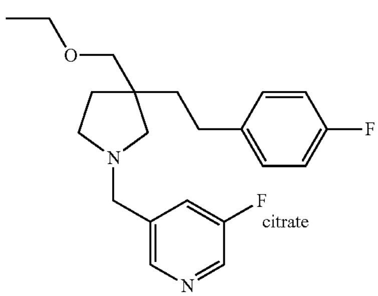 [SMILES: CCOCC1(CCc2ccc(F)cc2)CCN(Cc2cncc(F)c2)C1] | (R or S)-3-((3-(ethoxy-methyl)-3-(4-fluoro-phenethyl)pyrrolidin-1-yl)methyl)-5-fluoro-pyridine citrate | 361 | ¹H NMR (300 MHz, MeOD): δ 8.58 (s, 2H), 7.91 (d, J = 9.1 Hz, 1H), 7.26-7.15 (m, 2H), 6.98 (t, J = 8.6 Hz, 2H), 4.54-4.35 (m, 2H), 3.61-3.51 (m, 2H), 3.49-3.34 (m, 5H), 3.15 (d, J = 11.5 Hz, 1H), 2.81 (q, J = 15.6 Hz, 4H), 2.59 (s, 2H), 2.04 (s, 2H), 1.84 (d, J = 11.9 Hz, 2H), 1.22 (t, J = 7.0 Hz, 3H). |
| 46 | 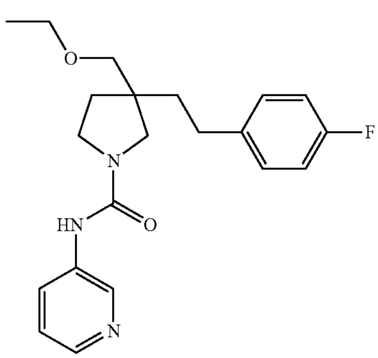 [SMILES: CCOCC1(CCc2ccc(F)cc2)CCN(C(=O)Nc2cccnc2)C1] | (R or S)-3-(ethoxymethyl)-3-(4-fluorophenethyl)-N-(pyridin-3-yl)pyrrolidine-1-carboxamide | | |

TABLE I-continued

Compounds with a pyrrolidine ring and a pyridine or pyridine-like molecule bonded to the pyrrolidine N-constituent

| Compound No. | Structure | Name | MS (ESI+): [M + H]⁺ | H-NMR |
|---|---|---|---|---|
| 47 | 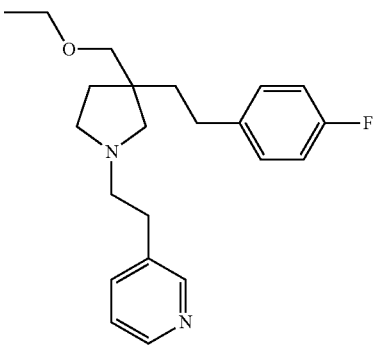 [SMILES: CCOCC1(CCc2ccc(F)cc2)CCN(CCc2cccnc2)C1] | (R or S)-3-(2-(3-(ethoxymethyl)-3-(4-fluorophenethyl)pyrrolidin-1-yl)ethyl)pyridine | | |
| 48 | 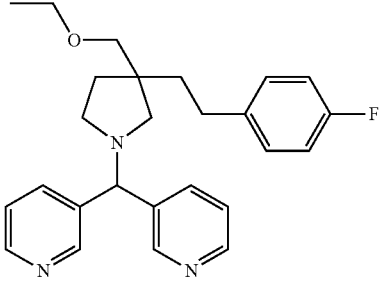 [SMILES: CCOCC1(CCc2ccc(F)cc2)CCN(C(c2cccnc2)c2cccnc2)C1] | (R or S)-3,3'-((3-(ethoxymethyl)-3-(4-fluorophenethyl)pyrrolidin-1-yl)methylene)dipyridine | | |
| 49 | 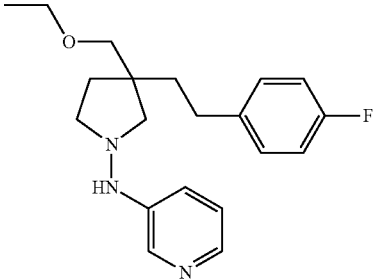 [SMILES: CCOCC1(CCc2ccc(F)cc2)CCN(Nc2cccnc2)C1] | (R or S)-N-(3-(ethoxymethyl)-3-(4-fluorophenethyl)pyrrolidin-1-yl)pyridin-3-amine | | |
| 50 | 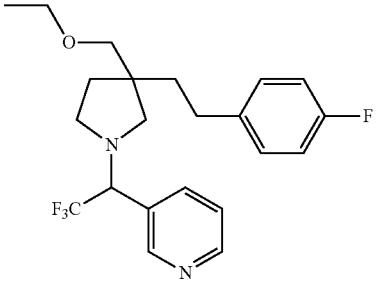 [SMILES: CCOCC1(CCc2ccc(F)cc2)CCN(C(c2cccnc2)C(F)(F)F)C1] | 3-(1-((R or S)-3-(ethoxymethyl)-3-(4-fluorophenethyl)pyrrolidin-1-yl)-2,2,2-trifluoroethyl)pyridine | | |
| 51 | 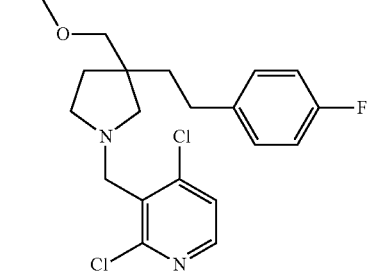 | (R or S)-3,5-dichloro-4-((3-(ethoxymethyl)-3-(4-fluorophenethyl)pyrrolidin-1-yl)methyl)pyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]$^+$ | H-NMR |
|---|---|---|---|---|
| 52 | 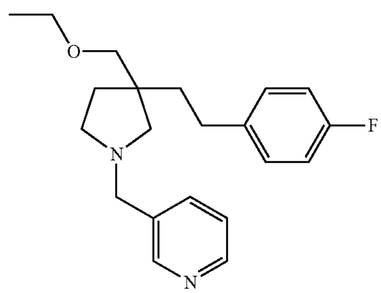 [SMILES: CCOCC1(CCc2ccc(F)cc2)CCN(Cc2cccnc2)C1] | (R or S)-4-(2-(3-(ethoxymethyl)-1-(pyridin-3-ylmethyl)pyrrolidin-3-yl)ethyl)benzonitrile | | |
| 53 | 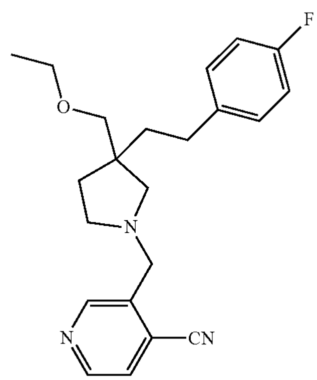 [SMILES: CCOCC1(CCc2ccc(F)cc2)CCN(Cc2cnccc2C#N)C1] | (R or S)-3-((3-(ethoxymethyl)-3-(4-fluorophenethyl)pyrrolidin-1-yl)methyl)isonicotinonitrile | | |
| 54 | 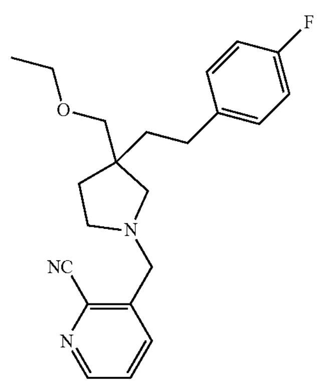 [SMILES: CCOCC1(CCc2ccc(F)cc2)CCN(Cc2cccnc2C#N)C1] | (R or S)-3-((3-(ethoxymethyl)-3-(4-fluorophenethyl)pyrrolidin-1-yl)methyl)picolinonitrile | | |
| 55 | 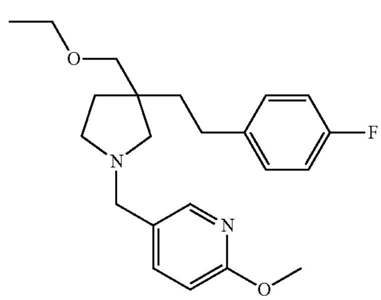 [SMILES: CCOCC1(CCc2ccc(F)cc2)CCN(Cc2ccc(OC)nc2)C1] | (R or S)-5-((3-(ethoxymethyl)-3-(4-fluorophenethyl)pyrrolidin-1-yl)methyl)-2-methoxy pyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 56 | 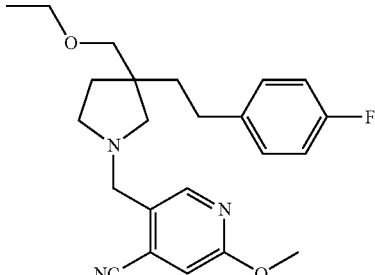 | (R or S)-5-((3-(ethoxy-methyl)-3-(4-fluoro-phenethyl)pyrrolidin-1-yl)methyl)-2-methoxyiso-nicotinonitrile | | |
| 57 | 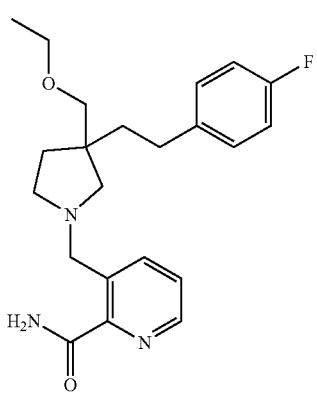 [SMILES: CCOCC1(CCc2ccc(F)cc2)CCN(Cc2cccnc2C(N)=O)C1] | (R or S)-3-((3-(ethoxy-methyl)-3-(4-fluoro-phenethyl)pyrrolidin-1-yl)methyl)pico-linamide | | |
| 58 | 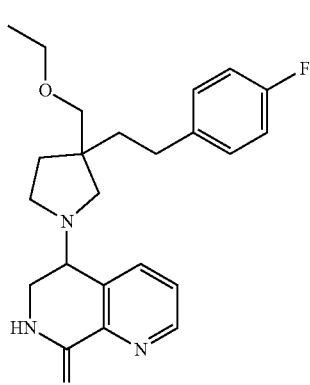 | 5-((R or S)-3-(ethoxy-methyl)-3-(4-fluoro-phenethyl)pyrrolidin-1-yl)-6,7-dihydro-1,7-naphthyridin-8(5H)-one | | |
| 59 | 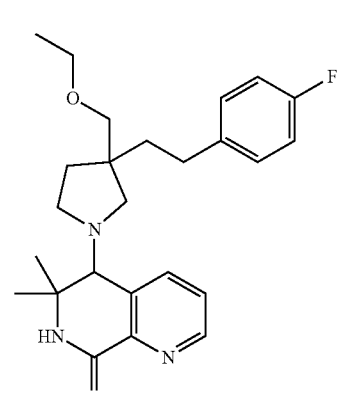 | 5-((R or S)-3-(ethoxy-methyl)-3-(4-fluoro-phenethyl)pyrrolidin-1-yl)-6,6-dimethyl-6,7-dihydro-1,7-naphthyridin-8(5H)-one | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 60 | 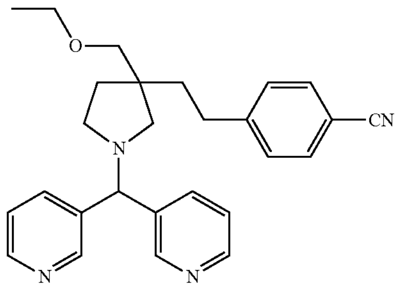 [SMILES: CCOCC1(CCc2ccc(C#N)cc2)CCN(C(c2cccnc2)c2cccnc2)C1] | (R or S)-4-(2-(1-(di(pyridin-3-yl)methyl)-3-(ethoxymethyl)pyrrolidin-3-yl)ethyl)benzonitrile | | |
| 61 | 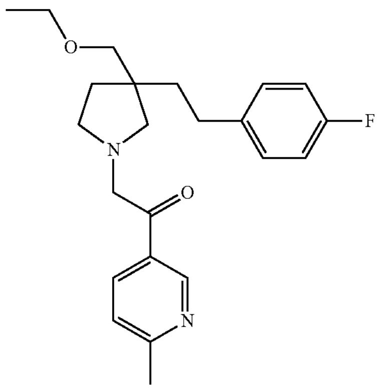 [SMILES: CCOCC1(CCc2ccc(F)cc2)CCN(CC(=O)c2ccc(C)nc2)C1] | (R or S)-2-(3-(ethoxymethyl)-3-(4-fluorophenethyl)pyrrolidin-1-yl)-1-(6-methylpyridin-3-yl)ethan-1-one | | |
| 62 | 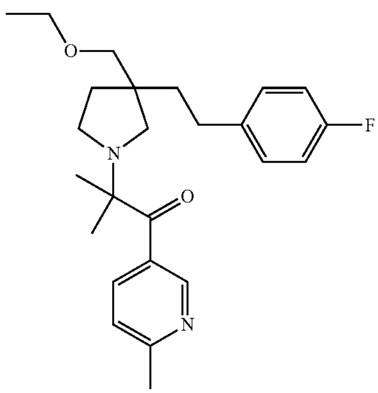 [SMILES: CCOCC1(CCc2ccc(F)cc2)CCN(C(C)(C)C(=O)c2ccc(C)nc2)C1] | (R or S)-2-(3-(ethoxymethyl)-3-(4-fluorophenethyl)pyrrolidin-1-yl)-2-methyl-1-(6-methylpyridin-3-yl)propan-1-one | | |
| 63 | 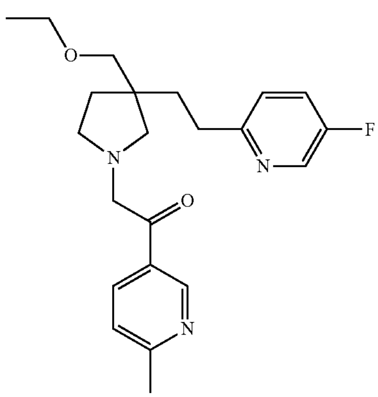 [SMILES: CCOCC1(CCc2ccc(F)cn2)CCN(CC(=O)c2ccc(C)nc2)C1] | (R or S)-2-(3-(ethoxymethyl)-3-(2-(5-fluoropyridin-2-yl)ethyl)pyrrolidin-1-yl)-1-(6-methylpyridin-3-yl)ethan-1-one | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 64 | 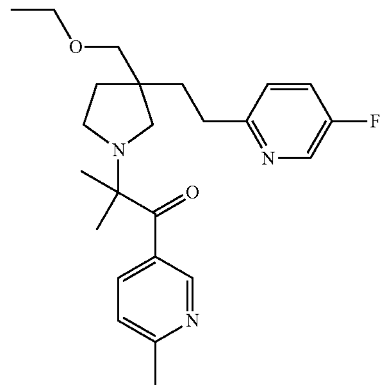 [SMILES: CCOCC1(CCc2ccc(F)cn2)CCN(C(C)(C)C(=O)c2ccc(C)nc2)C1] | (R or S)-2-(3-(ethoxymethyl)-3-(2-(5-fluoropyridin-2-yl)ethyl)pyrrolidin-1-yl)-2-methyl-1-(6-methylpyridin-3-yl)propan-1-one | | |
| 65 | 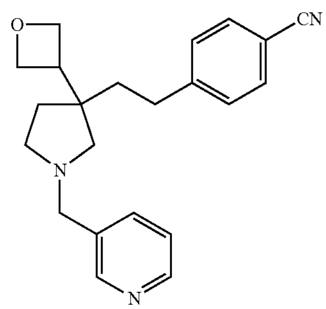 [SMILES: N#Cc1ccc(CCC2(C3COC3)CCN(Cc3cccnc3)C2)cc1] | (R or S)-4-(2-(3-(oxetan-3-yl)-1-(pyridin-3-ylmethyl)pyrrolidin-3-yl)ethyl)benzonitrile | | |
| 66 | 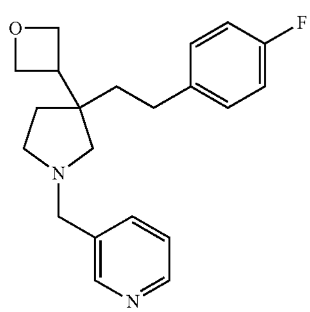 [SMILES: Fc1ccc(CCC2(C3COC3)CCN(Cc3cccnc3)C2)cc1] | (R or S)-3-((3-(4-fluorophenethyl)-3-(oxetan-3-yl)pyrrolidin-1-yl)methyl)pyridine | | |
| 67 | 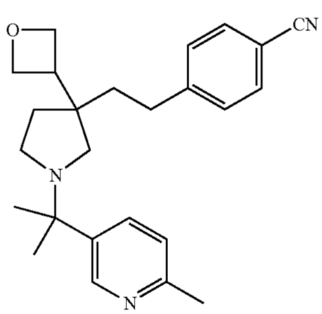 [SMILES: Cc1ccc(C(C)(C)N2CCC(CCc3ccc(C#N)cc3)(C3COC3)C2)cn1] | (R or S)-4-(2-(1-(2-(6-methylpyridin-3-yl)propan-2-yl)-3-(oxetan-3-yl)pyrrolidin-3-yl)ethyl)benzonitrile | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 68 | 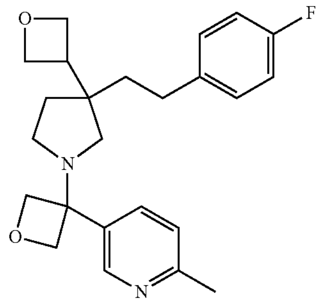 [SMILES: Cc1ccc(C2(N3CCC(CCc4ccc(F)cc4)(C4COC4)C3)COC2)cn1] | (R or S)5-(3-(3-(4-fluorophenethyl)-3-(oxetan-3-yl)pyrrolidin-1-yl)oxetan-3-yl)-2-methylpyridine | | |
| 69 | 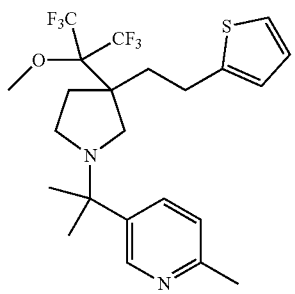 [SMILES: COC(C(F)(F)F)(C(F)(F)F)C1(CCc2cccs2)CCN(C(C)(C)c2ccc(C)nc2)C1] | (R or S)-5-(2-(3-(1,1,1,3,3,3-hexafluoro-2-methoxypropan-2-yl)-3-(2-(thiophen-2-yl)ethyl)pyrrolidin-1-yl)propan-2-yl)-2-methylpyridine | | |
| 70 | 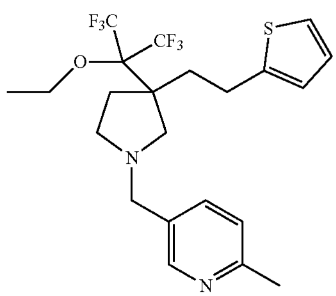 [SMILES: CCOC(C(F)(F)F)(C(F)(F)F)C1(CCc2cccs2)CCN(Cc2ccc(C)nc2)C1] | (R or S)-5-((3-(2-ethoxy-1,1,1,3,3,3-hexafluoropropan-2-yl)-3-(2-(thiophen-2-yl)ethyl)pyrrolidin-1-yl)methyl)-2-methylpyridine | | |
| 71 | 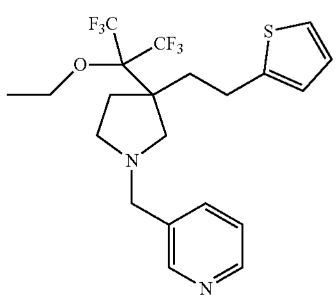 [SMILES: CCOC(C(F)(F)F)(C(F)(F)F)C1(CCc2cccs2)CCN(Cc2cccnc2)C1] | (R or S)-3-((3-(2-ethoxy-1,1,1,3,3,3-hexafluoropropan-2-yl)-3-(2-(thiophen-2-yl)ethyl)pyrrolidin-1-yl)methyl)pyridine | | |
| 72 | 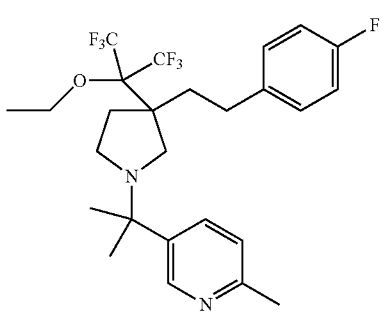 [SMILES: CCOC(C(F)(F)F)(C(F)(F)F)C1(CCc2ccc(F)cc2)CCN(C(C)(C)c2ccc(C)nc2)C1] | (R or S)-5-(2-(3-(2-ethoxy-1,1,1,3,3,3-hexafluoropropan-2-yl)-3-(4-fluorophenethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 73 | 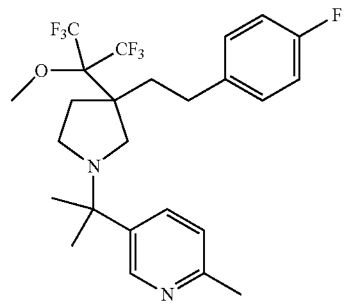 [SMILES: COC(C(F)(F)F)(C(F)(F)F)C1(CCc2ccc(F)cc2)CCN(C(C)(C)c2ccc(C)nc2)C1] | (R or S)-5-(2-(3-(4-fluoro-phenethyl)-3-(1,1,1,3,3,3-hexafluoro-2-methoxypropan-2-yl)pyrrolidin-1-yl)propan-2-yl)-2-methylpyridine | | |
| 74 | 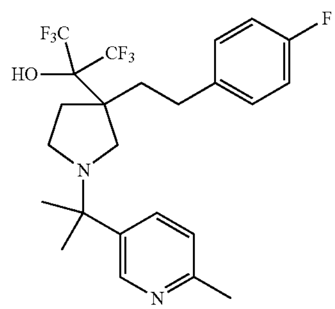 [SMILES: Cc1ccc(C(C)(C)N2CCC(CCc3ccc(F)cc3)(C(O)(C(F)(F)F)C(F)(F)F)C2)cn1] | (R or S)-1,1,1,3,3,3-hexa-fluoro-2-(3-(4-fluoro-phenethyl)-1-(2-(6-methylpyridin-3-yl)propan-2-yl)pyrrolidin-3-yl)propan-2-ol | | |
| 75 | 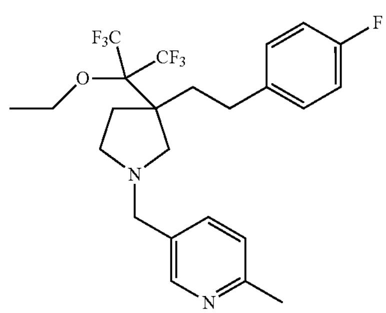 [SMILES: CCOC(C(F)(F)F)(C(F)(F)F)C1(CCc2ccc(F)cc2)CCN(Cc2ccc(C)nc2)C1] | (R or S)-5-((3-(2-ethoxy-1,1,1,3,3,3-hexafluoro-propan-2-yl)-3-(4-fluorophenethyl)pyrrolidin-1-yl)methyl)-2-methylpyridine | | |
| 76 | 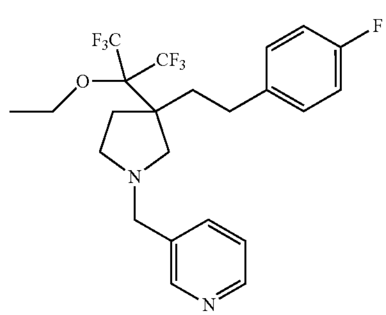 [SMILES: CCOC(C(F)(F)F)(C(F)(F)F)C1(CCc2ccc(F)cc2)CCN(Cc2cccnc2)C1] | (R or S)-3-((3-(2-ethoxy-1,1,1,3,3,3-hexafluoro-propan-2-yl)-3-(4-fluorophenethyl)pyrrolidin-1-yl)methyl)pyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]$^+$ | H-NMR |
|---|---|---|---|---|
| 77 | 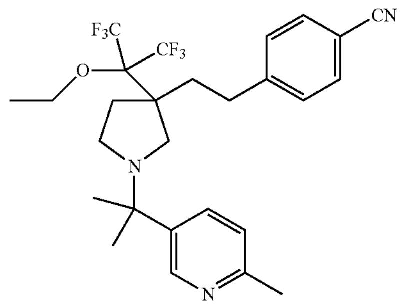 [SMILES: CCOC(C(F)(F)F)(C(F)(F)F)C1(CCc2ccc(C#N)cc2)CCN(C(C)(C)c2ccc(C)nc2)C1] | (R or S)-4-(2-(3-(2-ethoxy-1,1,1,3,3,3-hexafluoropropan-2-yl)-1-(2-(6-methylpyridin-3-yl)propan-2-yl)pyrrolidin-3-yl)ethyl)benzonitrile | | |
| 78 | 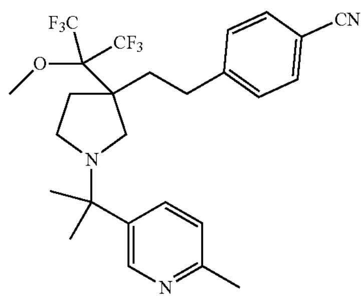 [SMILES: COC(C(F)(F)F)(C(F)(F)F)C1(CCc2ccc(C#N)cc2)CCN(C(C)(C)c2ccc(C)nc2)C1] | (R or S)-4-(2-(3-(1,1,1,3,3,3-hexafluoro-2-methoxypropan-2-yl)-1-(2-(6-methylpyridin-3-yl)propan-2-yl)pyrrolidin-3-yl)ethyl)benzonitrile | | |
| 79 | 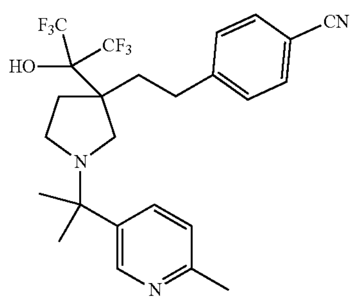 [SMILES: Cc1ccc(C(C)(C)N2CCC(CCc3ccc(C#N)cc3)(C(O)(C(F)(F)F)C(F)(F)F)C2)cn1] | (R or S)-4-(2-(3-(1,1,1,3,3,3-hexafluoro-2-hydroxypropan-2-yl)-1-(2-(6-methylpyridin-3-yl)propan-2-yl)pyrrolidin-3-yl)ethyl)benzonitrile | | |
| 80 | 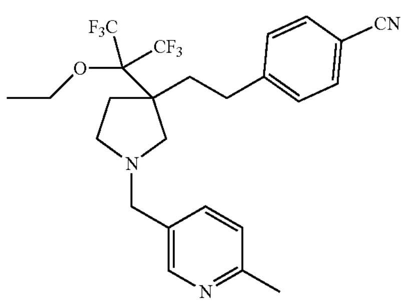 [SMILES: CCOC(C(F)(F)F)(C(F)(F)F)C1(CCc2ccc(C#N)cc2)CCN(Cc2ccc(C)nc2)C1] | (R or S)-4-(2-(3-(2-ethoxy-1,1,1,3,3,3-hexafluoropropan-2-yl)-1-((6-methylpyridin-3-yl)methyl)pyrrolidin-3-yl)ethyl)benzonitrile | | |
| 81 | 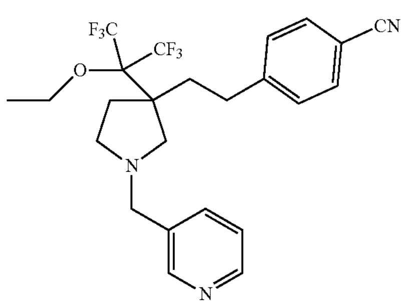 [SMILES: CCOC(C(F)(F)F)(C(F)(F)F)C1(CCc2ccc(C#N)cc2)CCN(Cc2cccnc2)C1] | (R or S)-4-(2-(3-(2-ethoxy-1,1,1,3,3,3-hexafluoropropan-2-yl)-1-(pyridin-3-ylmethyl)pyrrolidin-3-yl)ethyl)benzonitrile | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 82 | (structure) citrate | (R or S)-5-(2-(3-((difluoromethoxy)methyl)-3-(2-(thiophen-2-yl)ethyl)pyrrolidin-1-yl)propan-2-yl)-2-methylpyridine citarte | 395 | ¹H NMR (300 MHz, MeOD): δ 8.63 (s, 1H), 7.98 (dd, J = 5.7, 2.7 Hz, 1H), 7.36 (d, J = 8.4 Hz, 1H), 7.17 (dd, J = 3.9, 1.2 Hz, 1H), 6.88 (dd, J = 3.6, 1.2 Hz, 1H), 6.79 (d, J = 3.3 Hz, 1H), 6.38 (t, J = 75.3 Hz, 1H), 3.88-3.75 (m, 2H), 3.05-2.98 (m, 2H), 2.93-2.78 (m, 6H), 2.75-2.65 (m, 2H), 2.54 (s, 3H), 1.89-1.80 (m, 4H), 1.65 (s, 6H) |
| 83 | (structure) citrate | (R or S)-3-((3-(ethoxymethyl)-1-(2-(6-methylpyridin-3-yl)propan-2-yl)pyrrolidin-3-yl)methyl)-3H-imidazo[4,5-c]pyridine citarte | 422 | ¹H NMR (300 MHz, MeOD): δ 8.98 (s, 1H), 8.59 (d, J = 2.4 Hz, 1H), 8.45-8.31 (m, 2H), 7.96 (m, 1H), 7.79 (m, 1H), 7.34 (d, J = 8.2 Hz, 1H), 4.53-4.37 (m, 2H), 3.41 (t, J = 7.1 Hz, 2H), 3.21-3.09 (m, 2H), 3.02-2.96 (m, 1H), 2.93-2.75 (m, 4H), 2.75-2.66 (m, 3H), 2.55 (s, 3H), 1.96-1.85 (m, 1H), 1.70 (m, 1H), 1.57 (m, 6H), 1.16 (t, J = 7.0 Hz, 3H). |
| 84 | (structure) citrate | (R or S)-1-((3-(ethoxymethyl)-1-(2-(6-methylpyridin-3-yl)propan-2-yl)pyrrolidin-3-yl)methyl)-3-ethyl-5,6-difluoro-1,3-dihydro-2H-benzo[d]imidazol-2-one citarte | 473 | ¹H NMR (300 MHz, MeOD): δ 8.59 (s, 1H), 7.97 (dd, J = 8.3, 2.6 Hz, 1H), 7.31 (d, J = 8.3 Hz, 1H), 7.14-7.08 (m, 2H), 3.91-3.75 (m, 4H), 3.46-3.26 (m, 4H), 3.13 (m, 1H), 2.91 (m, 1H), 2.75-2.64 (m, 6H), 2.47 (s, 3H), 1.96 (m, 1H), 1.80 (m, 1H), 1.70 (d, J = 3.2 Hz, 6H), 1.18 (t, J = 7.2 Hz, 3H), 1.08 (t, J = 7.0 Hz, 3H). |
| 85 | (structure) citrate | (R or S)-1-((3-(ethoxymethyl)-1-(2-(6-methylpyridin-3-yl)propan-2-yl)pyrrolidin-3-yl)methyl)-1H-imidazo[4,5-c]pyridine citrate | 394 | ¹H NMR (300 MHz, MeOD): δ 9.04 (s, 1H), 8.60 (d, J = 2.3 Hz, 1H), 8.42 (s, 1H), 8.38 (d, J = 5.8 Hz, 1H), 8.01 (dd, J = 8.2, 2.4 Hz, 1H), 7.76 (d, J = 5.7 Hz, 1H), 7.37 (d, J = 8.2 Hz, 1H), 4.64-4.45 (m, 2H), 3.38 (m, 2H), 3.13 (m, 2H), 2.91 (m, 2H), 2.99-2.80 (m, 4H), 2.76 (m, 2H), 2.56 (s, 3H), 1.97 (m, 1H), 1.60-1.58 (m, 7H), 1.17 (t, J = 7.0 Hz, 3H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 86 | 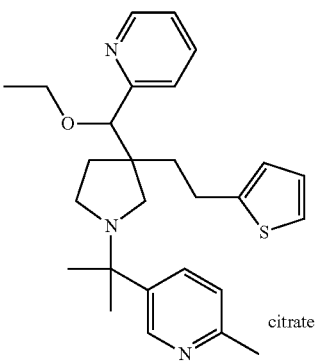 [SMILES: CCOC(c1ccccn1)C1(CCc2cccs2)CCN(C(C)(C)c2ccc(C)nc2)C1] | 5-(2-((S or R)-3-((R & S)-ethoxy(pyridin-2-yl)methyl)-3-(2-(thiophen-2-yl)ethyl)pyrrolidin-1-yl)propan-2-yl)-2-methylpyridine citrate | 450 | ¹HNMR (300 MHz, MeOD): δ 8.64 (t, J = 3.0 Hz, 1H), 8.54 (t, J = 3.9 Hz, 1H), 8.02-7.96 (m, 1H), 7.88-7.79 (m, 1H), 7.50-7.45 (m, 1H), 7.43-7.34 (m, 2H), 7.15-7.11 (m, 1H), 6.88-6.83 (m, 1H), 6.75-6.71 (m, 1H), 4.49 (s, 0.5H), 4.47 (s, 0.5H), 3.73 (d, J = 11.4 Hz, 0.5 H), 3.46 (d, J = 11.4 Hz, 0.5 H), 3.39-3.35 (m, 2H), 3.30-3.25 (m, 1H), 3.23-3.03 (m, 2H), 3.01-2.96 (m, 1H), 2.83-2.73 (m, 5H), 2.56 (m, 3H), 2.41-2.20 (m, 1H), 1.93-1.84 (m, 1H), 1.76 (m, 6H), 1.74-1.42 (m, 2H), 1.17-1.06 (m, 3H) |
| 87 | 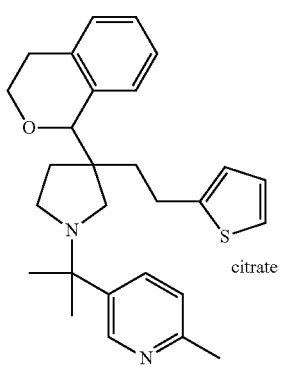 [SMILES: Cc1ccc(C(C)(C)N2CCC(CCc3cccs3)(C3OCCc4ccccc43)C2)cn1] | 5-(2-((R or S)-3-((S or R)-isochroman-1-yl)-3-(2-(thiophen-2-yl)ethyl)pyrrolidin-1-yl)propan-2-yl)-2-methylpyridine citrate | 447 | ¹H NMR (300 MHz, MeOD): δ 8.72 (s, 1H), 8.06 (s, 1H), 7.42 (s, 1H), 7.20-7.18 (m, 4H), 7.09 (d, J = 4.8 Hz, 1H), 6.82 (t, J = 3.3 Hz, 1H), 6.56 (s, 1H), 4.11-4.05 (m, 1H), 3.61-3.50 (m, 2H), 3.10-3.05 (m, 1H), 2.98-2.86 (m, 2H), 2.75 (q, J = 15.6 Hz, 4H), 2.65-2.55 (m, 4H), 2.54-2.45 (m, 4H), 2.20-2.00 (m, 2H), 1.83 (s, 6H), 1.70-2.55 (m, 2H) |
| 88 | 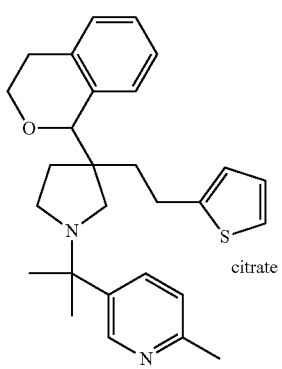 [SMILES: Cc1ccc(C(C)(C)N2CCC(CCc3cccs3)(C3OCCc4ccccc43)C2)cn1] | 5-(2-((R or S)-3-((R or S)-isochroman-1-yl)-3-(2-(thiophen-2-yl)ethyl)pyrrolidin-1-yl)propan-2-yl)-2-methylpyridine citrate | 447 | ¹H NMR (300 MHz, MeOD): δ 8.65 (s, 1H), 7.98 (d, J = 6.9 Hz, 1H), 7.39 (d, J = 7.8 Hz, 1H), 7.21-7.16 (m, 5H), 6.88 (t, J = 3.9 Hz, 1H), 6.75 (s, 1H), 4.08-4.06 (m, 1H), 3.56-3.46 (m, 2H), 3.16-3.08 (m, 1H), 2.85 (q, J = 15.5 Hz, 4H), 2.58 (s, 6H), 2.19 (t, J = 7.5 Hz, 1H), 2.09-1.97 (m, 3H), 1.87-1.81 (m, 8H), 1.66-1.54 (m, 2H) |
| 89 | 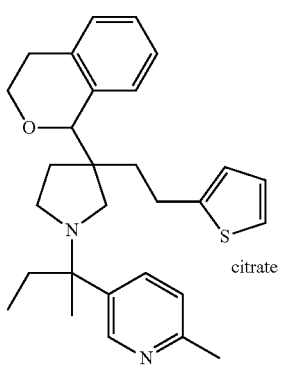 [SMILES: CCC(C)(c1ccc(C)nc1)N1CCC(CCc2cccs2)(C2OCCc3ccccc32)C1] | 5-(2-((R or S)-3-((S or R)-isochroman-1-yl)-3-(2-(thiophen-2-yl)ethyl)pyrrolidin-1-yl)butan-2-yl)-2-methylpyridine citrate | 461 | ¹H NMR (300 MHz, MeOD): δ 8.68 (s, 1H), 8.06 (s, 1H), 7.46 (s, 1H), 7.20 (m, 4H), 7.10 (t, J = 5.7 Hz, 1H), 6.81 (m, 1H), 6.55 (m, 1H), 4.15-4.02 (m, 1H), 3.62-3.45 (m, 4H), 3.21-2.95 (m, 2H), 2.80 (q, J = 15.5 Hz, 4H), 2.58-2.49 (m, 6H), 2.47-2.25 (m, 2H), 2.19-2.05 (m, 2H), 1.95-1.78 (m, 4H), 1.76-1.50 (m, 2H), 0.90-0.81 (m, 3H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 90 | 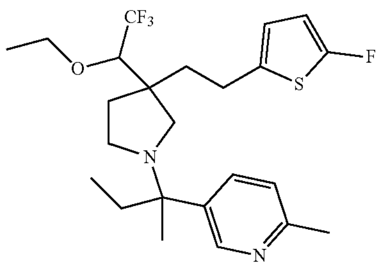 [SMILES: CCOC(C(F)(F)F)C1(CCc2ccc(F)s2)CCN(C(C)(CC)c2ccc(C)nc2)C1] | 5-(2-((R or S)-3-((S & R)-1-ethoxy-2,2,2-trifluoroethyl)-3-(2-(5-fluorothiophen-2-yl)ethyl)pyrrolidin-1-yl)butan-2-yl)-2-methylpyridine | 473 | $^1$H NMR (300 MHz, MeOD): δ 8.54 (m, 1H), 7.65-7.59 (m, 1H), 7.10 (d, J = 7.8 Hz, 1H), 6.33 (s, 1H), 6.23 (d, J = 1.8 Hz, 1H), 4.01-3.80 (m, 1H), 3.64-3.42 (m, 2H), 3.04-2.64 (m, 3H), 2.54 (s, 6H), 2.00-1.91 (m, 1H), 1.90-1.74 (m, 3H), 1.72-1.61 (m, 2H), 1.35 (s, 3H), 1.24-1.17 (m, 2H), 1.16-1.06 (m, 1H), 0.63 (t, J = 7.2 Hz, 3H) |
| 91 | 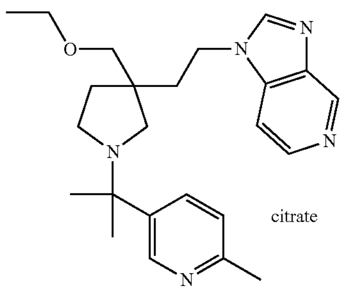 [SMILES: CCOCC1(CCn2cnc3cnccc32)CCN(C(C)(C)c2ccc(C)nc2)C1] | 1-(2-(3-(ethoxymethyl)-1-(2-(6-methylpyridin-3-yl)propan-2-yl)pyrrolidin-3-yl)ethyl)-1H-imidazo[4,5-c]pyridine citrate | 408 | $^1$H NMR (300 MHz, MeOD): δ 8.98 (s, 1H), 8.66 (s, 1H), 8.47 (s, 1H), 8.40 (d, J = 5.8 Hz, 1H), 8.08-7.97 (m, 1H), 7.75 (d, J = 5.7 Hz, 1H), 7.39 (d, J = 8.5 Hz, 1H), 4.45 (t, J = 8.2 Hz, 2H), 3.48 (q, J = 7.0 Hz, 3H), 3.39 (m, 2H), 3.24-3.12 (m, 2H), 3.10-3.02 (m, 1H), 2.81 (q, J = 15.6 Hz, 4H), 2.55 (s, 3H), 2.21-2.05 (m, 2H), 1.95-1.85 (m, 2H), 1.75 (s, 6H), 1.16 (t, J = 7.0 Hz, 3H). |
| 92 | 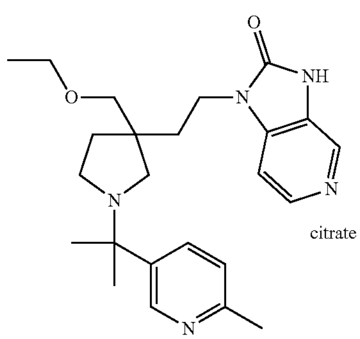 [SMILES: CCOCC1(CCn2c(=O)[nH]c3cnccc32)CCN(C(C)(C)c2ccc(C)nc2)C1] | 1-(2-(3-(ethoxymethyl)-1-(2-(6-methylpyridin-3-yl)propan-2-yl)pyrrolidin-3-yl)ethyl)-1,3-dihydro-2H-imidazo[4,5-c]pyridin-2-one citrate | 424 | $^1$H NMR (500 MHz, MeOD): δ 8.66 (d, J = 2.1 Hz, 1H), 8.33 (s, 1H), 8.22 (d, J = 5.4 Hz, 1H), 8.02 (dd, J = 8.3, 2.4 Hz, 1H), 7.39 (d, J = 8.3 Hz, 1H), 7.17 (d, J = 5.4 Hz, 1H), 3.94 (t, J = 7.7 Hz, 2H), 3.46 (t, J = 7.1 Hz, 2H), 3.38 (q, J = 9.2 Hz, 2H), 3.22-3.10 (m, 2H), 3.05 (d, J = 11.3 Hz, 1H), 2.90 (d, J = 11.4 Hz, 1H), 2.80 (q, J = 15.5 Hz, 4H), 2.55 (s, 3H), 2.01-1.82 (m, 4H), 1.74 (s, 6H), 1.14 (t, J = 7.0 Hz, 3H). |
| 93 | 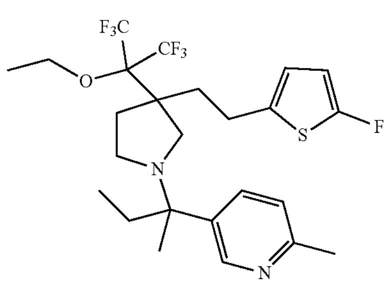 [SMILES: CCOC(C(F)(F)F)(C(F)(F)F)C1(CCc2ccc(F)s2)CCN(C(C)(CC)c2ccc(C)nc2)C1] | 5-(2-((R or S)-3-(2-ethoxy-1,1,1,3,3,3-hexafluoropropan-2-yl)-3-(2-(5-fluorothiophen-2-yl)ethyl)pyrrolidin-1-yl)butan-2-yl)-2-methylpyridine | 541 | $^1$HNMR (300 MHz, MeOD): δ 8.51 (dd, J = 11.4, 1.8 Hz, 1H), 7.68-7.55 (m, 1H), 7.11 (d, J = 8.1 Hz, 1H), 6.38-6.26 (m, 1H), 6.25 (d, J = 1.8 Hz, 1H), 4.01-3.82 (m, 2H), 3.11-2.75 (m, 4H), 2.55 (s, 3H), 2.51-2.45 (m, 1H), 2.40-2.27 (m, 2H), 2.23-1.98 (m, 1H), 1.97-1.70 (m, 4H), 1.41-1.32 (m, 3H), 1.21-1.15 (m, 3H), 0.63 (t, J = 7.2 Hz, 3H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 94 | 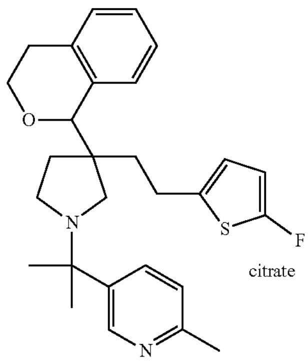 [SMILES: Cc1ccc(C(C)(C)N2CCC(CCc3ccc(F)s3)(C3OCCc4ccccc43)C2)cn1] | 5-(2-((R or S)-3-(2-(5-fluoro-thiophen-2-yl)ethyl)-3-((R or S)-isochroman-1-yl)pyrrolidin-1-yl)propan-2-yl)-2-methylpyridine citrate | 465 | ¹HNMR (300 MHz, MeOD): δ 8.61 (d, J = 2.1 Hz, 1H), 7.94 (m, 1H), 7.35 (d, J = 8.4 Hz, 1H), 7.19-7.08 (m, 4H), 6.31 (d, J = 3.0 Hz, 1H), 6.27 (t, J = 3.6 Hz, 1H), 4.15-4.02 (m, 1H), 3.55-3.49 (m, 1H), 3.20-3.11 (m, 2H), 3.07-3.01 (m, 1H), 2.98-2.88 (m, 2H), 2.87-2.84 (m, 1H), 2.79 (q, J = 15.6 Hz, 4H), 2.74-2.66 (m, 2H), 2.64-2.60 (m, 1H), 2.55 (s, 3H), 2.25-2.18 (m, 1H), 1.95-1.82 (m, 2H), 1.81-1.75 (m, 1H), 1.71 (m, 6H). |
| 95 | 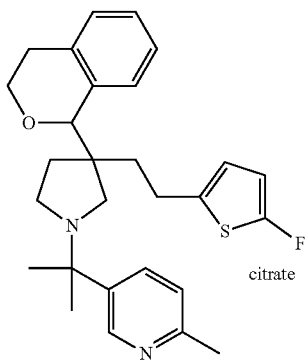 [SMILES: Cc1ccc(C(C)(C)N2CCC(CCc3ccc(F)s3)(C3OCCc4ccccc43)C2)cn1] | 5-(2-((R or S)-3-(2-(5-fluoro-thiophen-2-yl)ethyl)-3-((S or R)-isochroman-1-yl)pyrrolidin-1-yl)propan-2-yl)-2-methylpyridine citrate | 465 | ¹HNMR (300 MHz, MeOD): δ 8.74 (s, 1H), 8.10 (d, J = 6.0 Hz, 1H), 7.45 (d, J = 8.1 Hz, 1H), 7.26-7.20 (m, 4H), 6.23-6.22 (m, 1H), 6.18 (d, J = 2.7 Hz, 1H), 4.15-4.02 (m, 1H), 3.52-3.49 (m, 2H), 3.15-3.05 (m, 1H), 2.79 (q, J = 15.6 Hz, 4H), 2.74 (s, 3H), 2.54-2.43 (m, 2H), 2.38-2.28 (m, 2H), 2.20-2.08 (m, 2H), 1.87 (s, 6H), 1.80-1.75 (m, 1H), 1.65-1.60 (m, 1H), 1.18 (t, J = 6.9 Hz, 3H). |
| 96 | 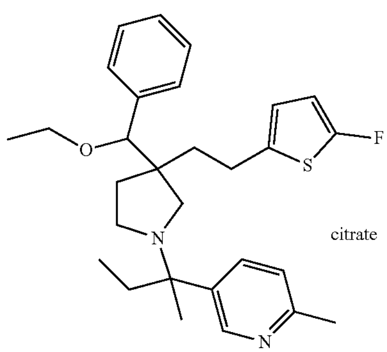 [SMILES: CCOC(c1ccccc1)C1(CCc2ccc(F)s2)CCN(C(C)(CC)c2ccc(C)nc2)C1] | 5-(2-((R or S)-3-((R or S)-ethoxy(phenyl)methyl)-3-(2-(5-fluoro-thiophen-2-yl)ethyl)pyrrolidin-1-yl)butan-2-yl)-2-methylpyridine citrate | 481 | ¹HNMR (300 MHz, MeOD): δ 8.69 (d, J = 2.1 Hz, 1H), 8.04 (d, J = 8.1 Hz, 1H), 7.52-7.47 (m, 1H), 7.40-7.34 (m, 3H), 7.26 (d, J = 6.9 Hz, 1H), 7.22 (t, J = 3.9 Hz, 1H), 6.37 (d, J = 3.9 Hz, 1H), 6.28 (m, 1H), 4.39 (m, 1H), 3.58-3.40 (m, 2H), 3.30-3.12 (m, 4H), 3.11-2.93 (m, 1H), 2.79 (q, J = 15.6 Hz, 4H), 2.78-2.70 (m, 3H), 2.60 (d, J = 6.3 Hz, 3H), 2.28-2.20 (m, 1H), 2.10-2.00 (m, 1H), 1.83 (m, 3H), 1.75-1.62 (m, 1H), 1.58 (m, 1H), 1.03 (t, J = 7.2 Hz, 3H), 0.82 (t, J = 6.9 Hz, 3H) |
| 97 | 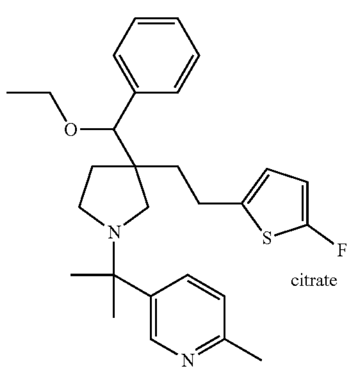 [SMILES: CCOC(c1ccccc1)C1(CCc2ccc(F)s2)CCN(C(C)(C)c2ccc(C)nc2)C1] | 5-(2-((R or S)-3-((R or S)-ethoxy(phenyl)methyl)-3-(2-(5-fluoro-thiophen-2-yl)ethyl)pyrrolidin-1-yl)propan-2-yl)-2-methylpyridine citrate | 467 | ¹HNMR (300 MHz, MeOD): δ 8.75 (s, 1H), 8.09 (d, J = 8.4 Hz, 1H), 7.48 (d, J = 8.4 Hz, 1H), 7.40-7.34 (m, 3H), 7.24 (d, J = 6.3 Hz, 2H), 6.37 (s, 1H), 6.29 (t, J = 2.9 Hz, 1H), 4.40 (s, 1H), 3.56-3.50 (m, 1H), 3.49-3.38 (m, 3H), 3.28-3.22 (m, 2H), 2.98-2.90 (m, 2H), 2.79 (q, J = 15.6 Hz, 4H), 2.60 (s, 3H), 2.32-2.21 (m, 1H), 2.08-1.97 (m, 1H), 1.88 (m, 6H), 1.70-1.52 (m, 2H), 1.03 (t, J = 6.9 Hz, 3H). |

TABLE I-continued

Compounds with a pyrrolidine ring and a pyridine or pyridine-like molecule bonded to the pyrrolidine N-constituent

| Compound No. | Structure | Name | MS (ESI+): [M + H]$^+$ | H-NMR |
|---|---|---|---|---|
| 98 | 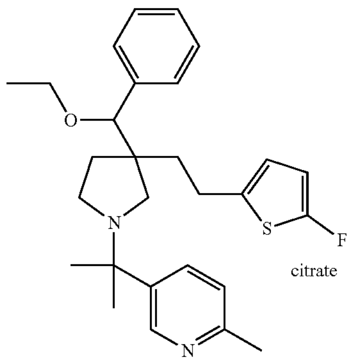 [SMILES: CCOC(c1ccccc1)C1(CCc2ccc(F)s2)CCN(C(C)(C)c2ccc(C)nc2)C1] | 5-(2-((R or S)-3-((S or R)-ethoxy(phenyl)methyl)-3-(2-(5-fluoro-thiophen-2-yl)ethyl)pyrrolidin-1-yl)propan-2-yl)-2-methylpyridine citrate | 467 | $^1$HNMR (300 MHz, MeOD): δ 8.70 (d, J = 1.8 Hz, 1H), 8.03 (m, 1H), 7.43 (d, J = 8.1 Hz, 1H), 7.35-7.28 (m, 5H), 6.37 (t, J = 3.3 Hz, 1H), 6.30-6.28 (m, 1H), 4.40 (s, 1H), 3.47-3.40 (m, 2H), 3.25-3.15 (m, 2H), 3.08-2.90 (m, 2H), 2.79 (q, J = 15.6 Hz, 4H), 2.75-2.65 (m, 2H), 2.59 (s, 3H), 2.38-2.30 (m, 1H), 2.15-1.92 (m, 1H), 1.84 (m, 6H), 1.70-1.62 (m, 1H), 1.58-1.49 (m, 1H), 1.11 (t, J = 7.2 Hz, 3H). |
| 99 | 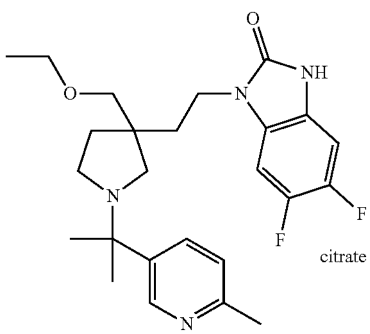 [SMILES: CCOCC1(CCn2c(=O)[nH]c3cc(F)c(F)cc32)CCN(C(C)(C)c2ccc(C)nc2)C1] | 1-(2-(3-(ethoxymethyl)-1-(2-(6-methylpyridin-3-yl)propan-2-yl)pyrrolidin-3-yl)ethyl)-5,6-difluoro-1,3-dihydro-2H-benzo[d]imidazol-2-one citrate | 459 | $^1$H NMR (300 MHz, MeOD): δ 8.67 (d, J = 1.8 Hz, 1H), 8.03 (dd, J = 8.3, 2.3 Hz, 1H), 7.40 (d, J = 8.3 Hz, 1H), 7.11 (t, J = 8.5 Hz, 1H), 7.01 (t, J = 8.5 Hz, 1H), 3.85 (t, J = 7.8 Hz, 2H), 3.46 (m, 3H), 3.38 (m, 2H), 3.24-3.15 (m, 2H), 3.08 (d, J = 11.4 Hz, 1H), 2.91 (d, J = 11.7 Hz, 1H), 2.80 (q, J = 15.5 Hz, 4H), 2.56 (s, 3H), 1.95-1.83 (m, 3H), 1.77 (s, 6H), 1.14 (t, J = 7.0 Hz, 3H). |
| 100 | 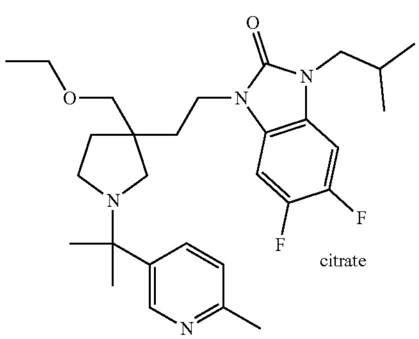 [SMILES: CCOCC1(CCn2c(=O)n(CC(C)C)c3cc(F)c(F)cc32)CCN(C(C)(C)c2ccc(C)nc2)C1] | 1-(2-(3-(ethoxymethyl)-1-(2-(6-methylpyridin-3-yl)propan-2-yl)pyrrolidin-3-yl)ethyl)-5,6-difluoro-3-isobutyl-1,3-dihydro-2H-benzo[d]imidazol-2-one citrate | 515 | $^1$H NMR (300 MHz, MeOD): δ 8.68 (s, 1H), 8.04 (d, J = 8.9 Hz, 1H), 7.41 (d, J = 8.3 Hz, 1H), 7.20 (ddd, J = 16.9, 10.0, 6.9 Hz, 2H), 3.89 (t, J = 7.5 Hz, 2H), 3.67 (d, J = 7.5 Hz, 2H), 3.46 (q, J = 7.0 Hz, 2H), 3.36 (m, 2H), 3.22 (m, 2H), 3.11 (d, J = 11.5 Hz, 1H), 2.96 (d, J = 11.7 Hz, 1H), 2.80 (q, J = 15.5 Hz, 4H), 2.56 (s, 3H), 2.19-2.08 (m, 1H), 2.01-1.82 (m, 4H), 1.79 (s, 6H), 1.14 (t, J = 7.0 Hz, 3H), 0.93 (d, J = 4.8 Hz, 6H). |
| 101 | 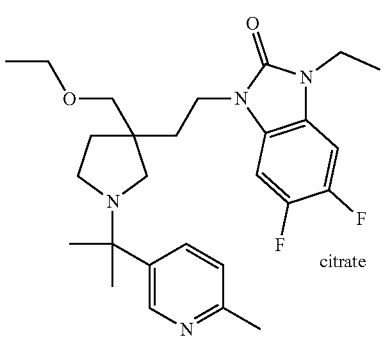 [SMILES: CCOCC1(CCn2c(=O)n(CC)c3cc(F)c(F)cc32)CCN(C(C)(C)c2ccc(C)nc2)C1] | 1-(2-(3-(ethoxymethyl)-1-(2-(6-methylpyridin-3-yl)propan-2-yl)pyrrolidin-3-yl)ethyl)-3-ethyl-5,6-difluoro-1,3-dihydro-2H-benzo[d]imidazol-2-one citrate | 487 | $^1$H NMR (300 MHz, MeOD): δ 8.65 (s, 1H), 8.00 (d, J = 6.2 Hz, 1H), 7.38 (d, J = 8.1 Hz, 1H), 7.24 (dd, J = 10.1, 6.9 Hz, 1H), 7.15 (dd, J = 10.1, 7.0 Hz, 1H), 3.96-3.84 (m, 4H), 3.46 (q, J = 6.9 Hz, 3H), 3.37 (s, 2H), 3.14 (m, 2H), 3.02 (m, 1H), 2.80 (q, J = 15.5 Hz, 4H), 2.55 (s, 3H), 1.97-1.78 (m, 4H), 1.73 (s, 6H), 1.27 (t, J = 7.1 Hz, 3H), 1.14 (t, J = 7.0 Hz, 3H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 102 | 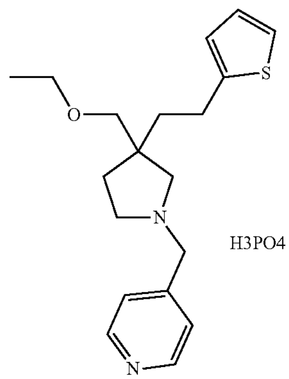 | (S)-4-((3-(ethoxymethyl)-3-(2-(thiophen-2-yl)ethyl)pyrrolidin-1-yl)methyl)pyridine H3PO4 salt | 331 | $^1$H NMR (300 MHz, MeOD): δ 8.46 (d, J = 5.2 Hz, 2H), 7.45 (s, 2H), 7.13 (dd, J = 5.2, 1.2 Hz, 1H), 6.87 (dd, J = 5.2, 3.4 Hz, 1H), 6.78 (d, J = 3.4 Hz, 1H), 3.66 (s, 2H), 3.49 (q, J = 7.0 Hz, 2H), 3.34 (d, J = 3.5 Hz, 2H), 2.81 (t, J = 7.8 Hz, 2H), 2.63 (q, J = 7.0 Hz, 2H), 2.56 (d, J = 9.6 Hz, 1H), 2.34 (d, J = 9.6 Hz, 1H), 1.86 (m, 2H), 1.68 (t, J = 6.9 Hz, 2H), 1.18 (t, J = 7.0 Hz, 3H). |
| 103 | 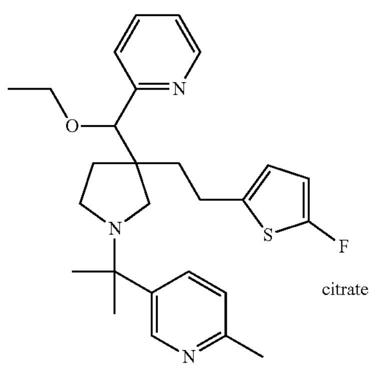 [SMILES: CCOC(c1ccccn1)C1(CCc2ccc(F)s2)CCN(C(C)(C)c2ccc(C)nc2)C1] | 5-(2-((R or S)-3-((S & R)-ethoxy(pyridin-2-yl)methyl)-3-(2-(5-fluorothiophen-2-yl)ethyl)pyrrolidin-1-yl)propan-2-yl)-2-methylpyridine citrate | 468 | $^1$H NMR (300 MHz, MeOD): δ 8.68 (s, 1H), 8.56 (s, 1H), 8.05 (m, 1H), 7.84 (m, 1H), 7.53-7.31 (m, 3H), 6.43-6.32 (m, 1H), 6.31-6.22 (m, 1H), 4.47 (m, 1H), 3.79 (d, J = 11.7 Hz, 1H), 3.51 (d, J = 11.5 Hz, 1H), 3.25-3.15 (m, 1H), 3.08 (d, J = 11.4 Hz, 1H), 3.02-2.87 (m, 2H), 2.79 (q, J = 15.5 Hz, 4H), 2.70-2.63 (m, 1H), 2.58 (s, 3H), 2.42-2.23 (m, 1H), 2.12-1.89 (m, 1H), 1.82 (s, 6H), 1.79-1.59 (m, 2H), 1.52-1.36 (m, 1H), 1.18-1.01 (m, 3H). |
| 104 | 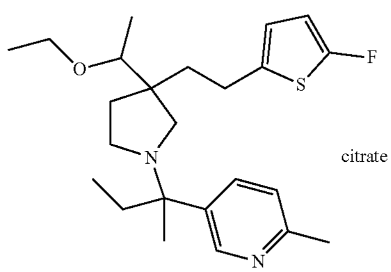 [SMILES: CCOC(C)C1(CCc2ccc(F)s2)CCN(C(C)(CC)c2ccc(C)nc2)C1] | 5-(2-((R or S)-3-((S or R)-1-ethoxyethyl)-3-(2-(5-fluorothiophen-2-yl)ethyl)pyrrolidin-1-yl)butan-2-yl)-2-methylpyridine citrate | 419 | $^1$H NMR (300 MHz, MeOD): δ 8.64 (s, 1H), 8.00 (d, J = 7.8 Hz, 1H), 7.45 (d, J = 8.1 Hz, 1H), 6.41 (m, 1H), 6.30 (m, 1H), 3.64-3.57 (m, 1H), 3.50-3.38 (m, 2H), 3.26-3.07 (m, 4H), 2.75 (q, J = 15.6 Hz, 4H), 2.71-2.61 (m, 2H), 2.57 (s, 3H), 2.53-2.44 (m, 1H), 2.21-2.11 (m, 1H), 2.07-2.00 (m, 1H), 1.80 (s, 3H), 1.76-1.57 (m, 3H), 1.13-1.02 (m, 6H), 0.78 (t, J = 7.2 Hz, 3H) |
| 105 | 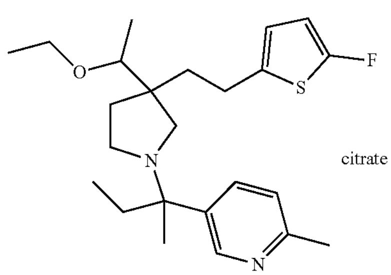 [SMILES: CCOC(C)C1(CCc2ccc(F)s2)CCN(C(C)(CC)c2ccc(C)nc2)C1] | 5-(2-((R or S)-3-((R or S)-1-ethoxyethyl)-3-(2-(5-fluorothiophen-2-yl)ethyl)pyrrolidin-1-yl)butan-2-yl)-2-methylpyridine citrate | 419 | $^1$HNMR (300 MHz, MeOD): δ 8.65 (s, 1H), 8.00 (d, J = 8.1 Hz, 1H), 7.45 (d, J = 8.1 Hz, 1H), 6.41 (d, J = 3.9 Hz, 1H), 6.30 (m, 1H), 3.64-3.56 (m, 1H), 3.50-3.42 (m, 2H), 3.22-3.08 (m, 2H), 2.77 (q, J = 15.6 Hz, 4H), 2.68-2.62 (m, 2H), 2.56 (s, 3H), 2.55-2.47 (m, 2H), 2.07-2.00 (m, 2H), 1.82 (s, 6H), 1.75-1.69 (m, 1H), 1.08-0.99 (m, 6H), 0.80 (t, J = 7.2 Hz, 3H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 106 | 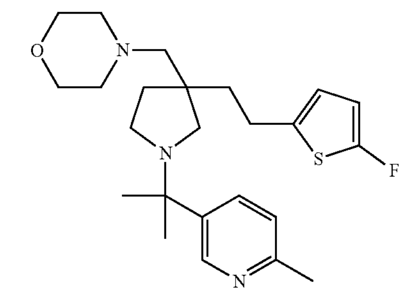 [SMILES: Cc1ccc(C(C)(C)N2CCC(CCc3ccc(F)s3)(CN3CCOCC3)C2)cn1] | (S or R)-4-((3-(2-(5-fluoro-thiophen-2-yl)ethyl)-1-(2-(6-methylpyridin-3-yl)propan-2-yl)pyrrolidin-3-yl)methyl)morpholine | 432 | $^1$HNMR (300 MHz, MeOD): δ 8.53 (d, J = 1.8 Hz, 1H), 7.85 (dd, J = 8.1, 2.1 Hz, 1H), 7.25 (d, J = 8.1 Hz, 1H), 6.38 (t, J = 3.3 Hz, 1H), 6.28 (m, 1H), 3.63 (t, J = 4.5 Hz, 4H), 2.68-2.58 (m, 4H), 2.52 (s, 3H), 2.50-2.38 (m, 6H), 2.36-2.28 (m, 2H), 1.82-1.70 (m, 2H), 1.66-1.54 (m, 2H), 1.42 (s, 6H) |
| 107 | 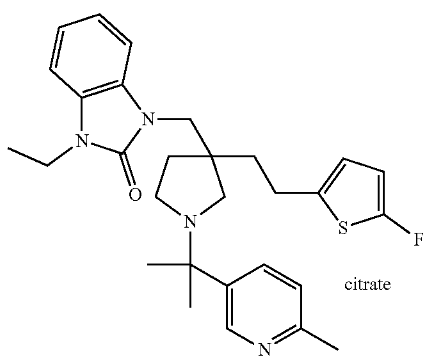 [SMILES: CCn1c(=O)n(CC2(CCc3ccc(F)s3)CCN(C(C)(C)c3ccc(C)nc3)C2)c2ccccc21] | (S or R)-1-ethyl-3-((3-(2-(5-fluorothiophen-2-yl)ethyl)-1-(2-(6-methylpyridin-3-yl)propan-2-yl)pyrrolidin-3-yl)methyl)-1,3-dihydro-2H-benzo[d]imidazol-2-one citrate | 507 | $^1$H NMR (300 MHz, MeOD): δ 8.59 (s, 1H), 7.90 (s, 1H), 7.30 (t, J = 5.1 Hz, 1H), 7.17 (d, J = 18.9 Hz, 4H), 6.43 (s, 1H), 6.29 (s, 1H), 3.99 (d, J = 4.0 Hz, 4H), 3.14-3.05 (m, 1H), 2.98 (s, 2H), 2.90-2.68 (m, 5H), 2.52 (d, J = 3.3 Hz, 3H), 2.07-1.95 (m, 1H), 1.87-1.77 (m, 3H), 1.65-1.55 (m, 6H), 1.35-1.29 (m, 5H). |
| 108 | 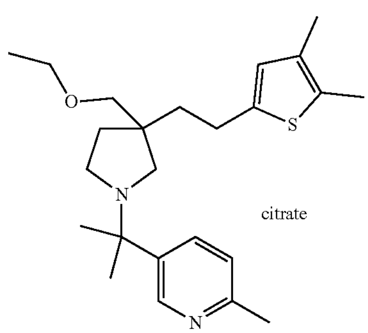 [SMILES: CCOCC1(CCc2cc(C)c(C)s2)CCN(C(C)(C)c2ccc(C)nc2)C1] | (R or S)-5-(2-(3-(2-(4,5-dimethylthiophen-2-yl)ethyl)-3-(ethoxy-methyl)pyrrolidin-1-yl)propan-2-yl)-2-methylpyridine citrate | 401 | $^1$H NMR (300 MHz, MeOD): δ 8.70 (s, 1H), 8.06 (d, J = 7.8 Hz, 1H), 7.43 (d, J = 8.3 Hz, 1H), 6.43 (s, 1H), 3.43 (q, J = 6.6 Hz, 2H), 3.18 (d, J = 11.8 Hz, 1H), 2.96 (d, J = 11.8 Hz, 1H), 2.80 (q, J = 15.5 Hz, 4H), 2.70-2.59 (m, 4H), 2.57 (s, 3H), 2.24 (s, 3H), 2.09-1.91 (m, 5H), 1.90-1.67 (m, 10H), 1.12 (t, J = 6.9 Hz, 3H). |
| 109 | 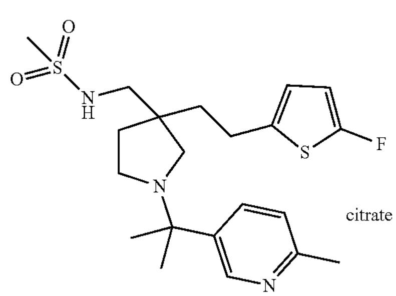 [SMILES: Cc1ccc(C(C)(C)N2CCC(CCc3ccc(F)s3)(CNS(C)(=O)=O)C2)cn1] | (R or S)-N-((3-(2-(5-fluoro-thiophen-2-yl)ethyl)-1-(2-(6-methylpyridin-3-yl)propan-2-yl)pyrrolidin-3-yl)methyl)methane-sulfonamide citrate | 440 | $^1$HNMR (300 MHz, MeOD): δ 8.63 (d, J = 1.8 Hz, 1H), 8.00 (dd, J = 8.1, 2.4 Hz, 1H), 7.36 (d, J = 8.1 Hz, 1H), 6.43 (t, J = 3.6 Hz, 1H), 6.29 (dd, J = 3.9, 2.1 Hz, 1H), 3.12-3.02 (m, 4H), 3.01-2.95 (m, 1H), 2.94 (s, 3H), 2.77 (q, J = 15.6 Hz, 4H), 2.72-2.64 (m, 3H), 2.54 (s, 3H), 1.92-1.75 (m, 4H), 1.74 (s, 6H) |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 110 | 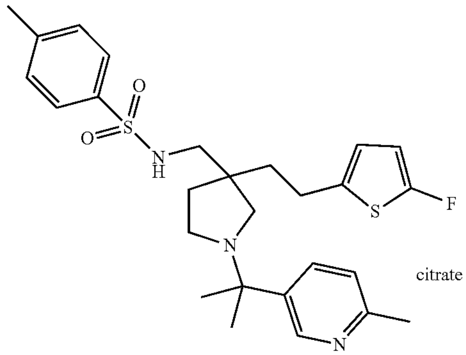 [SMILES: Cc1ccc(S(=O)(=O)NCC2(CCc3ccc(F)s3)CCN(C(C)(C)c3ccc(C)nc3)C2)cc1] | (R or S)-N-((3-(2-(5-fluoro-thiophen-2-yl)ethyl)-1-(2-(6-methylpyridin-3-yl)propan-2-yl)pyrrolidin-3-yl)methyl)-4-methylbenzene-sulfonamide citrate | 516 | ¹HNMR (300 MHz, MeOD): δ 8.67 (s, 1H), 8.07 (d, J = 8.1 Hz, 1H), 7.72 (d, J = 8.1 Hz, 2H), 7.39 (t, J = 8.4 Hz, 3H), 6.40 (t, J = 3.6 Hz, 1H), 6.27 (dd, J = 3.6, 2.1Hz, 1H), 3.32-3.30 (m, 3H), 3.29-3.18 (m, 2H), 3.15-3.05 (m, 1H), 2.90-2.80 (m, 3H), 2.75 (q, J = 15.6 Hz, 4H), 2.65-2.60 (m, 1H), 2.55 (s, 3H), 2.42 (s, 3H), 1.95-1.82 (m, 2H), 1.72 (s, 6H) |
| 111 | 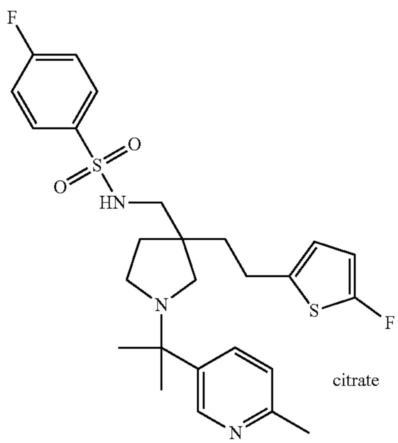 [SMILES: Cc1ccc(C(C)(C)N2CCC(CCc3ccc(F)s3)(CNS(=O)(=O)c3ccc(F)cc3)C2)cn1] | (S or R)-4-fluoro-N-((3-(2-(5-fluorothiophen-2-yl)ethyl)-1-(2-(6-methylpyridin-3-yl)propan-2-yl)pyrrolidin-3-yl)methyl)benzene-sulfonamide citrate | 520 | ¹H NMR (300 MHz, MeOD): δ 8.65 (s, 1H), 8.03 (d, J = 7.9 Hz, 1H), 7.90 (dd, J = 8.7, 4.9 Hz, 2H), 7.49-7.24 (m, 3H), 6.50-6.37 (m, 1H), 6.35-6.22 (m, 1H), 3.20-2.99 (m, 3H), 2.95-2.69 (m, 8H), 2.67-2.50 (m, 5H), 1.87-1.68 (m, 9H). |
| 112 | 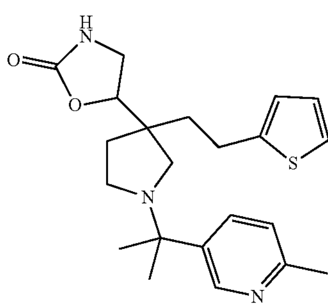 | (S & R)-5-((R or S)-3-(2-(5-fluoro-thiophen-2-yl)ethyl)-1-(2-(6-methylpyridin-3-yl)propan-2-yl)pyrrolidin-3-yl)oxazolidin-2-one citrate | 418 | ¹H NMR (300 MHz, MeOD): δ 8.61 (s, 1H), 8.00 (d, J = 8.1 Hz, 1H), 7.36 (d, J = 8.0 Hz, 1H), 6.44 (t, J = 3.4 Hz, 1H), 6.30 (dd, J = 3.7, 2.1 Hz, 1H), 4.88-4.70 (m, 1H), 3.69-3.42 (m, 2H), 2.98-2.61 (m, 10H), 2.54 (s, 3H), 1.97-1.68 (m, 4H), 1.61 (s, 6H). |
| 113 | 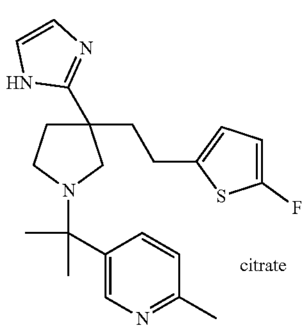 [SMILES: Cc1ccc(C(C)(C)N2CCC(CCc3ccc(F)s3)(c3ncc[nH]3)C2)cn1] | (R or S)-5-(2-(3-(2-(5-fluoro-thiophen-2-yl)ethyl)-3-(1H-imidazol-2-yl)pyrrolidin-1-yl)propan-2-yl)-2-methylpyridine citrate | 399 | ¹H NMR (300 MHz, MeOD): δ 8.43 (s, 1H), 7.79 (d, J = 8.3 Hz, 1H), 7.34-7.23 (m, 3H), 6.36-6.29 (m, 1H), 6.28-6.23 (m, 1H), 3.15 (m, 1H), 3.05-2.95 (m, 2H), 2.93-2.73 (m, 5H), 2.57-2.45 (m, 5H), 2.41-2.29 (m, 1H), 2.24-2.01 (m, 3H), 1.51 (d, J = 7.7 Hz, 6H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 114 | 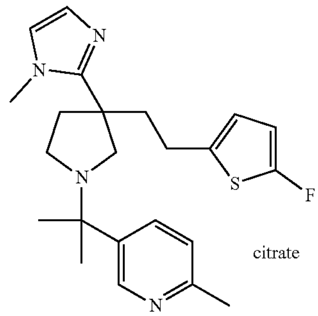 [SMILES: Cc1ccc(C(C)(C)N2CCC(CCc3ccc(F)s3)(c3nccn3C)C2)cn1] | (R or S)-5-(2-(3-(2-(5-fluoro-thiophen-2-yl)ethyl)-3-(1-methyl-1H-imidazol-2-yl)pyrrolidin-1-yl)propan-2-yl)-2-methylpyridine citrate | 413 | $^1$H NMR (300 MHz, MeOD): δ 8.55 (d, J = 1.9 Hz, 1H), 7.92 (dd, J = 8.3, 2.3 Hz, 1H), 7.32 (d, J = 8.3 Hz, 1H), 7.16 (d, J = 1.3 Hz, 1H), 7.04 (d, J = 1.2 Hz, 1H), 6.33-6.18 (m, 2H), 3.74 (s, 3H), 3.05 (m, 2H), 2.90-2.72 (m, 5H), 2.53 (s, 3H), 2.50-2.43 (m, 1H), 2.40-2.08 (m, 6H), 1.56 (s, 6H). |
| 115 | 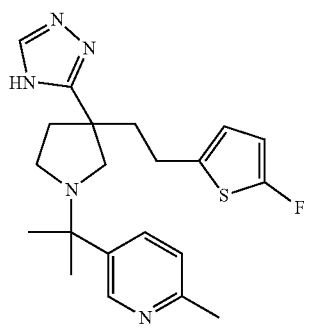 [SMILES: Cc1ccc(C(C)(C)N2CCC(CCc3ccc(F)s3)(c3nnc[nH]3)C2)cn1] | (R or S)-5-(2-(3-(2-(5-fluoro-thiophen-2-yl)ethyl)-3-(4H-1,2,4-triazol-3-yl)pyrrolidin-1-yl)propan-2-yl)-2-methylpyridine | 400 | $^1$HNMR (300 MHz, MeOD): δ 8.56 (s, 1H), 8.01 (s, 1H), 7.66 (t, J = 4.1 Hz, 1H), 7.12 (d, J = 8.1 Hz, 1H), 6.28-6.19 (m, 1H), 6.18 (d, J = 2.1 Hz, 1H), 3.10-3.00 (m, 1H), 2.99-2.85 (m, 1H), 2.80-2.68 (m, 1H), 2.66-2.55 (m, 2H), 2.53 (s, 3H), 2.50-2.42 (m, 1H), 2.40-2.25 (m, 2H), 2.15-2.05 (m, 1H), 1.98-1.88 (m, 1H), 1.45 (s, 3H), 1.45 (s, 3H). |
| 116 | 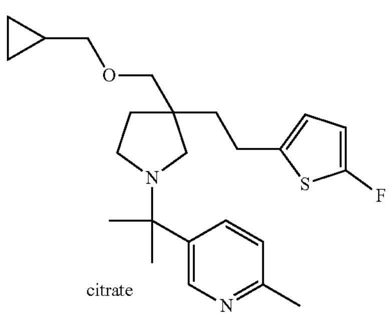 [SMILES: Cc1ccc(C(C)(C)N2CCC(CCc3ccc(F)s3)(COCC3CC3)C2)cn1] | (R or S)-5-(2-(3-((cyclopropylmethoxy)methyl)-3-(2-(5-fluorothiophen-2-yl)ethyl)pyrrolidin-1-yl)propan-2-yl)-2-methylpyridine citrate | 417 | $^1$H NMR (300 MHz, MeOD): δ 8.73 (s, 1H), 8.09 (dd, J = 8.4, 1.7 Hz, 1H), 7.45 (d, J = 8.0 Hz, 1H), 6.46-6.39 (m, 1H), 6.32-6.26 (m, 1H), 3.40-3.34 (m, 4H), 3.27-3.32 (m, 3H), 3.00 (d, J = 12.2 Hz, 1H), 2.82 (q, J = 15.6 Hz, 4H), 2.66 (t, J = 8.0 Hz, 2H), 2.57 (s, 3H), 2.06-1.99 (m, 1H), 1.93-1.83 (m, 8H), 1.79 (d, J = 8.3 Hz, 1H), 1.02-0.89 (m, 1H), 0.56-0.46 (m, 2H), 0.22-0.13 (m, 2H). |
| 117 | 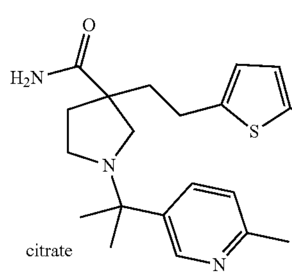 | (R or S)-3-(2-(5-fluoro-thiophen-2-yl)ethyl)-1-(2-(6-methylpyridin-3-yl)propan-2-yl)pyrrolidine-3-carboxamide citrate | 376 | $^1$H NMR (300 MHz, MeOD): δ 8.61 (s, 1H), 7.98 (d, J = 7.3 Hz, 1H), 7.36 (d, J = 8.5 Hz, 1H), 6.43-6.36 (m, 1H), 6.31-6.25 (m, 1H), 3.05-2.94 (m, 2H), 2.81 (q, J = 15.5 Hz, 4H), 2.68 (m, 1H), 2.62-2.57 (m, 1H), 2.55 (s, 3H), 2.42-2.28 (m, 1H), 2.16-2.00 (m, 2H), 1.97-1.72 (m, 3H), 1.64 (s, 6H). |

TABLE I-continued

Compounds with a pyrrolidine ring and a pyridine or pyridine-like molecule bonded to the pyrrolidine N-constituent

| Compound No. | Structure | Name | MS (ESI+): [M + H]$^+$ | H-NMR |
|---|---|---|---|---|
| 118 | (structure with citrate) | (R or S,E)-3-(2-(5-fluoro-thiophen-2-yl)ethyl)-1-(2-(6-methylpyridin-3-yl)propan-2-yl)pyrrolidine-3-carbaldehyde O-methyloxime citrate | 390 | $^1$H NMR (500 MHz, MeOD): δ 8.65 (d, J = 2.1 Hz, 1H), 8.03 (d, J = 8.3 Hz, 1H), 7.39 (d, J = 8.3 Hz, 1H), 7.30 (s, 1H), 6.40 (t, J = 3.6 Hz, 1H), 6.28 (dd, J = 3.9, 2.1 Hz, 1H), 3.78 (s, 3H), 3.36-3.32 (m, 1H), 3.24-3.15 (m, 1H), 3.05 (m, 1H), 2.93-2.88 (m, 1H), 2.81 (q, J = 15.5 Hz, 4H), 2.69-2.57 (m, 2H), 2.56 (s, 3H), 2.24-2.17 (m, 1H), 1.97-1.89 (m, 2H), 1.89-1.82 (m, 1H), 1.72 (s, 6H). |
| 119 | (structure) | (S or R)-((3-(2-(5-fluoro-thiophen-2-yl)ethyl)-1-(2-(6-methylpyridin-3-yl)propan-2-yl)pyrrolidin-3-yl)methyl)sulfamoyl amine | 441 | $^1$HNMR (300 MHz, MeOD): δ 8.51 (s, 1H), 7.87 (dd, J = 5.7, 2.4 Hz, 1H), 7.26 (d, J = 8.1 Hz, 1H), 6.42 (s, 1H), 6.28 (t, J = 3.0 Hz, 1H), 3.04 (s, 2H), 2.78-2.51 (m, 5H), 2.50 (s, 3H), 2.34 (m, 1H), 1.80-1.71 (m, 3H), 1.68-1.51 (m, 1H), 1.30 (s, 6H) |
| 120 | (structure with citrate) | (S or R)-((3-(2-(5-fluoro-thiophen-2-yl)ethyl)-1-(2-(6-methylpyridin-3-yl)propan-2-yl)pyrrolidin-3-yl)(pyridin-2-yl)methyl)sulfamoyl amine | 518 | $^1$H NMR (300 MHz, MeOD): δ 8.63 (s, 1H), 8.59-8.51 (m, 1H), 7.99 (d, J = 8.5 Hz, 1H), 7.78 (t, J = 7.6 Hz, 1H), 7.48 (dd, J = 22.1, 7.7 Hz, 1H), 7.41-7.26 (m, 2H), 6.40-6.34 (m, 1H), 6.28 (t, J = 3.1 Hz, 1H), 4.57 (d, J = 15.3 Hz, 1H), 3.52 (d, J = 10.4 Hz, 1H), 2.96-2.75 (m, 7H), 2.56 (s, 3H), 2.33-2.28 (m, 1H), 1.85-1.75 (m, 1H), 1.71 (d, J = 4.1 Hz, 6H), 1.58-1.43 (m, 2H). |
| 121 | (structure with citrate) | (S or R)-((3-(2-(5-fluoro-thiophen-2-yl)ethyl)-1-(2-(6-methylpyridin-3-yl)propan-2-yl)pyrrolidin-3-yl)methyl)sulfamoyl dimethyl amine | 469 | $^1$H NMR (300 MHz, MeOD): δ 8.64 (s, 1H), 8.01 (d, J = 7.5 Hz, 1H), 7.38 (d, J = 8.1 Hz, 1H), 6.43 (s, 1H), 6.29 (s, 1H), 3.11-3.00 (m, 5H), 2.91-2.61 (m, 14H), 2.55 (s, 3H), 1.95-1.74 (m, 3H), 1.61 (s, 6H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 122 | 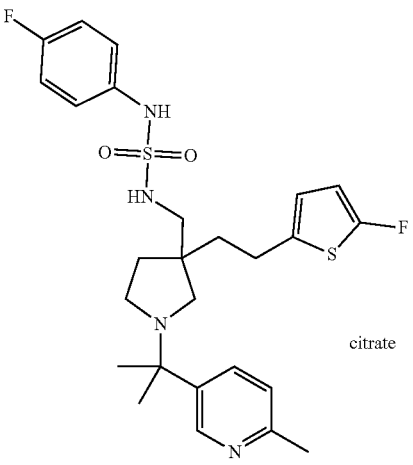 [SMILES: Cc1ccc(C(C)(C)N2CCC(CCc3ccc(F)s3)(CNS(=O)(=O)Nc3ccc(F)cc3)C2)cn1] | (R or S)-((3-(2-(5-fluoro-thiophen-2-yl)ethyl)-1-(2-(6-methylpyridin-3-yl)propan-2-yl)pyrrolidin-3-yl)methyl)sulfamoyl 4-fluorophenylamine citrate | 535 | ¹H NMR (300 MHz, MeOD): δ 8.65 (d, J = 2.3 Hz, 1H), 8.04 (dd, J = 8.7, 2.3 Hz, 1H), 7.40 (d, J = 8.2 Hz, 1H), 7.22 (dd, J = 8.9, 4.7 Hz, 2H), 7.04 (t, J = 8.5 Hz, 2H), 6.36 (d, J = 3.6 Hz, 1H), 6.27 (dd, J = 3.9, 2.1 Hz, 1H), 3.18 (t, J = 7.0 Hz, 2H), 3.09 (d, J = 11.6 Hz, 1H), 2.98 (s, 2H), 2.92-2.69 (m, 5H), 2.63-2.49 (m, 5H), 1.89-1.79 (m, 2H), 1.75 (s, 6H), 1.71-1.64 (m, 2H). |
| 123 | 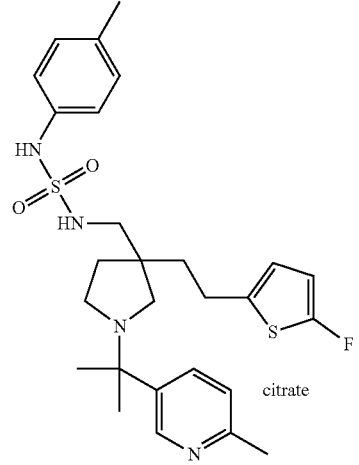 [SMILES: Cc1ccc(NS(=O)(=O)NCC2(CCc3ccc(F)s3)CCN(C(C)(C)c3ccc(C)nc3)C2)cc1] | (R or S)-((3-(2-(5-fluoro-thiophen-2-yl)ethyl)-1-(2-(6-methylpyridin-3-yl)propan-2-yl)pyrrolidin-3-yl)methyl)sulfamoyl 4-methylphenyl amine | | ¹H NMR (300 MHz, MeOD): δ 8.58 (s, 1H), 7.93 (d, J = 8.1 Hz, 1H), 7.35 (d, J = 7.9 Hz, 1H), 7.10 (s, 4H), 6.33 (s, 1H), 6.26 (s, 1H), 2.95 (s, 3H), 2.89-2.69 (m, 5H), 2.62-2.49 (m, 6H), 2.26 (s, 3H), 1.79-1.69 (m, 5H), 1.60 (s, 6H). |
| 124 | 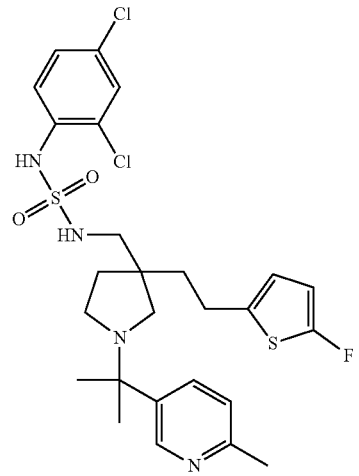<br>Exact Mass: 584.12<br>tPSA: 73.8<br>CLogP: 6.67 | (R or S)-((3-(2-(5-fluoro-thiophen-2-yl)ethyl)-1-(2-(6-methylpyridin-3-yl)propan-2-yl)pyrrolidin-3-yl)methyl)sulfamoyl 2,4-dichloro phenyl amine | 531 | ¹H NMR (300 MHz, MeOD): δ 8.60 (s, 1H), 7.96 (d, J = 8.5 Hz, 1H), 7.61 (d, J = 8.8 Hz, 1H), 7.49 (d, J = 2.4 Hz, 1H), 7.33 (dd, J = 19.1, 8.4 Hz, 2H), 6.36 (s, 1H), 6.31-6.24 (m, 1H), 3.05-2.98 (m, 3H), 2.89-2.73 (m, 6H), 2.66-2.57 (m, 3H), 2.55 (s, 3H), 1.83-1.70 (m, 4H), 1.64 (s, 6H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 125 | 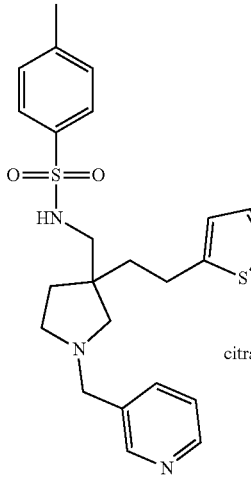 | (S or R)-4-methyl-N-((1-(pyridin-3-ylmethyl)-3-(2-(thiophen-2-yl)ethyl)pyrrolidin-3-yl)methyl)benzenesulfonamide citrate | 456 | ¹H NMR (300 MHz, MeOD): δ 8.63 (s, 1H), 8.57 (d, J = 4.9 Hz, 1H), 7.99 (d, J = 7.9 Hz, 1H), 7.74 (d, J = 8.0 Hz, 2H), 7.52-7.48 (m, 1H), 7.38 (d, J = 7.9 Hz, 2H), 7.19-7.11 (m, 1H), 6.88 (dd, J = 5.1, 3.5 Hz, 1H), 6.81 (d, J = 3.4 Hz, 1H), 4.19 (s, 2H), 3.23-3.11 (m, 3H), 2.91 (d, J = 7.0 Hz, 2H), 2.88-2.69 (m, 7H), 2.42 (s, 3H), 1.99-1.81 (m, 4H). |
| 126 | 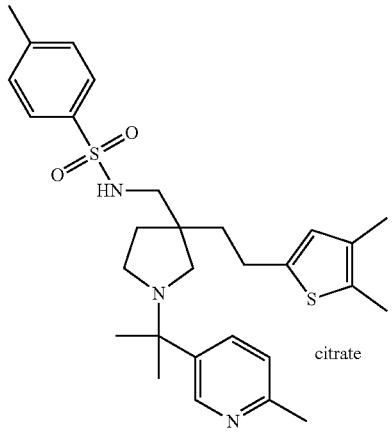 [SMILES: Cc1ccc(S(=O)(=O)NCC2(CCc3cc(C)c(C)s3)CCN(C(C)(C)c3ccc(C)nc3)C2)cc1] | (S or R)-N-((3-(2-(4,5-dimethylthiophen-2-yl)ethyl)-1-(2-(6-methylpyridin-3-yl)propan-2-yl)pyrrolidin-3-yl)methyl)-4-methyl benzenesulfonamide citrate | 526 | ¹H NMR (300 MHz, MeOD): δ 8.65 (s, 1H), 8.02 (d, J = 8.3 Hz, 1H), 7.71 (d, J = 8.0 Hz, 2H), 7.39 (t, J = 6.9 Hz, 3H), 6.41 (s, 1H), 3.22-3.15 (m, 2H), 3.10-3.06 (m, 1H), 2.89-2.71 (m, 8H), 2.62-2.53 (m, 5H), 2.43 (s, 3H), 2.23 (s, 3H), 2.02 (s, 3H), 1.87-1.83 (m, 1H), 1.77-1.69 (m, 8H). |
| 127 | 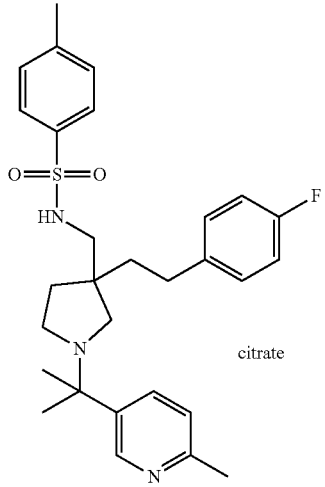 [SMILES: Cc1ccc(S(=O)(=O)NCC2(CCc3ccc(F)cc3)CCN(C(C)(C)c3ccc(C)nc3)C2)cc1] | (S or R)-N-((3-(4-fluoro-phenethyl)-1-(2-(6-methylpyridin-3-yl)propan-2-yl)pyrrolidin-3-yl)methyl)-4-methylbenzene-sulfonamide citrate | 510 | ¹H NMR (300 MHz, MeOD): δ 8.65 (s, 1H), 8.02 (d, J = 8.1 Hz, 1H), 7.73 (d, J = 8.0 Hz, 2H), 7.39 (d, J = 8.0 Hz, 3H), 7.20-7.11 (m, 2H), 6.95 (t, J = 8.7 Hz, 2H), 3.15 (t, J = 5.8 Hz, 2H), 3.05 (d, J = 11.0 Hz, 1H), 2.87-2.71 (m, 7H), 2.55 (s, 3H), 2.51-2.44 (m, 2H), 2.43 (s, 3H), 1.90-1.79 (m, 2H), 1.74 (s, 6H), 1.70-1.59 (m, 2H). |

TABLE I-continued

Compounds with a pyrrolidine ring and a pyridine or pyridine-like molecule bonded to the pyrrolidine N-constituent

| Compound No. | Structure | Name | MS (ESI+): [M + H]⁺ | H-NMR |
|---|---|---|---|---|
| 128 | 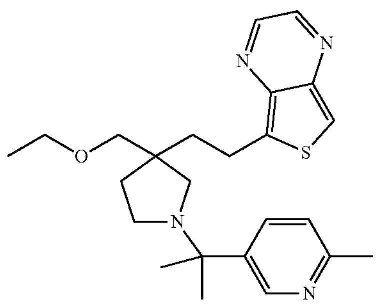 [SMILES: CCOCC1(CCc2scc3nccnc23)CCN(C(C)(C)c2ccc(C)nc2)C1] | (R or S)-5-(2-(3-(ethoxymethyl)-1-(2-(6-methylpyridin-3-yl)propan-2-yl)pyrrolidin-3-yl)ethyl)thieno[3,4-b]pyrazine | | |
| 129 | 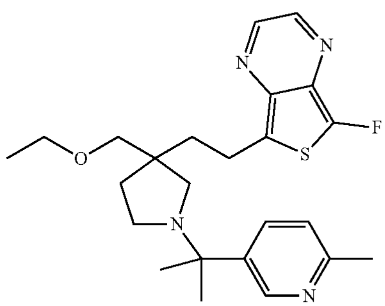 [SMILES: CCOCC1(CCc2sc(F)c3nccnc23)CCN(C(C)(C)c2ccc(C)nc2)C1] | (R or S)-5-(2-(3-(ethoxymethyl)-1-(2-(6-methylpyridin-3-yl)propan-2-yl)pyrrolidin-3-yl)ethyl)-7-fluoro-thieno[3,4-b]pyrazine | | |
| 130 | 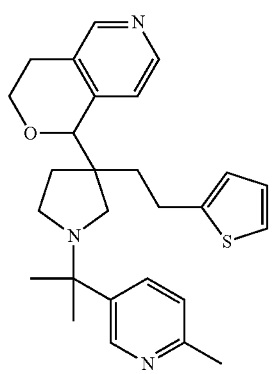 [SMILES: Cc1ccc(C(C)(C)N2CCC(CCc3cccs3)(C3OCCc4cnccc43)C2)cn1] | 1-((R or S)-1-(2-(6-methylpyridin-3-yl)propan-2-yl)-3-(2-(thiophen-2-yl)ethyl)pyrrolidin-3-yl)-3,4-dihydro-1H-pyrano[4,3-c]pyridine | | |
| 131 | 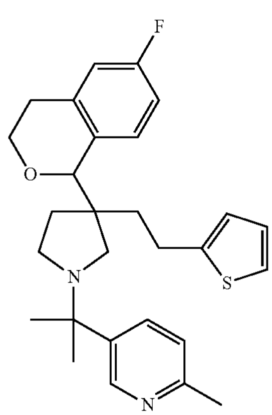 [SMILES: Cc1ccc(C(C)(C)N2CCC(CCc3cccs3)(C3OCCc4cc(F)ccc43)C2)cn1] | 5-(2-((3R or S)-3-(6-fluoroisochroman-1-yl)-3-(2-(thiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 132 | 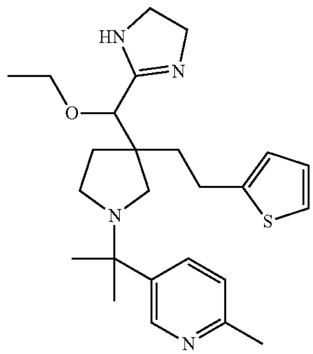 [SMILES: CCOC(C1=NCCN1)C1(CCc2cccs2)CCN(C(C)(C)c2ccc(C)nc2)C1] | 5-(2-((3R or S)-3-((4,5-dihydro-1H-imidazol-2-yl)(ethoxy)methyl)-3-(2-(thiophen-2-yl)ethyl)pyrrolidin-1-yl)propan-2-yl)-2-methylpyridine | | |
| 133 | 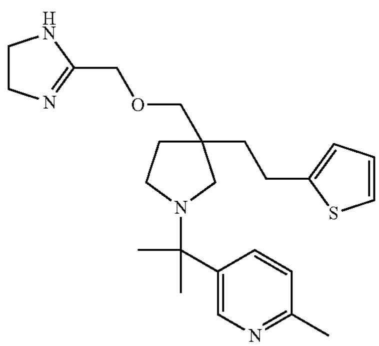 [SMILES: Cc1ccc(C(C)(C)N2CCC(CCc3cccs3)(COCC3=NCCN3)C2)cn1] | (R or S)-5-(2-(3-(((4,5-dihydro-1H-imidazol-2-yl)methoxy)methyl)-3-(2-(thiophen-2-yl)ethyl)pyrrolidin-1-yl)propan-2-yl)-2-methylpyridine | | |
| 134 | 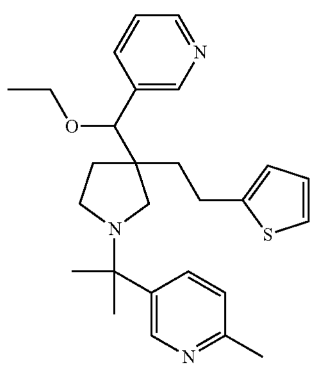 | 5-(2-((S or R)-3-((S or R)-ethoxy(pyridin-3-yl)methyl)-3-(2-(thiophen-2-yl)ethyl)pyrrolidin-1-yl)propan-2-yl)-2-methylpyridine | | |
| 135 | 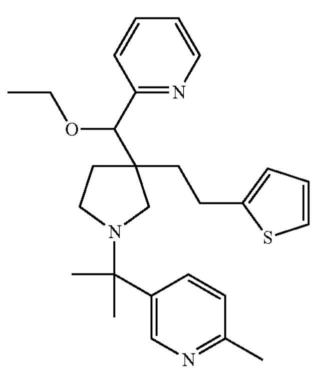 | 5-(2-((S or R)-3-((S or R)-ethoxy(pyridin-2-yl)methyl)-3-(2-(thiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 136 | 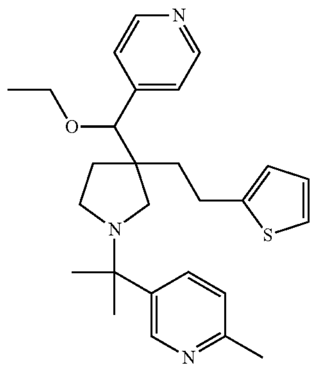 [SMILES: CCOC(c1ccncc1)C1(CCc2cccs2)CCN(C(C)(C)c2ccc(C)nc2)C1] | 5-(2-((3R or S)-3-(ethoxy(pyridin-4-yl)methyl)-3-(2-(thiophen-2-yl)ethyl)pyrrolidin-1-yl)propan-2-yl)-2-methylpyridine | | |
| 137 | 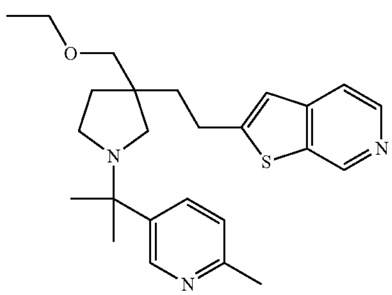 [SMILES: CCOCC1(CCc2cc3ccncc3s2)CCN(C(C)(C)c2ccc(C)nc2)C1] | (R or S)-2-(2-(3-(ethoxymethyl)-1-(2-(6-methylpyridin-3-yl)propan-2-yl)pyrrolidin-3-yl)ethyl)thieno[2,3-c]pyridine | | |
| 138 | 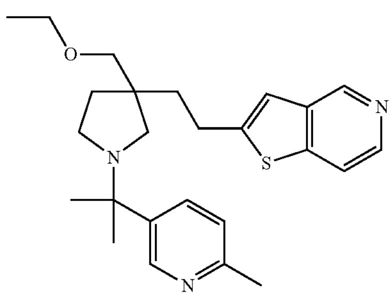 [SMILES: CCOCC1(CCc2cc3cnccc3s2)CCN(C(C)(C)c2ccc(C)nc2)C1] | (R or S)-2-(2-(3-(ethoxymethyl)-1-(2-(6-methylpyridin-3-yl)propan-2-yl)pyrrolidin-3-yl)ethyl)thieno[3,2-c]pyridine | | |
| 139 | 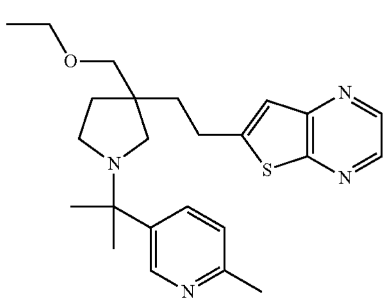 [SMILES: CCOCC1(CCc2cc3nccnc3s2)CCN(C(C)(C)c2ccc(C)nc2)C1] | (R or S)-6-(2-(3-(ethoxymethyl)-1-(2-(6-methylpyridin-3-yl)propan-2-yl)pyrrolidin-3-yl)ethyl)thieno[2,3-b]pyrazine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 140 | 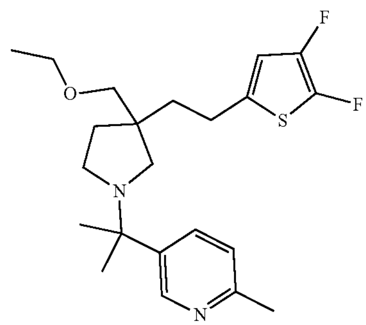 [SMILES: CCOCC1(CCc2cc(F)c(F)s2)CCN(C(C)(C)c2ccc(C)nc2)C1] | (R or S)-5-(2-(3-(2-(4,5-difluorothiophen-2-yl)ethyl)-3-(ethoxymethyl)pyrrolidin-1-yl)propan-2-yl)-2-methylpyridine | | |
| 141 | 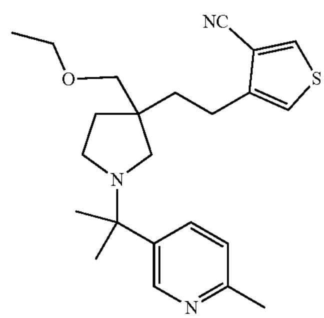 [SMILES: CCOCC1(CCc2cscc2C#N)CCN(C(C)(C)c2ccc(C)nc2)C1] | (R or S)-4-(2-(3-(ethoxymethyl)-1-(2-(6-methylpyridin-3-yl)propan-2-yl)pyrrolidin-3-yl)ethyl)thiophene-3-carbonitrile | | |
| 142 | 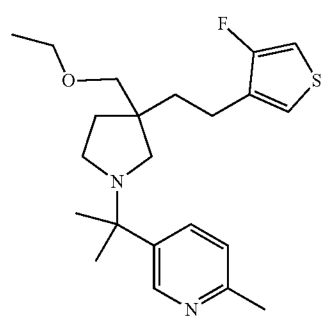 [SMILES: CCOCC1(CCc2cscc2F)CCN(C(C)(C)c2ccc(C)nc2)C1] | (R or S)-5-(2-(3-(ethoxymethyl)-3-(2-(4-fluoro-thiophen-3-yl)ethyl)pyrrolidin-1-yl)propan-2-yl)-2-methylpyridine | | |
| 143 | 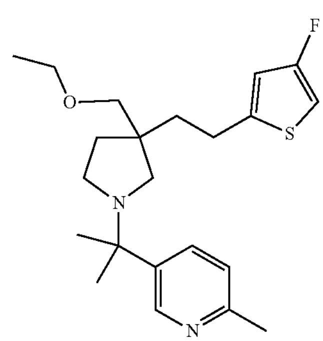 [SMILES: CCOCC1(CCc2cc(F)cs2)CCN(C(C)(C)c2ccc(C)nc2)C1] | (R or S)-5-(2-(3-(ethoxymethyl)-3-(2-(4-fluoro-thiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 144 | 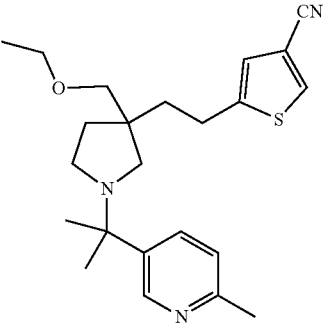 [SMILES: CCOCC1(CCc2cc(C#N)cs2)CCN(C(C)(C)c2ccc(C)nc2)C1] | (R or S)-5-(2-(3-(ethoxymethyl)-1-(2-(6-methylpyridin-3-yl)propan-2-yl)pyrrolidin-3-yl)ethyl)thiophene-3-carbonitrile | | |
| 145 | 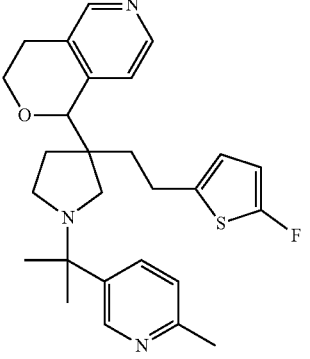 [SMILES: Cc1ccc(C(C)(C)N2CCC(CCc3ccc(F)s3)(C3OCCc4cnccc43)C2)cn1] | 1-((R or S)-3-(2-(5-fluoro-thiophen-2-yl)ethyl)-1-(2-(6-methylpyridin-3-yl)propan-2-yl)pyr-rolidin-3-yl)-3,4-dihydro-1H-pyrano[4,3-c]pyridine | | |
| 146 | 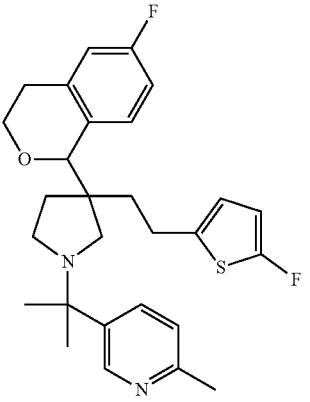 [SMILES: Cc1ccc(C(C)(C)N2CCC(CCc3ccc(F)s3)(C3OCCc4cc(F)ccc43)C2)cn1] | 5-(2-((3R or S)-3-(6-fluoroiso-chroman-1-yl)-3-(2-(5-fluorothiophen-2-yl)ethyl)pyrrolidin-1-yl)propan-2-yl)-2-methylpyridine | | |
| 147 | 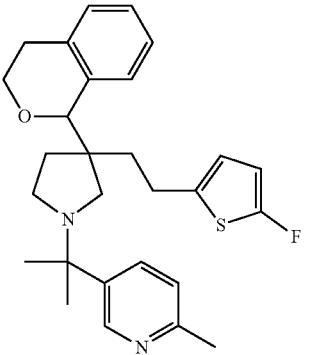 [SMILES: Cc1ccc(C(C)(C)N2CCC(CCc3ccc(F)s3)(C3OCCc4ccccc43)C2)cn1] | 5-(2-((3R or S)-3-(2-(5-fluoro-thiophen-2-yl)ethyl)-3-(isochroman-1-yl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 148 | 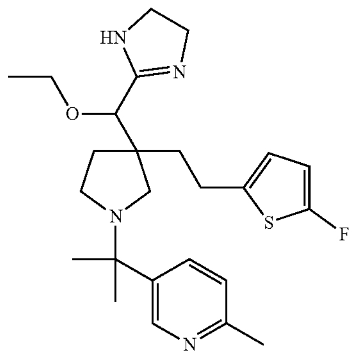 [SMILES: CCOC(C1=NCCN1)C1(CCc2ccc(F)s2)CCN(C(C)(C)c2ccc(C)nc2)C1] | 5-(2-((3R or S)-3-((4,5-dihydro-1H-imidazol-2-yl)(ethoxy)methyl)-3-(2-(5-fluorothiophen-2-yl)ethyl)pyrrolidin-1-yl)propan-2-yl)-2-methylpyridine | | |
| 149 | 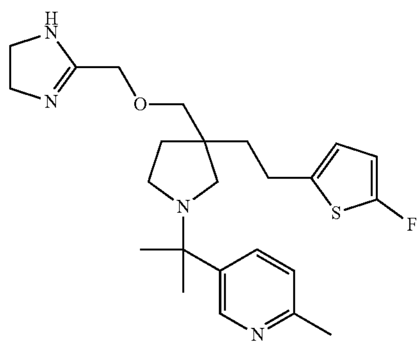 [SMILES: Cc1ccc(C(C)(C)N2CCC(CCc3ccc(F)s3)(COCC3=NCCN3)C2)cn1] | (R or S)-5-(2-(3-(((4,5-dihydro-1H-imidazol-2-yl)methoxy)methyl)-3-(2-(5-fluorothiophen-2-yl)ethyl)pyrrolidin-1-yl)propan-2-yl)-2-methylpyridine | | |
| 150 | 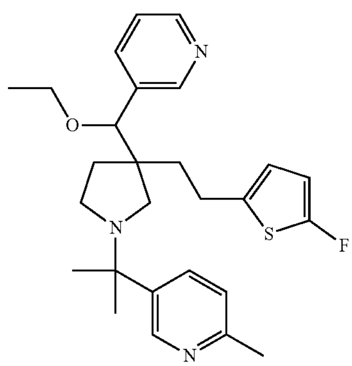 [SMILES: CCOC(c1cccnc1)C1(CCc2ccc(F)s2)CCN(C(C)(C)c2ccc(C)nc2)C1] | 5-(2-((S or R)-3-((R or S)-ethoxy(pyridin-3-yl)methyl)-3-(2-(5-fluorothiophen-2-yl)ethyl)pyrrolidin-1-yl)propan-2-yl)-2-methylpyridine | | |
| 151 | 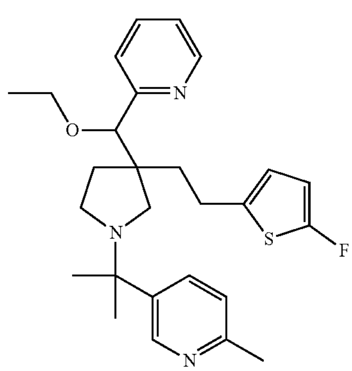 [SMILES: CCOC(c1ccccn1)C1(CCc2ccc(F)s2)CCN(C(C)(C)c2ccc(C)nc2)C1] | 5-(2-((S or R)-3-((R or S)-ethoxy(pyridin-2-yl)methyl)-3-(2-(5-fluorothiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 152 | 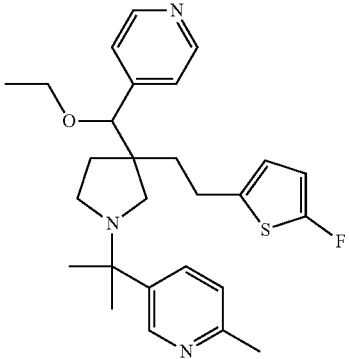 [SMILES: CCOC(c1ccncc1)C1(CCc2ccc(F)s2)CCN(C(C)(C)c2ccc(C)nc2)C1] | 5-(2-((S or R)-3-((R or S)-ethoxy(pyridin-4-yl)methyl)-3-(2-(5-fluorothiophen-2-yl)ethyl)pyrrolidin-1-yl)propan-2-yl)-2-methylpyridine | | |
| 153 | 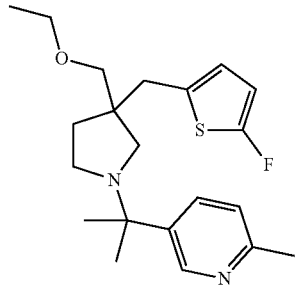 [SMILES: CCOCC1(Cc2ccc(F)s2)CCN(C(C)(C)c2ccc(C)nc2)C1] | (S or R)-5-(2-(3-(ethoxymethyl)-3-((5-fluorothiophen-2-yl)methyl)pyrrolidin-1-yl)propan-2-yl)-2-methylpyridine | | |
| 154 | 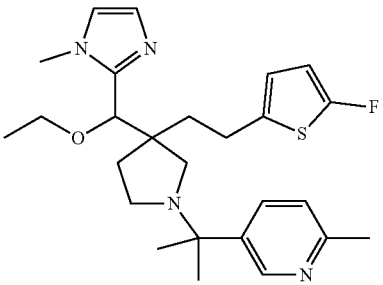 [SMILES: CCOC(c1nccn1C)C1(CCc2ccc(F)s2)CCN(C(C)(C)c2ccc(C)nc2)C1] | 5-(2-((3R or S)-3-(ethoxy(1-methyl-1H-imidazol-2-yl)methyl)-3-(2-(5-fluorothiophen-2-yl)ethyl)pyrrolidin-1-yl)propan-2-yl)-2-methylpyridine | | |
| 155 | 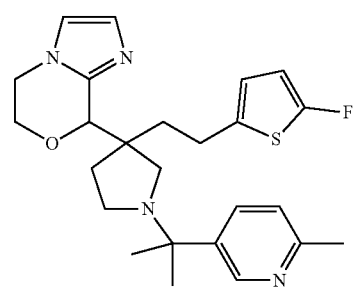 [SMILES: Cc1ccc(C(C)(C)N2CCC(CCc3ccc(F)s3)(C3OCCn4ccnc43)C2)cn1] | 8-((R or S)-3-(2-(5-fluoro-thiophen-2-yl)ethyl)-1-(2-(6-methylpyridin-3-yl)propan-2-yl)pyrrolidin-3-yl)-5,6-dihydro-8H-imidazo[2,1-c][1,4]oxazine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 156 | 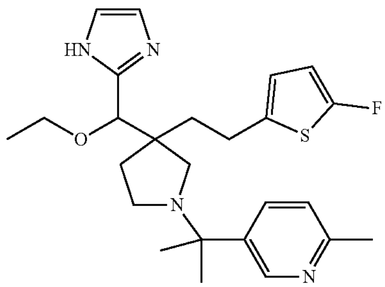 [SMILES: CCOC(c1ncc[nH]1)C1(CCc2ccc(F)s2)CCN(C(C)(C)c2ccc(C)nc2)C1] | 5-(2-((3R or S)-3-(ethoxy(1H-imidazol-2-yl)methyl)-3-(2-(5-fluoro-thiophen-2-yl)ethyl)pyrrolidin-1-yl)propan-2-yl)-2-methylpyridine | | |
| 157 | 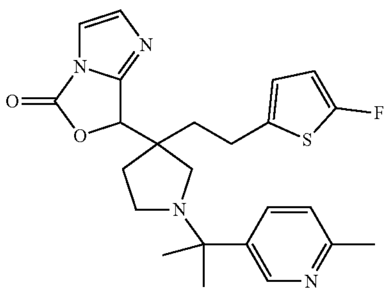 [SMILES: Cc1ccc(C(C)(C)N2CCC(CCc3ccc(F)s3)(C3OC(=O)n4ccnc43)C2)cn1] | 7-((R or S)-3-(2-(5-fluoro-thiophen-2-yl)ethyl)-1-(2-(6-methylpyridin-3-yl)propan-2-yl)pyrrolidin-3-yl)-5H,7H-imidazo[1,2-c]oxazol-5-one | | |
| 158 | 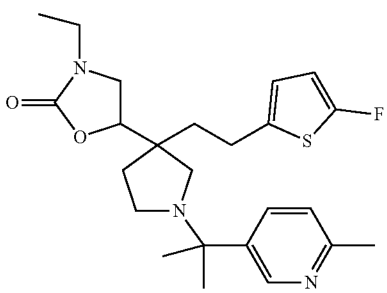 [SMILES: CCN1CC(C2(CCc3ccc(F)s3)CCN(C(C)(C)c3ccc(C)nc3)C2)OC1=O] | 3-ethyl-5-((R or S)-3-(2-(5-fluoro-thiophen-2-yl)ethyl)-1-(2-(6-methylpyridin-3-yl)propan-2-yl)pyrrolidin-3-yl)oxazolidin-2-one | | |
| 159 | 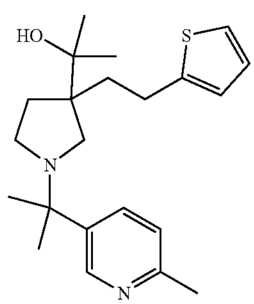 [SMILES: Cc1ccc(C(C)(C)N2CCC(CCc3cccs3)(C(C)(C)O)C2)cn1] | (R or S)-2-(1-(2-(6-methylpyridin-3-yl)propan-2-yl)-3-(2-(thiophen-2-yl)ethyl)pyrrolidin-3-yl)propan-2-ol | | |
| 160 | 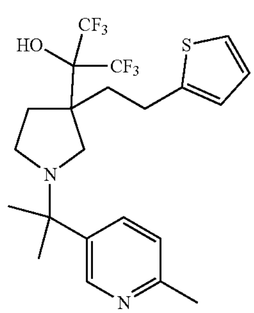 [SMILES: Cc1ccc(C(C)(C)N2CCC(CCc3cccs3)(C(O)(C(F)(F)F)C(F)(F)F)C2)cn1] | (R or S)-1,1,1,3,3,3-hexa-fluoro-2-(1-(2-(6-methylpyridin-3-yl)propan-2-yl)-3-(2-(thiophen-2-yl)ethyl)pyrrolidin-3-yl)propan-2-ol | | |

TABLE I-continued

Compounds with a pyrrolidine ring and a pyridine or pyridine-like molecule bonded to the pyrrolidine N-constituent

| Compound No. | Structure | Name | MS (ESI+): [M + H]⁺ | H-NMR |
|---|---|---|---|---|
| 161 | 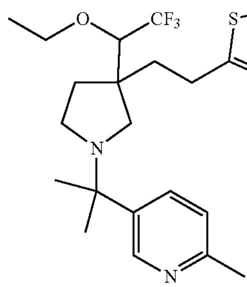 | (R or S)-5-(2-(3-(1-ethoxy-2,2,2-trifluoroethyl)-3-(2-(thiophen-2-yl)ethyl)pyrrolidin-1-yl)propan-2-yl)-2-methylpyridine | | |
| 162 | 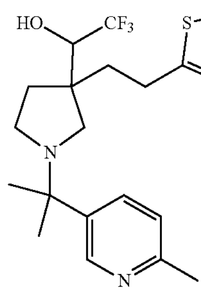 | (R or S)-2,2,2-trifluoro-1-(1-(2-(6-methylpyridin-3-yl)propan-2-yl)-3-(2-(thiophen-2-yl)ethyl)pyrrolidin-3-yl)ethan-1-ol | | |
| 163 | 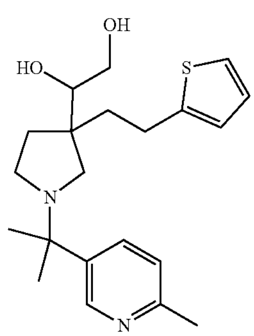 [SMILES: Cc1ccc(C(C)(C)N2CCC(CCc3cccs3)(C(O)CO)C2)cn1] | (R or S)-1-(1-(2-(6-methylpyridin-3-yl)propan-2-yl)-3-(2-(thiophen-2-yl)ethyl)pyrrolidin-3-yl)ethane-1,2-diol | | |
| 164 | 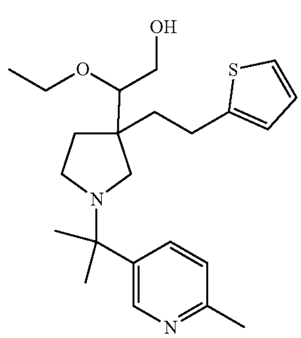 [SMILES: CCOC(CO)C1(CCc2cccs2)CCN(C(C)(C)c2ccc(C)nc2)C1] | (R or S)-2-ethoxy-2-(1-(2-(6-methylpyridin-3-yl)propan-2-yl)-3-(2-(thiophen-2-yl)ethyl)pyrrolidin-3-yl)ethan-1-ol | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 165 | 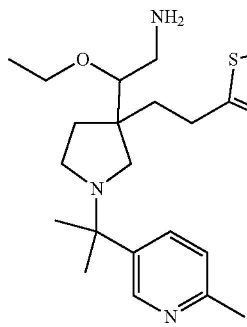 | (R or S)-2-ethoxy-2-(1-(2-(6-methylpyridin-3-yl)propan-2-yl)-3-(2-(thiophen-2-yl)ethyl)pyrrolidin-3-yl)ethan-1-amine | | |
| 166 | 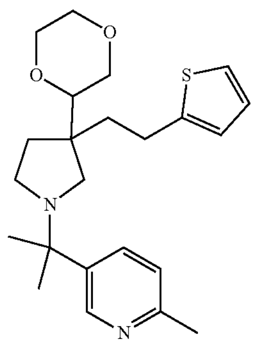 [SMILES: Cc1ccc(C(C)(C)N2CCC(CCc3cccs3)(C3COCCO3)C2)cn1] | (R or S)-5-(2-(3-(1,4-dioxan-2-yl)-3-(2-(thiophen-2-yl)ethyl)pyrrolidin-1-yl)propan-2-yl)-2-methylpyridine | | |
| 167 | 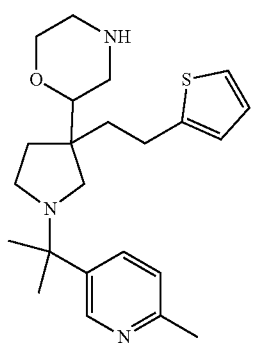 [SMILES: Cc1ccc(C(C)(C)N2CCC(CCc3cccs3)(C3CNCCO3)C2)cn1] | (R or S)-2-(1-(2-(6-methylpyridin-3-yl)propan-2-yl)-3-(2-(thiophen-2-yl)ethyl)pyrrolidin-3-yl)morpholine | | |
| 168 | 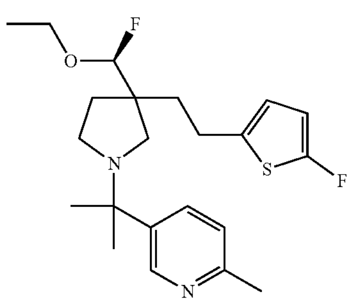 [SMILES: CCO[C@@H](F)C1(CCc2ccc(F)s2)CCN(C(C)(C)c2ccc(C)nc2)C1] | 5-(2-((R or S)-3-((S)-ethoxyfluoromethyl)-3-(2-(5-fluorothiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 169 | 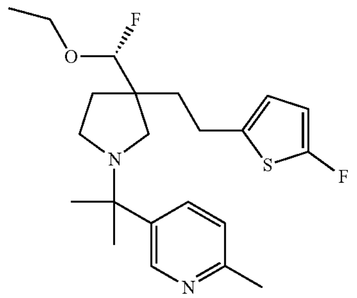 [SMILES: CCO[C@H](F)C1(CCc2ccc(F)s2)CCN(C(C)(C)c2ccc(C)nc2)C1] | 5-(2-((R or S)-3-((R)-ethoxy-fluoromethyl)-3-(2-(5-fluorothiophen-2-yl)ethyl)pyrrolidin-1-yl)propan-2-yl)-2-methylpyridine | | |
| 170 | 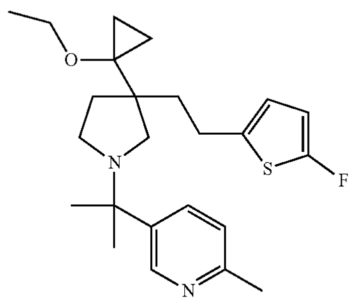 [SMILES: CCOC1(C2(CCc3ccc(F)s3)CCN(C(C)(C)c3ccc(C)nc3)C2)CC1] | (R or S)-5-(2-(3-(1-ethoxy-cyclopropyl)-3-(2-(5-fluorothiophen-2-yl)ethyl)pyrrolidin-1-yl)propan-2-yl)-2-methylpyridine | | |
| 171 | 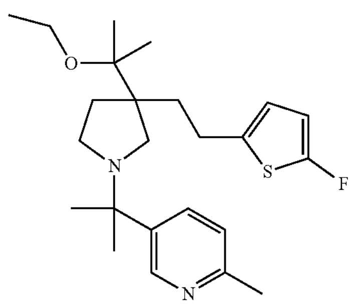 [SMILES: CCOC(C)(C)C1(CCc2ccc(F)s2)CCN(C(C)(C)c2ccc(C)nc2)C1] | (R or S)-5-(2-(3-(2-ethoxy-propan-2-yl)-3-(2-(5-fluorothiophen-2-yl)ethyl)pyrrolidin-1-yl)propan-2-yl)-2-methylpyridine | | |
| 172 | 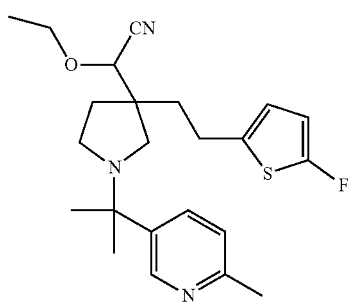 [SMILES: CCOC(C#N)C1(CCc2ccc(F)s2)CCN(C(C)(C)c2ccc(C)nc2)C1] | 2-ethoxy-2-((R or S)-3-(2-(5-fluoro-thiophen-2-yl)ethyl)-1-(2-(6-methylpyridin-3-yl)propan-2-yl)pyrrolidin-3-yl)acetonitrile | | |
| 173 | 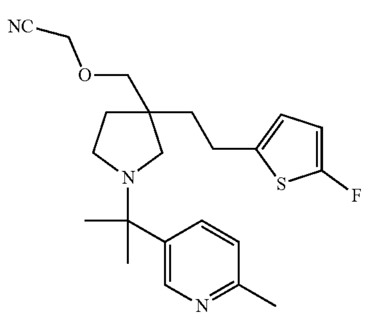 [SMILES: Cc1ccc(C(C)(C)N2CCC(CCc3ccc(F)s3)(COCC#N)C2)cn1] | (R or S)-2-((3-(2-(5-fluoro-thiophen-2-yl)ethyl)-1-(2-(6-methylpyridin-3-yl)propan-2-yl)pyrrolidin-3-yl)methoxy)acetonitrile | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 174 | 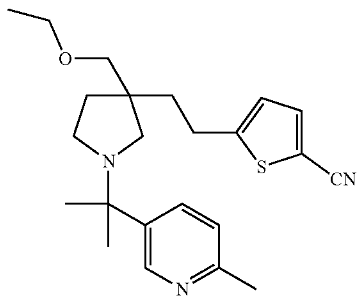 [SMILES: CCOCC1(CCc2ccc(C#N)s2)CCN(C(C)(C)c2ccc(C)nc2)C1] | (R or S)-5-(2-(3-(ethoxymethyl)-1-(2-(6-methylpyridin-3-yl)propan-2-yl)pyrrolidin-3-yl)ethyl)thiophene-2-carbonitrile | | |
| 175 | 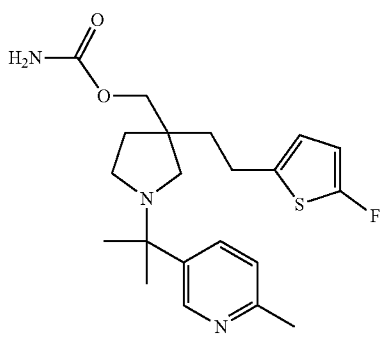 [SMILES: Cc1ccc(C(C)(C)N2CCC(CCc3ccc(F)s3)(COC(N)=O)C2)cn1] | (R or S)-(3-(2-(5-fluorothiophen-2-yl)ethyl)-1-(2-(6-methylpyridin-3-yl)propan-2-yl)pyrrolidin-3-yl)methyl carbamate | | |
| 176 | 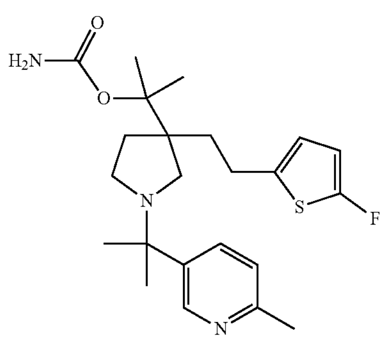 [SMILES: Cc1ccc(C(C)(C)N2CCC(CCc3ccc(F)s3)(C(C)(C)OC(N)=O)C2)cn1] | (R or S)-2-(3-(2-(5-fluorothiophen-2-yl)ethyl)-1-(2-(6-methylpyridin-3-yl)propan-2-yl)pyrrolidin-3-yl)propan-2-yl carbamate | | |
| 177 | 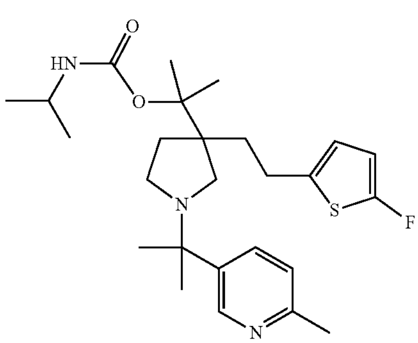 [SMILES: Cc1ccc(C(C)(C)N2CCC(CCc3ccc(F)s3)(C(C)(C)OC(=O)NC(C)C)C2)cn1] | (R or S)-2-(3-(2-(5-fluorothiophen-2-yl)ethyl)-1-(2-(6-methylpyridin-3-yl)propan-2-yl)pyrrolidin-3-yl)propan-2-yl isopropylcarbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 178 | 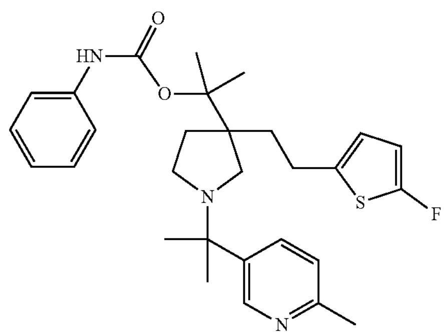 [SMILES: Cc1ccc(C(C)(C)N2CCC(CCc3ccc(F)s3)(C(C)(C)OC(=O)Nc3ccccc3)C2)cn1] | (R or S)-2-(3-(2-(5-fluoro-thiophen-2-yl)ethyl)-1-(2-(6-methylpyridin-3-yl)propan-2-yl)pyrrolidin-3-yl)propan-2-yl phenylcarbamate | | |
| 179 | 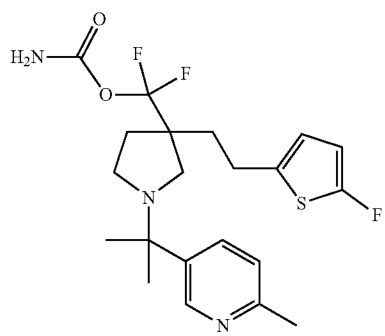 [SMILES: Cc1ccc(C(C)(C)N2CCC(CCc3ccc(F)s3)(C(F)(F)OC(N)=O)C2)cn1] | (R or S)-difluoro(3-(2-(5-fluorothiophen-2-yl)ethyl)-1-(2-(6-methylpyridin-3-yl)propan-2-yl)pyrrolidin-3-yl)methyl carbamate | | |
| 180 | 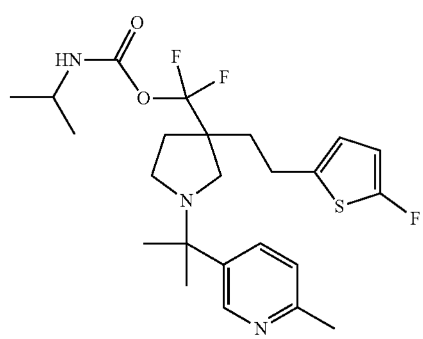 | (R or S)-difluoro(3-(2-(5-fluorothiophen-2-yl)ethyl)-1-(2-(6-methylpyridin-3-yl)propan-2-yl)pyrrolidin-3-yl)methyl isopropylcarbamate | | |
| 181 | 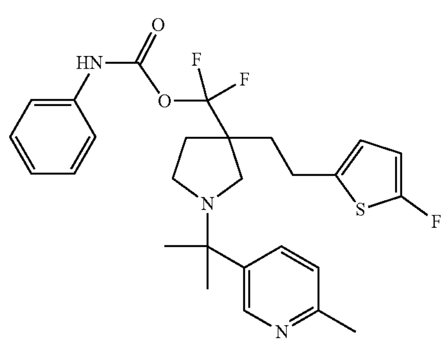 [SMILES: Cc1ccc(C(C)(C)N2CCC(CCc3ccc(F)s3)(C(F)(F)OC(=O)Nc3ccccc3)C2)cn1] | (R or S)-difluoro(3-(2-(5-fluorothiophen-2-yl)ethyl)-1-(2-(6-methylpyridin-3-yl)propan-2-yl)pyrrolidin-3-yl)methyl phenylcarbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 182 | 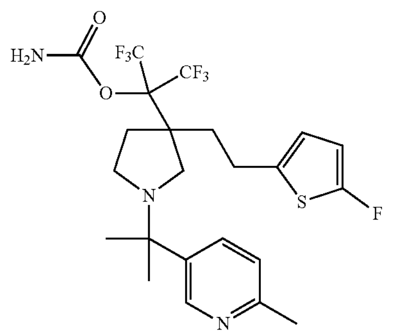 [SMILES: Cc1ccc(C(C)(C)N2CCC(CCc3ccc(F)s3)(C(OC(N)=O)(C(F)(F)F)C(F)(F)F)C2)cn1] | (R or S)-1,1,1,3,3,3-hexafluoro-2-(3-(2-(5-fluorothiophen-2-yl)ethyl)-1-(2-(6-methylpyridin-3-yl)propan-2-yl)pyrrolidin-3-yl)propan-2-yl carbamate | | |
| 183 | 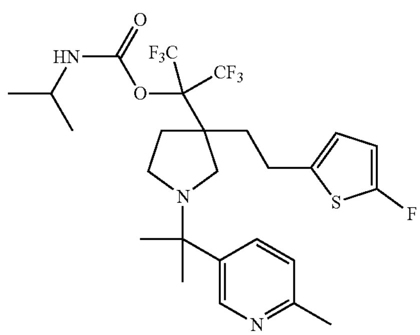 [SMILES: Cc1ccc(C(C)(C)N2CCC(CCc3ccc(F)s3)(C(OC(=O)NC(C)C)(C(F)(F)F)C(F)(F)F)C2)cn1] | (R or S)-1,1,1,3,3,3-hexafluoro-2-(3-(2-(5-fluorothiophen-2-yl)ethyl)-1-(2-(6-methylpyridin-3-yl)propan-2-yl)pyrrolidin-3-yl)propan-2-yl isopropylcarbamate | | |
| 184 | 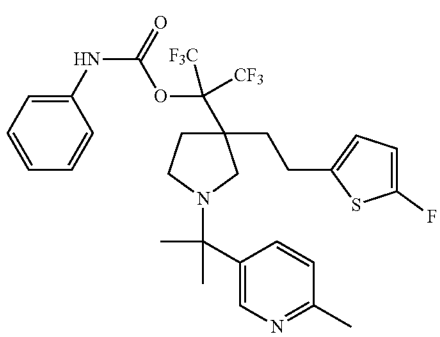 [SMILES: Cc1ccc(C(C)(C)N2CCC(CCc3ccc(F)s3)(C(OC(=O)Nc3ccccc3)(C(F)(F)F)C(F)(F)F)C2)cn1] | (R or S)-1,1,1,3,3,3-hexafluoro-2-(3-(2-(5-fluorothiophen-2-yl)ethyl)-1-(2-(6-methylpyridin-3-yl)propan-2-yl)pyrrolidin-3-yl)propan-2-yl phenylcarbamate | | |
| 185 | 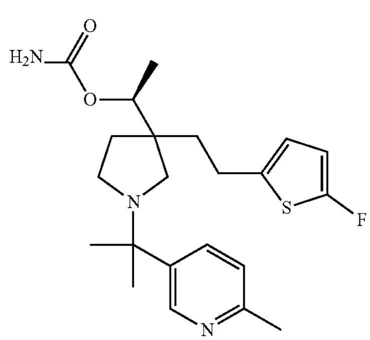 [SMILES: Cc1ccc(C(C)(C)N2CCC(CCc3ccc(F)s3)([C@H](C)OC(N)=O)C2)cn1] | (S)-1-((R or S)-3-(2-(5-fluorothiophen-2-yl)ethyl)-1-(2-(6-methylpyridin-3-yl)propan-2-yl)pyrrolidin-3-yl)ethylcarbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 186 | 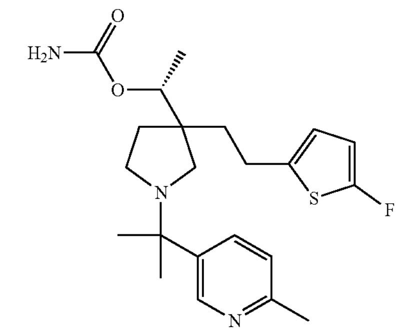 [SMILES: Cc1ccc(C(C)(C)N2CCC(CCc3ccc(F)s3)([C@@H](C)OC(N)=O)C2)cn1] | (R)-1-((R or S)-3-(2-(5-fluoro-thiophen-2-yl)ethyl)-1-(2-(6-methylpyridin-3-yl)propan-2-yl)pyrrolidin-3-yl)ethylcarbamate | | |
| 187 | 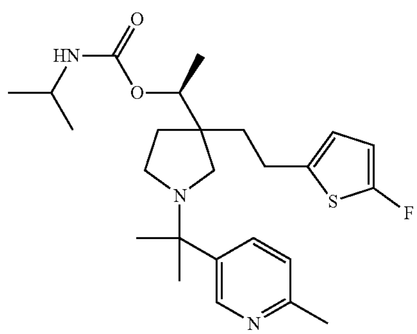 [SMILES: Cc1ccc(C(C)(C)N2CCC(CCc3ccc(F)s3)([C@H](C)OC(=O)NC(C)C)C2)cn1] | (S)-1-((R or S)-3-(2-(5-fluoro-thiophen-2-yl)ethyl)-1-(2-(6-methylpyridin-3-yl)propan-2-yl)pyrrolidin-3-yl)ethyl isopropylcarbamate | | |
| 188 | 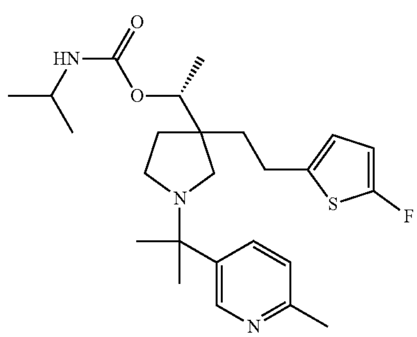 [SMILES: Cc1ccc(C(C)(C)N2CCC(CCc3ccc(F)s3)([C@@H](C)OC(=O)NC(C)C)C2)cn1] | (R)-1-((R or S)-3-(2-(5-fluoro-thiophen-2-yl)ethyl)-1-(2-(6-methylpyridin-3-yl)propan-2-yl)pyrrolidin-3-yl)ethyl isopropylcarbamate | | |
| 189 | 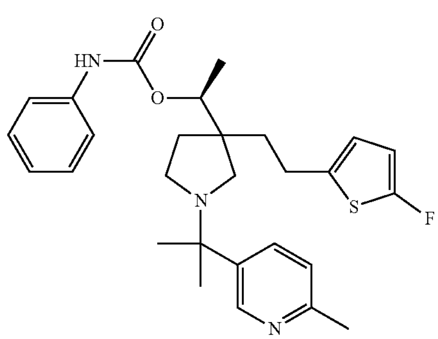 [SMILES: Cc1ccc(C(C)(C)N2CCC(CCc3ccc(F)s3)([C@H](C)OC(=O)Nc3ccccc3)C2)cn1] | (S)-1-((R or S)-3-(2-(5-fluoro-thiophen-2-yl)ethyl)-1-(2-(6-methylpyridin-3-yl)propan-2-yl)pyrrolidin-3-yl)ethyl phenylcarbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 190 | 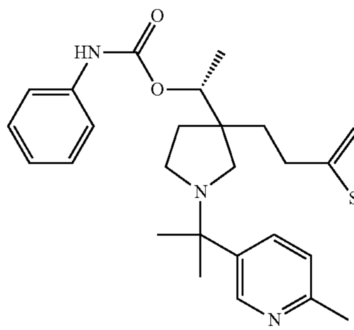 | (R)-1-((R or S)-3-(2-(5-fluorothiophen-2-yl)ethyl)-1-(2-(6-methylpyridin-3-yl)propan-2-yl)pyrrolidin-3-yl)ethyl phenylcarbamate | | |
| 191 | 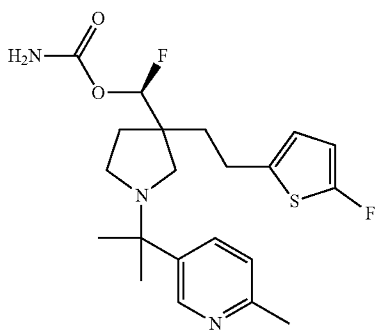 [SMILES: Cc1ccc(C(C)(C)N2CCC(CCc3ccc(F)s3)([C@H](F)OC(N)=O)C2)cn1] | (S)-fluoro((R or S)-3-(2-(5-fluorothiophen-2-yl)ethyl)-1-(2-(6-methylpyridin-3-yl)propan-2-yl)pyrrolidin-3-yl)methylcarbamate | | |
| 192 | 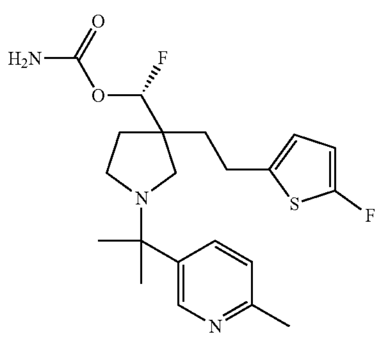 [SMILES: Cc1ccc(C(C)(C)N2CCC(CCc3ccc(F)s3)([C@@H](F)OC(N)=O)C2)cn1] | (R)-fluoro((R or S)-3-(2-(5-fluorothiophen-2-yl)ethyl)-1-(2-(6-methylpyridin-3-yl)propan-2-yl)pyrrolidin-3-yl)methylcarbamate | | |
| 193 | 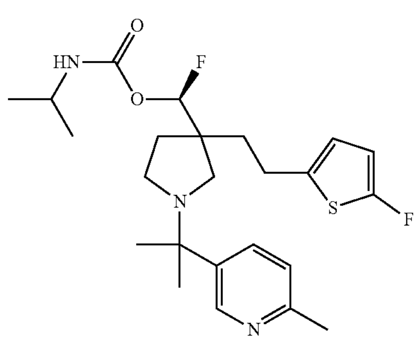 [SMILES: Cc1ccc(C(C)(C)N2CCC(CCc3ccc(F)s3)([C@H](F)OC(=O)NC(C)C)C2)cn1] | (S)-fluoro((R or S)-3-(2-(5-fluorothiophen-2-yl)ethyl)-1-(2-(6-methylpyridin-3-yl)propan-2-yl)pyrrolidin-3-yl)methyl isopropylcarbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 194 | 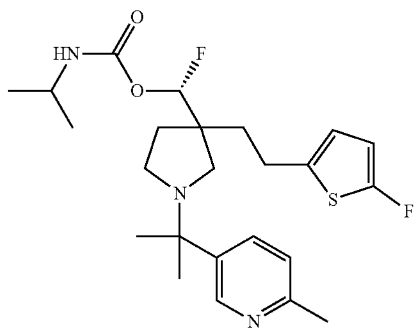 [SMILES: Cc1ccc(C(C)(C)N2CCC(CCc3ccc(F)s3)([C@@H](F)OC(=O)NC(C)C)C2)cn1] | (R)-fluoro((R or S)-3-(2-(5-fluoro-thiophen-2-yl)ethyl)-1-(2-(6-methylpyridin-3-yl)propan-2-yl)pyrrolidin-3-yl)methyl isopropylcarbamate | | |
| 195 | 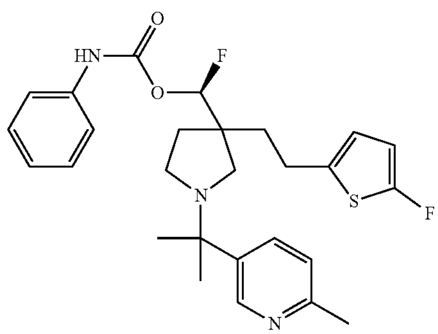 [SMILES: Cc1ccc(C(C)(C)N2CCC(CCc3ccc(F)s3)([C@H](F)OC(=O)Nc3ccccc3)C2)cn1] | (S)-fluoro((R or S)-3-(2-(5-fluoro-thiophen-2-yl)ethyl)-1-(2-(6-methylpyridin-3-yl)propan-2-yl)pyrrolidin-3-yl)methyl phenylcarbamate | | |
| 196 | 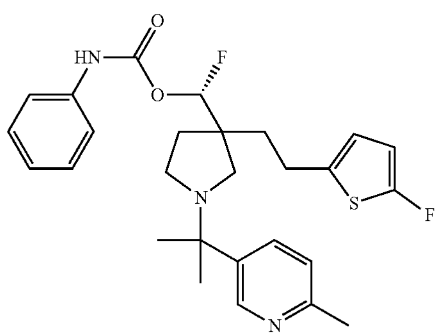 [SMILES: Cc1ccc(C(C)(C)N2CCC(CCc3ccc(F)s3)([C@@H](F)OC(=O)Nc3ccccc3)C2)cn1] | (R)-fluoro((R or S)-3-(2-(5-fluoro-thiophen-2-yl)ethyl)-1-(2-(6-methylpyridin-3-yl)propan-2-yl)pyrrolidin-3-yl)methyl phenylcarbamate | | |
| 197 | 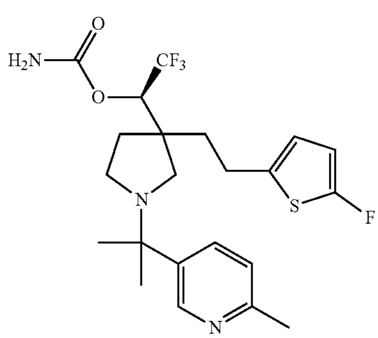 [SMILES: Cc1ccc(C(C)(C)N2CCC(CCc3ccc(F)s3)([C@@H](OC(N)=O)C(F)(F)F)C2)cn1] | (R)-2,2,2-trifluoro-1-((R or S)-3-(2-(5-fluoro-thiophen-2-yl)ethyl)-1-(2-(6-methylpyridin-3-yl)propan-2-yl)pyrrolidin-3-yl)ethyl-carbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 198 | 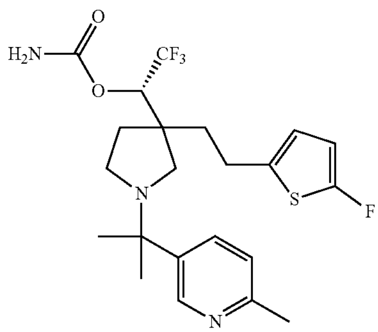 | (S)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl-carbamate | | |
| 199 | 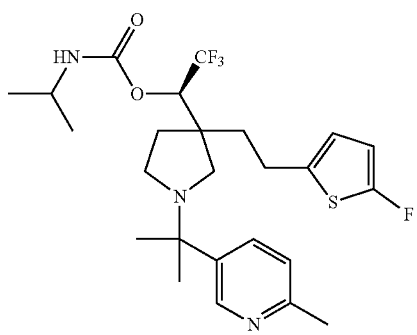 [SMILES: Cc1ccc(C(C)(C)N2CCC(CCc3ccc(F)s3)([C@@H](OC(=O)NC(C)C)C(F)(F)F)C2)cn1] | (R)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl isopropylcarbamate | | |
| 200 | 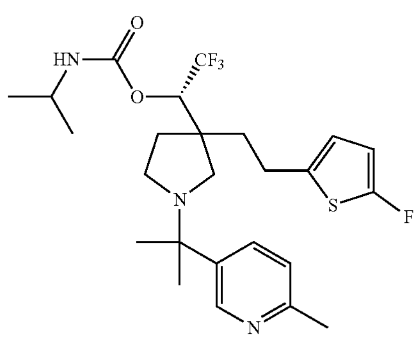 [SMILES: Cc1ccc(C(C)(C)N2CCC(CCc3ccc(F)s3)([C@H](OC(=O)NC(C)C)C(F)(F)F)C2)cn1] | (S)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl isopropylcarbamate | | |
| 201 | 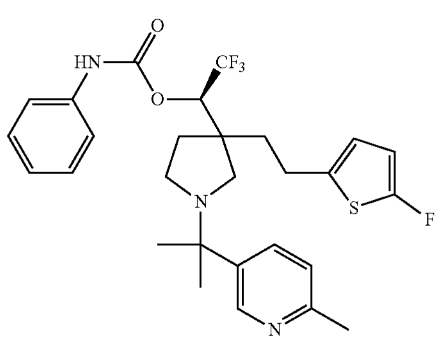 [SMILES: Cc1ccc(C(C)(C)N2CCC(CCc3ccc(F)s3)([C@@H](OC(=O)Nc3ccccc3)C(F)(F)F)C2)cn1] | (R)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl phenylcarbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 202 | 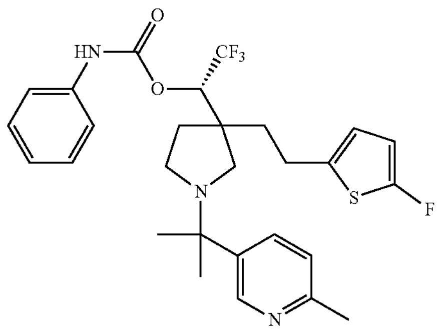 | (S)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl phenylcarbamate | | |
| 203 | 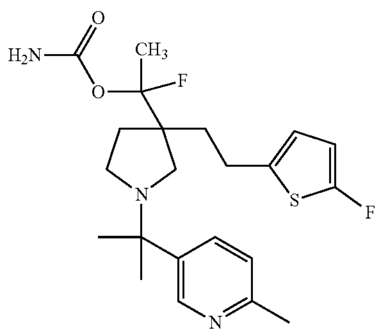 [SMILES: Cc1ccc(C(C)(C)N2CCC(CCc3ccc(F)s3)(C(C)(F)OC(N)=O)C2)cn1] | 1-fluoro-1-((R or S)-3-(2-(5-fluoro-thiophen-2-yl)ethyl)-1-(2-(6-methylpyridin-3-yl)propan-2-yl)pyr-rolidin-3-yl)ethyl carbamate | | |
| 204 | 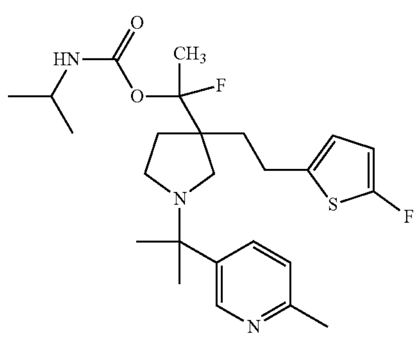 [SMILES: Cc1ccc(C(C)(C)N2CCC(CCc3ccc(F)s3)(C(C)(F)OC(=O)NC(C)C)C2)cn1] | 1-fluoro-1-((R or S)-3-(2-(5-fluoro-thiophen-2-yl)ethyl)-1-(2-(6-methylpyridin-3-yl)propan-2-yl)pyr-rolidin-3-yl)ethyl isopropylcarbamate | | |
| 205 | 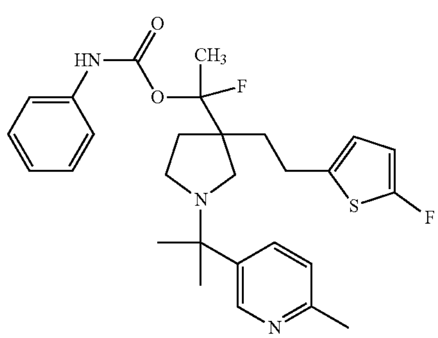 [SMILES: Cc1ccc(C(C)(C)N2CCC(CCc3ccc(F)s3)(C(C)(F)OC(=O)Nc3ccccc3)C2)cn1] | 1-fluoro-1-((R or S)-3-(2-(5-fluoro-thiophen-2-yl)ethyl)-1-(2-(6-methylpyridin-3-yl)propan-2-yl)pyr-rolidin-3-yl)ethyl phenylcarbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]⁺ | H-NMR |
|---|---|---|---|---|
| 206 | 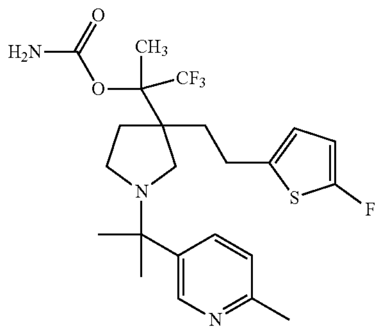 [SMILES: Cc1ccc(C(C)(C)N2CCC(CCc3ccc(F)s3)(C(C)(OC(N)=O)C(F)(F)F)C2)cn1] | 1,1,1-trifluoro-2-((R or S)-3-(2-(5-fluoro-thiophen-2-yl)ethyl)-1-(2-(6-methylpyridin-3-yl)propan-2-yl)pyr-rolidin-3-yl)propan-2-yl carbamate | | |
| 207 | 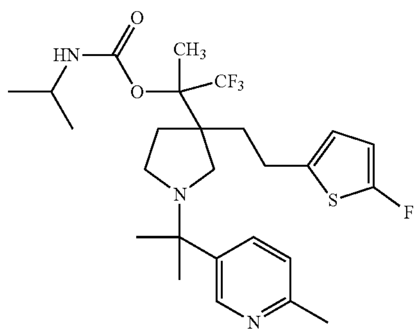 [SMILES: Cc1ccc(C(C)(C)N2CCC(CCc3ccc(F)s3)(C(C)(OC(=O)NC(C)C)C(F)(F)F)C2)cn1] | 1,1,1-trifluoro-2-((R or S)-3-(2-(5-fluoro-thiophen-2-yl)ethyl)-1-(2-(6-methylpyridin-3-yl)propan-2-yl)pyr-rolidin-3-yl)propan-2-yl isopropylcarbamate | | |
| 208 | 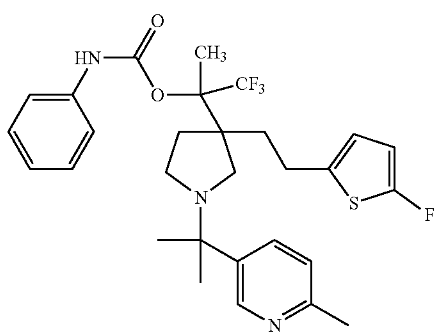 [SMILES: Cc1ccc(C(C)(C)N2CCC(CCc3ccc(F)s3)(C(C)(OC(=O)Nc3ccccc3)C(F)(F)F)C2)cn1] | 1,1,1-trifluoro-2-((R or S)-3-(2-(5-fluoro-thiophen-2-yl)ethyl)-1-(2-(6-methylpyridin-3-yl)propan-2-yl)pyr-rolidin-3-yl)propan-2-yl phenylcarbamate | | |
| 209 | 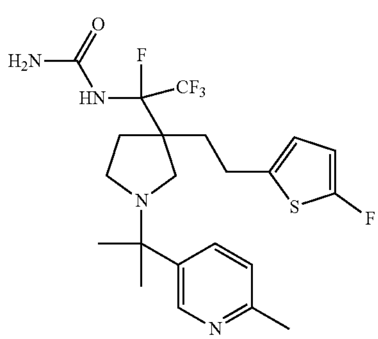 [SMILES: Cc1ccc(C(C)(C)N2CCC(CCc3ccc(F)s3)(C(F)(NC(N)=O)C(F)(F)F)C2)cn1] | 1-(1,2,2,2-tetrafluoro-1-((R or S)-3-(2-(5-fluoro-thiophen-2-yl)ethyl)-1-(2-(6-methylpyridin-3-yl)propan-2-yl)pyr-rolidin-3-yl)ethyl)urea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 210 | 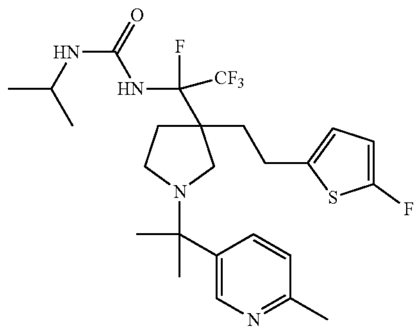 [SMILES: Cc1ccc(C(C)(C)N2CCC(CCc3ccc(F)s3)(C(F)(NC(=O)NC(C)C)C(F)(F)F)C2)cn1] | 1-isopropyl-3-(1,2,2,2-tetrafluoro-1-((R or S)-3-(2-(5-fluoro-thiophen-2-yl)ethyl)-1-(2-(6-methylpyridin-3-yl)propan-2-yl)pyr-rolidin-3-yl)ethyl)urea | | |
| 211 | 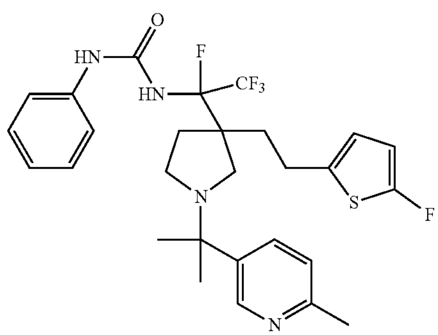 [SMILES: Cc1ccc(C(C)(C)N2CCC(CCc3ccc(F)s3)(C(F)(NC(=O)Nc3ccccc3)C(F)(F)F)C2)cn1] | 1-phenyl-3-(1,2,2,2-tetrafluoro-1-((R or S)-3-(2-(5-fluoro-thiophen-2-yl)ethyl)-1-(2-(6-methylpyridin-3-yl)propan-2-yl)pyr-rolidin-3-yl)ethyl)urea | | |
| 212 | 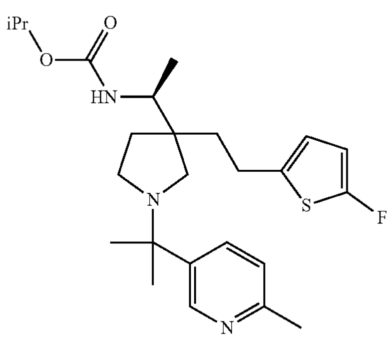 [SMILES: Cc1ccc(C(C)(C)N2CCC(CCc3ccc(F)s3)([C@H](C)NC(=O)OC(C)C)C2)cn1] | isopropyl ((S)-1-((R or S)-3-(2-(5-fluoro-thiophen-2-yl)ethyl)-1-(2-(6-methylpyridin-3-yl)propan-2-yl)pyr-rolidin-3-yl)ethyl)carbamate isopropyl ((1S)-1-(3-(2-(5-fluoro-thiophen-2-yl)ethyl)-1-(2-(6-methylpyridin-3-yl)propan-2-yl)pyrrolidin-3-yl)ethyl)carbamate | | |
| 213 | 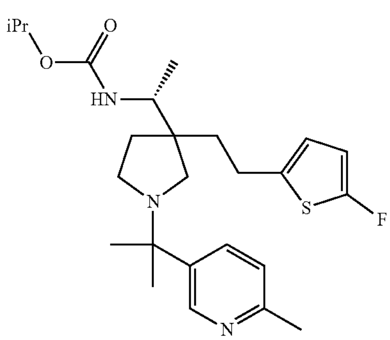 [SMILES: Cc1ccc(C(C)(C)N2CCC(CCc3ccc(F)s3)([C@@H](C)NC(=O)OC(C)C)C2)cn1] | isopropyl ((R)-1-((R or S)-3-(2-(5-fluoro-thiophen-2-yl)ethyl)-1-(2-(6-methylpyridin-3-yl)propan-2-yl)pyr-rolidin-3-yl)ethyl)carbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]⁺ | H-NMR |
|---|---|---|---|---|
| 214 | 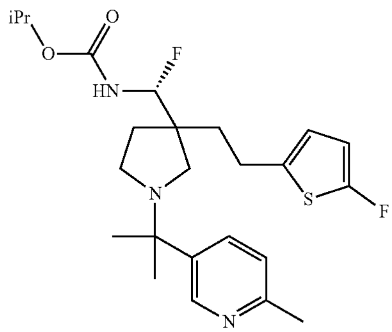 [SMILES: Cc1ccc(C(C)(C)N2CCC(CCc3ccc(F)s3)([C@@H](F)NC(=O)OC(C)C)C2)cn1] | isopropyl ((R)-fluoro((R or S)-3-(2-(5-fluoro-thiophen-2-yl)ethyl)-1-(2-(6-methylpyridin-3-yl)propan-2-yl)pyrrolidin-3-yl)methyl)carbamate | | |
| 215 | 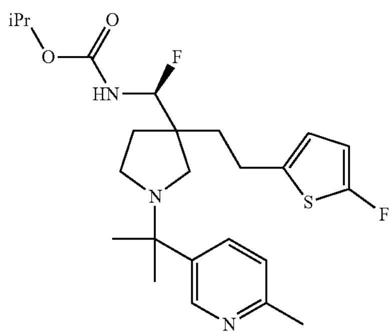 [SMILES: Cc1ccc(C(C)(C)N2CCC(CCc3ccc(F)s3)([C@H](F)NC(=O)OC(C)C)C2)cn1] | isopropyl ((S)-fluoro((R or S)-3-(2-(5-fluoro-thiophen-2-yl)ethyl)-1-(2-(6-methylpyridin-3-yl)propan-2-yl)pyrrolidin-3-yl)methyl)carbamate | | |
| 216 | 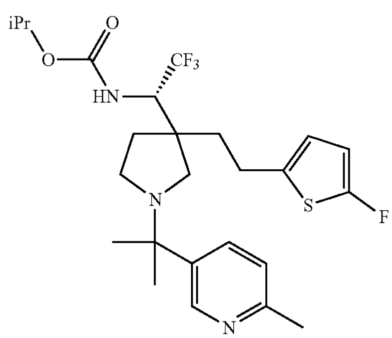 [SMILES: Cc1ccc(C(C)(C)N2CCC(CCc3ccc(F)s3)([C@H](NC(=O)OC(C)C)C(F)(F)F)C2)cn1] | isopropyl ((S)-2,2,2-trifluoro-1-((R or S)-3-(2-(5-fluoro-thiophen-2-yl)ethyl)-1-(2-(6-methylpyridin-3-yl)propan-2-yl)pyrrolidin-3-yl)ethyl)carbamate | | |
| 217 | 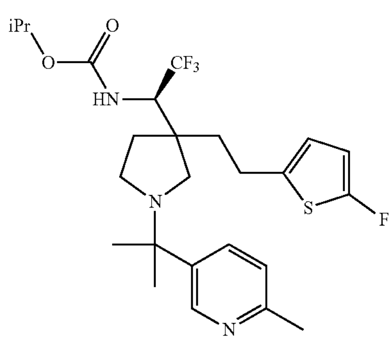 [SMILES: Cc1ccc(C(C)(C)N2CCC(CCc3ccc(F)s3)([C@@H](NC(=O)OC(C)C)C(F)(F)F)C2)cn1] | isopropyl ((R)-2,2,2-trifluoro-1-((R or S)-3-(2-(5-fluoro-thiophen-2-yl)ethyl)-1-(2-(6-methylpyridin-3-yl)propan-2-yl)pyrrolidin-3-yl)ethyl)carbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 218 | 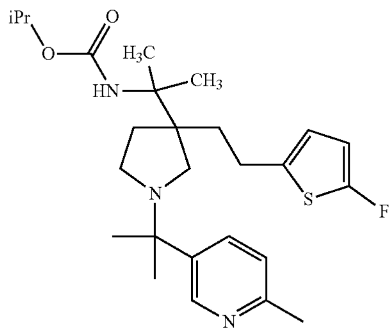 [SMILES: Cc1ccc(C(C)(C)N2CCC(CCc3ccc(F)s3)(C(C)(C)NC(=O)OC(C)C)C2)cn1] | isopropyl (R or S)-(2-(3-(2-(5-fluoro-thiophen-2-yl)ethyl)-1-(2-(6-methylpyridin-3-yl)propan-2-yl)pyrrolidin-3-yl)propan-2-yl)carbamate | | |
| 219 | 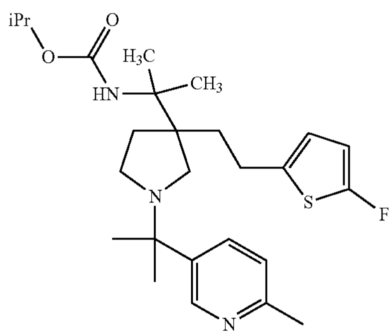 [SMILES: Cc1ccc(C(C)(C)N2CCC(CCc3ccc(F)s3)(C(C)(C)NC(=O)OC(C)C)C2)cn1] | isopropyl (1,1,1-trifluoro-2-((R or S)-3-(2-(5-fluoro-thiophen-2-yl)ethyl)-1-(2-(6-methylpyridin-3-yl)propan-2-yl)pyrrolidin-3-yl)propan-2-yl)carbamate | | |
| 220 | 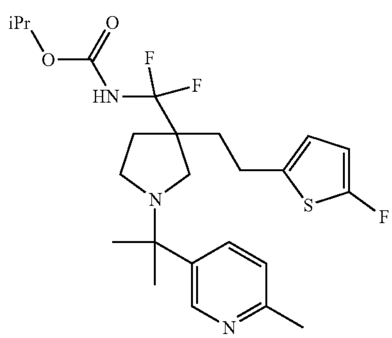 [SMILES: Cc1ccc(C(C)(C)N2CCC(CCc3ccc(F)s3)(C(F)(F)NC(=O)OC(C)C)C2)cn1] | isopropyl (R or S)-(difluoro(3-(2-(5-fluorothiophen-2-yl)ethyl)-1-(2-(6-methylpyridin-3-yl)propan-2-yl)pyrrolidin-3-yl)methyl)carbamate | | |
| 221 | 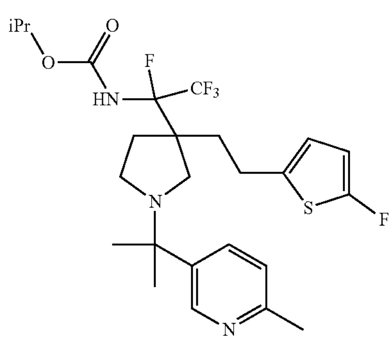 [SMILES: Cc1ccc(C(C)(C)N2CCC(CCc3ccc(F)s3)(C(F)(NC(=O)OC(C)C)C(F)(F)F)C2)cn1] | isopropyl (1,2,2,2-tetrafluoro-1-((R or S)-3-(2-(5-fluoro-thiophen-2-yl)ethyl)-1-(2-(6-methylpyridin-3-yl)propan-2-yl)pyrrolidin-3-yl)ethyl)carbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 222 | 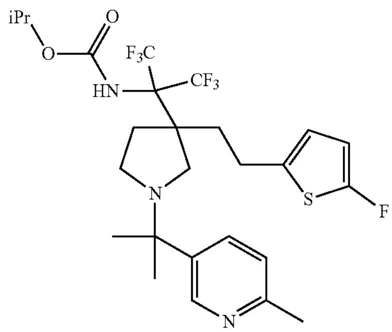 [SMILES: Cc1ccc(C(C)(C)N2CCC(CCc3ccc(F)s3)(C(NC(=O)OC(C)C)(C(F)(F)F)C(F)(F)F)C2)cn1] | isopropyl (R or S)-(1,1,1,3,3,3-hexa-fluoro-2-(3-(2-(5-fluorothiophen-2-yl)ethyl)-1-(2-(6-methylpyridin-3-yl)propan-2-yl)pyrrolidin-3-yl)propan-2-yl)carbamate | | |
| 223 | 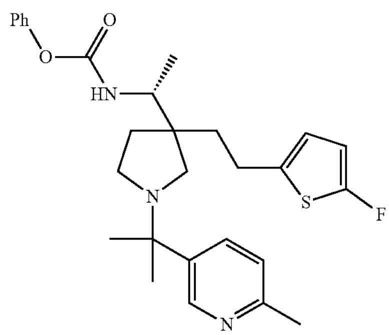 [SMILES: Cc1ccc(C(C)(C)N2CCC(CCc3ccc(F)s3)([C@@H](C)NC(=O)Oc3ccccc3)C2)cn1] | phenyl ((R)-1-((R or S)-3-(2-(5-fluoro-thiophen-2-yl)ethyl)-1-(2-(6-methylpyridin-3-yl)propan-2-yl)pyrrolidin-3-yl)ethyl)carbamate | | |
| 224 | 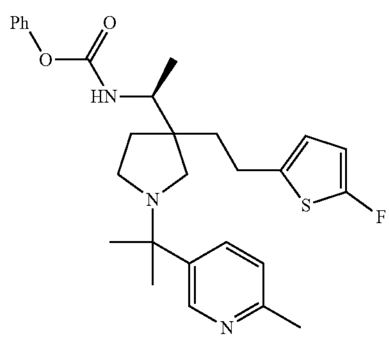 [SMILES: Cc1ccc(C(C)(C)N2CCC(CCc3ccc(F)s3)([C@H](C)NC(=O)Oc3ccccc3)C2)cn1] | phenyl ((S)-1-((R or S)-3-(2-(5-fluoro-thiophen-2-yl)ethyl)-1-(2-(6-methylpyridin-3-yl)propan-2-yl)pyrrolidin-3-yl)ethyl)carbamate | | |
| 225 | 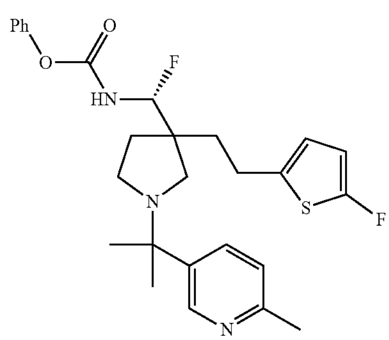 [SMILES: Cc1ccc(C(C)(C)N2CCC(CCc3ccc(F)s3)([C@@H](F)NC(=O)Oc3ccccc3)C2)cn1] | phenyl ((R)-fluoro((R or S)-3-(2-(5-fluoro-thiophen-2-yl)ethyl)-1-(2-(6-methylpyridin-3-yl)propan-2-yl)pyrrolidin-3-yl)methyl)carbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 226 | 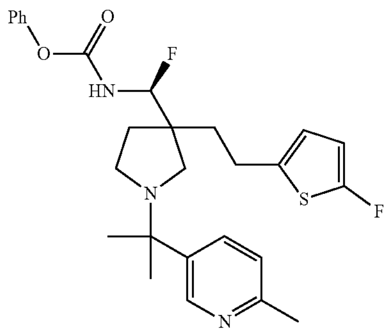 [SMILES: Cc1ccc(C(C)(C)N2CCC(CCc3ccc(F)s3)([C@H](F)NC(=O)Oc3ccccc3)C2)cn1] | phenyl ((S)-fluoro((R or S)-3-(2-(5-fluoro-thiophen-2-yl)ethyl)-1-(2-(6-methylpyridin-3-yl)propan-2-yl)pyr-rolidin-3-yl)methyl)carbamate | | |
| 227 | 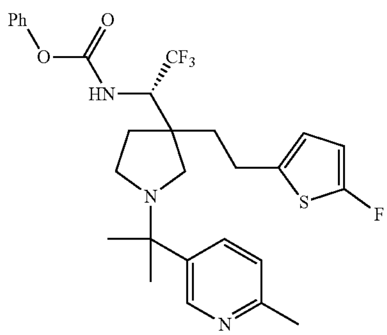 [SMILES: Cc1ccc(C(C)(C)N2CCC(CCc3ccc(F)s3)([C@H](NC(=O)Oc3ccccc3)C(F)(F)F)C2)cn1] | phenyl ((S)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl)carbamate | | |
| 228 | 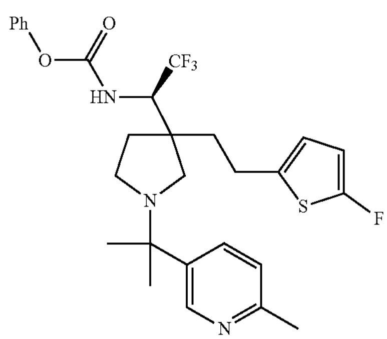 [SMILES: Cc1ccc(C(C)(C)N2CCC(CCc3ccc(F)s3)([C@@H](NC(=O)Oc3ccccc3)C(F)(F)F)C2)cn1] | phenyl ((R)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl)carbamate | | |
| 229 | 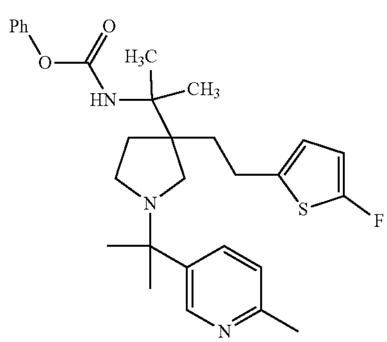 [SMILES: Cc1ccc(C(C)(C)N2CCC(CCc3ccc(F)s3)(C(C)(C)NC(=O)Oc3ccccc3)C2)cn1] | phenyl (R or S)-(2-(3-(2-(5-fluoro-thiophen-2-yl)ethyl)-1-(2-(6-methylpyridin-3-yl)propan-2-yl)pyrrolidin-3-yl)propan-2-yl)carbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 230 | 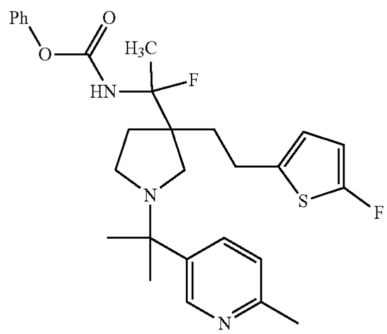 [SMILES: Cc1ccc(C(C)(C)N2CCC(CCc3ccc(F)s3)(C(C)(F)NC(=O)Oc3ccccc3)C2)cn1] | phenyl (1-fluoro-1-((R or S)-3-(2-(5-fluorothiophen-2-yl)ethyl)-1-(2-(6-methylpyridin-3-yl)propan-2-yl)pyrrolidin-3-yl)ethyl)carbamate | | |
| 231 | 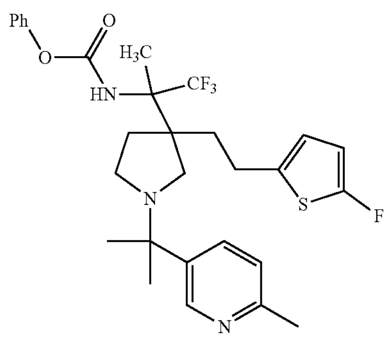 [SMILES: Cc1ccc(C(C)(C)N2CCC(CCc3ccc(F)s3)(C(C)(NC(=O)Oc3ccccc3)C(F)(F)F)C2)cn1] | phenyl (1,1,1-trifluoro-2-((R or S)-3-(2-(5-fluorothiophen-2-yl)ethyl)-1-(2-(6-methylpyridin-3-yl)propan-2-yl)pyrrolidin-3-yl)propan-2-yl)carbamate | | |
| 232 | 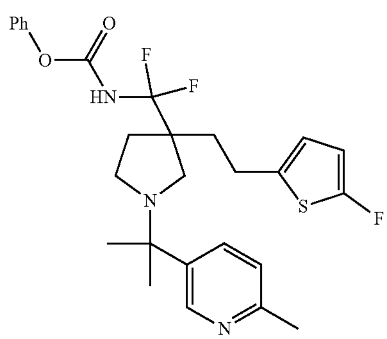 [SMILES: Cc1ccc(C(C)(C)N2CCC(CCc3ccc(F)s3)(C(F)(F)NC(=O)Oc3ccccc3)C2)cn1] | phenyl (R or S)-(difluoro(3-(2-(5-fluorothiophen-2-yl)ethyl)-1-(2-(6-methylpyridin-3-yl)propan-2-yl)pyrrolidin-3-yl)methyl)carbamate | | |
| 233 | 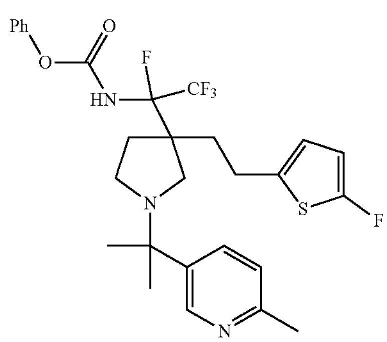 [SMILES: Cc1ccc(C(C)(C)N2CCC(CCc3ccc(F)s3)(C(F)(NC(=O)Oc3ccccc3)C(F)(F)F)C2)cn1] | phenyl (1,2,2,2-tetrafluoro-1-((R or S)-3-(2-(5-fluorothiophen-2-yl)ethyl)-1-(2-(6-methylpyridin-3-yl)propan-2-yl)pyrrolidin-3-yl)ethyl)carbamate | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 234 | 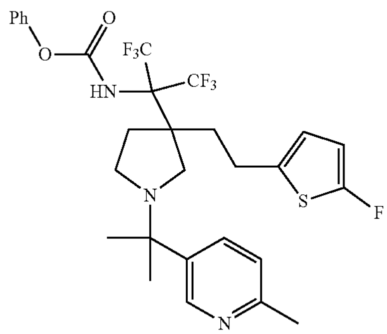 [SMILES: Cc1ccc(C(C)(C)N2CCC(CCc3ccc(F)s3)(C(NC(=O)Oc3ccccc3)(C(F)(F)F)C(F)(F)F)C2)cn1] | phenyl (R or S)-(1,1,1,3,3,3-hexafluoro-2-(3-(2-(5-fluorothiophen-2-yl)ethyl)-1-(2-(6-methylpyridin-3-yl)propan-2-yl)pyrrolidin-3-yl)propan-2-yl)carbamate | | |
| 235 | 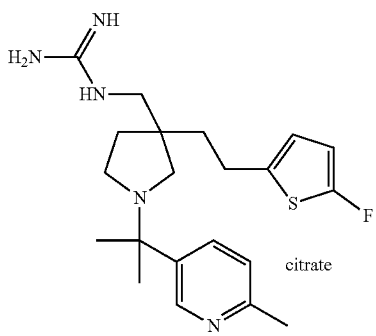 [SMILES: Cc1ccc(C(C)(C)N2CCC(CCc3ccc(F)s3)(CNC(=N)N)C2)cn1] | (R or S)-1-((3-(2-(5-fluoro-thiophen-2-yl)ethyl)-1-(2-(6-methylpyridin-3-yl)propan-2-yl)pyrrolidin-3-yl)methyl)guanidine citrate | 404 | $^1$H NMR (300 MHz, MeOD): δ 8.78 (s, 1H), 8.27 (d, J = 6.6 Hz, 1H), 7.52 (d, J = 7.8 Hz, 1H), 6.46 (s, 1H), 6.32 (s, 1H), 3.11-2.99 (m, 2H), 2.94-2.76 (m, 7H), 2.71-2.55 (m, 5H), 2.05-1.90 (m, 2H), 1.88-1.72 (m, 9H). |
| 236 | 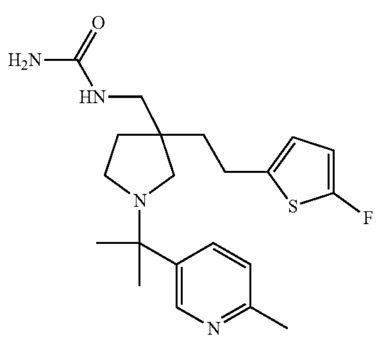 [SMILES: Cc1ccc(C(C)(C)N2CCC(CCc3ccc(F)s3)(CNC(N)=O)C2)cn1] | (S or R)-1-((3-(2-(5-fluoro-thiophen-2-yl)ethyl)-1-(2-(6-methylpyridin-3-yl)propan-2-yl)pyrrolidin-3-yl)methyl)urea | | |
| 237 | 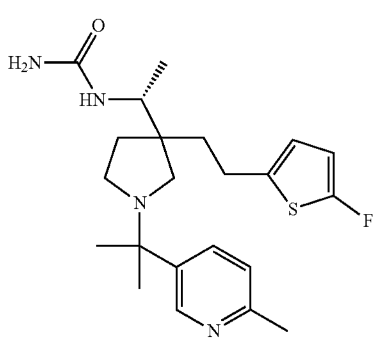 [SMILES: Cc1ccc(C(C)(C)N2CCC(CCc3ccc(F)s3)([C@@H](C)NC(N)=O)C2)cn1] | 1-((R)-1-((R or S)-3-(2-(5-fluoro-thiophen-2-yl)ethyl)-1-(2-(6-methylpyridin-3-yl)propan-2-yl)pyrrolidin-3-yl)ethyl)urea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 238 | 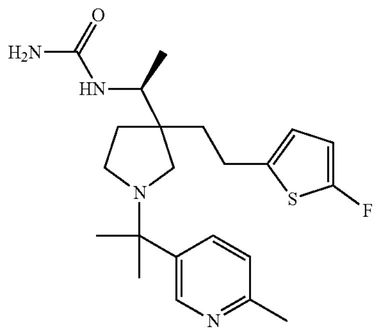 [SMILES: Cc1ccc(C(C)(C)N2CCC(CCc3ccc(F)s3)([C@H](C)NC(N)=O)C2)cn1] | 1-((S)-1-((R or S)-3-(2-(5-fluoro-thiophen-2-yl)ethyl)-1-(2-(6-methylpyridin-3-yl)propan-2-yl)pyr-rolidin-3-yl)ethyl)urea | | |
| 239 | 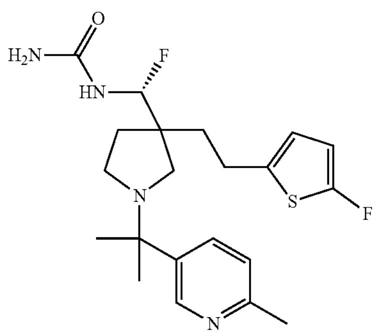 [SMILES: Cc1ccc(C(C)(C)N2CCC(CCc3ccc(F)s3)([C@@H](F)NC(N)=O)C2)cn1] | 1-((R)-fluoro((R or S)-3-(2-(5-fluoro-thiophen-2-yl)ethyl)-1-(2-(6-methylpyridin-3-yl)propan-2-yl)pyr-rolidin-3-yl)methyl)urea | | |
| 240 | 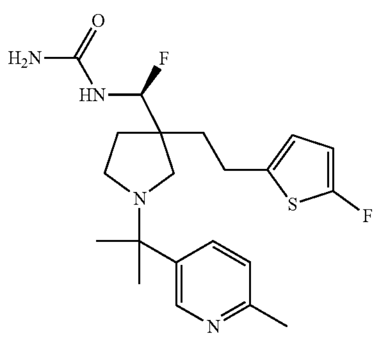 [SMILES: Cc1ccc(C(C)(C)N2CCC(CCc3ccc(F)s3)([C@H](F)NC(N)=O)C2)cn1] | 1-((S)-fluoro((R or S)-3-(2-(5-fluoro-thiophen-2-yl)ethyl)-1-(2-(6-methylpyridin-3-yl)propan-2-yl)pyr-rolidin-3-yl)methyl)urea | | |
| 241 | 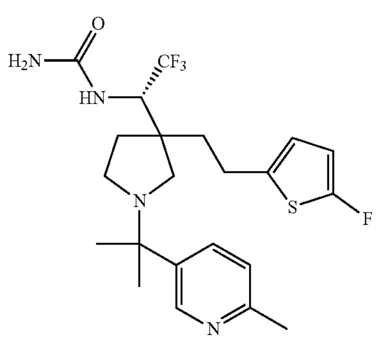 [SMILES: Cc1ccc(C(C)(C)N2CCC(CCc3ccc(F)s3)([C@H](NC(N)=O)C(F)(F)F)C2)cn1] | 1-((S)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl)urea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 242 | 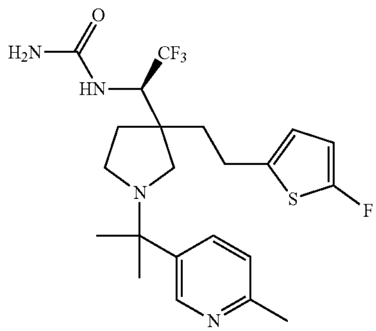 [SMILES: Cc1ccc(C(C)(C)N2CCC(CCc3ccc(F)s3)([C@@H](NC(N)=O)C(F)(F)F)C2)cn1] | 1-((R)-2,2,2-trifluoro-1-((R or S)-3-(2-(5-fluoro-thiophen-2-yl)ethyl)-1-(2-(6-methylpyridin-3-yl)propan-2-yl)pyr-rolidin-3-yl)ethyl)urea | | |
| 243 | 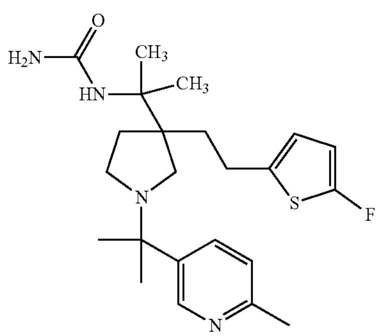 | (R or S)-1-(2-(3-(2-(5-fluoro-thiophen-2-yl)ethyl)-1-(2-(6-methylpyridin-3-yl)propan-2-yl)pyrrolidin-3-yl)propan-2-yl)urea | | |
| 244 | 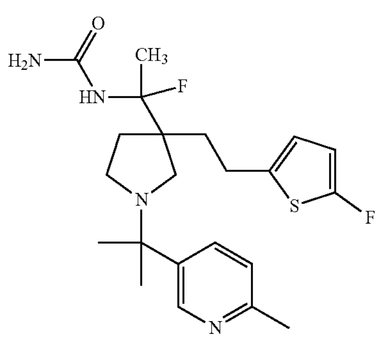 | 1-(1-fluoro-1-((R or S)-3-(2-(5-fluoro-thiophen-2-yl)ethyl)-1-(2-(6-methylpyridin-3-yl)propan-2-yl)pyr-rolidin-3-yl)ethyl)urea | | |
| 245 | 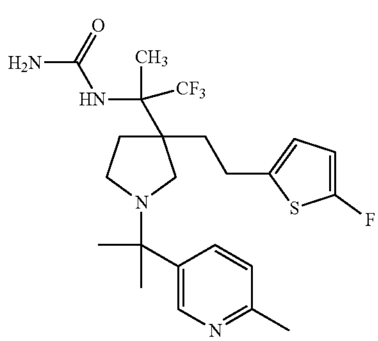 [SMILES: Cc1ccc(C(C)(C)N2CCC(CCc3ccc(F)s3)(C(C)(C)NC(N)=O)C2)cn1] | 1-(1,1,1-trifluoro-2-((R or S)-3-(2-(5-fluoro-thiophen-2-yl)ethyl)-1-(2-(6-methylpyridin-3-yl)propan-2-yl)pyr-rolidin-3-yl)propan-2-yl)urea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 246 | 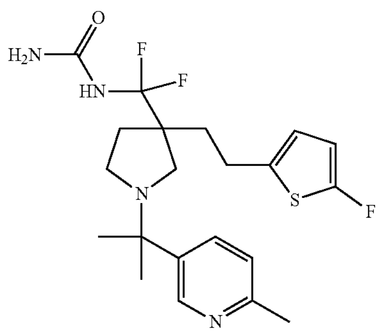 [SMILES: Cc1ccc(C(C)(C)N2CCC(CCc3ccc(F)s3)(C(F)(F)NC(N)=O)C2)cn1] | (R or S)-1-(difluoro(3-(2-(5-fluorothiophen-2-yl)ethyl)-1-(2-(6-methylpyridin-3-yl)propan-2-yl)pyrrolidin-3-yl)methyl)urea | | |
| 247 | 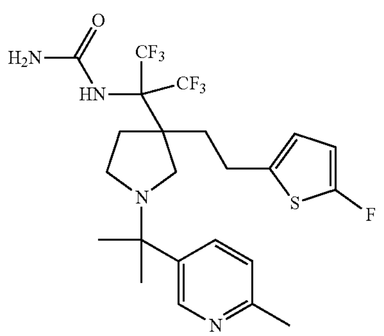 [SMILES: Cc1ccc(C(C)(C)N2CCC(CCc3ccc(F)s3)(C(NC(N)=O)(C(F)(F)F)C(F)(F)F)C2)cn1] | (R or S)-1-(1,1,1,3,3,3-hexafluoro-2-(3-(2-(5-fluorothiophen-2-yl)ethyl)-1-(2-(6-methylpyridin-3-yl)propan-2-yl)pyrrolidin-3-yl)propan-2-yl)urea | | |
| 248 | 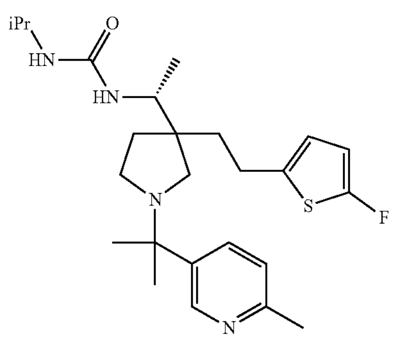 [SMILES: Cc1ccc(C(C)(C)N2CCC(CCc3ccc(F)s3)([C@@H](C)NC(=O)NC(C)C)C2)cn1] | 1-((R)-1-((R or S)-3-(2-(5-fluoro-thiophen-2-yl)ethyl)-1-(2-(6-methylpyridin-3-yl)propan-2-yl)pyrrolidin-3-yl)ethyl)-3-isopropylurea | | |
| 249 | 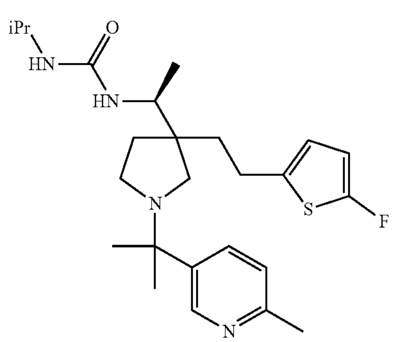 [SMILES: Cc1ccc(C(C)(C)N2CCC(CCc3ccc(F)s3)([C@H](C)NC(=O)NC(C)C)C2)cn1] | 1-((S)-1-((R or S)-3-(2-(5-fluoro-thiophen-2-yl)ethyl)-1-(2-(6-methylpyridin-3-yl)propan-2-yl)pyrrolidin-3-yl)ethyl)-3-isopropylurea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 250 | 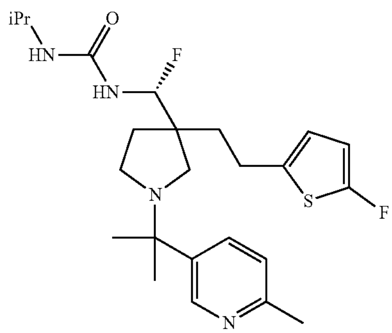 [SMILES: Cc1ccc(C(C)(C)N2CCC(CCc3ccc(F)s3)([C@@H](F)NC(=O)NC(C)C)C2)cn1] | 1-((R)-fluoro((R or S)-3-(2-(5-fluoro-thiophen-2-yl)ethyl)-1-(2-(6-methylpyridin-3-yl)propan-2-yl)pyrrolidin-3-yl)methyl)-3-isopropylurea | | |
| 251 | 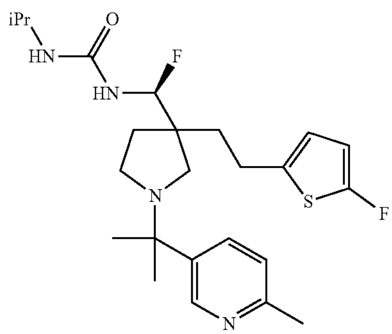 [SMILES: Cc1ccc(C(C)(C)N2CCC(CCc3ccc(F)s3)([C@H](F)NC(=O)NC(C)C)C2)cn1] | 1-((S)-fluoro((R or S)-3-(2-(5-fluoro-thiophen-2-yl)ethyl)-1-(2-(6-methylpyridin-3-yl)propan-2-yl)pyrrolidin-3-yl)methyl)-3-isopropylurea | | |
| 252 | 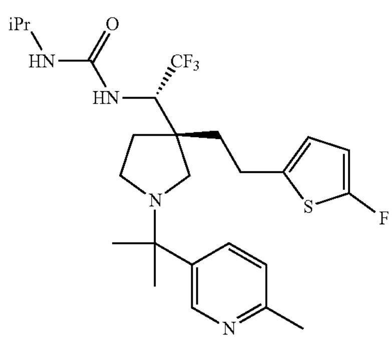 [SMILES: Cc1ccc(C(C)(C)N2CC[C@](CCc3ccc(F)s3)([C@H](NC(=O)NC(C)C)C(F)(F)F)C2)cn1] | 1-isopropyl-3-((S)-2,2,2-trifluoro-1-((R or S)-3-(2-(5-fluoro-thiophen-2-yl)ethyl)-1-(2-(6-methylpyridin-3-yl)propan-2-yl)pyrrolidin-3-yl)ethyl)urea | | |
| 253 | 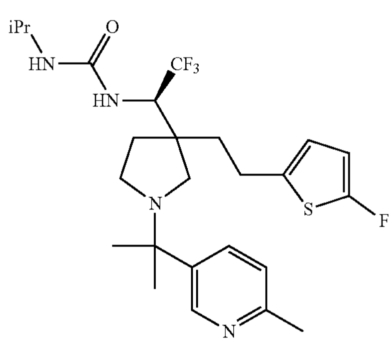 | 1-isopropyl-3-((R)-2,2,2-trifluoro-1-((R or S)-3-(2-(5-fluoro-thiophen-2-yl)ethyl)-1-(2-(6-methylpyridin-3-yl)propan-2-yl)pyrrolidin-3-yl)ethyl)urea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 254 | 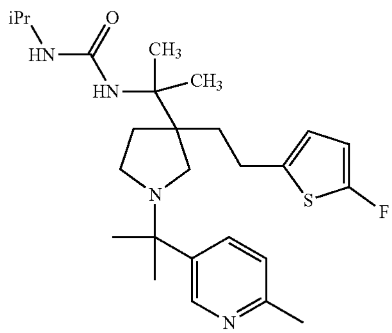 [SMILES: Cc1ccc(C(C)(C)N2CCC(CCc3ccc(F)s3)(C(C)(C)NC(=O)NC(C)C)C2)cn1] | (R or S)-1-(2-(3-(2-(5-fluorothiophen-2-yl)ethyl)-1-(2-(6-methylpyridin-3-yl)propan-2-yl)pyrrolidin-3-yl)propan-2-yl)-3-isopropylurea | | |
| 255 | 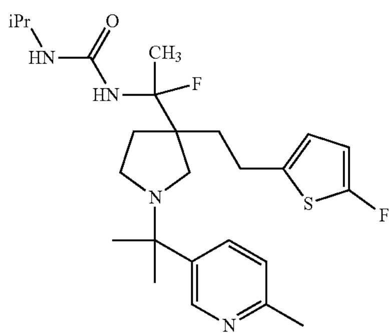 [SMILES: Cc1ccc(C(C)(C)N2CCC(CCc3ccc(F)s3)(C(C)(F)NC(=O)NC(C)C)C2)cn1] | 1-(1-fluoro-1-((R or S)-3-(2-(5-fluoro-thiophen-2-yl)ethyl)-1-(2-(6-methylpyridin-3-yl)propan-2-yl)pyrrolidin-3-yl)ethyl)-3-isopropylurea | | |
| 256 | 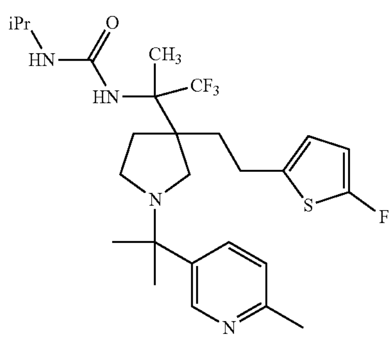 | 1-isopropyl-3-(1,1,1-trifluoro-2-((R or S)-3-(2-(5-fluoro-thiophen-2-yl)ethyl)-1-(2-(6-methylpyridin-3-yl)propan-2-yl)pyrrolidin-3-yl)propan-2-yl)urea | | |
| 257 | 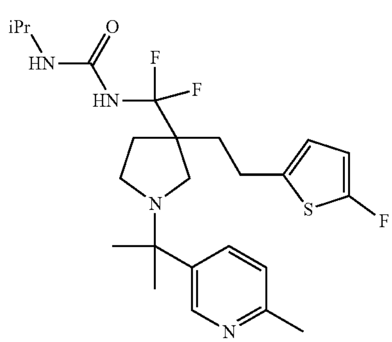 [SMILES: Cc1ccc(C(C)(C)N2CCC(CCc3ccc(F)s3)(C(F)(F)NC(=O)NC(C)C)C2)cn1] | (R or S)-1-(difluoro(3-(2-(5-fluorothiophen-2-yl)ethyl)-1-(2-(6-methylpyridin-3-yl)propan-2-yl)pyrrolidin-3-yl)methyl)-3-isopropylurea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 258 | 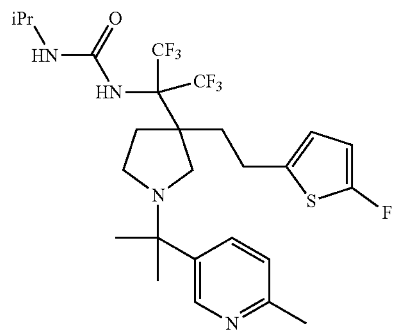 [SMILES: Cc1ccc(C(C)(C)N2CCC(CCc3ccc(F)s3)(C(NC(=O)NC(C)C)(C(F)(F)F)C(F)(F)F)C2)cn1] | (R or S)-1-(1,1,1,3,3,3-hexafluoro-2-(3-(2-(5-fluorothiophen-2-yl)ethyl)-1-(2-(6-methylpyridin-3-yl)propan-2-yl)pyrrolidin-3-yl)propan-2-yl)-3-isopropylurea | | |
| 259 | 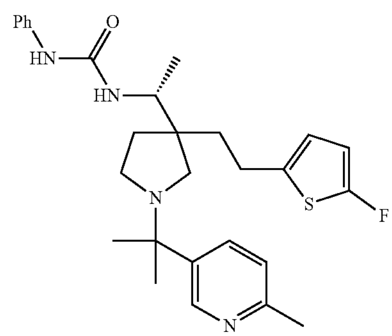 [SMILES: Cc1ccc(C(C)(C)N2CCC(CCc3ccc(F)s3)([C@@H](C)NC(=O)Nc3ccccc3)C2)cn1] | 1-((R)-1-((R or S)-3-(2-(5-fluoro-thiophen-2-yl)ethyl)-1-(2-(6-methylpyridin-3-yl)propan-2-yl)pyr-rolidin-3-yl)ethyl)-3-phenylurea | | |
| 260 | 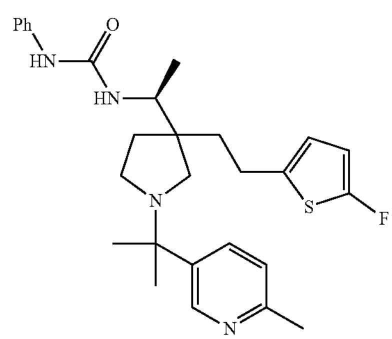 [SMILES: Cc1ccc(C(C)(C)N2CCC(CCc3ccc(F)s3)([C@H](C)NC(=O)Nc3ccccc3)C2)cn1] | 1-((S)-1-((R or S)-3-(2-(5-fluoro-thiophen-2-yl)ethyl)-1-(2-(6-methylpyridin-3-yl)propan-2-yl)pyr-rolidin-3-yl)ethyl)-3-phenylurea | | |
| 261 | 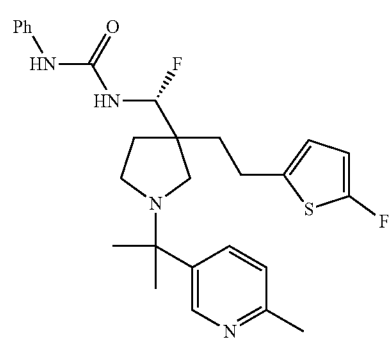 [SMILES: Cc1ccc(C(C)(C)N2CCC(CCc3ccc(F)s3)([C@@H](F)NC(=O)Nc3ccccc3)C2)cn1] | 1-((R)-fluoro((R or S)-3-(2-(5-fluoro-thiophen-2-yl)ethyl)-1-(2-(6-methylpyridin-3-yl)propan-2-yl)pyr-rolidin-3-yl)methyl)-3-phenylurea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 262 | 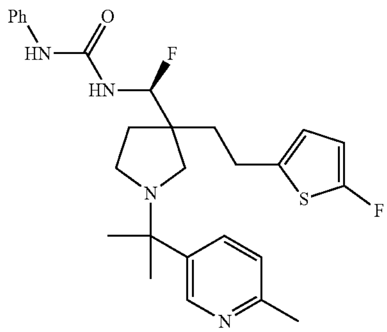 [SMILES: Cc1ccc(C(C)(C)N2CCC(CCc3ccc(F)s3)([C@H](F)NC(=O)Nc3ccccc3)C2)cn1] | 1-((S)-fluoro((R or S)-3-(2-(5-fluorothiophen-2-yl)ethyl)-1-(2-(6-methylpyridin-3-yl)propan-2-yl)pyrrolidin-3-yl)methyl)-3-phenylurea | | |
| 263 | 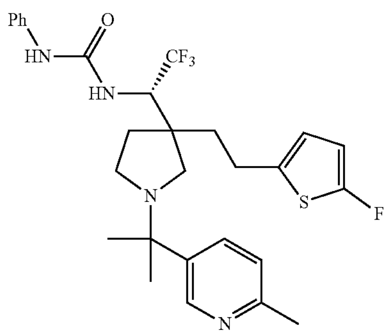 [SMILES: Cc1ccc(C(C)(C)N2CCC(CCc3ccc(F)s3)([C@H](NC(=O)Nc3ccccc3)C(F)(F)F)C2)cn1] | 1-phenyl-3-((S)-2,2,2-trifluoro-1-((R or S)-3-(2-(5-fluorothiophen-2-yl)ethyl)-1-(2-(6-methylpyridin-3-yl)propan-2-yl)pyrrolidin-3-yl)ethyl)urea | | |
| 264 | 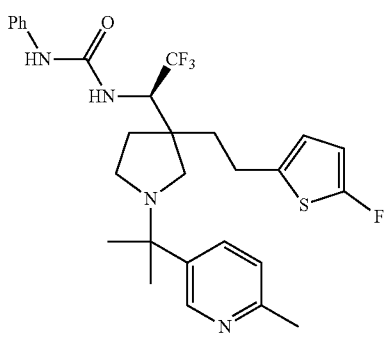 [SMILES: Cc1ccc(C(C)(C)N2CCC(CCc3ccc(F)s3)([C@@H](NC(=O)Nc3ccccc3)C(F)(F)F)C2)cn1] | 1-phenyl-3-((R)-2,2,2-trifluoro-1-((R or S)-3-(2-(5-fluorothiophen-2-yl)ethyl)-1-(2-(6-methylpyridin-3-yl)propan-2-yl)pyrrolidin-3-yl)ethyl)urea | | |
| 265 | 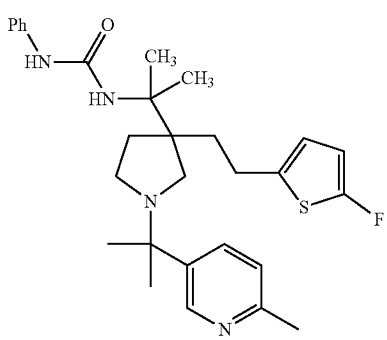 [SMILES: Cc1ccc(C(C)(C)N2CCC(CCc3ccc(F)s3)(C(C)(C)NC(=O)Nc3ccccc3)C2)cn1] | (R or S)-1-(2-(3-(2-(5-fluorothiophen-2-yl)ethyl)1-(2-(6-methylpyridin-3-yl)propan-2-yl)pyrrolidin-3-yl)propan-2-yl)-3-phenylurea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 266 | 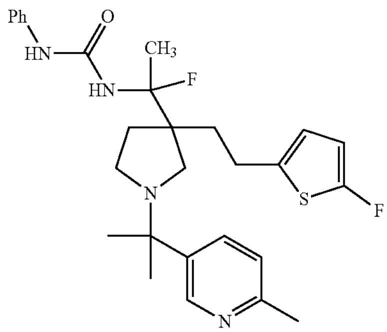 [SMILES: Cc1ccc(C(C)(C)N2CCC(CCc3ccc(F)s3)(C(C)(F)NC(=O)Nc3ccccc3)C2)cn1] | 1-(1-fluoro-1-((R or S)-3-(2-(5-fluoro-thiophen-2-yl)ethyl)-1-(2-(6-methylpyridin-3-yl)propan-2-yl)pyrrolidin-3-yl)ethyl)-3-phenylurea | | |
| 267 | 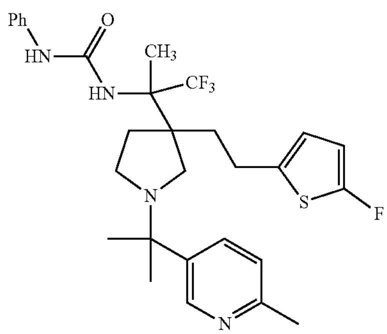 [SMILES: Cc1ccc(C(C)(C)N2CCC(CCc3ccc(F)s3)(C(C)(NC(=O)Nc3ccccc3)C(F)(F)F)C2)cn1] | 1-phenyl-3-(1,1,1-trifluoro-2-((R or S)-3-(2-(5-fluorothiophen-2-yl)ethyl)-1-(2-(6-methylpyridin-3-yl)propan-2-yl)pyrrolidin-3-yl)propan-2-yl)urea | | |
| 268 | 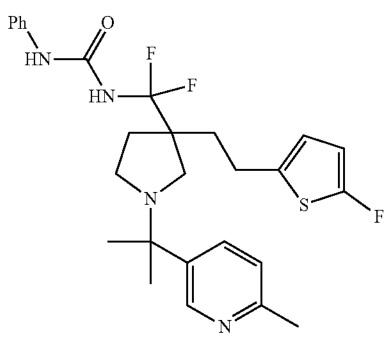 [SMILES: Cc1ccc(C(C)(C)N2CCC(CCc3ccc(F)s3)(C(F)(F)NC(=O)Nc3ccccc3)C2)cn1] | (R or S)-1-(difluoro(3-(2-(5-fluorothiophen-2-yl)ethyl)-1-(2-(6-methylpyridin-3-yl)propan-2-yl)pyrrolidin-3-yl)methyl)-3-phenylurea | | |
| 269 | 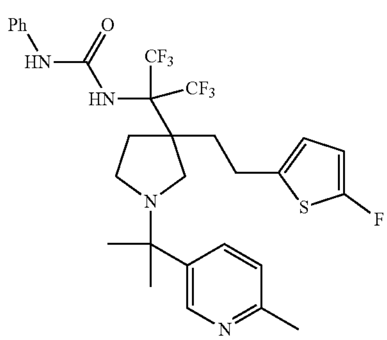 [SMILES: Cc1ccc(C(C)(C)N2CCC(CCc3ccc(F)s3)(C(NC(=O)Nc3ccccc3)(C(F)(F)F)C(F)(F)F)C2)cn1] | (R or S)-1-(1,1,1,3,3,3-hexafluoro-2-(3-(2-(5-fluorothiophen-2-yl)ethyl)-1-(2-(6-methylpyridin-3-yl)propan-2-yl)pyrrolidin-3-yl)propan-2-yl)-3-phenylurea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 270 | 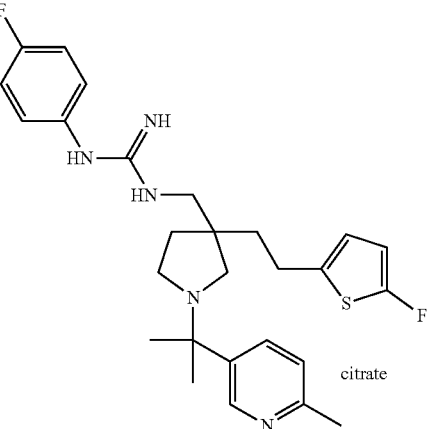 | (R or S)-1-(4-fluorophenyl)-3-((3-(2-(5-fluoro-thiophen-2-yl)ethyl)-1-(2-(6-methylpyridin-3-yl)propan-2-yl)pyrrolidin-3-yl)methyl)guanidine citrate | 498 | $^1$H NMR (300 MHz, MeOD): δ 8.76 (s, 1H), 8.21 (s, 1H), 7.47 (d, J = 8.3 Hz, 1H), 7.32 (dd, J = 8.8, 4.5 Hz, 2H), 7.21 (t, J = 8.5 Hz, 2H), 6.47 (s, 1H), 6.35-6.27 (m, 1H), 3.48-3.41 (m, 2H), 2.94-2.74 (m, 7H), 2.72-2.64 (m, 2H), 2.58 (s, 3H), 2.10-1.91 (m, 2H), 1.83-1.74 (m, 9H). |
| 271 | 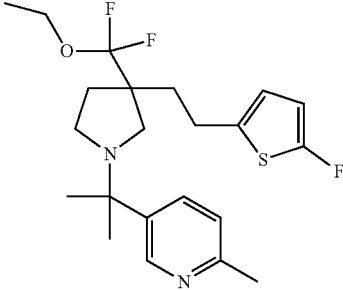 [SMILES: CCOC(F)(F)C1(CCc2ccc(F)s2)CCN(C(C)(C)c2ccc(C)nc2)C1] | (R or S)-5-(2-(3-(ethoxydi-fluoromethyl)-3-(2-(5-fluorothiophen-2-yl)ethyl)pyrrolidin-1-yl)propan-2-yl)-2-methylpyridine | | |
| 272 | 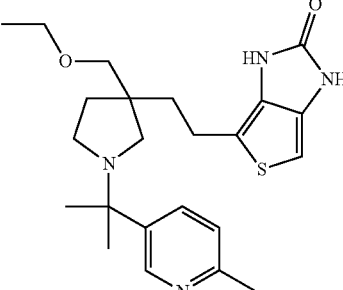 | (R or S)-4-(2-(3-(ethoxy-methyl)-1-(2-(6-methylpyridin-3-yl)propan-2-yl)pyrrolidin-3-yl)ethyl)-1H-thieno[3,4-d]imidazol-2(3H)-one | | |
| 273 | 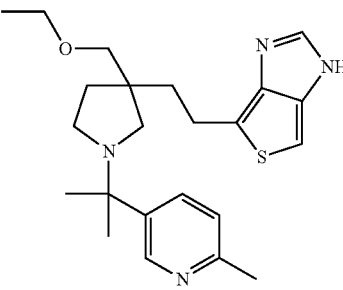 | (R or S)-4-(2-(3-(ethoxy-methyl)-1-(2-(6-methylpyridin-3-yl)propan-2-yl)pyrrolidin-3-yl)ethyl)-1H-thieno[3,4-d]imidazole | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 274 | 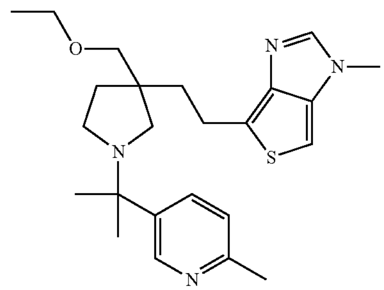 [SMILES: CCOCC1(CCc2scc3c2ncn3C)CCN(C(C)(C)c2ccc(C)nc2)C1] | (R or S)-4-(2-(3-(ethoxy-methyl)-1-(2-(6-methylpyridin-3-yl)propan-2-yl)pyrrolidin-3-yl)ethyl)-1-methyl-1H-thieno[3,4-d]imidazole | | |
| 275 | 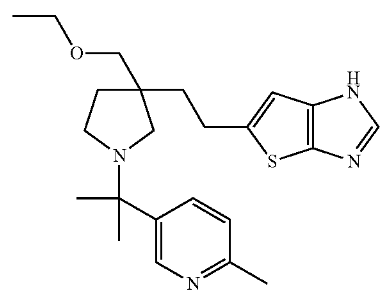 [SMILES: CCOCC1(CCc2cc3[nH]cnc3s2)CCN(C(C)(C)c2ccc(C)nc2)C1] | (R or S)-5-(2-(3-(ethoxy-methyl)-1-(2-(6-methylpyridin-3-yl)propan-2-yl)pyrrolidin-3-yl)ethyl)-1H-thieno[2,3-d]imidazole | | |
| 276 | 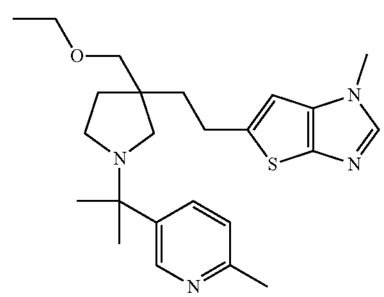 [SMILES: CCOCC1(CCc2cc3c(ncn3C)s2)CCN(C(C)(C)c2ccc(C)nc2)C1] | (R or S)-5-(2-(3-(ethoxy-methyl)-1-(2-(6-methylpyridin-3-yl)propan-2-yl)pyrrolidin-3-yl)ethyl)-1-methyl-1H-thieno[2,3-d]imidazole | | |
| 277 | 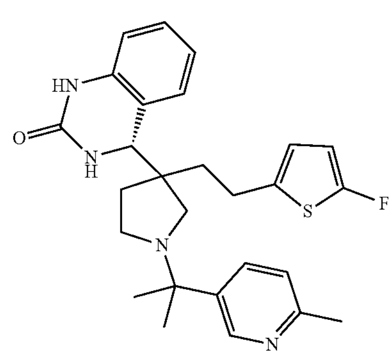 [SMILES: Cc1ccc(C(C)(C)N2CCC(CCc3ccc(F)s3)([C@@H]3NC(=O)Nc4ccccc43)C2)cn1] | (S)-4-((R or S)-3-(2-(5-fluorothio-phen-2-yl)ethyl)-1-(2-(6-methylpyridin-3-yl)propan-2-yl)pyrrolidin-3-yl)-3,4-di-hydroquinazolin-2(1H)-one | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 278 | 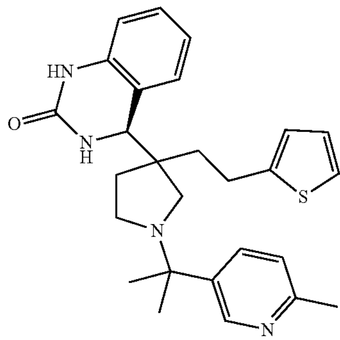 | (R)-4-((R or S)-3-(2-(5-fluorothiophen-2-yl)ethyl)-1-(2-(6-methylpyridin-3-yl)propan-2-yl)pyrrolidin-3-yl)-3,4-dihydroquinazolin-2(1H)-one | | |
| 279 | 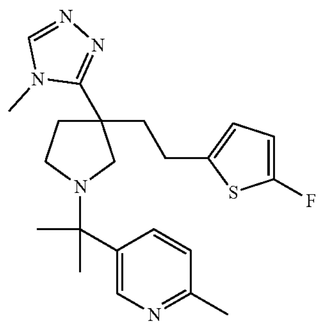 [SMILES: Cc1ccc(C(C)(C)N2CCC(CCc3ccc(F)s3)(c3nncn3C)C2)cn1] | (R or S)-5-(2-(3-(2-(5-fluorothiophen-2-yl)ethyl)-3-(4-methyl-4H-1,2,4-triazol-3-yl)pyrrolidin-1-yl)propan-2-yl)-2-methylpyridine | | |
| 280 | 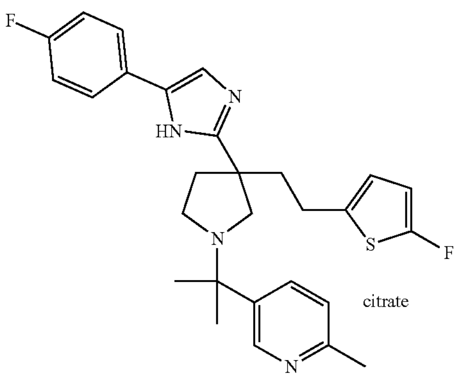 [SMILES: Cc1ccc(C(C)(C)N2CCC(CCc3ccc(F)s3)(c3ncc(-c4ccc(F)cc4)[nH]3)C2)cn1] | (S or R)-5-(2-(3-(5-(4-fluorophenyl)-1H-imidazol-2-yl)-3-(2-(5-fluorothiophen-2-yl)ethyl)pyrrolidin-1-yl)propan-2-yl)-2-methylpyridine citrate | 493 | $^1$H NMR (300 MHz, MeOD): δ 8.62 (s, 1H), 7.99 (dd, J = 8.4, 2.3 Hz, 1H), 7.70 (dd, J = 8.5, 5.3 Hz, 2H), 7.46-7.31 (m, 2H), 7.14 (t, J = 8.8 Hz, 2H), 6.31 (t, J = 3.6 Hz, 1H), 6.22 (dd, J = 3.9, 2.1 Hz, 1H), 3.72 (d, J = 11.1 Hz, 1H), 3.41- 3.28 (m, 1H), 3.21 (d, J = 10.9 Hz, 2H), 2.92-2.73 (m, 4H), 2.68-2.59 (m, 1H), 2.48 (s, 4H), 2.41-2.27 (m, 1H), 2.22 (m, 3H), 1.74 (d, J = 5.0 Hz, 6H). |
| 281 | 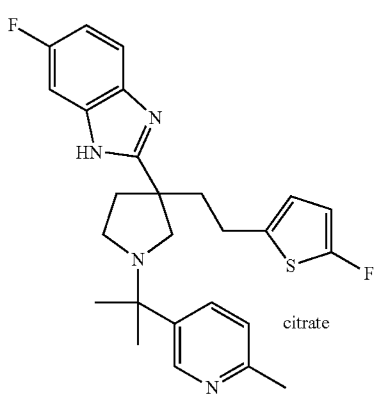 [SMILES: Cc1ccc(C(C)(C)N2CCC(CCc3ccc(F)s3)(c3nc4ccc(F)cc4[nH]3)C2)cn1] | (S or R)-6-fluoro-2-(3-(2-(5-fluorothiophen-2-yl)ethyl)-1-(2-(6-methylpyridin-3-yl)propan-2-yl)pyrrolidin-3-yl)-1H-benzo[d]imidazole citrate | 467 | $^1$H NMR (300 MHz, MeOD): δ 8.62 (s, 1H), 8.00 (d, J = 8.0 Hz, 1H), 7.51 (dd, J = 8.7, 4.6 Hz, 1H), 7.27 (dd, J = 22.7, 8.5 Hz, 2H), 7.04 (s, 1H), 6.27 (s, 1H), 6.19 (s, 1H), 3.73 (d, J = 10.0 Hz, 1H), 3.39-3.33 (m, 1H), 3.25-3.10 (m, 2H), 2.93-2.74 (m, 6H), 2.48 (s, 3H), 2.35-2.11 (m, 4H), 1.72 (d, J = 6.7 Hz, 6H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 282 | 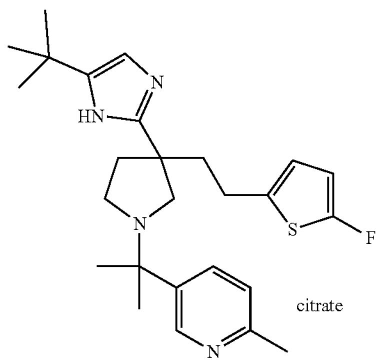 [SMILES: Cc1ccc(C(C)(C)N2CCC(CCc3ccc(F)s3)(c3ncc(C(C)(C)C)[nH]3)C2)cn1] | (S or R)-5-(2-(3-(5-(tert-butyl)-1H-imidazol-2-yl)-3-(2-(5-fluoro-thiophen-2-yl)ethyl)pyrrolidin-1-yl)propan-2-yl)-2-methylpyridine citrate | 455 | $^1$H NMR (300 MHz, MeOD): δ 8.45 (s, 1H), 7.85 (d, J = 8.2 Hz, 1H), 7.34 (d, J = 8.1 Hz, 1H), 7.06 (s, 1H), 6.30 (s, 1H), 6.24 (s, 1H), 3.11 (d, J = 9.3 Hz, 1H), 3.05-2.96 (m, 2H), 2.93-2.74 (m, 4H), 2.65-2.43 (m, 6H), 2.36-2.25 (m, 1H), 2.22-2.11 (m, 2H), 1.99 (s, 1H), 1.50 (d, J = 6.2 Hz, 6H), 1.34 (s, 9H). |
| 283 | 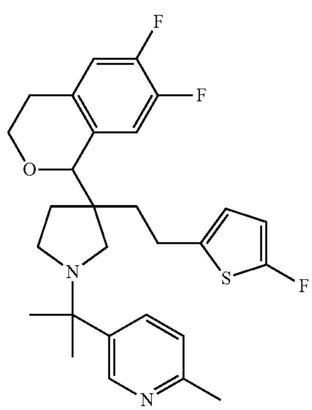 [SMILES: Cc1ccc(C(C)(C)N2CCC(CCc3ccc(F)s3)(C3OCCc4cc(F)c(F)cc43)C2)cn1] | 5-(2-((R or S)-3-((R)-6,7-difluoro-isochroman-1-yl)-3-(2-(5-fluorothiophen-2-yl)ethyl)pyrrolidin-1-yl)propan-2-yl)-2-methylpyridine | | |
| 284 | 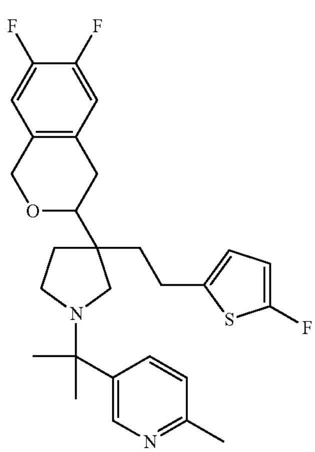 [SMILES: Cc1ccc(C(C)(C)N2CCC(CCc3ccc(F)s3)(C3Cc4cc(F)c(F)cc4CO3)C2)cn1] | 5-(2-((R or S)-3-((R)-6,7-difluoro-isochroman-3-yl)-3-(2-(5-fluorothiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 285 | 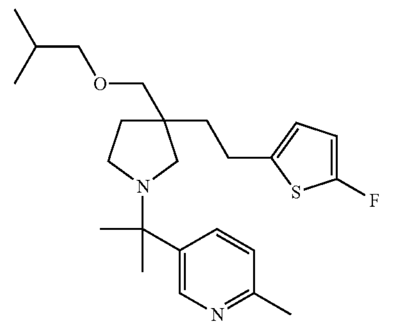 [SMILES: Cc1ccc(C(C)(C)N2CCC(CCc3ccc(F)s3)(COCC(C)C)C2)cn1] | (R or S)-5-(2-(3-(2-(5-fluoro-thiophen-2-yl)ethyl)-3-(isobutoxy-methyl)pyrrolidin-1-yl)propan-2-yl)-2-methylpyridine | | |
| 286 | 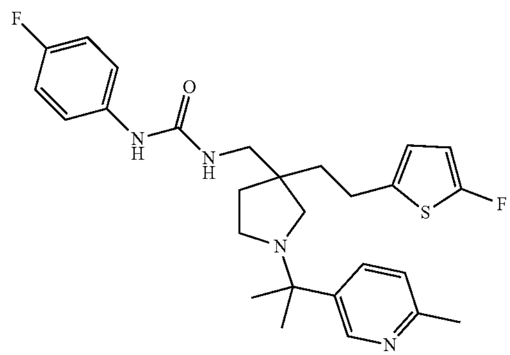 [SMILES: Cc1ccc(C(C)(C)N2CCC(CCc3ccc(F)s3)(CNC(=O)Nc3ccc(F)cc3)C2)cn1] | (S or R)-1-(4-fluorophenyl)-3-((3-(2-(5-fluoro-thiophen-2-yl)ethyl)-1-(2-(6-methylpyridin-3-yl)propan-2-yl)pyrrolidin-3-yl)methyl)urea | | |
| 287 | 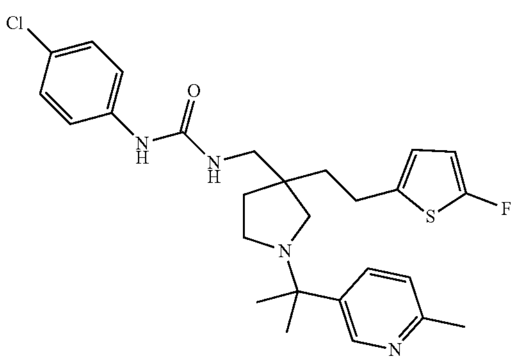 [SMILES: Cc1ccc(C(C)(C)N2CCC(CCc3ccc(F)s3)(CNC(=O)Nc3ccc(Cl)cc3)C2)cn1] | (S or R)-1-(4-chlorophenyl)-3-((3-(2-(5-fluoro-thiophen-2-yl)ethyl)-1-(2-(6-methylpyridin-3-yl)propan-2-yl)pyrrolidin-3-yl)methyl)urea | | |
| 288 | 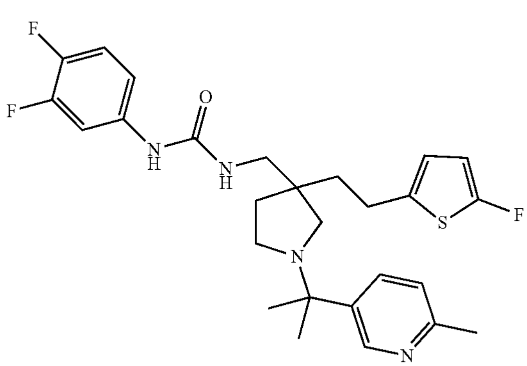 [SMILES: Cc1ccc(C(C)(C)N2CCC(CCc3ccc(F)s3)(CNC(=O)Nc3ccc(F)c(F)c3)C2)cn1] | (S or R)-1-(3,4-difluoro-phenyl)-3-((3-(2-(5-fluorothiophen-2-yl)ethyl)-1-(2-(6-methylpyridin-3-yl)propan-2-yl)pyrrolidin-3-yl)methyl)urea | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 289 | 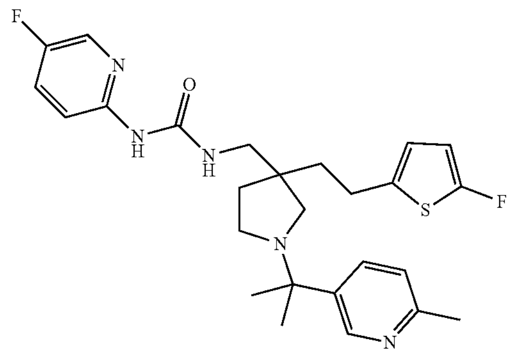 [SMILES: Cc1ccc(C(C)(C)N2CCC(CCc3ccc(F)s3)(CNC(=O)Nc3ccc(F)cn3)C2)cn1] | (S or R)-1-(5-fluoropyridin-2-yl)-3-((3-(2-(5-fluorothiophen-2-yl)ethyl)-1-(2-(6-methylpyridin-3-yl)propan-2-yl)pyrrolidin-3-yl)methyl)urea | | |
| 290 | 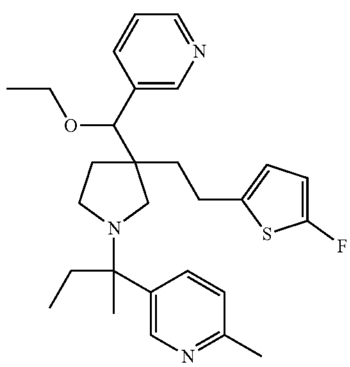 [SMILES: CCOC(c1cccnc1)C1(CCc2ccc(F)s2)CCN(C(C)(CC)c2ccc(C)nc2)C1] | 5-(2-((R or S)-3-(ethoxy(pyridin-3-yl)methyl)-3-(2-(5-fluorothiophen-2-yl)ethyl)pyrrolidin-1-yl)butan-2-yl)-2-methylpyridine | | |
| 291 | 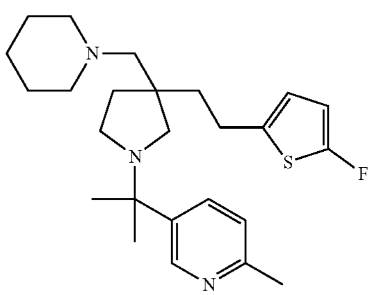 [SMILES: Cc1ccc(C(C)(C)N2CCC(CCc3ccc(F)s3)(CN3CCCCC3)C2)cn1] | (S or R)-5-(2-(3-(2-(5-fluoro-thiophen-2-yl)ethyl)-3-(piperidin-1-ylmethyl)pyrrolidin-1-yl)propan-2-yl)-2-methylpyridine | | |
| 292 | 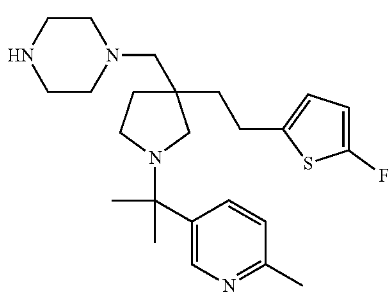 [SMILES: Cc1ccc(C(C)(C)N2CCC(CCc3ccc(F)s3)(CN3CCNCC3)C2)cn1] | (S or R)-1-((3-(2-(5-fluoro-thiophen-2-yl)ethyl)-1-(2-(6-methylpyridin-3-yl)propan-2-yl)pyrrolidin-3-yl)methyl)piperazine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 293 | 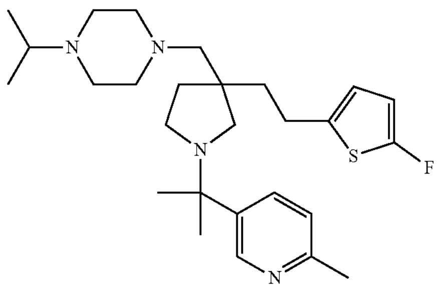 [SMILES: Cc1ccc(C(C)(C)N2CCC(CCc3ccc(F)s3)(CN3CCN(C(C)C)CC3)C2)cn1] | (S or R)-1-((3-(2-(5-fluoro-thiophen-2-yl)ethyl)-1-(2-(6-methylpyridin-3-yl)propan-2-yl)pyrrolidin-3-yl)methyl)-4-isopropylpiperazine | | |
| 294 | 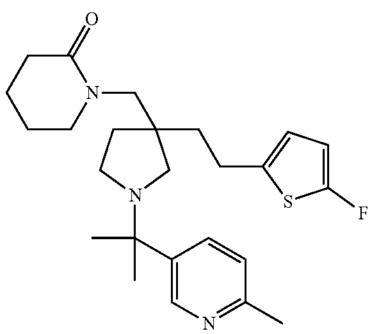 [SMILES: Cc1ccc(C(C)(C)N2CCC(CCc3ccc(F)s3)(CN3CCCCC3=O)C2)cn1] | (R or S)-1-((3-(2-(5-fluoro-thiophen-2-yl)ethyl)-1-(2-(6-methylpyridin-3-yl)propan-2-yl)pyrrolidin-3-yl)methyl)piperidin-2-one | | |
| 295 | 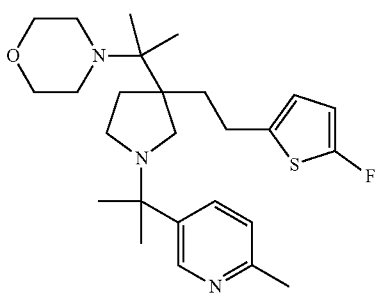 [SMILES: Cc1ccc(C(C)(C)N2CCC(CCc3ccc(F)s3)(C(C)(C)N3CCOCC3)C2)cn1] | (R or S)-4-(2-(3-(2-(5-fluoro-thiophen-2-yl)ethyl)-1-(2-(6-methylpyridin-3-yl)propan-2-yl)pyrrolidin-3-yl)propan-2-yl)morpholine | | |
| 296 | 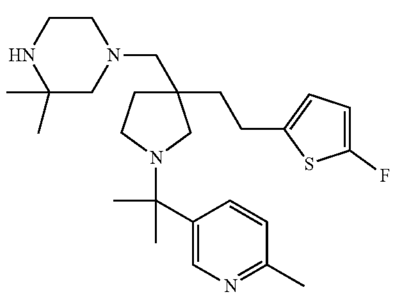 [SMILES: Cc1ccc(C(C)(C)N2CCC(CCc3ccc(F)s3)(CN3CCNC(C)(C)C3)C2)cn1] | (S or R)-1-((3-(2-(5-fluoro-thiophen-2-yl)ethyl)-1-(2-(6-methylpyridin-3-yl)propan-2-yl)pyrrolidin-3-yl)methyl)-3,3-dimethylpiperazine | | |
| 297 | 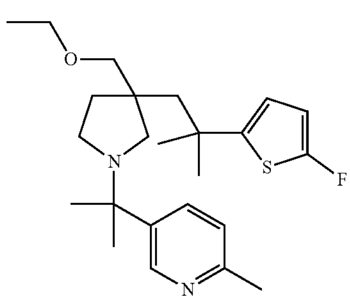 [SMILES: CCOCC1(CC(C)(C)c2ccc(F)s2)CCN(C(C)(C)c2ccc(C)nc2)C1] | 5-(2-(3-(ethoxymethyl)-3-(2-(5-fluorothio-phen-2-yl)-2-methyl-propyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 298 | 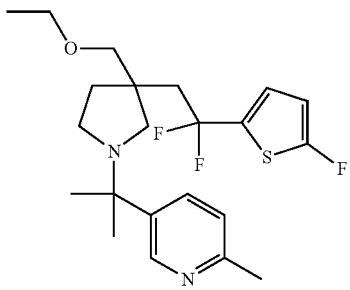 [SMILES: CCOCC1(CC(F)(F)c2ccc(F)s2)CCN(C(C)(C)c2ccc(C)nc2)C1] | 5-(2-(3-(2,2-difluoro-2-(5-fluorothiophen-2-yl)ethyl)-3-(ethoxymethyl)pyrrolidin-1-yl)propan-2-yl)-2-methylpyridine | | |
| 299 | 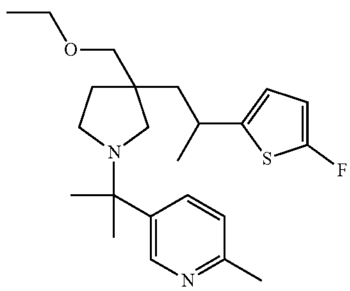 [SMILES: CCOCC1(CC(C)c2ccc(F)s2)CCN(C(C)(C)c2ccc(C)nc2)C1] | 5-(2-(3-(ethoxymethyl)-3-(2-(5-fluorothiophen-2-yl)propyl)pyrrolidin-1-yl)propan-2-yl)-2-methylpyridine | | |
| 300 | 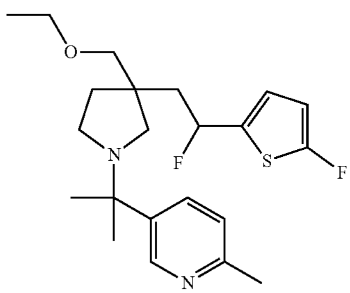 [SMILES: CCOCC1(CC(F)c2ccc(F)s2)CCN(C(C)(C)c2ccc(C)nc2)C1] | 5-(2-(3-(ethoxymethyl)-3-(2-fluoro-2-(5-fluorothiophen-2-yl)ethyl)pyrrolidin-1-yl)propan-2-yl)-2-methylpyridine | | |
| 301 | 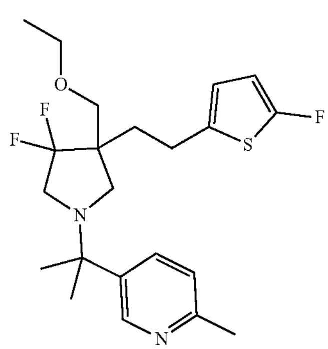 [SMILES: CCOCC1(CCc2ccc(F)s2)CN(C(C)(C)c2ccc(C)nc2)CC1(F)F] | 5-(2-(3-(ethoxymethyl)-4,4-difluoro-3-(2-(5-fluorothiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 302 | 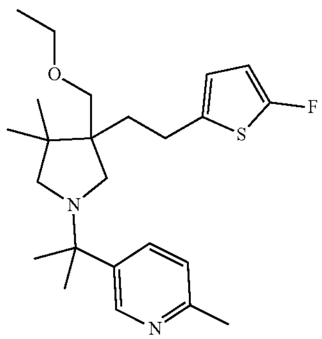 [SMILES: CCOCC1(CCc2ccc(F)s2)CN(C(C)(C)c2ccc(C)nc2)CC1(C)C] | 5-(2-(3-(ethoxymethyl)-3-(2-(5-fluorothiophen-2-yl)ethyl)-4,4-dimethylpyrrolidin-1-yl)propan-2-yl)-2-methylpyridine | | |
| 303 | 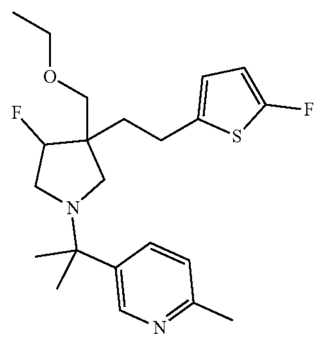 | 5-(2-(3-(ethoxymethyl)-4-fluoro-3-(2-(5-fluorothiophen-2-yl)ethyl)pyrrolidin-1-yl)propan-2-yl)-2-methylpyridine | | |
| 304 | 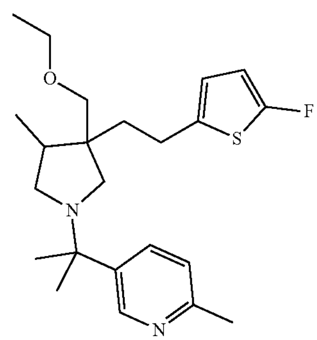 [SMILES: CCOCC1(CCc2ccc(F)s2)CN(C(C)(C)c2ccc(C)nc2)CC1C] | 5-(2-(3-(ethoxymethyl)-3-(2-(5-fluorothiophen-2-yl)ethyl)-4-methylpyrrolidin-1-yl)propan-2-yl)-2-methylpyridine | | |
| 305 | 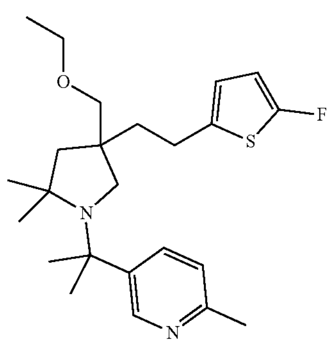 [SMILES: CCOCC1(CCc2ccc(F)s2)CN(C(C)(C)c2ccc(C)nc2)C(C)(C)C1] | 5-(2-(4-(ethoxymethyl)-4-(2-(5-fluorothiophen-2-yl)ethyl)-2,2-dimethylpyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 306 | 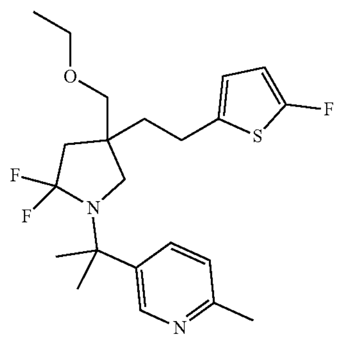 [SMILES: CCOCC1(CCc2ccc(F)s2)CN(C(C)(C)c2ccc(C)nc2)C(F)(F)C1] | 5-(2-(4-(ethoxymethyl)-2,2-difluoro-4-(2-(5-fluorothiophen-2-yl)ethyl)pyrrolidin-1-yl)propan-2-yl)-2-methylpyridine | | |
| 307 | 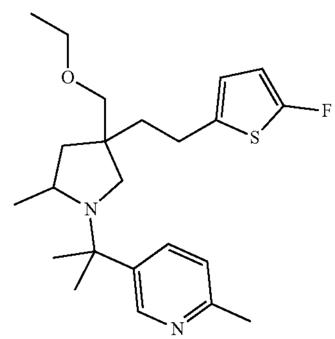 [SMILES: CCOCC1(CCc2ccc(F)s2)CC(C)N(C(C)(C)c2ccc(C)nc2)C1] | 5-(2-(4-(ethoxymethyl)-4-(2-(5-fluorothiophen-2-yl)ethyl)-2-methylpyrrolidin-1-yl)propan-2-yl)-2-methylpyridine | | |
| 308 | 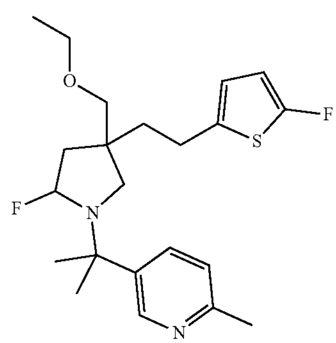 [SMILES: CCOCC1(CCc2ccc(F)s2)CC(F)N(C(C)(C)c2ccc(C)nc2)C1] | 5-(2-(4-(ethoxymethyl)-2-fluoro-4-(2-(5-fluorothiophen-2-yl)ethyl)pyrrolidin-1-yl)propan-2-yl)-2-methylpyridine | | |
| 309 | 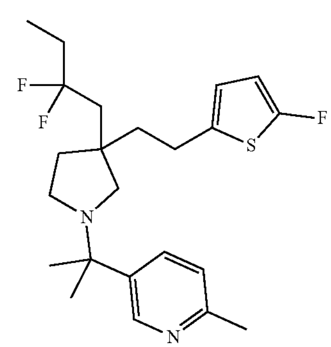 [SMILES: CCC(F)(F)CC1(CCc2ccc(F)s2)CCN(C(C)(C)c2ccc(C)nc2)C1] | (S or R)-5-(2-(3-(2,2-difluorobutyl)-3-(2-(5-fluorothiophen-2-yl)ethyl)pyrrolidin-1-yl)propan-2-yl)-2-methylpyridine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 310 | 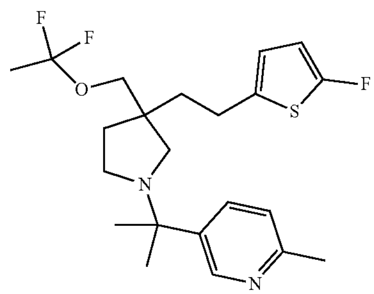 [SMILES: Cc1ccc(C(C)(C)N2CCC(CCc3ccc(F)s3)(COC(C)(F)F)C2)cn1] | (R or S)-5-(2-(3-((1,1-di-fluoroethoxy)methyl)-3-(2-(5-fluorothiophen-2-yl)ethyl)pyrrolidin-1-yl)propan-2-yl)-2-methylpyridine | | |
| 311 | 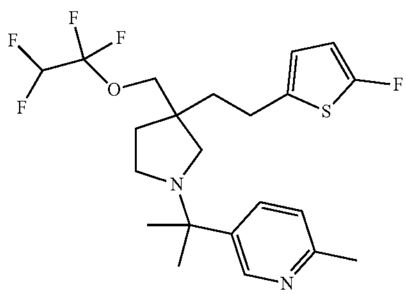 [SMILES: Cc1ccc(C(C)(C)N2CCC(CCc3ccc(F)s3)(COC(F)(F)C(F)F)C2)cn1] | (R or S)-5-(2-(3-(2-(5-fluoro-thiophen-2-yl)ethyl)-3-((1,1,2,2-tetrafluoro-ethoxy)methyl)pyr-rolidin-1-yl)propan-2-yl)-2-methylpyridine | | |
| 312 | 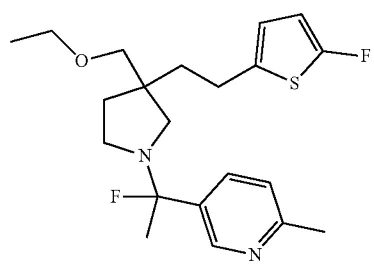 [SMILES: CCOCC1(CCc2ccc(F)s2)CCN(C(C)(F)c2ccc(C)nc2)C1] | 5-(1-((R or S)-3-(ethoxymethyl)-3-(2-(5-fluorothio-phen-2-yl)ethyl)pyr-rolidin-1-yl)-1-fluoro-ethyl)-2-methylpyridine | | |
| 313 | 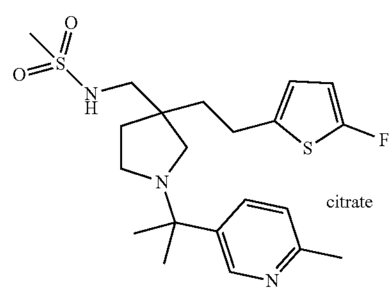 [SMILES: Cc1ccc(C(C)(C)N2CCC(CCc3ccc(F)s3)(CNS(C)(=O)=O)C2)cn1] | (S or R)-N-((3-(2-(5-fluoro-thiophen-2-yl)ethyl)-1-(2-(6-methylpyridin-3-yl)propan-2-yl)pyrrolidin-3-yl)methyl)methane-sulfonamide citrate | 440 | $^1$H NMR (300 MHz, MeOD): δ 8.67 (s, 1H), 8.06 (d, J = 8.1 Hz, 1H), 7.41 (d, J = 8.2 Hz, 1H), 6.44 (t, J = 3.6 Hz, 1H), 6.29 (dd, J = 3.9, 2.1 Hz, 1H), 3.26-3.17 (m, 2H), 3.15-3.06 (m, 3H), 2.94 (s, 3H), 2.90-2.72 (m, 6H), 2.71-2.64 (m, 2H), 2.56 (s, 3H), 1.92-1.83 (m, 2H), 1.78 (s, 6H), 1.75-1.72 (m, 1H). |
| 314 | 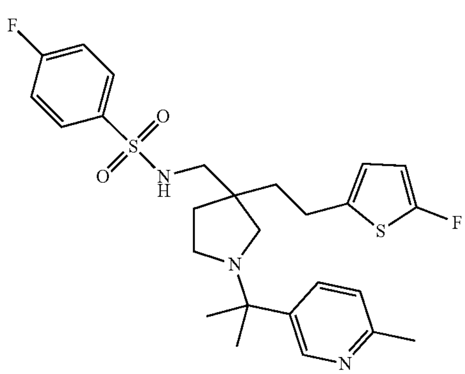 [SMILES: Cc1ccc(C(C)(C)N2CCC(CCc3ccc(F)s3)(CNS(=O)(=O)c3ccc(F)cc3)C2)cn1] | (S or R)-4-fluoro-N-((3-(2-(5-fluorothiophen-2-yl)ethyl)-1-(2-(6-methylpyridin-3-yl)propan-2-yl)pyrrolidin-3-yl)methyl)benzene-sulfonamide | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 315 | 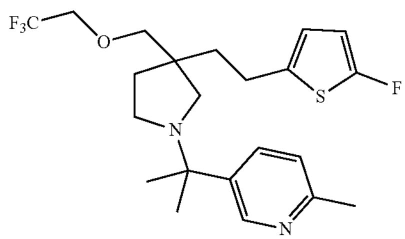 [SMILES: Cc1ccc(C(C)(C)N2CCC(CCc3ccc(F)s3)(COCC(F)(F)F)C2)cn1] | (S or R)-5-(2-(3-(2-(5-fluoro-thiophen-2-yl)ethyl)-3-((2,2,2-trifluoro-ethoxy)methyl)pyr-rolidin-1-yl)propan-2-yl)-2-methylpyridine | | |
| 316 | 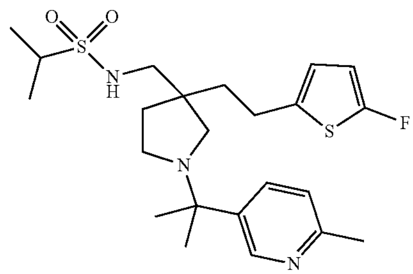 [SMILES: Cc1ccc(C(C)(C)N2CCC(CCc3ccc(F)s3)(CNS(=O)(=O)C(C)C)C2)cn1] | (S or R)-N-((3-(2-(5-fluoro-thiophen-2-yl)ethyl)-1-(2-(6-methyl-pyridin-3-yl)propan-2-yl)pyrrolidin-3-yl)methyl)propane-2-sulfonamide | | |
| 317 | 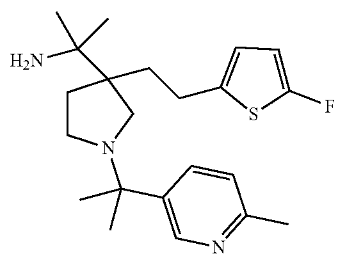 [SMILES: Cc1ccc(C(C)(C)N2CCC(CCc3ccc(F)s3)(C(C)(C)N)C2)cn1] | (S or R)-2-(3-(2-(5-fluoro-thiophen-2-yl)ethyl)-1-(2-(6-methylpyridin-3-yl)propan-2-yl)pyrrolidin-3-yl)propan-2-amine | | |
| 318 | 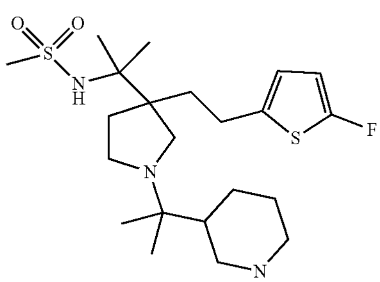 [SMILES: CC(C)(C1CCCNC1)N1CCC(CCc2ccc(F)s2)(C(C)(C)NS(C)(=O)=O)C1] | (S or R)-N-(2-(3-(2-(5-fluoro-thiophen-2-yl)ethyl)-1-(2-(6-methylpyridin-3-yl)propan-2-yl)pyrrolidin-3-yl)propan-2-yl)methanesulfonamide | | |
| 319 | 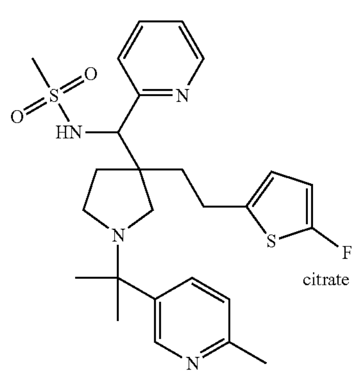 [SMILES: Cc1ccc(C(C)(C)N2CCC(CCc3ccc(F)s3)(C(NS(C)(=O)=O)c3ccccn3)C2)cn1] | N-((R & S)-((S or R)-3-(2-(5-fluorothio-phen-2-yl)ethyl)-1-(2-(6-methylpyridin-3-yl)propan-2-yl)pyr-rolidin-3-yl)(pyridin-2-yl)methyl)methane-sulfonamide citrate | 517 | $^1$H NMR (300 MHz, MeOD): δ 8.58 (d, J = 7.5 Hz, 2H), 7.96 (d, J = 8.4 Hz, 1H), 7.82 (t, J = 7.9 Hz, 1H), 7.53 (d, J = 7.7 Hz, 1H), 7.37 (d, J = 7.8 Hz, 2H), 6.39 (s, 1H), 6.28 (s, 1H), 4.64 (s, 1H), 3.50 (m, 1H), 2.88-2.72 (m, 8H), 2.70-2.62 (m, 1H), 2.56-2.52 (m, 6H), 2.32-2.18 (m, 1H), 1.93-1.90 (m, 1H), 1.87-1.50 (m, 8H). |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 320 | 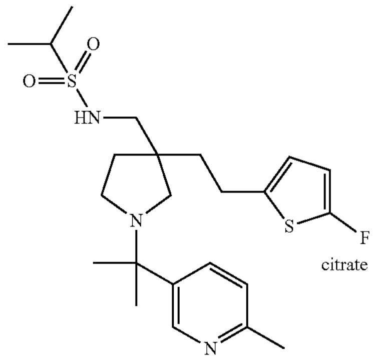 [SMILES: Cc1ccc(C(C)(C)N2CCC(CCc3ccc(F)s3)(CNS(=O)(=O)C(C)C)C2)cn1] | (S or R)-N-((3-(2-(5-fluoro-thiophen-2-yl)ethyl)-1-(2-(6-methylpyridin-3-yl)propan-2-yl)pyrrolidin-3-yl)methyl)propane-2-sulfonamide citrate | 468 | ¹H NMR (300 MHz, MeOD): δ 8.64 (s, 1H), 8.00 (d, J = 8.2 Hz, 1H), 7.38 (d, J = 8.1 Hz, 1H), 6.44 (s, 1H), 6.30 (d, J = 3.0 Hz, 1H), 3.34 (s, 3H), 3.15-3.03 (m, 4H), 2.80 (q, J = 15.5 Hz, 4H), 2.70-2.63 (m, 3H), 2.55 (s, 3H), 1.85-1.75 (m, 3H), 1.72 (s, 6H), 1.33 (d, J = 6.7 Hz, 6H). |
| 321 | 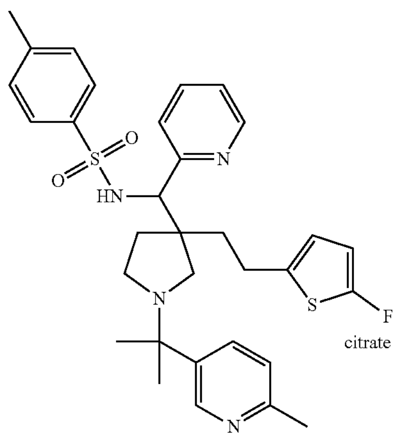 [SMILES: Cc1ccc(S(=O)(=O)NC(c2ccccn2)C2(CCc3ccc(F)s3)CCN(C(C)(C)c3ccc(C)nc3)C2)cc1] | N-((R & S)-((S or R)-3-(2-(5-fluorothio-phen-2-yl)ethyl)-1-(2-(6-methylpyridin-3-yl)propan-2-yl)pyr-rolidin-3-yl)(pyridin-2-yl)methyl)-4-methyl-benzenesulfonamide citrate | 593 | ¹H NMR (300 MHz, MeOD): δ 8.61 (s, 1H), 8.40-8.28 (m, 1H), 8.09-7.81 (m, 1H), 7.41 (q, J = 7.9, 7.1 Hz, 4H), 7.14-7.08 (m, 1H), 6.98 (dd, J = 34.6, 8.0 Hz, 3H), 6.37 (s, 1H), 6.27 (t, J = 3.1 Hz, 1H), 4.41 (s, 1H), 3.55 (m, 1H), 3.08-2.67 (m, 1H), 2.88-2.72 (m, 8H), 2.55 (d, J = 7.2 Hz, 3H), 2.27 (m, 3H), 2.22-2.17 (m, 1H), 1.93-1.60 (m, 9H). |
| 322 | 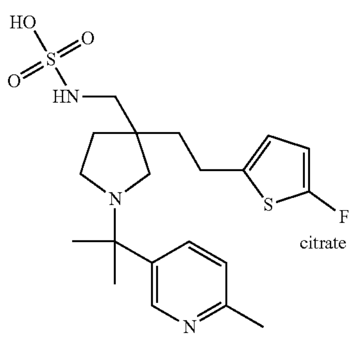 [SMILES: Cc1ccc(C(C)(C)N2CCC(CCc3ccc(F)s3)(CNS(=O)(=O)O)C2)cn1] | (S or R)-((3-(2-(5-fluoro-thiophen-2-yl)ethyl)-1-(2-(6-methylpyridin-3-yl)propan-2-yl)pyrrolidin-3-yl)methyl)sulfamic acid citrate | 442 | ¹H NMR (300 MHz, MeOD): δ 8.70 (s, 1H), 8.11 (d, J = 4.8 Hz, 1H), 8.46 (d, J = 8.1 Hz, 1H), 6.45 (s, 1H), 6.30 (s, 1H), 3.60-3.54 (m, 2H), 3.11-3.03 (m, 2H), 2.88-2.81 (m, 6H), 2.79-2.62 (m, 2H), 2.58 (s, 3H), 2.15-1.93 (m, 2H), 1.87 (s, 6H), 1.76 (d, J = 8.4 Hz, 2H). |
| 323 | 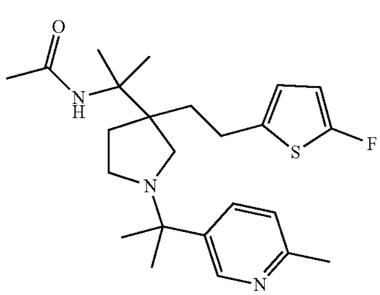 [SMILES: CC(=O)NC(C)(C)C1(CCc2ccc(F)s2)CCN(C(C)(C)c2ccc(C)nc2)C1] | (S or R)-N-(2-(3-(2-(5-fluoro-thiophen-2-yl)ethyl)-1-(2-(6-methylpyridin-3-yl)propan-2-yl)pyrrolidin-3-yl)propan-2-yl)acetamide | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 324 | 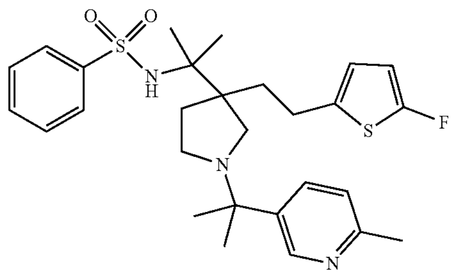 [SMILES: Cc1ccc(C(C)(C)N2CCC(CCc3ccc(F)s3)(C(C)(C)NS(=O)(=O)c3ccccc3)C2)cn1] | (S or R)-N-(2-(3-(2-(5-fluoro-thiophen-2-yl)ethyl)-1-(2-(6-methylpyridin-3-yl)propan-2-yl)pyrrolidin-3-yl)propan-2-yl)benzenesulfonamide | | |
| 325 | 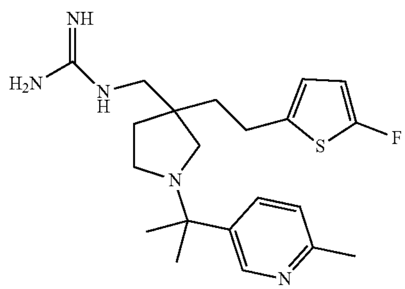 [SMILES: Cc1ccc(C(C)(C)N2CCC(CCc3ccc(F)s3)(CNC(=N)N)C2)cn1] | (R or S)-1-((3-(2-(5-fluoro-thiophen-2-yl)ethyl)-1-(2-(6-methylpyridin-3-yl)propan-2-yl)pyrrolidin-3-yl)methyl)guanidine | | |
| 326 | 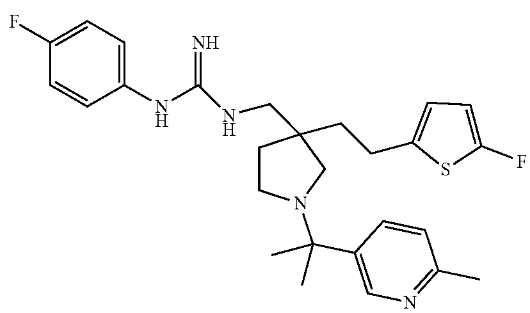 [SMILES: Cc1ccc(C(C)(C)N2CCC(CCc3ccc(F)s3)(CNC(=N)Nc3ccc(F)cc3)C2)cn1] | (R or S)-1-(4-fluorophenyl)-3-((3-(2-(5-fluoro-thiophen-2-yl)ethyl)-1-(2-(6-methylpyridin-3-yl)propan-2-yl)pyrrolidin-3-yl)methyl)guanidine | | |
| 327 | 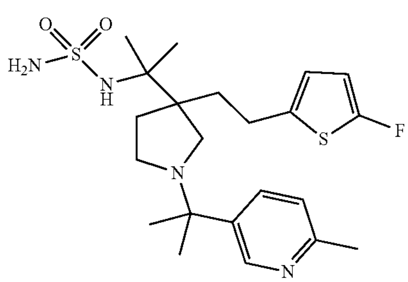 [SMILES: Cc1ccc(C(C)(C)N2CCC(CCc3ccc(F)s3)(C(C)(C)NS(N)(=O)=O)C2)cn1] | (R or S)-2-(3-(2-(5-fluoro-thiophen-2-yl)ethyl)-1-(2-(6-methylpyridin-3-yl)propan-2-yl)pyrrolidin-3-yl)propan-2-yl sulfamoylamine | | |
| 328 | 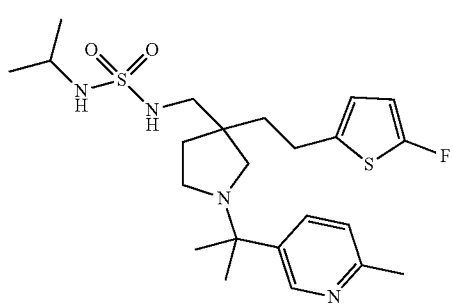 [SMILES: Cc1ccc(C(C)(C)N2CCC(CCc3ccc(F)s3)(CNS(=O)(=O)NC(C)C)C2)cn1] | (R or S)-((3-(2-(5-fluoro-thiophen-2-yl)ethyl)-1-(2-(6-methylpyridin-3-yl)propan-2-yl)pyrrolidin-3-yl)methyl)sulfamoyl propan-2-yl-amine | | |

TABLE I-continued

Compounds with a pyrrolidine ring and a pyridine or pyridine-like molecule bonded to the pyrrolidine N-constituent

| Compound No. | Structure | Name | MS (ESI+): [M + H]+ | H-NMR |
|---|---|---|---|---|
| 329 | 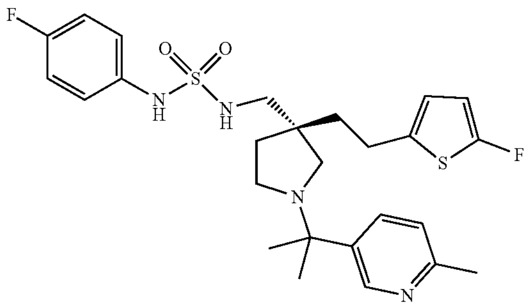 [SMILES: Cc1ccc(C(C)(C)N2CC[C@](CCc3ccc(F)s3)(CNS(=O)(=O)Nc3ccc(F)cc3)C2)cn1] | (R or S)-((3-(2-(5-fluoro-thiophen-2-yl)ethyl)-1-(2-(6-methylpyridin-3-yl)propan-2-yl)pyrrolidin-3-yl)methyl)sulfamoyl 4-fluorophenylamine | | |
| 330 | 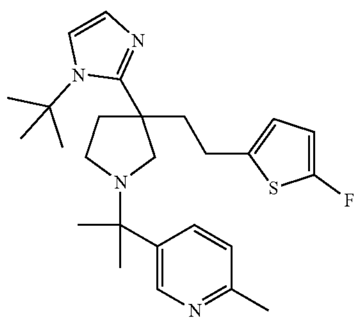 [SMILES: Cc1ccc(C(C)(C)N2CCC(CCc3ccc(F)s3)(c3nccn3C(C)(C)C)C2)cn1] | (S or R)-5-(2-(3-(1-(tert-butyl)-1H-imidazol-2-yl)-3-(2-(5-fluoro-thiophen-2-yl)ethyl)pyrrolidin-1-yl)propan-2-yl)-2-methylpyridine | | |
| 331 | 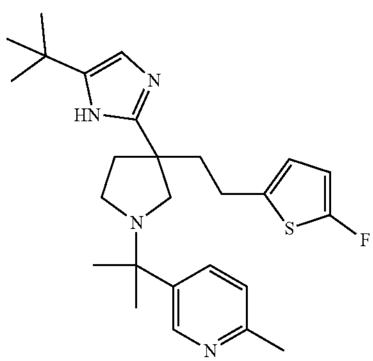 [SMILES: Cc1ccc(C(C)(C)N2CCC(CCc3ccc(F)s3)(c3ncc(C(C)(C)C)[nH]3)C2)cn1] | (S or R)-5-(2-(3-(5-(tert-butyl)-1H-imidazol-2-yl)-3-(2-(5-fluoro-thiophen-2-yl)ethyl)pyrrolidin-1-yl)propan-2-yl)-2-methylpyridine | | |
| 332 | 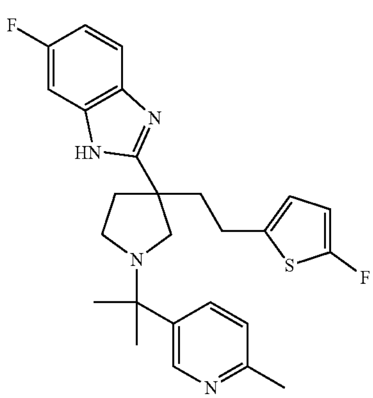 [SMILES: Cc1ccc(C(C)(C)N2CCC(CCc3ccc(F)s3)(c3nc4ccc(F)cc4[nH]3)C2)cn1] | (S or R)-6-fluoro-2-(3-(2-(5-fluorothiophen-2-yl)ethyl)-1-(2-(6-methylpyridin-3-yl)propan-2-yl)pyrrolidin-3-yl)-1H-benzo[d]imidazole | | |

Legend for Tables I, III, V; 4th & 5th Columns: Electrospray ionization (ESI) was used in mass spectrometry for the compounds with a measured mass result shown in the fourth column. The right-most (fifth) column shows the H NMR of such compounds in MeOD at 300 MHz.

TABLE II

Chirality and in vivo testing of certain compounds of Table I

| Compound No. | Configuration | ED$_{50}$ (mg/kg) at 30 min on C57BL/6 mice in Warm-water Tail-flick Test |
|---|---|---|
| 1 | S | ++ |
| 2 | S | ++ |
| 3 | S | ++ |
| 4 | S | ++ |
| 5 | (S&R, S) | ++ |
| 6 | S | ++ |
| 7 | S | ++ |
| 8 | S | ++ |
| 9 | S | ++ |
| 10 | (S, S or R) | ++ |
| 11 | (S, S or R) | ++ |
| 12 | (S, S or R) | ++ |
| 13 | (S, S or R) | ++ |
| 14 | S | ++ |
| 15 | S | ++ |
| 16 | S | ++ |
| 17 | S | + |
| 18 | S | ++ |
| 19 | S | ++ |
| 20 | S | ++ |
| 21 | S | ++ |
| 22 | S | ++ |
| 23 | S | ++ |
| 24 | S | ++ |
| 25 | S | ++ |
| 26 | S | ++ |
| 27 | S | ++ |
| 28 | S | ++ |
| 29 | (S&R) | ++ |
| 30 | S | ++ |
| 31 | S | ++ |
| 32 | S | ++ |
| 33 | S | ++ |
| 34 | (R&S, S) | ++ |
| 35 | (S or R, S) | ++ |
| 36 | S | ++ |
| 37 | (S or R, S) | ++ |
| 38 | S | ++ |
| 39 | S | ++ |
| 40 | S | ++ |
| 41 | S | ++ |
| 42 | S | ++ |
| 43 | S | ++ |
| 44 | R | ++ |
| 45 | R | + |
| 82 | S | ++ |
| 83 | S | ++ |
| 84 | S | ++ |
| 85 | S | ++ |
| 86 | (S, R&S) | ++ |
| 87 | (S, S or R) | ++ |
| 88 | (S, S or R) | ++ |
| 89 | (S, S or R) | ++ |
| 90 | (S, R&S) | ++ |
| 91 | (R&S) | ++ |
| 92 | (R&S) | ++ |
| 93 | S | ++ |
| 94 | (S, S or R) | ++ |
| 95 | (S, S or R) | ++ |
| 96 | (S, S or R) | ++ |
| 97 | (S, S or R) | ++ |
| 98 | (S, S or R) | ++ |
| 99 | (R&S) | ++ |
| 100 | (R&S) | ++ |
| 101 | (R&S) | ++ |
| 102 | S | + |
| 103 | (S, R&S) | ++ |
| 104 | (S, S or R) | ++ |
| 105 | (S, S or R) | ++ |
| 106 | S | ++ |
| 107 | S | ++ |
| 108 | S | ++ |
| 109 | S | ++ |
| 110 | S | + |
| 111 | S | ++ |
| 112 | (R&S, S) | ++ |
| 113 | S | ++ |
| 114 | S | ++ |
| 115 | S | ++ |
| 116 | S | ++ |
| 117 | S | ++ |
| 118 | S | ++ |
| 119 | S | ++ |
| 120 | S | ++ |
| 121 | S | ++ |
| 122 | R | ++ |
| 123 | R | ++ |
| 124 | R | + |
| 125 | S | + |
| 126 | S | ++ |
| 127 | S | ++ |
| 235 | R | + |
| 270 | R | + |
| 280 | S | ++ |
| 281 | S | ++ |
| 282 | S | ++ |
| 313 | S | ++ |
| 319 | (R&S, S) | ++ |
| 320 | S | ++ |
| 321 | (R&S, S) | ++ |
| 322 | S | ++ |

Legend for Table II, Middle Column:

"S" means the S enantiomer was tested with the result shown in the right-most column.

"R" means the R enantiomer was tested with the result shown in the right-most column.

"R&S" means the racemate was tested.

"S, S or R" means the compound has two chiral centers and can possibly have four diastereomers. The compound with S at the 1st chiral center and S or R at the 2nd chiral center was tested.

"R, R&S" means the compound has two chiral centers and can possibly have four diastereomers. The compound with R at the 1st chiral center and the racemate at the 2nd chiral center was tested.

"S, R&S" means the compound has two chiral centers and can possibly have four diastereomers. The compound with S at the 1st chiral center and the racemate at the 2nd chiral center was tested.

Right-Most Column in Table II:

Shows results from an antinociception and warm-water tail-flick test, using male C57BL/6 mice (20-30 g; 6-12 wks), maintained on a 12-h light/dark cycle with rodent chow and water available ad libitum, and housed separately until testing. Antinociception was assessed using the 55° C. warm-water tail-flick test. The latency to the first sign of a rapid tail flick was taken as the behavioral endpoint. Each mouse was first tested for baseline latency by immersing its tail in the water and recording the time to response. Mice not responding within 2 secs were excluded from further testing. Responsive mice were then s.c. administered the test compound and tested for antinociception at 30 min, 60 min, 90 min, and 120 min time points afterward. Antinociception was calculated using the following formula: percentage of antinociception=100×(test latency-control latency)/(20-control latency). To avoid tissue damage, a maximum score was assigned (100%) to animals that failed to respond within 20 secs.

TABLE III

New Compounds with a pyrrolidine ring and a non-pyridine-like molecule bonded to the pyrrolidine N-constituent

| Compound No. | Structure | Name | MS (ESI+): [M + H]+ | H-NMR |
|---|---|---|---|---|
| 1 | 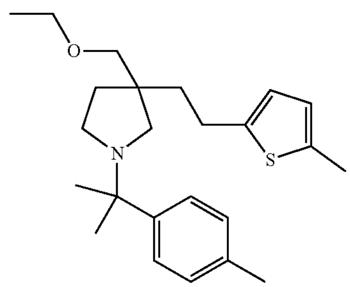 [SMILES: CCOCC1(CCc2ccc(C)s2)CCN(C(C)(C)c2ccc(C)cc2)C1] | (R or S)-3-(ethoxymethyl)-3-(2-(5-methylthiophen-2-yl)ethyl)-1-(2-(p-tolyl)propan-2-yl)pyrrolidine | 386 | $^1$H NMR (300 MHz, CDCl$_3$: δ 7.39-7.28 (m, 2H), 7.03 (d, J = 8.0 Hz, 2H), 6.46 (s, 2H), 3.43-3.36 (m, 2H), 3.19 (q, J = 8.8 Hz, 2H), 2.62 (t, J = 8.4 Hz, 2H), 2.49 (dd, J = 11.1, 6.9 Hz, 2H), 2.39 (d, J = 9.0 Hz, 1H), 2.35 (s, 3H), 2.25 (d, J = 9.1 Hz, 1H), 1.78-1.67 (m, 2H), 1.47 (t, J = 6.8 Hz, 2H), 1.33 (t, J = 7.2 Hz, 3H), 1.28 (s, 6H), 1.09 (t, J = 7.2 Hz, 3H). |
| 2 | 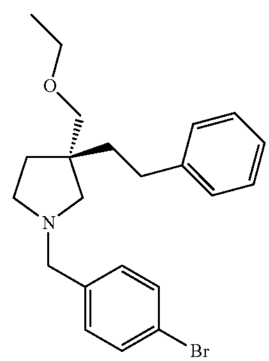 [SMILES: CCOC[C@@]1(CCc2ccccc2)CCN(Cc2ccc(Br)cc2)C1] | (S)-1-(4-bromobenzyl)-3-(ethoxymethyl)-3-phenethylpyrrolidine | 402 | $^1$H NMR (300 MHz, MeOD): δ 7.53 (d, J = 8.1 Hz, 2H), 7.32 (d, J = 8.1 Hz, 2H), 7.30-7.21 (m, 2H), 7.19-7.10 (m, 3H), 3.86-3.77 (m, 2H), 3.51 (q, J = 7.2 Hz, 2H), 3.37 (s, 2H), 2.91-2.77 (m, 3H), 2.60-2.51 (m, 3H), 1.86-1.71 (m, 4H), 1.21 (t, J = 6.9 Hz, 3H). |
| 3 | 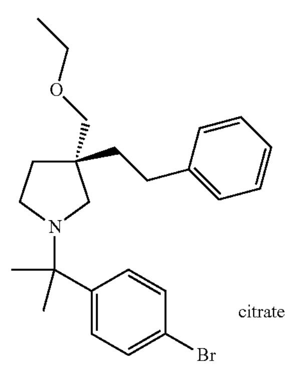 [SMILES: CCOC[C@@]1(CCc2ccccc2)CCN(C(C)(C)c2ccc(Br)cc2)C1] | (S)-1-(2-(4-bromophenyl)propan-2-yl)-3-(ethoxymethyl)-3-phenethylpyrrolidine citrate | 430 | $^1$H NMR (300 MHz, MeOD): δ 7.68-7.59 (m, 4H), 7.27-7.22 (m, 2H), 7.17-7.12 (m, 3H), 3.52 (q, J = 8.4 Hz, 2H), 3.42-3.39 (m, 3H), 3.25-3.14 (m, 2H), 2.97-2.88 (m, 1H), 2.85-2.69 (m, 4H), 2.55-2.49 (m, 2H), 2.04-1.81 (m, 2H), 1.78 (s, 6H), 1.18 (t, J = 6.9 Hz, 3H). |

TABLE III-continued

New Compounds with a pyrrolidine ring and a
non-pyridine-like molecule bonded to the pyrrolidine N-constituent

| Compound No. | Structure | Name | MS (ESI+): [M + H]$^+$ | H-NMR |
|---|---|---|---|---|
| 4 | 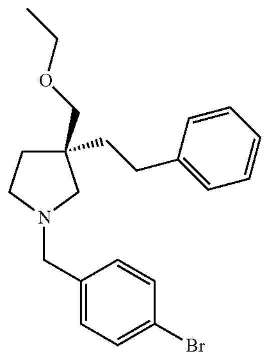 [SMILES: CCOC[C@]1(CCc2ccccc2)CCN(Cc2ccc(Br)cc2)C1] | (R)-1-(4-bromobenzyl)-3-(ethoxymethyl)-3-phenethylpyrrolidine | 402 | $^1$H NMR (300 MHz, MeOD): δ 7.43 (d, J = 8.1 Hz, 2H), 7.33-7.25 (m, 2H), 7.22-7.14 (m, 5H), 3.52-3.43 (m, 4H), 3.35-3.25 (m, 2H), 2.62-2.57 (m, 5H), 2.28 (d, J = 9.6 Hz, 1H), 1.81-1.68 (m, 2H), 1.69-1.61 (m, 2H), 1.18 (t, J = 6.9 Hz, 3H). |
| 5 | 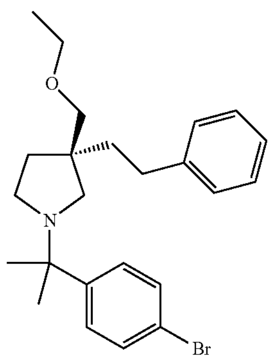 [SMILES: CCOC[C@]1(CCc2ccccc2)CCN(C(C)(C)c2ccc(Br)cc2)C1] | (R)-1-(2-(4-bromophenyl)propan-2-yl)-3-(ethoxymethyl)-3-phenethylpyrrolidine | 430 | $^1$H NMR (300 MHz, MeOD): δ 7.41-7.36 (m, 4H), 7.28-7.22 (m, 2H), 7.18-7.11 (m, 3H), 3.48 (q, J = 6.9 Hz, 2H), 3.33-3.25 (m, 2H), 2.62-2.52 (m, 4H), 2.48 (d, J = 9.0 Hz, 1H), 2.31 (d, J = 9.0 Hz, 1H), 1.82-1.65 (m, 2H), 1.68-1.51 (m, 2H), 1.33 (s, 6H), 1.18 (t, J = 6.9 Hz, 3H). |
| 6 | 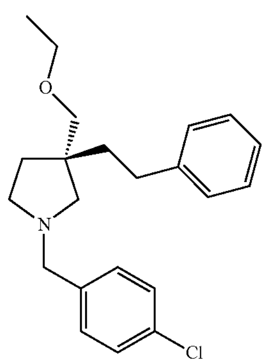 | (S)-1-(4-chlorobenzyl)-3-(ethoxymethyl)-3-phenethylpyrrolidine | 358 | $^1$H NMR (300 MHz, MeOD): δ 7.34-7.31 (m, 4H), 7.25-7.21 (m, 2H), 7.16-7.12 (m, 3H), 3.52 (s, 2H), 3.48 (q, J = 6.9 Hz, 2H), 3.33-3.30 (m, 2H), 2.65-2.59 (m, 3H), 2.58-2.51 (m, 2H), 2.33-2.30 (m, 1H), 1.78-1.64 (m, 4H), 1.18 (t, J = 6.9 Hz, 3H). |
| 7 | 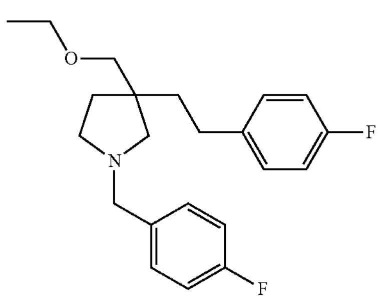 [SMILES: CCOCC1(CCc2ccc(F)cc2)CCN(Cc2ccc(F)cc2)C1] | (R or S)-3-(ethoxymethyl)-1-(4-fluorobenzyl)-3-(4-fluorophenethyl)pyrrolidine | | |

TABLE III-continued

New Compounds with a pyrrolidine ring and a
non-pyridine-like molecule bonded to the pyrrolidine N-constituent

| Compound No. | Structure | Name | MS (ESI+): [M + H]+ | H-NMR |
|---|---|---|---|---|
| 8 | 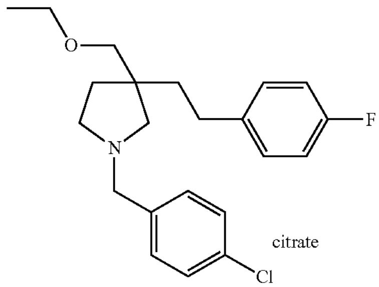 [SMILES: CCOCC1(CCc2ccc(F)cc2)CCN(Cc2ccc(Cl)cc2)C1] | (R or S)-1-(4-chlorobenzyl)-3-(ethoxymethyl)-3-(4-fluorophenethyl)pyrrolidine citrate | 376 | $^1$H NMR (300 MHz, MeOD): δ 7.50 (s, 4H), 7.20 (t, J = 6.8 Hz, 2H), 6.98 (t, J = 8.6 Hz, 2H), 4.50-4.20 (m, 2H), 3.64-3.51 (m, 3H), 3.49-3.39 (m, 4H), 3.21-3.08 (m, 1H), 2.81 (q, J = 15.6 Hz, 4H), 2.65-2.51 (m, 2H), 2.17-1.96 (m, 2H), 1.92-1.74 (m, 2H), 1.21 (t, J = 6.9 Hz, 3H). |
| 9 | 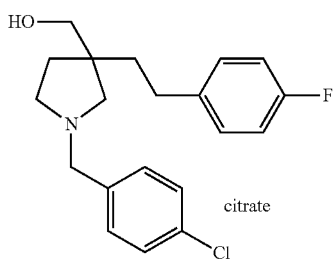 [SMILES: OCC1(CCc2ccc(F)cc2)CCN(Cc2ccc(Cl)cc2)C1] | (R or S)-(1-(4-chlorobenzyl)-3-(4-fluorophenethyl)pyrrolidin-3-yl)methanolcitrate | 348 | $^1$H NMR (300 MHz, MeOD): δ 7.50 (s, 4H), 7.21 (dd, J = 8.4, 5.4 Hz, 2H), 6.98 (t, J = 8.6 Hz, 2H), 4.86-4.68 (m, 2H), 4.44-4.23 (m, 2H), 3.60-3.53 (m, 2H), 2.92-2.72 (m, 6H), 2.59 (t, J = 8.4 Hz, 2H), 2.13-1.99 (m, 2H), 1.87-1.72 (m, 2H). |
| 10 | 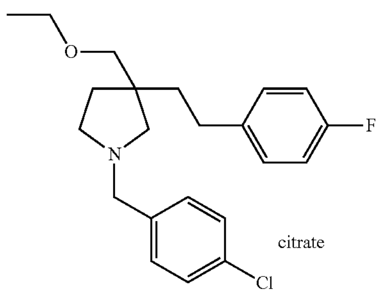 [SMILES: CCOCC1(CCc2ccc(F)cc2)CCN(Cc2ccc(Cl)cc2)C1] | (S or R)-1-(4-chlorobenzyl)-3-(ethoxymethyl)-3-(4-fluorophenethyl)pyrrolidine citrate | 376 | $^1$H NMR (300 MHz, MeOD): δ 7.50 (s, 4H), 7.20 (dd, J = 8.3, 5.4 Hz, 2H), 6.98 (t, J = 8.6 Hz, 2H), 4.36 (q, J = 12.9 Hz, 2H), 3.56 (dd, J = 7.2, 2.2 Hz, 2H), 3.45 (s, 2H), 3.35 (s, 3H), 3.14 (d, J = 11.9 Hz, 1H), 2.94-2.71 (m, 4H), 2.59 (s, 2H), 2.05 (s, 2H), 1.83 (q, J = 8.5 Hz, 2H), 1.22 (t, J = 7.0 Hz, 3H). |
| 11 | 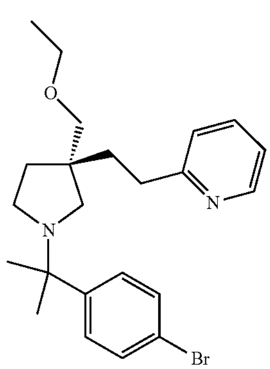 [SMILES: CCOC[C@@]1(CCc2ccccn2)CCN(C(C)(C)c2ccc(Br)cc2)C1] | (S)-2-(2-(1-(2-(4-bromophenyl)propan-2-yl)-3-(ethoxymethyl)pyrrolidin-3-yl)ethyl)pyridine | 431 | $^1$H NMR (300 MHz, MeOD): δ 8.43 (d, J = 4.2 Hz, 1H), 7.79-7.73 (m, 1H), 7.68-7.59 (m, 4H), 7.31-7.24 (m, 2H), 3.45 (q, J = 6.9 Hz, 2H), 3.40-3.32 (m, 3H), 3.19-3.13 (m, 1H), 2.98-2.95 (m, 1H), 2.70 (t, J = 8.1 Hz, 2H), 2.03-1.95 (m, 1H), 1.83-1.74 (m, 10H), 1.14 (t, J = 6.9 Hz, 3H). |

TABLE III-continued

New Compounds with a pyrrolidine ring and a
non-pyridine-like molecule bonded to the pyrrolidine N-constituent

| Compound No. | Structure | Name | MS (ESI+): [M + H]$^+$ | H-NMR |
|---|---|---|---|---|
| 12 | 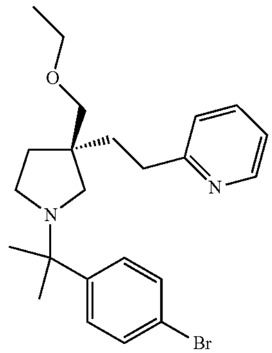 [SMILES: CCOC[C@]1(CCc2ccccn2)CCN(C(C)(C)c2ccc(Br)cc2)C1] | (R)-2-(2-(1-(2-(4-bromophenyl)propan-2-yl)-3-(ethoxymethyl)pyrrolidin-3-yl)ethyl)pyridine | 431 | $^1$H NMR (300 MHz, MeOD): δ 8.43 (d, J = 4.2 Hz, 1H), 7.79-7.73 (m, 1H), 7.68-7.60 (m, 4H), 7.31-7.24 (m, 2H), 3.45 (q, J = 6.9 Hz, 2H), 3.36-3.32 (m, 3H), 3.19-3.13 (m, 1H), 2.98-2.91 (m, 1H), 2.70 (t, J = 8.1 Hz, 2H), 2.03-1.95 (m, 1H), 1.83-1.74 (m, 10H), 1.14 (t, J = 6.9 Hz, 3H). |
| 13 | 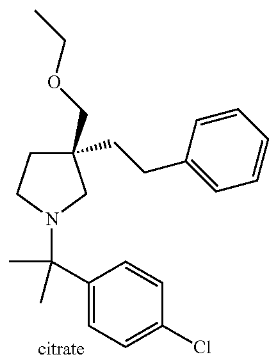 [SMILES: CCOC[C@]1(CCc2ccccc2)CCN(C(C)(C)c2ccc(Cl)cc2)C1] | (S)-1-(2-(4-chlorophenyl)propan-2-yl)-3-(ethoxymethyl)-3-phenethylpyrrolidine citrate | 386 | $^1$H NMR (300 MHz, MeOD): δ 7.50 (d, J = 2.1 Hz, 2H), 7.28-7.20 (m, 4H), 7.13-7.10 (m, 3H), 3.49 (q, J = 6.9 Hz, 2H), 3.32-3.31 (m, 2H), 2.62-2.59 (m, 2H), 2.53-2.47 (m, 3H), 2.29 (d, J = 9Hz, 1H), 1.69-1.60 (m, 4H), 1.38 (s, 6H), 1.14 (t, J = 6.9 Hz, 3H). |
| 14 | 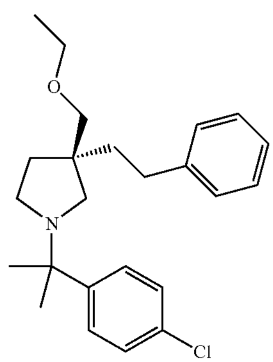 | (R)-1-(2-(4-chlorophenyl)propan-2-yl)-3-(ethoxymethyl)-3-phenethylpyrrolidine | 386 | $^1$H NMR (300 MHz, MeOD): δ 7.65 (d, J = 8.7 Hz, 2H), 7.44 (d, J = 8.7 Hz, 2H), 7.23-7.21 (m, 2H), 7.15-7.13 (m, 3H), 3.49 (q, J = 6.9 Hz, 2H), 3.34-3.30 (m, 4H), 3.14-3.09 (m, 2H), 2.98 (d, J = 10.5 Hz, 1H), 2.75 (d, J = 11.1 Hz, 1H), 2.54 (t, J = 8.4 Hz, 2H), 1.90-1.74 (m, 2H), 1.68 (s, 6H), 1.17 (t, J = 6.9 Hz, 3H). |
| 15 | 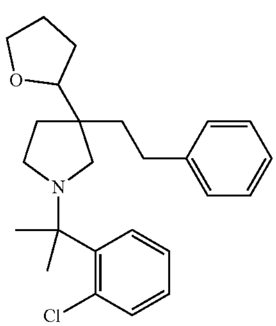 [SMILES: CC(C)(c1ccccc1Cl)N1CCC(CCc2ccccc2)(C2CCCO2)C1] | (S or R)-1-(2-(2-chlorophenyl)propan-2-yl)-3-phenethyl-3-((S&R)-tetrahydrofuran-2-yl)pyrrolidine | 398 | $^1$H NMR (300 MHz, MeOD): δ 7.72-7.68 (m, 1H), 7.68-7.58 (m, 1H), 7.49-7.47 (m, 2H), 7.27-7.16 (m, 5H), 4.01-3.96 (m, 2H), 3.80 (m, 1H), 3.45-3.34 (m, 3H), 3.08-3.04 (m, 1H), 2.80 (q, J = 15.3 Hz, 4H), 2.69-2.63 (m, 2H), 2.28 (t, J = 8.4 Hz, 2H), 2.02 (m, 3H), 2.00 (d, J = 8.7 Hz, 6H), 1.96-1.83 (m, 2H), 1.76-1.51 (m, 1H). |

TABLE III-continued

New Compounds with a pyrrolidine ring and a
non-pyridine-like molecule bonded to the pyrrolidine N-constituent

| Compound No. | Structure | Name | MS (ESI+): [M + H]+ | H-NMR |
|---|---|---|---|---|
| 16 | 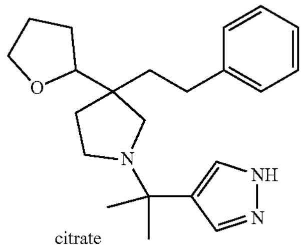 [SMILES: CC(C)(c1cn[nH]c1)N1CCC(CCc2ccccc2)(C2CCCO2)C1] | 4-(2-((S or R)-3-phenethyl-3-((S&R)-tetrahydrofuran-2-yl)pyrrolidin-1-yl)propan-2-yl)-1H-pyrazole citrate | 354 | $^1$H NMR (300 MHz, MeOD): δ 7.98 (s, 1H), 7.93 (s, 1H), 7.25-7.03 (m, 5H), 3.93-3.85 (m, 2H), 3.59-3.49 (m, 3H), 3.16-3.10 (m, 2H), 2.80 (q, J = 15.3 Hz, 4H), 2.75 (m, 1H), 2.63-2.60 (m, 1H), 2.16-0.98 (m, 5H), 1.70 (s, 6H), 1.60 (m, 1H), 1.54-1.29 (m, 2H). |
| 17 | 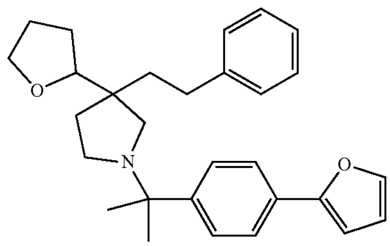 [SMILES: CC(C)(c1ccc(-c2ccco2)cc1)N1CCC(CCc2ccccc2)(C2CCCO2)C1] | (S or R)-1-(2-(4-(furan-2-yl)phenyl)propan-2-yl)-3-phenethyl-3-((S&R)-tetrahydrofuran-2-yl)pyrrolidine | 431 | $^1$H NMR (300 MHz, MeOD): δ 7.84-7.61 (m, 5H), 7.30-7.00 (m, 5H), 6.89 (d, J = 3.3 Hz, 1H), 6.56 (d, J = 4.5 Hz, 1H), 4.93 (hr s, 1H), 3.45-3.31 (m, 2H), 2.80 (q, J = 15.3 Hz, 4H), 2.68-2.45 (m, 2H), 2.30-1.95 (m, 4H), 1.88 (s, 6H), 1.86-1.60 (m, 4H), 1.39-1.29 (m, 4H). |
| 18 | 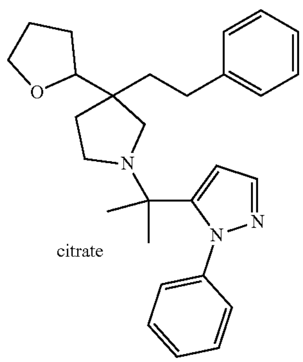 [SMILES: CC(C)(c1ccnn1-c1ccccc1)N1CCC(CCc2ccccc2)(C2CCCO2)C1] | 5-(2-((S or R)-3-phenethyl-3-((S&R)-tetrahydrofuran-2-yl)pyrrolidin-1-yl)propan-2-yl)-1-phenyl-1H-pyrazole citrate | 431 | $^1$H NMR (300 MHz, MeOD): δ 7.62 (s, 1H), 7.61-7.47 (m, 5H), 7.28-7.14 (m, 5H), 6.60 (d, J = 5.1 Hz, 1H), 3.88-3.70 (m, 3H), 2.90-2.70 (m, 8H), 2.58-2.53 (t, J = 9.0 Hz, 2H), 1.93-1.84 (m, 4H), 1.71-1.57 (m, 3H), 1.49-1.46 (m, 7H). |
| 19 | 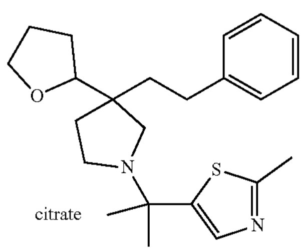 [SMILES: Cc1ncc(C(C)(C)N2CCC(CCc3ccccc3)(C3CCCO3)C2)s1] | 2-methyl-5-(2-((S or R)-3-phenethyl-3-((S&R)-tetrahydrofuran-2-yl)pyrrolidin-1-yl)propan-2-yl)thiazole citrate | 385 | $^1$H NMR (300 MHz, MeOD): δ 7.87 (d, J = 6.3 Hz, 1H), 7.27-7.12 (m, 5H), 3.89-3.81 (m, 1H), 3.49-3.41 (m, 2H), 3.40 (m, 3H), 3.30 (s, 1H), 3.32-3.10 (m, 1H), 2.80 (q, J = 15.3 Hz, 4H), 3.71 (s, 3H), 3.61-3.50 (m, 2H), 2.20-2.01 (m, 2H), 2.00-1.90 (m, 2H), 1.85-1.80 (m, 6H), 1.78-1.73 (m, 3H). |
| 20 | 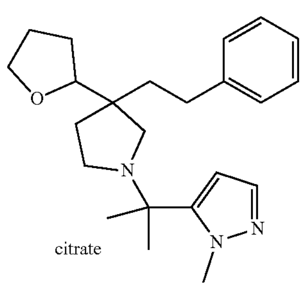 [SMILES: Cn1nccc1C(C)(C)N1CCC(CCc2ccccc2)(C2CCCO2)C1] | 1-methyl-5-(2-((S or R)-3-phenethyl-3-((S&R)-tetrahydrofuran-2-yl)pyrrolidin-1-yl)propan-2-yl)-1H-pyrazole citrate | 368 | $^1$H NMR (300 MHz, MeOD): δ 7.38 (s, 1H), 7.28-7.23 (m, 2H), 7.17-7.15 (m, 3H), 6.31 (m, 1H), 4.11 (s, 3H), 3.93-3.79 (m, 1H), 3.76-3.70 (m, 2H), 2.91-2.75 (m, 4H), 2.71-2.58 (m, 6H), 2.00-1.75 (m, 8H), 1.63-1.62 (m, 6H). |

TABLE III-continued

New Compounds with a pyrrolidine ring and a
non-pyridine-like molecule bonded to the pyrrolidine N-constituent

| Compound No. | Structure | Name | MS (ESI+): [M + H]+ | H-NMR |
|---|---|---|---|---|
| 21 | 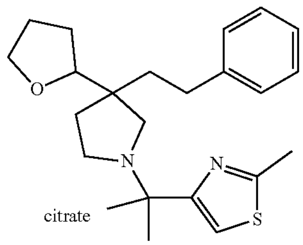 [SMILES: Cc1nc(C(C)(C)N2CCC(CCc3ccccc3)(C3CCCO3)C2)cs1] | 2-methyl-4-(2-((S or R)-3-phenethyl-3-((S&R)-tetrahydrofuran-2-yl)pyrrolidin-1-yl)propan-2-yl)thiazole citrate | 385 | $^1$H NMR (300 MHz, MeOD): δ 7.61 (s, 1H), 7.29-7.24 (m, 2H), 7.19-7.14 (m, 3H), 4.04-3.81 (m, m, 2H), 3.66-3.39 (m, 3H), 3.26 (s, 3H), 3.03 (m, 1H), 2.43 (q, J = 15.6 Hz, 4H), 2.72-2.66 (m, 5H), 2.24-2.16 (m, 2H), 2.14-2.00 (m, 2H), 1.80 (s, 6H), 1.62-1.53 (m, 2H). |
| 22 | 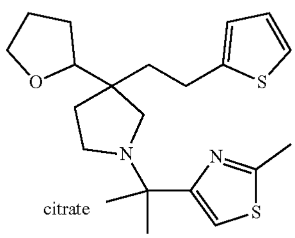 [SMILES: Cc1nc(C(C)(C)N2CCC(CCc3cccs3)(C3CCCO3)C2)cs1] | 2-methyl-4-(2-((S or R)-3-((S&R)-tetrahydrofuran-2-yl)-3-(2-(thiophen-2-yl)ethyl)pyrrolidin-1-yl)propan-2-yl)thiazole citrate | 391 | $^1$H NMR (300 MHz, MeOD): δ 7.61 (d, J = 5.1 Hz, 1H), 7.19 (dd, J = 2.4, 1.2 Hz, 1H), 6.90 (dd, J = 3.6, 1.5 Hz, 1H), 6.82 (s, 1H), 3.93-3.90 (m, 2H), 3.88-3.65 (m, 1H), 3.56-3.44 (m, 3H), 2.92-2.80 (m, 7H), 2.77-2.68 (m, 3H), 2.11-1.95 (m, 6H), 1.80-1.73 (m, 8H). |
| 23 | 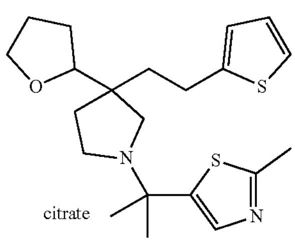 [SMILES: Cc1ncc(C(C)(C)N2CCC(CCc3cccs3)(C3CCCO3)C2)s1] | 2-methyl-5-(2-((S or R)-3-((S&R)-tetrahydrofuran-2-yl)-3-(2-(thiophen-2-yl)ethyl)pyrrolidin-1-yl)propan-2-yl)thiazole citrate | 391 | $^1$H NMR (300 MHz, MeOD): δ 7.81-7.76 (m, 1H), 7.17 (d, J = 4.8 Hz, 1H), 6.89 (s, 1H), 6.80 (s, 1H), 3.89-3.81 (m, 1H), 3.70-3.57 (m, 2H), 3.22-3.19 (m, 2H), 3.09-3.05 (m, 1H), 2.87-2.77 (m, 6H), 2.71-2.68 (m, 3H), 2.03-1.87 (m, 6H), 1.82-1.73 (m, 8H), 1.72-1.56 (m, 1H). |
| 24 | 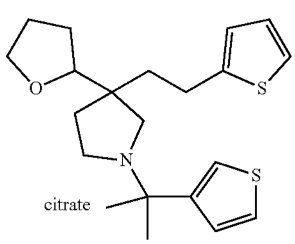 [SMILES: CC(C)(c1ccsc1)N1CCC(CCc2cccs2)(C2CCCO2)C1] | (S or R)-3-((S&R)-tetrahydrofuran-2-yl)-3-(2-(thiophen-2-yl)ethyl)-1-(2-(thiophen-3-yl)propan-2-yl)pyrrolidine citrate | 376 | $^1$H NMR (300 MHz, MeOD): δ 7.79-7.78 (m, 1H), 7.61-7.59 (m, 1H), 7.40-7.39 (m, 1H), 7.17 (d, J = 5.1 Hz, 1H), 6.90-6.87 (m, 1H), 6.80-6.78 (m, 1H), 3.89-3.84 (m, 2H), 3.78-3.55 (m, 2H), 3.78-3.55 (m, 1H), 3.42-3.31 (m, 3H), 3.24-3.06 (m, 1H), 2.78 (q, J = 15.3 Hz, 4H), 2.23-1.93 (m, 1H), 1.95-1.90 (m, 4H), 1.84 (s, 6H), 1.80-1.61 (m, 2H), 1.55-1.31 (m, 1H). |

TABLE III-continued

New Compounds with a pyrrolidine ring and a
non-pyridine-like molecule bonded to the pyrrolidine N-constituent

| Compound No. | Structure | Name | MS (ESI+): [M + H]+ | H-NMR |
|---|---|---|---|---|
| 25 | 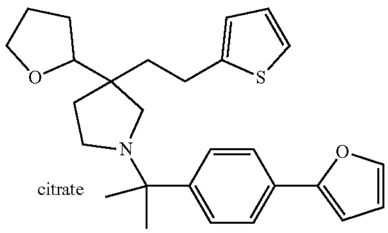 [SMILES: CC(C)(c1ccc(-c2ccco2)cc1)N1CCC(CCc2cccs2)(C2CCCO2)C1] | (S or R)-1-(2-(4-(furan-2-yl)phenyl)propan-2-yl)-3-((S&R)-tetrahydrofuran-2-yl)-3-(2-(thiophen-2-yl)ethyl)pyrrolidine citrate | 436 | $^1$H NMR (300 MHz, MeOD): δ 7.84-7.81 (m, 2H), 7.76-7.70 (m, 2H), 7.61 (s, 1H), 7.11-7.01 (m, 1H), 6.89 (d, J = 3.3 Hz, 1H), 6.81-6.80 (m, 2H), 6.56-6.55 (m, 1H), 3.90-3.72 (m, 2H), 3.69-3.65 (m, 1H), 3.55-3.36 (m, 2H), 3.26-3.00 (m, 2H), 2.91-2.75 (m, 6H), 2.25-2.02 (m, 2H), 1.99-1.89 (m, 2H), 1.87 (s, 6H), 1.82-1.75 (m, 4H). |
| 26 | 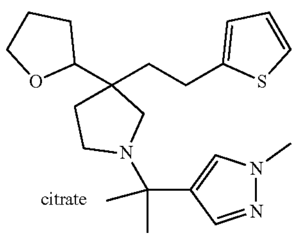 [SMILES: Cn1cc(C(C)(C)N2CCC(CCc3cccs3)(C3CCCO3)C2)cn1] | 1-methyl-4-(2-((S or R)-3-((S&R)-tetrahydrofuran-2-yl)-3-(2-(thiophen-2-yl)ethyl)pyrrolidin-1-yl)propan-2-yl)-1H-pyrazole citrate | 374 | $^1$H NMR (300 MHz, MeOD): δ 7.97 (s, 1H), 7.74 (s, 1H), 7.19 (s, 1H), 6.91 (s, 1H), 6.91-6.75 (m, 1H), 3.99-3.88 (m, 5H), 3.75-3.35 (m, 5H), 3.12-3.03 (m, 1H), 2.84 (q, J = 15.3 Hz, 4H), 2.73-2.66 (m, 1H), 2.22-2.16 (m, 6H), 1.96 (s, 6H), 1.77-1.30 (m, 2H). |
| 27 | 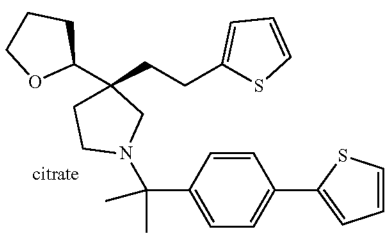 [SMILES: CC(C)(c1ccc(-c2cccs2)cc1)N1CC[C@](CCc2cccs2)([C@@H]2CCCO2)C1] | (S or R)-3-((S&R)-tetrahydrofuran-2-yl)-3-(2-(thiophen-2-yl)ethyl)-1-(2-(4-(thiophen-2-yl)phenyl)propan-2-yl)pyrrolidine citrate | 452 | $^1$H NMR (300 MHz, MeOD): δ 7.80-7.69 (m, 4H), 7.49-7.44 (m, 2H), 7.13-7.08 (m, 2H), 6.85-6.74 (m, 2H), 4.88-3.37 (m, 5H), 3.25-2.91 (m, 2H), 2.86-2.74 (m, 6H), 2.17-1.73 (m, 14H). |
| 28 | 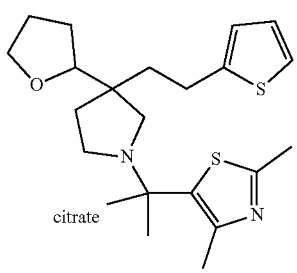 [SMILES: Cc1nc(C)c(C(C)(C)N2CCC(CCc3cccs3)(C3CCCO3)C2)s1] | 2,4-dimethyl-5-(2-((S or R)-3-((S&R)-tetrahydrofuran-2-yl)-3-(2-(thiophen-2-yl)ethyl)pyrrolidin-1-yl)propan-2-yl)thiazole citrate | 405 | $^1$H NMR (300 MHz, MeOD): δ 7.17 (d, J = 4.8 Hz, 1H), 6.90 (br s, 1H), 6.81 (br s, 1H), 3.90-3.86 (m, 2H), 3.75-3.70 (m, 2H), 3.20-2.95 (m, 3H), 2.94-2.86 (m, 4H), 2.85-2.70 (m, 4H), 2.60-2.58 (m, 3H), 2.53-2.51 (m, 3H), 1.93-1.79 (m, 6H), 1.72-1.68 (m, 6H). |
| 29 | 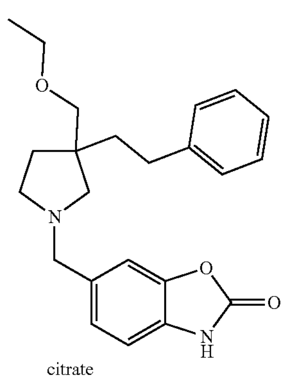 [SMILES: CCOCC1(CCc2ccccc2)CCN(Cc2ccc3[nH]c(=O)oc3c2)C1] | (R or S)-6-((3-(ethoxymethyl)-3-phenethylpyrrolidin-1-yl)methyl)benzo[d]oxazol-2(3H)-one citrate | 381 | $^1$H NMR (300 MHz, MeOD): 87.40 (s, 1H), 7.32 (d, J = 8.1 Hz, 1H), 7.28-7.23 (m, 2H), 7.20-7.13 (m, 4H), 4.44-4.31 (q, J = 12.9 Hz, 2H), 3.54 (q, J = 7.2 Hz, 2H), 3.45-3.31 (m, 5H), 3.12 (m, 1H), 2.78 (q, J = 15.6 Hz, 4H), 2.60-2.57 (m, 2H), 2.10-1.99 (m, 2H), 1.89-1.80 (m, 2H), 1.21 (t, J = 7.2 Hz, 3H). |

TABLE III-continued

New Compounds with a pyrrolidine ring and a
non-pyridine-like molecule bonded to the pyrrolidine N-constituent

| Compound No. | Structure | Name | MS (ESI+): [M + H]+ | H-NMR |
|---|---|---|---|---|
| 30 | 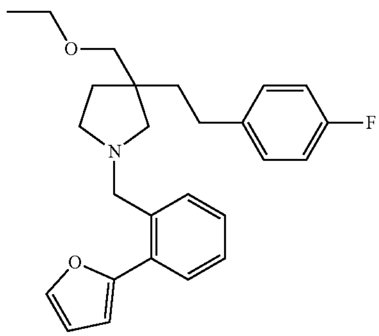 [SMILES: CCOCC1(CCc2ccc(F)cc2)CCN(Cc2ccccc2-c2ccco2)C1] | (R or S)-3-(ethoxymethyl)-3-(4-fluorophenethyl)-1-(2-(furan-2-yl)benzyl)pyrrolidine | | |
| 31 | 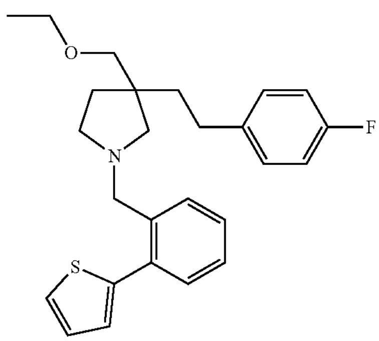 [SMILES: CCOCC1(CCc2ccc(F)cc2)CCN(Cc2ccccc2-c2cccs2)C1] | (R or S)-3-(ethoxymethyl)-3-(4-fluorophenethyl)-1-(2-(thiophen-2-yl)benzyl)pyrrolidine | | |
| 32 | 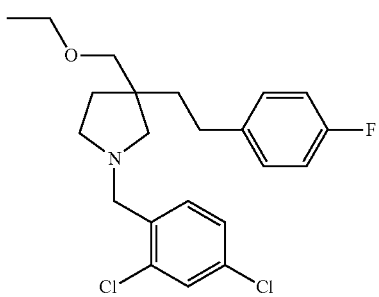 [SMILES: CCOCC1(CCc2ccc(F)cc2)CCN(Cc2ccc(Cl)cc2Cl)C1] | (R or S)-1-(2,4-dichlorobenzyl)-3-(ethoxymethyl)-3-(4-fluorophenethyl)pyrrolidine | | |
| 33 | 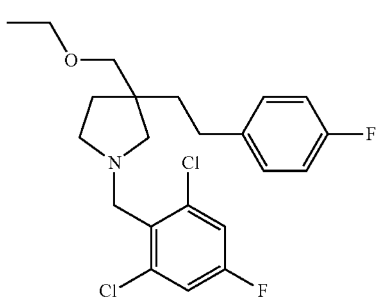 [SMILES: CCOCC1(CCc2ccc(F)cc2)CCN(Cc2c(Cl)cc(F)cc2Cl)C1] | (R or S)-1-(2,6-dichloro-4-fluorobenzyl)-3-(ethoxymethyl)-3-(4-fluorophenethyl)pyrrolidine | | |

TABLE III-continued

New Compounds with a pyrrolidine ring and a
non-pyridine-like molecule bonded to the pyrrolidine N-constituent

| Compound No. | Structure | Name | MS (ESI+): [M + H]⁺ | H-NMR |
|---|---|---|---|---|
| 34 | 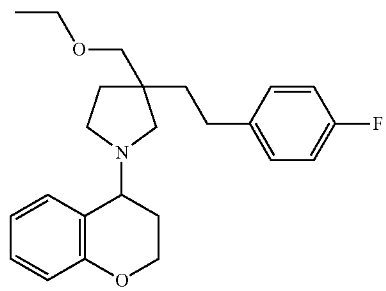 [SMILES: CCOCC1(CCc2ccc(F)cc2)CCN(C2CCOc3ccccc32)C1] | (3R or S)-1-(chroman-4-yl)-3-(ethoxymethyl)-3-(4-fluorophenethyl)pyrrolidine | | |
| 35 | 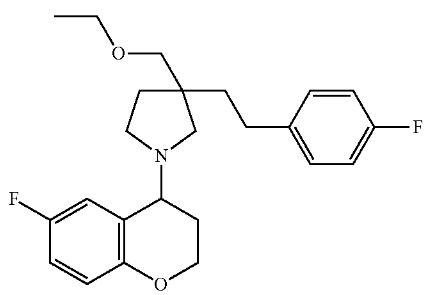 [SMILES: CCOCC1(CCc2ccc(F)cc2)CCN(C2CCOc3ccc(F)cc32)C1] | (3R or S)-3-(ethoxymethyl)-1-(6-fluorochroman-4-yl)-3-(4-fluorophenethyl)pyrrolidine | | |
| 36 | 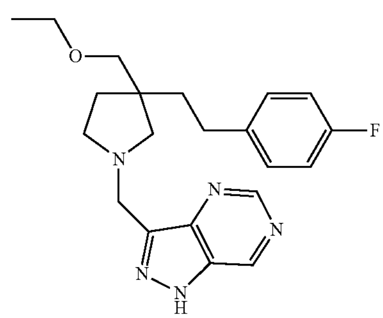 [SMILES: CCOCC1(CCc2ccc(F)cc2)CCN(Cc2n[nH]c3cncnc23)C1] | (R or S)-3-((3-(ethoxymethyl)-3-(4-fluorophenethyl)pyrrolidin-1-yl)methyl)-1H-pyrazolo[4,3-d]pyrimidine | | |
| 37 | 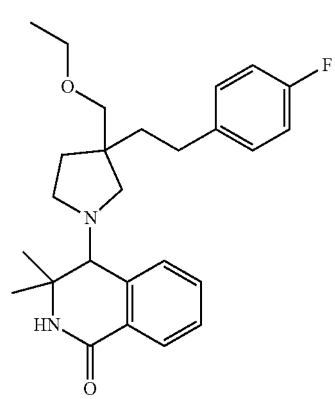 [SMILES: CCOCC1(CCc2ccc(F)cc2)CCN(C2c3ccccc3C(=O)NC2(C)C)C1] | 4-((R or S)-3-(ethoxymethyl)-3-(4-fluorophenethyl)pyrrolidin-1-yl)-3,3-dimethyl-3,4-dihydroisoquinolin-1(2H)-one | | |

TABLE III-continued

New Compounds with a pyrrolidine ring and a
non-pyridine-like molecule bonded to the pyrrolidine N-constituent

| Compound No. | Structure | Name | MS (ESI+): [M + H]+ | H-NMR |
|---|---|---|---|---|
| 38 | 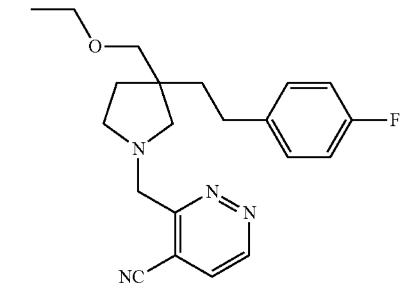 [SMILES: CCOCC1(CCc2ccc(F)cc2)CCN(Cc2nnccc2C#N)C1] | (R or S)-3-((3-(ethoxymethyl)-3-(4-fluorophenethyl)pyrrolidin-1-yl)methyl)pyridazine-4-carbonitrile | | |
| 39 | 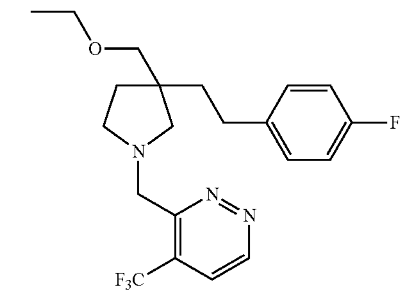 [SMILES: CCOCC1(CCc2ccc(F)cc2)CCN(Cc2nnccc2C(F)(F)F)C1] | (R or S)-3-((3-(ethoxymethyl)-3-(4-fluorophenethyl)pyrrolidin-1-yl)methyl)-4-(trifluoromethyl)pyridazine | | |
| 40 | 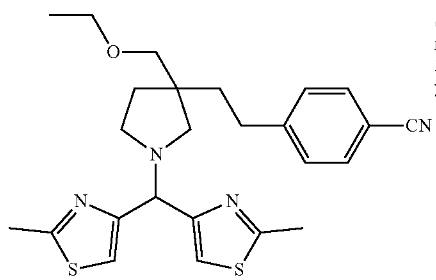 [SMILES: CCOCC1(CCc2ccc(C#N)cc2)CCN(C(c2csc(C)n2)c2csc(C)n2)C1] | (R or S)-4-(2-(1-(bis(2-methylthiazol-4-yl)methyl)-3-(ethoxymethyl)pyrrolidin-3-yl)ethyl)benzonitrile | | |
| 41 | 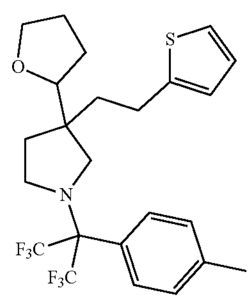 [SMILES: Cc1ccc(C(N2CCC(CCc3cccs3)(C3CCCO3)C2)(C(F)(F)F)C(F)(F)F)cc1] | (3R or S)-1-(1,1,1,3,3,3-hexafluoro-2-(p-tolyl)propan-2-yl)-3-(tetrahydrofuran-2-yl)-3-(2-(thiophen-2-yl)ethyl)pyrrolidine | | |

*Legend for 4th & 5th columns in Table III is same as for Table I.

TABLE IV

Chirality and in vivo testing of compound Nos. 1 to 25 of Table III

| Compound | Configuration tested | ED$_{50}$ (mg/kg) at 30 min on C57BL/6 mice in Warm-water Tail-flick Test (same as Table II) |
|---|---|---|
| 1 | S | ++ |
| 2 | S | + |
| 3 | S | ++ |
| 4 | R | + |
| 5 | R | ++ |
| 6 | S | + |
| 7 | S | ++ |
| 8 | R | + |
| 9 | R | + |
| 10 | S | + |

TABLE IV-continued

Chirality and in vivo testing of compound Nos. 1 to 25 of Table III

| Compound | Configuration tested | $ED_{50}$ (mg/kg) at 30 min on C57BL/6 mice in Warm-water Tail-flick Test (same as Table II) |
|---|---|---|
| 11 | S | ++ |
| 12 | S | ++ |
| 13 | S | ++ |
| 14 | S | ++ |
| 15 | (S, S&R) | + |
| 16 | (S, S&R) | ++ |
| 17 | (S, S&R) | ++ |
| 18 | (S, S&R) | + |
| 19 | (S, S&R) | ++ |
| 21 | (S, S&R) | ++ |
| 22 | (S, S&R) | ++ |
| 23 | (S, S&R) | ++ |
| 24 | (S, S&R) | ++ |
| 24 | (S, S&R) | ++ |
| 25 | (S, S&R) | ++ |
| 26 | (S, S&R) | ++ |
| 27 | (S, S&R) | + |
| 28 | (S, S&R) | + |
| 29 | S | + |

Legend for Table IV, Middle Column
"S, S&R" means the compound has two chiral centers and can possibly have four diastereomers. The compound with S at the 1st chiral center and the racemate at the 2nd chiral center was tested.

TABLE V

New Compounds with a pyridine ring and other groups bonded to the pyridine N-constituent

| Compound | Structure | Name | MS (ESI+): $[M + H]^+$ | H-NMR |
|---|---|---|---|---|
| 1 | 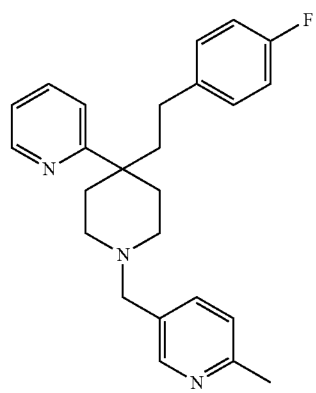 [SMILES: Cc1ccc(CN2CCC(CCc3ccc(F)cc3)(c3ccccn3)CC2)cn1] | 5-((4-(4-fluorophenethyl)-4-(pyridin-2-yl)piperidin-1-yl)methyl)-2-methylpyridine | 390 | $^1$H NMR (300 MHz, MeOD): δ 8.56 (d, J = 4.2 Hz, 1H), 8.31 (d, J = 1.5 Hz, 1H), 7.80 (td, J = 7.5, 1.5 Hz, 1H), 7.69 (dd, J = 8.1, 2.0 Hz, 1H), 7.49 (d, J = 8.1 Hz, 1H), 7.39-7.21 (m, 2H), 7.02-6.82 (m, 4H), 3.45 (s, 2H), 2.75-2.68 (m, 2H), 2.50 (s, 3H), 2.47-2.43 (m, 2H), 2.19-2.14 (m, 4H), 1.93-1.85 (m, 4H). |
| 2 | 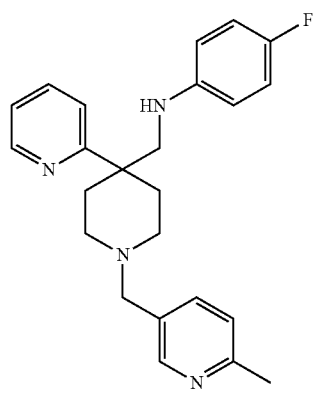 [SMILES: Cc1ccc(CN2CCC(CNc3ccc(F)cc3)(c3ccccn3)CC2)cn1] | 4-fluoro-N-((1-((6-methylpyridin-3-yl)methyl)-4-(pyridin-2-yl)piperidin-4-yl)methyl)aniline | 391 | $^1$H NMR (300 MHz, MeOD): δ 8.55 (d, J = 3.6 Hz, 1H), 8.30 (d, J = 1.8 Hz, 1H), 7.72-7.65 (m, 2H), 7.48 (d, J = 7.8 Hz, 1H), 7.24-7.18 (m, 2H), 6.70 (t, J = 8.7 Hz, 2H), 6.40-6.30 (m, 2H), 3.43 (s, 2H), 3.29 (s, 2H), 2.72-2.66 (m, 2H), 2.49-2.47 (m, 5H), 1.88 (t, J = 8.4 Hz, 2H), 1.98-1.94 (m, 2H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 3 | 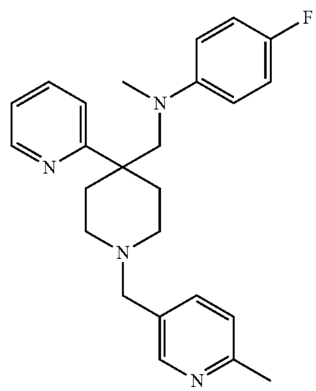 [SMILES: Cc1ccc(CN2CCC(CN(C)c3ccc(F)cc3)(c3ccccn3)CC2)cn1] | 4-fluoro-N-methyl-N-((1-((6-methylpyridin-3-yl)methyl)-4-(pyridin-2-yl)piperidin-4-yl)methyl)aniline | 405 | $^1$H NMR (300 MHz, MeOD): δ 8.55 (dd, J = 4.5, 0.9 Hz, 1H), 8.27 (d, J = 1.8 Hz, 1H), 7.65-7.60 (m, 2H), 7.40 (d, J = 8.1 Hz, 1H), 7.24-7.18 (m, 2H), 6.73-6.67 (m, 2H), 6.4-6.35 (m, 2H), 3.42 (s, 2H), 3.34 (s, 2H), 2.73 (d, J = 8.7 Hz, 2H), 2.62 (s, 3H), 2.60-2.56 (m, 2H), 2.48 (s, 3H), 2.02-1.87 (m, 4H). |
| 4 | 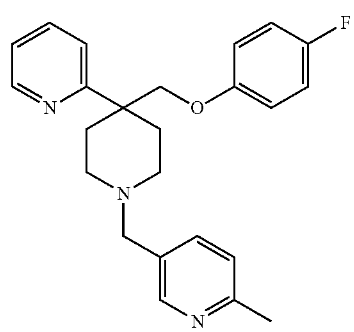 [SMILES: Cc1ccc(CN2CCC(COc3ccc(F)cc3)(c3ccccn3)CC2)cn1] | 5-((4-((4-fluorophenoxy)methyl)-4-(pyridin-2-yl)piperidin-1-yl)methyl)-2-methyl pyridine | 392 | $^1$H NMR (300 MHz, MeOD): δ 8.52 (s, 1H), 8.32 (s, 1H), 7.80-7.75 (m, 1H), 7.69 (d, J = 8.1 Hz, 1H), 7.56 (d, J = 8.1 Hz, 1H), 7.28-7.21 (m, 2H), 6.93-6.86 (m, 2H), 6.75-6.72 (m, 2H), 4.00 (s, 2H), 3.45 (s, 2H), 2.72-2.68 (m, 2H), 2.57-2.46 (m, 5H), 2.28-2.20 (m, 2H), 2.18-2.03 (m, 2H). |
| 5 | 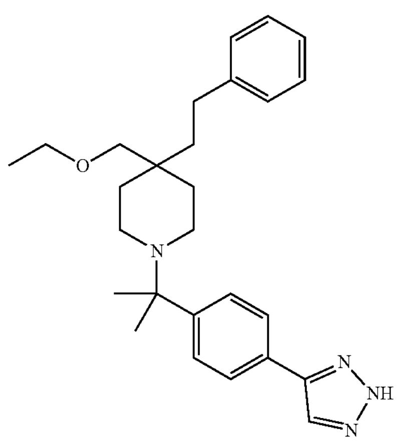 [SMILES: CCOCC1(CCc2ccccc2)CCN(C(C)(C)c2ccc(-c3cn[nH]n3)cc2)CC1] | 1-(2-(4-(2H-1,2,3-triazol-4-yl)phenyl)propan-2-yl)-4-(ethoxymethyl)-4-phenethyl-piperidine | 433 | $^1$H NMR (300 MHz, MeOD): δ 8.26 (s, 1H), 8.01 (d, J = 8.4 Hz, 2H), 7.78 (d, J = 8.4 Hz, 2H), 7.24-7.20 (m, 2H), 7.15-7.12 (m, 3H), 3.48-3.42 (m, 4H), 3.28-3.22 (m, 2H), 2.54-2.48 (m, 2H), 1.90 (s, 6H), 1.84-1.70 (m, 4H), 1.67-1.55 (m, 2H), 1.35-1.28 (m, 2H), 1.19-1.17 (m, 3H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 6 | citrate | 5-(2-(4-(ethoxymethyl)-4-(2-(thiophen-2-yl)ethyl)piperidin-1-yl)propan-2-yl)-2-methylpyridine citrate | 387 | ¹H NMR (300 MHz, MeOD): δ 8.70 (s, 1H), 8.05-8.03 (m, 1H), 7.45 (d, J = 8.1 Hz, 1H), 7.16 (d, J = 5.1 Hz, 1H), 6.90-6.87 (m, 1H), 6.80-6.79 (m, 1H), 3.52-3.41 (m, 4H), 3.24-3.13 (m, 4H), 2.90-2.72 (m, 6H), 2.58 (s, 3H), 1.97-1.86 (m, 2H), 1.85 (s, 6H), 1.77-1.70 (m, 4H), 1.23 (t, J = 7.2 Hz, 3H). |
| 7 | 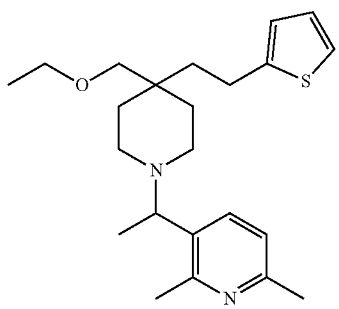 [SMILES: CCOCC1(CCc2cccs2)CCN(C(C)c2ccc(C)nc2C)CC1] | 3-(1-(4-(ethoxymethyl)-4-(2-(thiophen-2-yl)ethyl)piperidin-1-yl)ethyl)-2,6-dimethylpyridine | 387 | ¹H NMR (300 MHz, MeOD): δ 8.21 (s, 1H), 7.25 (s, 1H), 7.14 (dd, J = 5.1, 1.2 Hz, 1H), 6.88 (dd, J = 5.1, 2.4 Hz, 1H), 6.81-6.80 (m, 1H), 3.79 (br s. 2H), 3.53 (q, J = 6.9 Hz, 2H), 3.38 (s, 2H), 3.29-3.26 (m, 5H), 2.85-2.79 (m, 2H), 2.51 (s, 3H), 2.31 (s, 3H), 1.85-1.80 (m, 2H), 1.70-1.43 (m, 5H), 1.17 (t, J = 6.9 Hz, 3H). |
| 8 | citrate | 5-((4-(ethoxymethyl)-4-phenethylpiperidin-1-yl)methyl)-1-methyl-1,3-dihydro-2H-benzo[d]imidazol-2-one citrate | 407 | ¹H NMR (300 MHz, MeOD): δ 7.27-7.12 (m, 8H), 4.30 (s, 2H), 3.54 (q, J = 7.2 Hz, 2H), 3.32-3.30 (m, 5H), 3.21 (m, 4H), 2.79 (q, J = 15.6 Hz, 4H), 2.61-2.53 (m, 2H), 1.90-1.71 (m, 6H), 1.18 (t, J = 7.2 Hz, 3H). |
| 9 | HCl | 6-((4-(ethoxymethyl)-4-phenethylpiperidin-1-yl)methyl)-3-methylbenzo[d]oxazol-2(3H)-one HCl | 406 | ¹H NMR (300 MHz, D₂O): δ 7.32-7.24 (m, 4H), 7.22-7.18 (m, 4H), 4.26-4.25 (m, 2H), 3.50-3.44 (m, 3H), 3.35 (s, 3H), 3.32-3.28 (m, 3H), 3.06-2.98 (m, 2H), 2.51-2.47 (m, 2H), 1.89-1.51 (m, 6H), 1.08 (t, J = 7.2 Hz, 3H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 10 | 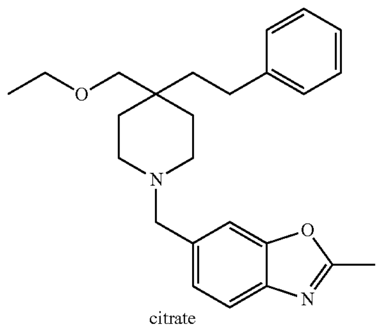 [SMILES: CCOCC1(CCc2ccccc2)CCN(Cc2ccc3nc(C)oc3c2)CC1] | 6-((4-(ethoxymethyl)-4-phenethylpiperidin-1-yl)methyl)-2-methylbenzo[d]oxazole citrate | 392 | $^1$H NMR (300 MHz, MeOD): δ 7.78 (s, 1H), 7.71 (d, J = 8.1 Hz, 1H), 7.49 (d, J = 8.4 Hz, 1H), 7.27-7.12 (m, 5H), 4.42 (s, 2H), 3.54 (q, J = 7.2 Hz, 2H), 3.47-3.45 (m, 2H), 3.22 (m, 4H), 2.79 (q, J = 15.3 Hz, 4H), 2.66 (s, 3H), 2.59-2.54 (m, 2H), 1.91-1.86 (m, 2H), 1.77-1.72 (m, 4H), 1.18 (t, J = 7.2 Hz, 3H). |
| 11 | 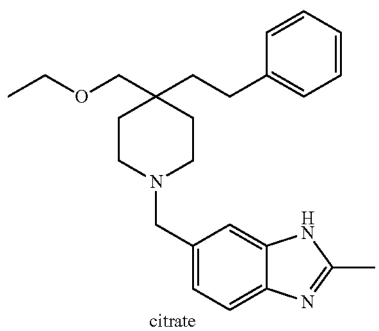 [SMILES: CCOCC1(CCc2ccccc2)CCN(Cc2ccc3nc(C)[nH]c3c2)CC1] | 6-((4-(ethoxymethyl)-4-phenethylpiperidin-1-yl)methyl)-2-methyl-1H-benzo[d]imidazole citrate | 391 | $^1$H NMR (300 MHz, MeOD): δ 7.68 (s, 1H), 7.57 (d, J = 8.1 Hz, 1H), 7.32 (d, J = 8.4 Hz, 1H), 7.27-7.12 (m, 5H), 4.40 (s, 2H), 3.54 (q, J = 7.2 Hz, 2H), 3.40 (s, 2H), 3.26 (m, 4H), 2.78 (q, J = 15.6 Hz, 4H), 2.60 (s, 3H), 2.58-2.54 (m, 2H), 1.86-1.75 (m, 6H), 1.17 (t, J = 7.2 Hz, 3H). |
| 12 | 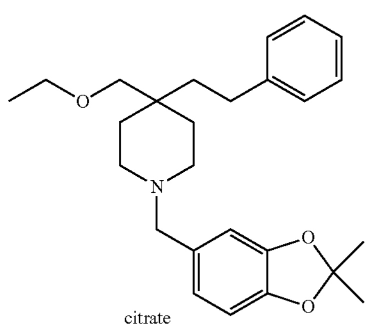 [SMILES: CCOCC1(CCc2ccccc2)CCN(Cc2ccc3c(c2)OC(C)(C)O3)CC1] | 1-((2,2-dimethylbenzo[d][1,3]dioxol-5-yl)methyl)-4-(ethoxymethyl)-4-phenethylpiperidine citrate | 409 | $^1$H NMR (300 MHz, MeOD): δ 7.28-7.15 (m, 5H), 6.93-6.90 (m, 2H), 6.81 (d, J = 7.8 Hz, 1H), 4.18(s, 2H), 3.54 (q, J = 7.2 Hz, 2H), 3.40 (m, 2H), 3.22 (m, 4H), 2.78 (q, J = 15.6 Hz, 4H), 2.60-2.54 (m, 2H), 1.87-1.71 (m, 6H), 1.66 (s, 6H), 1.18 (t, J = 7.2 Hz, 3H). |
| 13 | 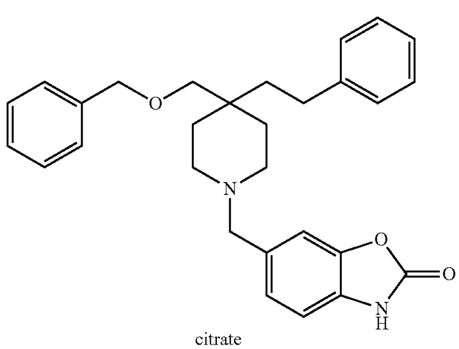 [SMILES: O=c1[nH]c2ccc(CN3CCC(CCc4ccccc4)(COCc4ccccc4)CC3)cc2o1] | 6-((4-((benzyloxy)methyl)-4-phenethylpiperidin-1-yl)methyl)benzo[d]oxazol-2(3H)-one citrate | 459 | $^1$H NMR (300 MHz, MeOD): δ 7.37-7.30 (m, 5H), 7.28-7.22 (m, 4H), 7.17-7.12 (m, 4H), 4.52 (s, 2H), 4.27 (s, 2H), 3.54 (s, 2H), 3.17 (m, 4H), 2.78 (q, J = 15.6 Hz, 4H), 2.55-2.49 (m, 2H), 1.91-1.86 (m, 2H), 1.82-1.71 (m, 4H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 14 | citrate | 2-chloro-5-((4-(ethoxy-methyl)-4-phenethyl-piperidin-1-yl)methyl) phenol citrate | 388 | $^1$H NMR (300 MHz, MeOD): δ 7.33 (d, J = 8.7 Hz, 1H), 7.28-7.09 (m, 5H), 7.05 (s, 1H), 6.87 (d, J = 8.7 Hz, 1H), 4.33 (s, 2H), 3.54 (q, J = 7.2 Hz, 2H), 3.42 (s, 2H), 3.34-3.29 (m, 4H), 2.78 (q, J = 15.6 Hz, 4H), 2.60-2.54 (m, 2H), 1.91-1.87 (m, 2H), 1.78-1.68 (m, 4H), 1.29 (t, J = 7.2 Hz, 3H). |
| 15 | citrate | 4-chloro-3-((4-(ethoxy-methyl)-4-phenethyl-piperidin-1-yl)methyl) phenol citrate | 388 | $^1$H NMR (300 MHz, MeOD): δ 7.32-7.23 (m, 3H), 7.20-7.14 (m, 2H), 7.12-7.10 (m, 2H), 7.04 (d, J = 8.1 Hz, 1H), 4.44 (s, 2H), 3.54 (q, J = 7.2 Hz, 2H), 3.42 (s, 2H), 3.34 (m, 4H), 2.78 (q, J = 15.6 Hz, 4H), 2.60-2.54 (m, 2H), 1.93-1.88 (m, 2H), 1.79-1.69 (m, 4H), 1.21 (t, J = 7.2 Hz, 3H). |
| 16 | citrate | 6-(2-(4-(ethoxymethyl)-4-phenethylpiperidin-1-yl)ethyl)benzo[d]oxazol-2(3H)-one citrate | 409 | $^1$H NMR (300 MHz, MeOD): δ 7.40-7.19 (m, 4H), 7.15-7.10 (m, 2H), 7.05 (d, J = 7.8 Hz, 2H) 3.67-3.34 (q, J = 7.2 Hz, 2H), 3.31-3.30 (m, 4H), 3.18-3.00 (m, 4H), 3.11-3.00 (m, 2H), 2.78 (q, J = 15.6 Hz, 4H), 2.61-2.56 (m, 2H), 1.92-1.55 (m, 6H), 1.22 (t, J = 6.9 Hz, 3H). |
| 17 | citrate | 6-((4-(ethoxymethyl)-4-phenethylpiperidin-1-yl)methyl)iso-benzofuran-1(3H)-one citrate | 394 | $^1$H NMR (300 MHz, MeOD): δ 8.02 (s, 1H), 7.90 (d, J = 7.2 Hz, 1H), 7.73 (d, J = 7.2 Hz, 1H), 7.29-7.12 (m, 5H), 5.43 (s, 2H), 4.37 (s, 2H), 3.54 (q, J = 7.2 Hz, 2H), 3.40 (s, 2H), 3.18 (m, 4H), 2.78 (q, J = 15.6 Hz, 4H), 2.59-2.54 (m, 2H), 1.89-1.84 (m, 2H), 1.75-1.69 (m, 4H), 1.29 (t, J = 6.9 Hz, 3H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 18 | 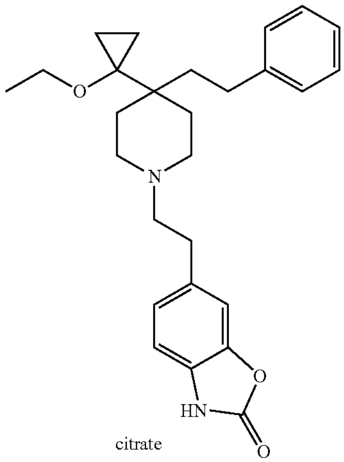 [SMILES: CCOC1(C2(CCc3ccccc3)CCN(CCc3ccc4[nH]c(=O)oc4c3)CC2)CC1] | 6-(2-(4-(1-ethoxycyclo-propyl)-4-phenethyl-piperidin-1-yl)ethyl)benzo[d]oxazol-2(3H)-one citrate | 435 | 1H NMR (300 MHz, MeOD): δ 7.26-7.20 (m, 4H), 7.16-7.10 (m, 3H), 7.04 (d, J = 7.8 Hz, 1H), 3.54 (q, J = 7.2 Hz, 2H), 3.44 (m, 2H), 3.31-3.21 (m, 2H), 3.23-3.08 (m, 4H), 2.86-2.71 (m, 6H), 2.05-2.00 (m, 2H), 1.87 (d, J = 14.4 Hz, 2H), 1.67-1.59 (m, 2H), 1.14 (t, J = 6.9 Hz, 3H), 0.89 (m, 2H), 0.74 (m, 2H). |
| 19 | 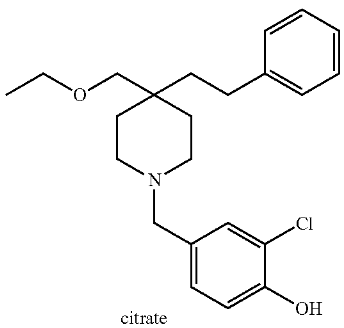 [SMILES: CCOCC1(CCc2ccccc2)CCN(Cc2ccc(O)c(Cl)c2)CC1] | 2-chloro-4-((4-(ethoxy-methyl)-4-phenethyl-piperidin-1-yl)methyl)phenol citrate | 388 | 1H NMR (300 MHz, MeOD): δ 7.49 (s, 1H), 7.28-7.23 (m, 3H), 7.20-7.12 (m, 3H), 6.98 (d, J = 8.4 Hz, 1H), 4.18 (s, 2H), 3.54 (q, J = 7.2 Hz, 2H), 3.39 (m, 2H), 3.20 (m, 4H), 2.78 (q, J = 15.6 Hz, 4H), 2.64-2.53 (m, 2H), 1.85-1.71 (m, 6H), 1.19 (t, J = 7.2 Hz, 3H). |
| 20 | 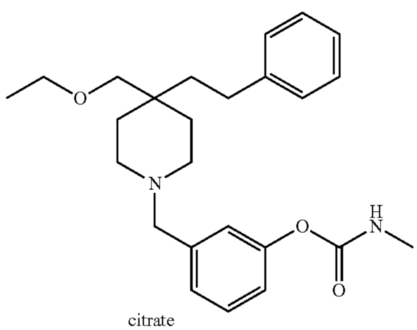 [SMILES: CCOCC1(CCc2ccccc2)CCN(Cc2cccc(OC(=O)NC)c2)CC1] | 3-((4-(ethoxymethyl)-4-phenethylpiperidin-1-yl)methyl)phenyl methylcarbamate citrate | 410 | 1H NMR (300 MHz, MeOD): δ 7.49 (t, J = 7.6 Hz, 1H), 7.34-7.12 (m, 8H), 4.28 (s, 2H), 3.54 (q, J = 7.2 Hz, 2H), 3.40 (s, 2H), 3.23 (br s, 4H), 2.80-2.71 (m, 7H), 2.60-2.54 (m, 2H), 1.86-1.75 (m, 6H), 1.20 (t, J = 6.9 Hz, 3H). |
| 21 | 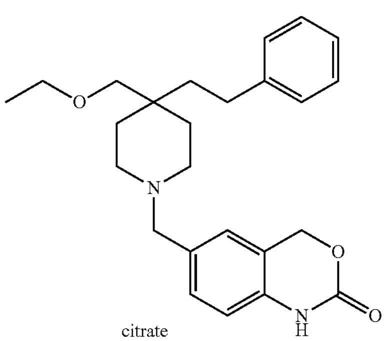 [SMILES: CCOCC1(CCc2ccccc2)CCN(Cc2ccc3c(c2)COC(=O)N3)CC1] | 6-((4-(ethoxymethyl)-4-phenethylpiperidin-1-yl)methyl)-1,4-dihydro-2H-benzo[d][1,3]oxazin-2-one citrate | 408 | 1H NMR (300 MHz, MeOD): δ 7.40 (d, J = 8.1 Hz, 1H), 7.34 (s, 1H), 7.28-7.12 (m, 5H), 6.96 (d, J = 7.8 Hz, 1H), 5.35 (s, 2H), 4.22 (s, 2H), 3.54 (q, J = 7.2 Hz, 2H), 3.39 (br s, 2H), 3.20 (br s, 4H), 2.78 (q, J = 15.6 Hz, 4H), 2.59-2.54 (m, 2H), 1.90-1.59 (m, 6H), 1.20 (t, J = 6.9 Hz, 3H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 22 | (citrate) | 7-((4-(ethoxymethyl)-4-phenethylpiperidin-1-yl)methyl)-2H-benzo[b][1,4]oxazin-3(4H)-one citrate | 408 | $^1$H NMR (300 MHz, MeOD): δ 7.28-7.07 (m, 7H), 6.97 (d, J = 8.1 Hz, 1H), 4.61 (s, 2H), 4.19 (s, 2H), 3.54 (q, J = 7.2 Hz, 2H), 3.40 (br s, 2H), 3.20 (br s, 4H), 2.78 (q, J = 15.6 Hz, 4H), 2.59-2.54 (m, 2H), 1.85-1.62 (m, 6H), 1.19 (t, J = 7.2 Hz, 3H). |
| 23 | (citrate) | 1-((2,3-dihydrobenzofuran-6-yl)methyl)-4-(ethoxymethyl)-4-phenethylpiperidine citrate | 379 | $^1$H NMR (300 MHz, MeOD): δ 7.31-7.23 (m, 3H), 7.20-7.12 (m, 3H), 6.94 (d, J = 6.6 Hz, 1H), 6.87 (s, 1H), 4.58 (t, J = 8.7 Hz, 2H), 4.20 (s, 2H), 3.54 (q, J = 7.2 Hz, 2H), 3.34 (br s, 2H), 3.29-3.20 (m, 6H), 2.78 (q, J = 15.6 Hz, 4H), 2.59-2.54 (m, 2H), 1.86-1.74 (m, 6H), 1.19 (t, J = 6.9 Hz, 3H). |
| 24 | (citrate) | methyl (4-((4-(ethoxymethyl)-4-phenethylpiperidin-1-yl)methyl)phenyl)carbamate citrate | 410 | $^1$H NMR (300 MHz, MeOD): δ 7.56 (d, J = 8.1 Hz, 2H), 7.41 (d, J = 8.1 Hz, 2H), 7.28-7.12 (m, 5H), 4.23 (s, 2H), 3.74 (s, 3H), 3.57 (q, J = 7.2 Hz, 2H), 3.39 (br s, 2H), 3.22 (br s, 4H), 2.78 (q, J = 15.6 Hz, 4H), 2.59-2.54 (m, 2H), 1.86-1.74 (m, 6H), 1.19 (t, J = 6.9 Hz, 3H). |
| 25 | (citrate) | 5-((4-(ethoxymethyl)-4-phenethylpiperidin-1-yl)methyl)benzo[d]oxazol-2(3H)-one citrate | 394 | $^1$H NMR (300 MHz, MeOD): δ 7.39-7.23 (m, 5H), 7.22-7.12 (m, 3H), 4.19 (s, 2H), 3.54 (q, J = 7.2 Hz, 2H), 3.47 (br s, 2H), 3.21 (br s, 4H), 2.78 (q, J = 15.6 Hz, 4H), 2.59-2.54 (m, 2H), 1.85-1.75 (m, 6H), 1.19 (t, J = 6.9 Hz, 3H). |

TABLE V-continued

New Compounds with a pyridine ring and other groups bonded to the pyridine N-constituent

| Compound | Structure | Name | MS (ESI+): [M + H]$^+$ | H-NMR |
|---|---|---|---|---|
| 26 | (citrate) | 5-((4-(ethoxymethyl)-4-phenethylpiperidin-1-yl)methyl)-3-methylbenzo[d]oxazol-2(3H)-one citrate | 408 | $^1$H NMR (300 MHz, MeOD): δ 7.35-7.29 (m, 2H), 7.25-7.12 (m, 6H), 4.32 (s, 2H), 3.54 (q, J = 7.2 Hz, 2H), 3.43-3.20 (m, 5H), 3.22 (br s, 4H), 2.78 (q, J = 15.6 Hz, 4H), 2.60-2.54 (m, 2H), 1.91-1.65 (m, 6H), 1.19 (t, J = 6.9 Hz, 3H). |
| 27 | (citrate) | 6-((4-(ethoxymethyl)-4-phenethylpiperidin-1-yl)methyl)-1-methyl-1,4-dihydro-2H-benzo[d][1,3]oxazin-2-one citrate | 422 | $^1$H NMR (300 MHz, MeOD): δ 7.52 (d, J = 8.4 Hz, 1H), 7.39 (s, 1H), 7.28-7.12 (m, 6H), 5.28 (s, 2H), 4.31 (s, 2H), 3.54 (q, J = 7.2 Hz, 2H), 3.40-3.34 (m, 5H), 3.20 (br s, 4H), 2.78 (q, J = 15.6 Hz, 4H), 2.60-2.54 (m, 2H), 1.90-1.71 (m, 6H), 1.19 (t, J = 6.9 Hz, 3H) |
| 28 | (citrate) | 7-((4-(ethoxymethyl)-4-phenethylpiperidin-1-yl)methyl)-3,4-dihydro-2H-benzo[e][1,3]oxazin-2-one citrate | 408 | $^1$H NMR (300 MHz, MeOD): δ 7.33-7.12 (m, 8H), 4.51 (s, 2H), 4.22 (s, 2H), 3.54 (q, J = 7.2 Hz, 2H), 3.39 (s, 2H), 3.16 (br s, 4H), 2.78 (q, J = 15.6 Hz, 4H), 2.59-2.54 (m, 2H), 1.89-1.70 (m, 6H), 1.19 (t, J = 6.9 Hz, 3H). |
| 29 | (citrate) | 6-((4-(ethoxymethyl)-4-phenethylpiperidin-1-yl)methyl)benzo[d]thiazol-2(3H)-one citrate | 410 | $^1$H NMR (300 MHz, MeOD): δ 7.64 (s, 1H), 7.42 (d, J = 8.1 Hz, 1H), 7.28-7.12 (m, 6H), 4.28 (s, 2H), 3.53 (q, J = 7.2 Hz, 2H), 3.40 (br s, 2H), 3.22 (br s, 4H), 2.78 (q, J = 15.6 Hz, 4H), 2.59-2.21 (m, 2H), 1.90-1.71 (m, 6H), 1.19 (t, J = 6.9 Hz, 3H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 30 | 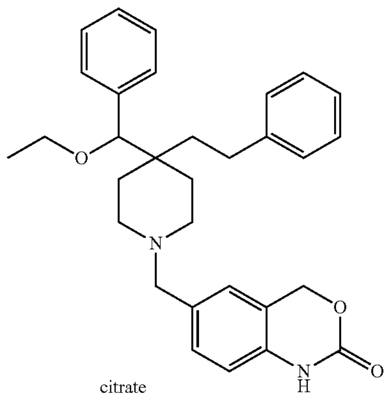 [SMILES: CCOC(c1ccccc1)C1(CCc2ccccc2)CCN(Cc2ccc3c(c2)COC(=O)N3)CC1] | 6-((4-(ethoxy(phenyl)methyl)-4-phenethyl-piperidin-1-yl)methyl)-1,4-dihydro-2H-benzo[d][1,3]oxazin-2-one citrate | 484 | $^1$H NMR (300 MHz, MeOD): δ 7.38-7.30 (m, 7H), 7.25-7.20 (m, 2H), 7.17-7.13 (m, 3H), 6.94 (d, J = 8.1 Hz, 1H), 5.33 (s, 2H), 4.37 (s, 1H), 4.21 (s, 2H), 3.41-3.36 (m, 2H), 3.30-3.26 (m, 2H), 3.10-3.08 (m, 2H), 2.78 (q, J = 15.6 Hz, 4H), 2.67-2.61 (m, 2H), 2.04-1.61 (m, 6H), 1.67 (t, J = 6.9 Hz, 3H). |
| 31 | 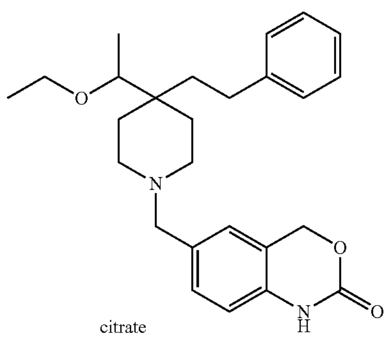 [SMILES: CCOC(C)C1(CCc2ccccc2)CCN(Cc2ccc3c(c2)COC(=O)N3)CC1] | 6-((4-(1-ethoxyethyl)-4-phenethylpiperidin-1-yl)methyl)-1,4-dihydro-2H-benzo[d][1,3]oxazin-2-one citrate | 422 | $^1$H NMR (300 MHz, MeOD): δ 7.41 (d, J = 8.4 Hz, 1H), 7.36 (s, 1H), 7.29-7.13 (m, 5H), 6.96 (d, J = 8.1 Hz, 1H), 5.35 (s, 2H), 4.23 (s, 2H), 3.71-3.66 (m, 1H), 3.42-3.34 (m, 4H), 3.12 (br s, 2H), 2.78 (q, J = 15.6 Hz, 4H), 2.71-2.50 (m, 2H), 2.03-1.82 (m, 3H), 1.72-1.62 (m, 3H), 1.17-1.13 (m, 6H). |
| 32 | 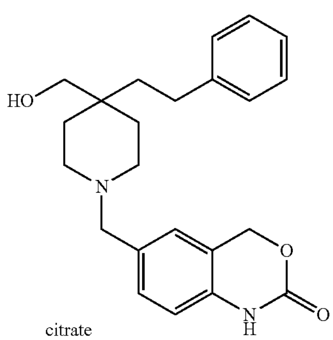 [SMILES: O=C1Nc2ccc(CN3CCC(CO)(CCc4ccccc4)CC3)cc2CO1] | 6-((4-(hydroxymethyl)-4-phenethylpiperidin-1-yl)methyl)-1,4-dihydro-2H-benzo[d][1,3]oxazin-2-one citrate | 380 | $^1$H NMR (300 MHz, MeOD): δ 7.41 (d, J = 8.7 Hz, 1H), 7.36 (s, 1H), 7.28-7.11 (m, 5H), 6.96 (d, J = 7.8 Hz, 1H), 5.35 (s, 2H), 4.24 (s, 2H), 3.53 (s, 2H), 3.11 (br s, 4H), 2.78 (q, J = 15.6 Hz, 4H), 2.60-2.54 (m, 2H), 1.84-1.73 (m, 6H). |
| 33 | 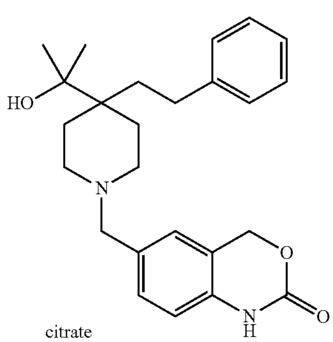 [SMILES: CC(C)(O)C1(CCc2ccccc2)CCN(Cc2ccc3c(c2)COC(=O)N3)CC1] | 6-((4-(2-hydroxypropan-2-yl)-4-phenethyl-piperidin-1-yl)methyl)-1,4-dihydro-2H-benzo[d][1,3]oxazin-2-one citrate | 408 | $^1$H NMR (300 MHz, MeOD): δ 7.42 (d, J = 8.1 Hz, 1H), 7.37 (s, 1H), 7.29-7.13 (m, 5H), 6.96 (d, J = 8.1 Hz, 1H), 5.35 (s, 2H), 4.25 (s, 2H), 3.39 (s, 2H), 3.05 (q, J = 12.9 Hz, 2H), 2.85-2.68 (m, 6H), 2.08 (t, J = 11.7 Hz, 2H), 1.79-1.75 (m, 4H), 1.27 (s, 6H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 34 | 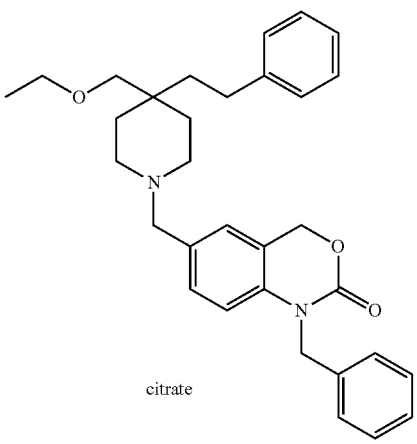 [SMILES: CCOCC1(CCc2ccccc2)CCN(Cc2ccc3c(c2)COC(=O)N3Cc2ccccc2)CC1] citrate | 1-benzyl-6-((4-(ethoxy-methyl)-4-phenethyl-piperidin-1-yl)methyl)-1,4-dihydro-2H-benzo[d][1,3]oxazin-2-one citrate | 498 | $^1$H NMR (300 MHz, MeOD): δ 7.39-7.32 (m, 2H), 7.30-7.22 (m, 4H), 7.18-7.11 (m, 6H), 7.00 (d, J = 8.4 Hz, 1H), 5.38 (s, 2H), 5.19 (s, 2H), 4.19 (s, 2H), 3.54 (q, J = 7.2 Hz, 2H), 3.45 (s, 2H), 3.16 (br s, 4H), 2.78 (q, J = 15.6 Hz, 4H), 2.57-2.52 (m, 2H), 1.87-1.68 (m, 6H), 1.17 (t, J = 6.9 Hz, 3H). |
| 35 | 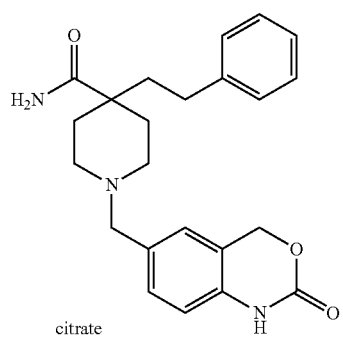 [SMILES: NC(=O)C1(CCc2ccccc2)CCN(Cc2ccc3c(c2)COC(=O)N3)CC1] citrate | 1-((2-oxo-1,4-dihydro-2H-benzo[d][1,3]oxazin-6-yl)methyl)-4-phenethylpiperidine-4-carboxamide citrate | 393 | $^1$H NMR (300 MHz, MeOD): δ 7.42 (d, J = 8.1 Hz, 1H), 7.33 (s, 1H), 7.28-7.15 (m, 5H), 6.98 (d, J = 7.8 Hz, 1H), 5.35 (s, 2H), 4.28 (s, 2H), 3.41-3.10 (m, 2H), 3.07-3.06 (m, 2H), 2.80 (q, J = 15.6 Hz, 4H), 2.58-2.45 (m, 4H), 1.82-1.68 (m, 4H). |
| 36 | 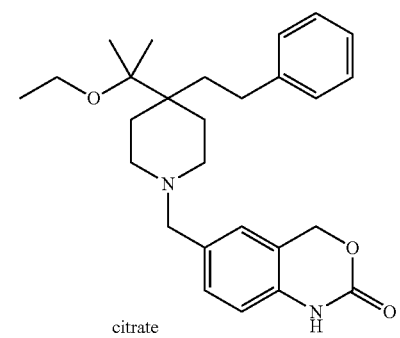 [SMILES: CCOC(C)(C)C1(CCc2ccccc2)CCN(Cc2ccc3c(c2)COC(=O)N3)CC1] citrate | 6-((4-(2-ethoxypropan-2-yl)-4-phenethyl-piperidin-1-yl)methyl)-1,4-dihydro-2H-benzo[d][1,3]oxazin-2-one citrate | 436 | $^1$H NMR (300 MHz, MeOD): δ 7.42 (d, J = 7.8 Hz, 1H), 7.35 (s, 1H), 7.29-7.13 (m, 5H), 6.98 (d, J = 7.5 Hz, 1H), 5.35 (s, 2H), 4.27 (s, 2H), 3.54-3.42 (m, 4H), 3.11 (br s, 2H), 2.89-2.73 (m, 6H), 2.09 (m, 2H), 1.84-1.79 (m, 4H), 1.22 (s, 6H), 1.15 (t, J = 7.2 Hz, 3H). |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 37 | 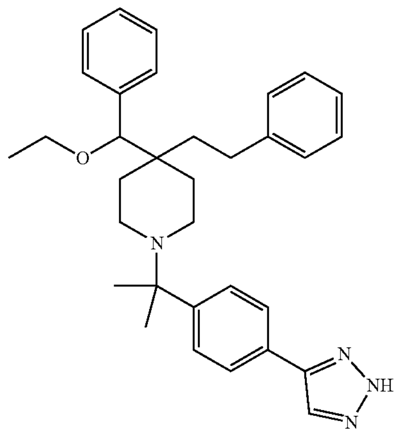 [SMILES: CCOC(c1ccccc1)C1(CCc2ccccc2)CCN(C(C)(C)c2ccc(-c3cn[nH]n3)cc2)CC1] | 1-(2-(4-(2H-1,2,3-triazol-4-yl)phenyl)propan-2-yl)-4-(ethoxy(phenyl)methyl)-4-phenethylpiperidine | | |
| 38 | 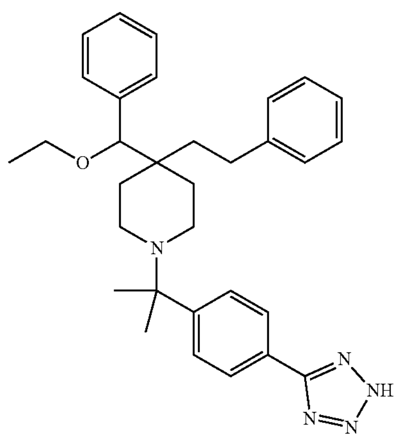 [SMILES: CCOC(c1ccccc1)C1(CCc2ccccc2)CCN(C(C)(C)c2ccc(-c3nn[nH]n3)cc2)CC1] | 1-(2-(4-(2H-tetrazol-5-yl)phenyl)propan-2-yl)-4-(ethoxy(phenyl)methyl)-4-phenethyl-piperidine | | |
| 39 | 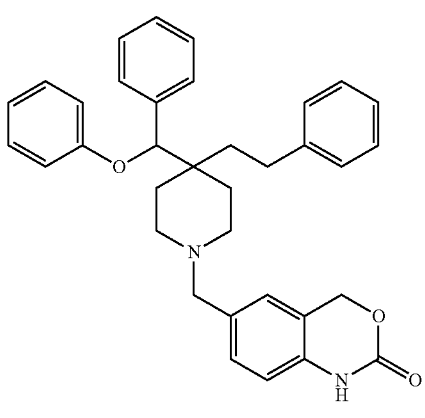 [SMILES: O=C1Nc2ccc(CN3CCC(CCc4ccccc4)(C(Oc4ccccc4)c4ccccc4)CC3)cc2CO1] | 6-((4-phenethyl-4-(phenoxy(phenyl)methyl)piperidin-1-yl)methyl)-1H-benzo[d][1,3]oxazin-2(4H)-one | | |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 40 | 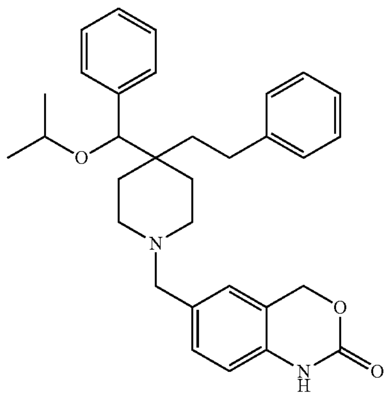 [SMILES: CC(C)OC(c1ccccc1)C1(CCc2ccccc2)CCN(Cc2ccc3c(c2)COC(=O)N3)CC1] | 6-((4-(isopropoxy (phenyl)methyl)-4-phenethylpiperidin-1-yl)methyl)-1H-benzo[d][1,3]oxazin-2(4H)-one | | |
| 41 | 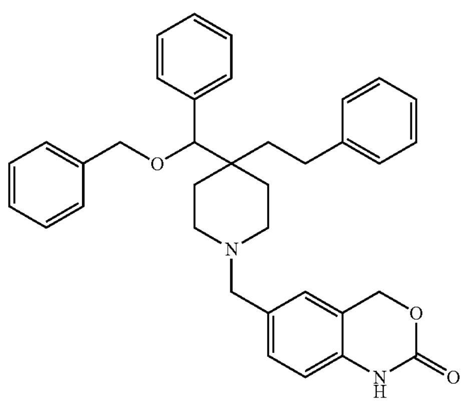 [SMILES: O=C1Nc2ccc(CN3CCC(CCc4ccccc4)(C(OCc4ccccc4)c4ccccc4)CC3)cc2CO1] | 6-((4-((benzyloxy)(phenyl)methyl)-4-phenethylpiperidin-1-yl)methyl)-1H-benzo[d][1,3]oxazin-2(4H)-one | | |
| 42 | 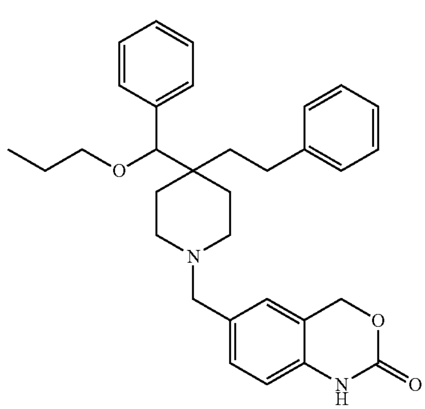 [SMILES: CCCOC(c1ccccc1)C1(CCc2ccccc2)CCN(Cc2ccc3c(c2)COC(=O)N3)CC1] | 6-((4-phenethyl-4-(phenyl(propoxy)methyl)piperidin-1-yl)methyl)-1H-benzo[d][1,3]oxazin-2(4H)-one | | |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 43 | 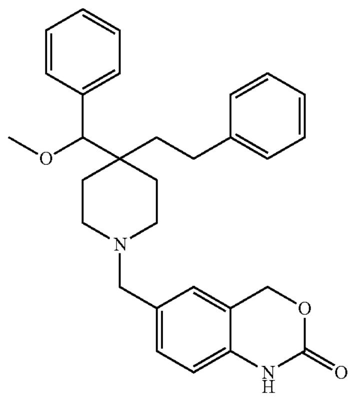 [SMILES: COC(c1ccccc1)C1(CCc2ccccc2)CCN(Cc2ccc3c(c2)COC(=O)N3)CC1] | 6-((4-(methoxy(phenyl)methyl)-4-phenethylpiperidin-1-yl)methyl)-1H-benzo[d][1,3]oxazin-2(4H)-one | | |
| 44 | 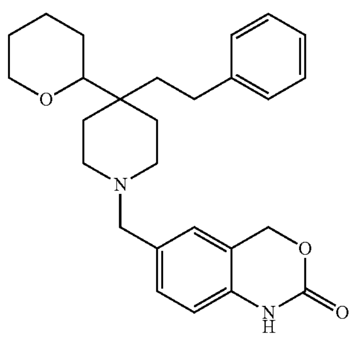 [SMILES: O=C1Nc2ccc(CN3CCC(CCc4ccccc4)(C4CCCCO4)CC3)cc2CO1] | 6-((4-phenethyl-4-(tetrahydro-2H-pyran-2-yl)piperidin-1-yl)methyl)-1H-benzo[d][1,3]oxazin-2(4H)-one | | |
| 45 | 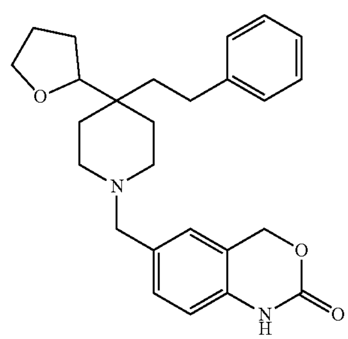 [SMILES: O=C1Nc2ccc(CN3CCC(CCc4ccccc4)(C4CCCO4)CC3)cc2CO1] | 6-((4-phenethyl-4-(tetrahydrofuran-2-yl)piperidin-1-yl)methyl)-1H-benzo[d][1,3]oxazin-2(4H)-one | | |
| 46 | 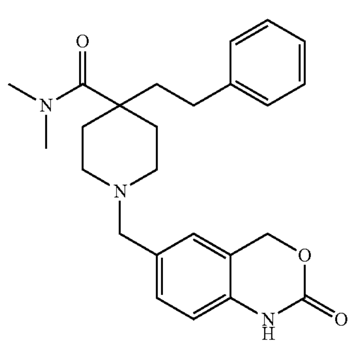 [SMILES: CN(C)C(=O)C1(CCc2ccccc2)CCN(Cc2ccc3c(c2)COC(=O)N3)CC1] | N,N-dimethyl-1-((2-oxo-2,4-dihydro-1H-benzo[d][1,3]oxazin-6-yl)methyl)-4-phenethyl-piperidine-4-carboxamide | | |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 47 | 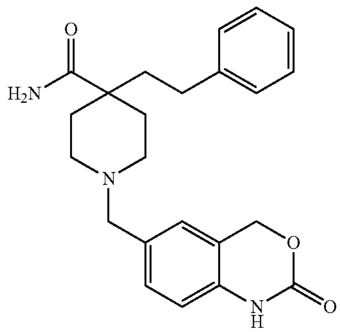 [SMILES: NC(=O)C1(CCc2ccccc2)CCN(Cc2ccc3c(c2)COC(=O)N3)CC1] | 1-((2-oxo-2,4-dihydro-1H-benzo[d][1,3]oxazin-6-yl)methyl)-4-phenethylpiperidine-4-carboxamide | | |
| 48 | 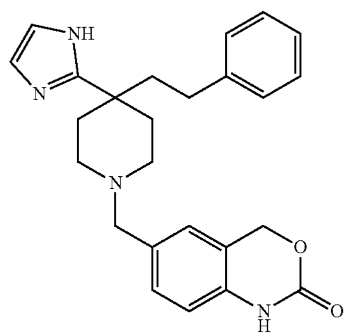 [SMILES: O=C1Nc2ccc(CN3CCC(CCc4ccccc4)(c4ncc[nH]4)CC3)cc2CO1] | 6-((4-(1H-imidazol-2-yl)-4-phenethyl-piperidin-1-yl)methyl)-1H-benzo[d][1,3]oxazin-2(4H)-one | | |
| 49 | 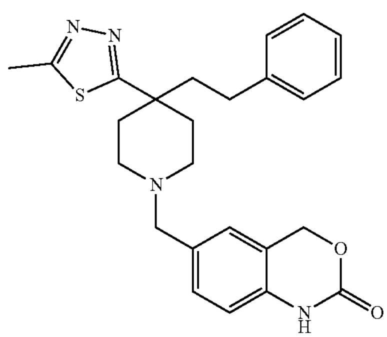 [SMILES: Cc1nnc(C2(CCc3ccccc3)CCN(Cc3ccc4c(c3)COC(=O)N4)CC2)s1] | 6-((4-(5-methyl-1,3,4-thiadiazol-2-yl)-4-phenethylpiperidin-1-yl)methyl)-1H-benzo[d][1,3]oxazin-2(4H)-one | | |
| 50 | 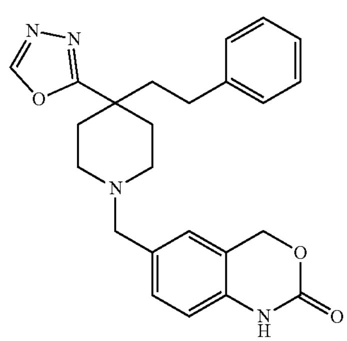 [SMILES: O=C1Nc2ccc(CN3CCC(CCc4ccccc4)(c4nnco4)CC3)cc2CO1] | 6-((4-(1,3,4-oxadiazol-2-yl)-4-phenethyl piperidin-1-yl)methyl)-1H-benzo[d][1,3]oxazin-2(4H)-one | | |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 51 | 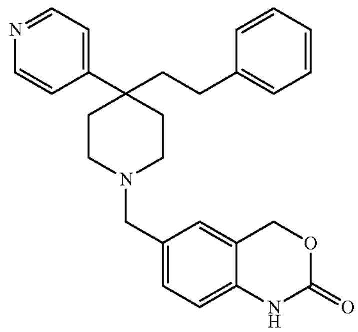 [SMILES: O=C1Nc2ccc(CN3CCC(CCc4ccccc4)(c4ccncc4)CC3)cc2CO1] | 6-((4-phenethyl-4-(pyridin-4-yl)piperidin-1-yl)methyl)-1H-benzo[d][1,3]oxazin-2(4H)-one | | |
| 52 | 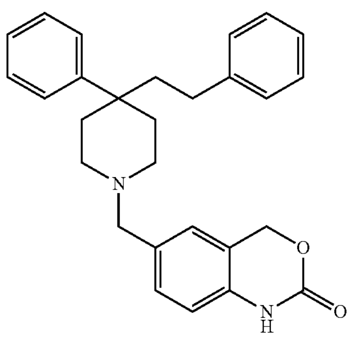 [SMILES: O=C1Nc2ccc(CN3CCC(CCc4ccccc4)(c4ccccc4)CC3)cc2CO1] | 6-((4-phenethyl-4-phenylpiperidin-1-yl)methyl)-1H-benzo[d][1,3]oxazin-2(4H)-one | | |
| 53 | 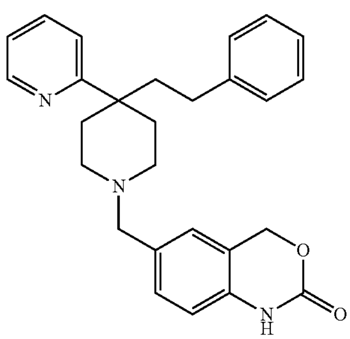 [SMILES: O=C1Nc2ccc(CN3CCC(CCc4ccccc4)(c4ccccn4)CC3)cc2CO1] | 6-((4-phenethyl-4-(pyridin-2-yl)piperidin-1-yl)methyl)-1H-benzo[d][1,3]oxazin-2(4H)-one | | |
| 54 | 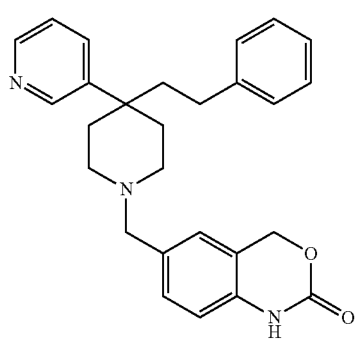 [SMILES: O=C1Nc2ccc(CN3CCC(CCc4ccccc4)(c4cccnc4)CC3)cc2CO1] | 6-((4-phenethyl-4-(pyridin-3-yl)piperidin-1-yl)methyl)-1H-benzo[d][1,3]oxazin-2(4H)-one | | |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 55 | 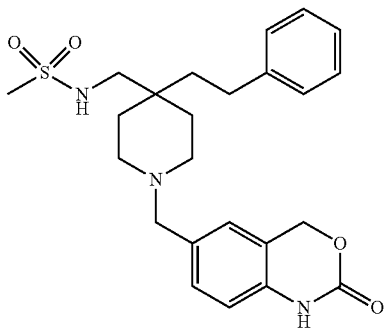 [SMILES: CS(=O)(=O)NCC1(CCc2ccccc2)CCN(Cc2ccc3c(c2)COC(=O)N3)CC1] | N-((1-((2-oxo-2,4-dihydro-1H-benzo[d][1,3]oxazin-6-yl)methyl)-4-phenethylpiperidin-4-yl)methyl)methanesulfonamide | | |
| 56 | 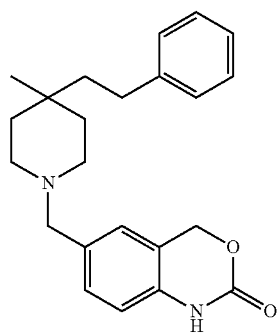 [SMILES: CC1(CCc2ccccc2)CCN(Cc2ccc3c(c2)COC(=O)N3)CC1] | 6-((4-methyl-4-phenethylpiperidin-1-yl)methyl)-1H-benzo[d][1,3]oxazin-2(4H)-one | | |
| 57 | 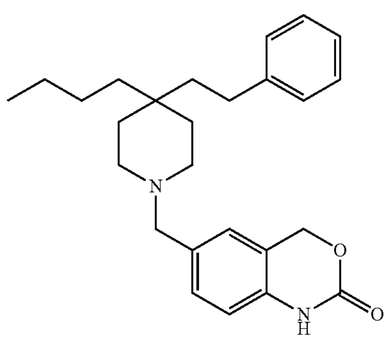 [SMILES: CCCCC1(CCc2ccccc2)CCN(Cc2ccc3c(c2)COC(=O)N3)CC1] | 6-((4-butyl-4-phenethylpiperidin-1-yl)methyl)-1H-benzo[d][1,3]oxazin-2(4H)-one | | |
| 58 | 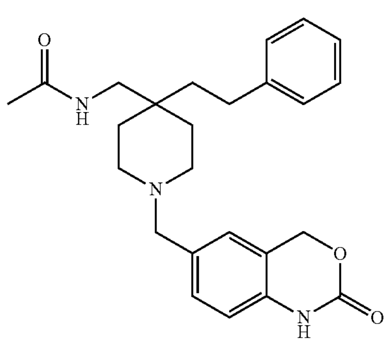 [SMILES: CC(=O)NCC1(CCc2ccccc2)CCN(Cc2ccc3c(c2)COC(=O)N3)CC1] | N-((1-((2-oxo-2,4-dihydro-1H-benzo[d][1,3]oxazin-6-yl)methyl)-4-phenethylpiperidin-4-yl)methyl)acetamide | | |

TABLE V-continued

New Compounds with a pyridine ring and other groups bonded to the pyridine N-constituent

| Compound | Structure | Name | MS (ESI+): [M + H]⁺ | H-NMR |
|---|---|---|---|---|
| 59 | 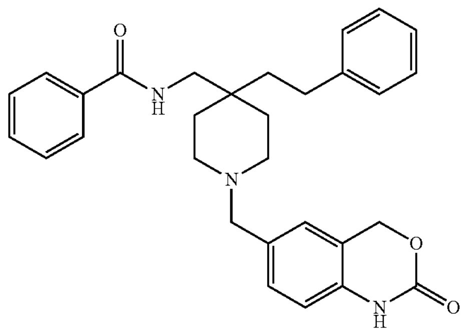 [SMILES: O=C1Nc2ccc(CN3CCC(CCc4ccccc4)(CNC(=O)c4ccccc4)CC3)cc2CO1] | N-((1-((2-oxo-2,4-dihydro-1H-benzo[d][1,3]oxazin-6-yl)methyl)-4-phenethylpiperidin-4-yl)methyl)benzamide | | |
| 60 | 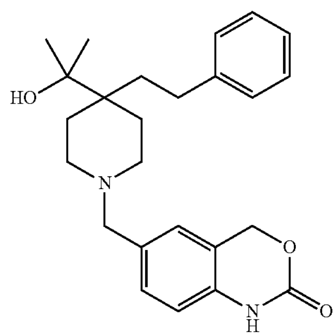 [SMILES: CC(C)(O)C1(CCc2ccccc2)CCN(Cc2ccc3c(c2)COC(=O)N3)CC1] | 6-((4-(2-hydroxypropan-2-yl)-4-phenethyl-piperidin-1-yl)methyl)-1H-benzo[d][1,3]oxazin-2(4H)-one | | |
| 61 | 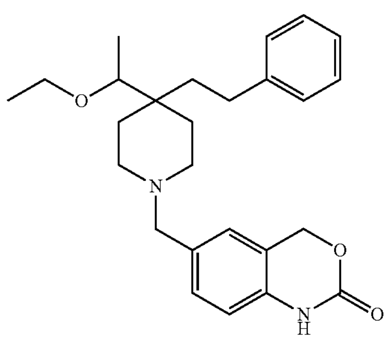 [SMILES: CCOC(C)C1(CCc2ccccc2)CCN(Cc2ccc3c(c2)COC(=O)N3)CC1] | 6-((4-(1-ethoxyethyl)-4-phenethylpiperidin-1-yl)methyl)-1H-benzo[d][1,3]oxazin-2(4H)-one | | |
| 62 | 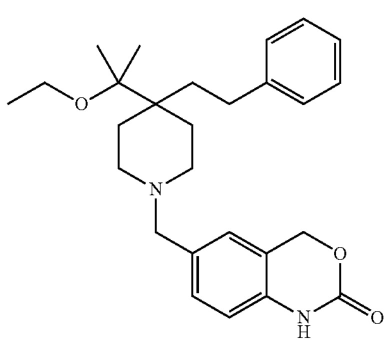 [SMILES: CCOC(C)(C)C1(CCc2ccccc2)CCN(Cc2ccc3c(c2)COC(=O)N3)CC1] | 6-((4-(2-ethoxypropan-2-yl)-4-phenethyl-piperidin-1-yl)methyl)-1H-benzo[d][1,3]oxazin-2(4H)-one | | |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 63 | 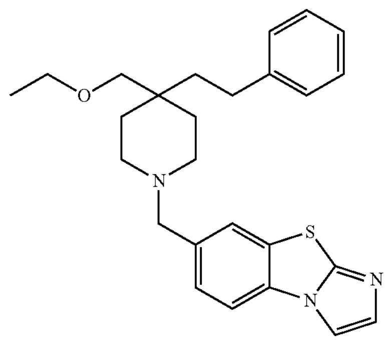 [SMILES: CCOCC1(CCc2ccccc2)CCN(Cc2ccc3c(c2)sc2nccn23)CC1] | 7-((4-(ethoxymethyl)-4-phenethylpiperidin-1-yl)methyl)benzo[d]imidazo[2,1-b]thiazole | | |
| 64 | 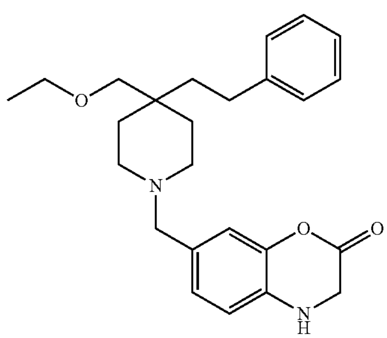 [SMILES: CCOCC1(CCc2ccccc2)CCN(Cc2ccc3c(c2)OC(=O)CN3)CC1] | 7-((4-(ethoxymethyl)-4-phenethylpiperidin-1-yl)methyl)-3,4-dihydro-2H-benzo[b][1,4]oxazin-2-one | | |
| 65 | 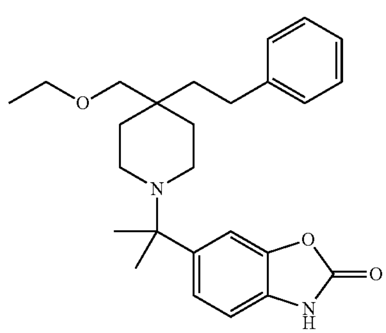 [SMILES: CCOCC1(CCc2ccccc2)CCN(C(C)(C)c2ccc3[nH]c(=O)oc3c2)CC1] | 6-(2-(4-(ethoxymethyl)-4-phenethylpiperidin-1-yl)propan-2-yl)benzo[d]oxazol-2(3H)-one | | |
| 66 | 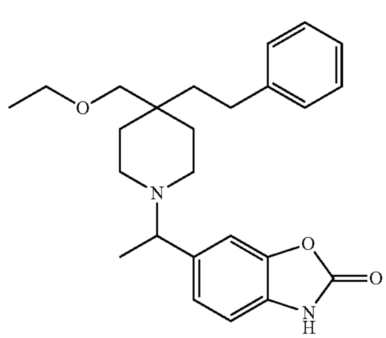 [SMILES: CCOCC1(CCc2ccccc2)CCN(C(C)c2ccc3[nH]c(=O)oc3c2)CC1] | 6-(1-(4-(ethoxymethyl)-4-phenethylpiperidin-1-yl)ethyl)benzo[d]oxazol-2(3H)-one | | |

TABLE V-continued

New Compounds with a pyridine ring and other groups bonded to the pyridine N-constituent

| Compound | Structure | Name | MS (ESI+): [M + H]+ | H-NMR |
|---|---|---|---|---|
| 67 | 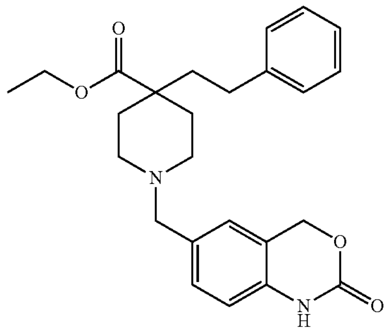 [SMILES: CCOC(=O)C1(CCc2ccccc2)CCN(Cc2ccc3c(c2)COC(=O)N3)CC1] | ethyl 1-((2-oxo-2,4-dihydro-1H-benzo[d][1,3]oxazin-6-yl)methyl)-4-phenethylpiperidine-4-carboxylate | | |
| 68 | 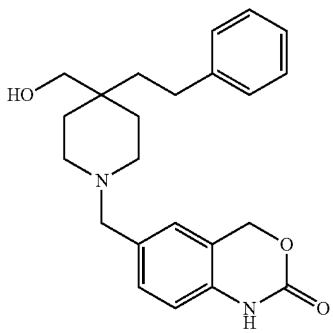 [SMILES: O=C1Nc2ccc(CN3CCC(CO)(CCc4ccccc4)CC3)cc2CO1] | 6-((4-(hydroxymethyl)-4-phenethylpiperidin-1-yl)methyl)-1H-benzo[d][1,3]oxazin-2(4H)-one | | |

*Legend for 4th & 5th columns in Table V is same as for Table I.

TABLE VI in vivo testing of compound Nos. 1 to 36 of Table V

| Compound No. | ED50 (mg/kg) at 30 min on C57BL/6 mice in Warm-water Tail-flick Test (same as Table II) |
|---|---|
| 1 | + |
| 2 | + |
| 3 | ++ |
| 4 | ++ |
| 5 | + |
| 6 | + |
| 7 | ++ |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | ++ |
| 29 | + |
| 30 | + |
| 31 | + |
| 32 | + |
| 33 | + |
| 34 | + |
| 35 | + |
| 36 | + |

The specific methods, processes, compounds and compositions described herein are representative of preferred and other embodiments, and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that various substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", "having"

etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound selected from compounds having one of the following formulae or a pharmaceutically acceptable salt thereof, wherein, unless otherwise indicated, each chiral compound below is in either the R or the S configuration:

| Compound No. | Structure | Name |
|---|---|---|
| 6 | | 2-methyl-5-(2-((3R or S)-3-phenethyl-3-(tetrahydrofuran-2-yl)pyrrolidin-1-yl)propan-2-yl)pyridine citrate |
| 44 | | (R or S)-(3-(4-fluorophenethyl)-1-(pyridin-3-ylmethyl)-pyrrolidin-3-yl)methanol citrate |
| 45 | 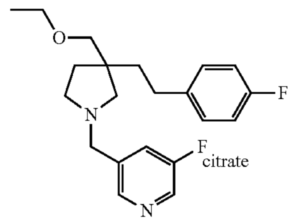 [SMILES: CCOCC1(CCc2ccc(F)cc2)CCN(Cc2cncc(F)c2)C1] | (R or S)-3-((3-(ethoxymethyl)-3-(4-fluorophenethyl)-pyrrolidin-1-yl)methyl)-5-fluoropyridine citrate |
| 46 | 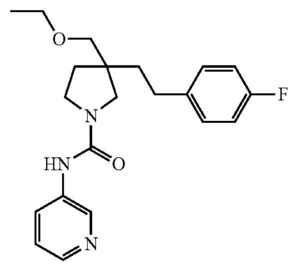 [SMILES: CCOCC1(CCc2ccc(F)cc2)CCN(C(=O)Nc2cccnc2)C1] | (R or S)-3-(2-(3-(ethoxymethyl)-3-(4-fluorophenethyl)-pyrrolidin-1-yl)ethyl)pyridine |
| 47 | 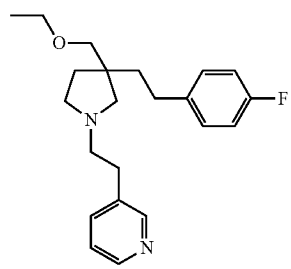 [SMILES: CCOCC1(CCc2ccc(F)cc2)CCN(CCc2cccnc2)C1] | (R or S)-3-(2-(3-(ethoxymethyl)-3-(4-fluorophenethyl)-pyrrolidin-1-yl)ethyl)pyridine |
| 48 | 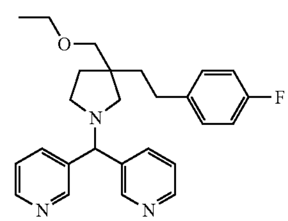 [SMILES: CCOCC1(CCc2ccc(F)cc2)CCN(C(c2cccnc2)c2cccnc2)C1] | (R or S)-3,3'-((3-(ethoxymethyl)-3-(4-fluorophenethyl)-pyrrolidin-1-yl)methylene)-dipyridine |
| 49 | 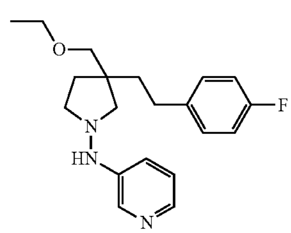 [SMILES: CCOCC1(CCc2ccc(F)cc2)CCN(Nc2cccnc2)C1] | (R or S)-N-(3-(ethoxymethyl)-3-(4-fluorophenethyl)-pyrrolidin-1-yl)pyridin-3-amine |
| 50 | 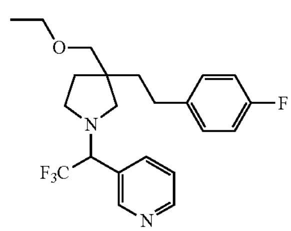 [SMILES: CCOCC1(CCc2ccc(F)cc2)CCN(C(c2cccnc2)C(F)(F)F)C1] | 3-(1-((R or S)-3-(ethoxymethyl)-3-(4-fluorophenethyl)-pyrrolidin-1-yl)-2,2,2-trifluoroethyl)-pyridine |

| Compound No. | Name |
|---|---|
| 51 | (R or S)-3,5-dichloro-4-((3-(ethoxymethyl)-3-(4-fluorophenethyl)-pyrrolidin-1-yl)methyl)pyridine |
| 52 | (R or S)-4-(2-(3-(ethoxymethyl)-1-(pyridin-3-ylmethyl)-pyrrolidin-3-yl)-ethyl)benzonitrile |
| 53 | (R or S)-3-((3-(ethoxymethyl)-3-(4-fluorophenethyl)-pyrrolidin-1-yl)methyl)-isonicotinonitrile |
| 54 | (R or S)-3-((3-(ethoxymethyl)-3-(4-fluorophenethyl)-pyrrolidin-1-yl)methyl)-picolinonitrile |
| 55 | (R or S)-5-((3-(ethoxymethyl)-3-(4-fluorophenethyl)-pyrrolidin-1-yl)methyl)-2-methoxypyridine |
| 56 | (R or S)-5-((3-(ethoxymethyl)-3-(4-fluorophenethyl)-pyrrolidin-1-yl)methyl)-2-methoxyisonicotinonitrile |
| 57 | (R or S)-3-((3-(ethoxymethyl)-3-(4-fluorophenethyl)-pyrrolidin-1-yl)methyl)-picolinamide |
| 60 | (R or S)-4-(2-(1-(di(pyridin-3-yl)methyl)-3-(ethoxymethyl)-pyrrolidin-3-yl)ethyl)-benzonitrile |
| 61 | (R or S)-2-(3-(ethoxymethyl)-3-(4-fluorophenethyl)-pyrrolidin-1-yl)-1-(6-methylpyridin-3-yl)ethan-1-one |
| 62 | (R or S)-2-(3-(ethoxymethyl)-3-(4-fluorophenethyl)-pyrrolidin-1-yl)-2-methyl-1-(6-methylpyridin-3-yl)propan-1-one |

| Compound No. | Structure | Name |
|---|---|---|
| 65 | 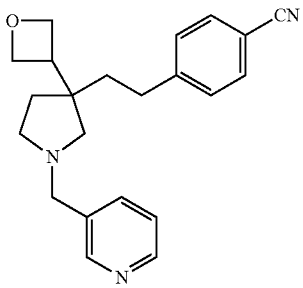 [SMILES: N#Cc1ccc(CCC2(C3COC3)CCN(Cc3cccnc3)C2)cc1] | (R or S)-4-(2-(3-(oxetan-3-yl)-1-(pyridin-3-ylmethyl)-pyrrolidin-3-yl)ethyl)-benzonitrile |
| 66 | 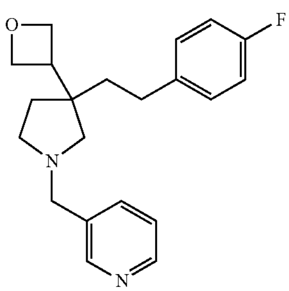 [SMILES: Fc1ccc(CCC2(C3COC3)CCN(Cc3cccnc3)C2)cc1] | (R or S)-3-((3-(4-fluorophenethyl)-3-(oxetan-3-yl)pyrrolidin-1-yl)methyl)pyridine |
| 67 | 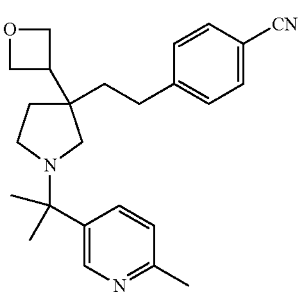 [SMILES: Cc1ccc(C(C)(C)N2CCC(CCc3ccc(C#N)cc3)(C3COC3)C2)cn1] | (R or S)-4-(2-(1-(2-(6-methylpyridin-3-yl)propan-2-yl)-3-(oxetan-3-yl)pyrrolidin-3-yl)ethyl)-benzonitrile |
| 68 | 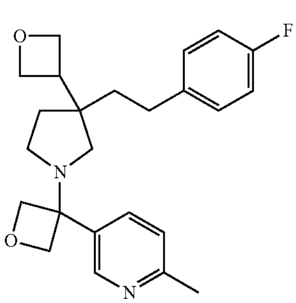 [SMILES: Cc1ccc(C2(N3CCC(CCc4ccc(F)cc4)(C4COC4)C3)COC2)cn1] | (R or S)5-(3-(3-(4-fluorophenethyl)-3-(oxetan-3-yl)pyrrolidin-1-yl)oxetan-3-yl)-2-methylpyridine |
| 72 | 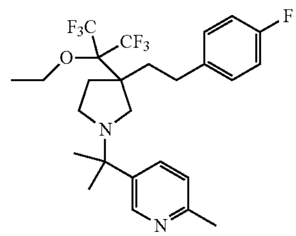 [SMILES: CCOC(C(F)(F)F)(C(F)(F)F)C1(CCc2ccc(F)cc2)CCN(C(C)(C)c2ccc(C)nc2)C1] | (R or S)-5-(2-(3-(2-ethoxy-1,1,1,3,3,3-hexafluoropropan-2-yl)-3-(4-fluorophenethyl)pyrrolidin-1-yl)propan-2-yl)-2-methylpyridine |
| 73 | 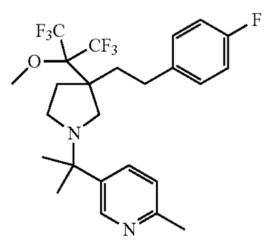 [SMILES: COC(C(F)(F)F)(C(F)(F)F)C1(CCc2ccc(F)cc2)CCN(C(C)(C)c2ccc(C)nc2)C1] | (R or S)-5-(2-(3-(4-fluorophenethyl)-3-(1,1,1,3,3,3-hexafluoro-2-methoxypropan-2-yl)pyrrolidin-1-yl)propan-2-yl)-2-methylpyridine |
| 74 | 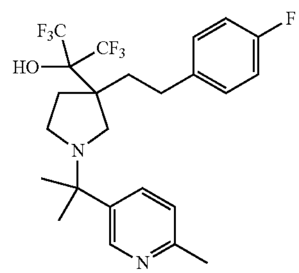 [SMILES: Cc1ccc(C(C)(C)N2CCC(CCc3ccc(F)cc3)(C(O)(C(F)(F)F)C(F)(F)F)C2)cn1] | (R or S)-1,1,1,3,3,3-hexafluoro-2-(3-(4-fluorophenethyl)-1-(2-(6-methylpyridin-3-yl)propan-2-yl)pyrrolidin-3-yl)propan-2-ol |
| 75 | 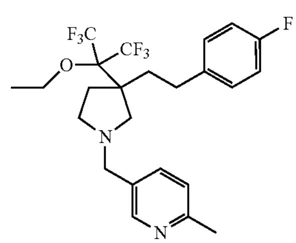 [SMILES: CCOC(C(F)(F)F)(C(F)(F)F)C1(CCc2ccc(F)cc2)CCN(Cc2ccc(C)nc2)C1] | (R or S)-5-((3-(2-ethoxy-1,1,1,3,3,3-hexafluoropropan-2-yl)-3-(4-fluorophenethyl)-pyrrolidin-1-yl)methyl)-2-methylpyridine |
| 76 | 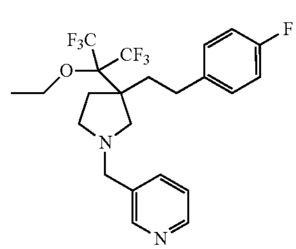 [SMILES: CCOC(C(F)(F)F)(C(F)(F)F)C1(CCc2ccc(F)cc2)CCN(Cc2cccnc2)C1] | (R or S)-3-((3-(2-ethoxy-1,1,1,3,3,3-hexafluoropropan-2-yl)-3-(4-fluorophenethyl)-pyrrolidin-1-yl)methyl)pyridine |

| Compound No. | Structure | Name |
|---|---|---|
| 77 | 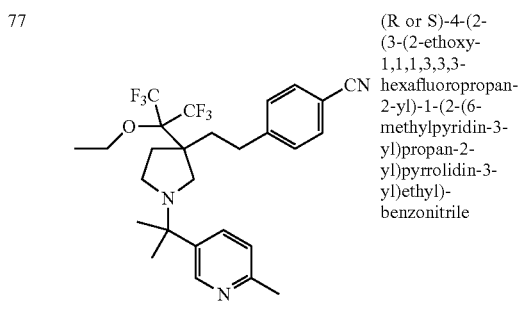 | (R or S)-4-(2-(3-(2-ethoxy-1,1,1,3,3,3-hexafluoropropan-2-yl)-1-(2-(6-methylpyridin-3-yl)propan-2-yl)pyrrolidin-3-yl)ethyl)-benzonitrile |
| 78 | 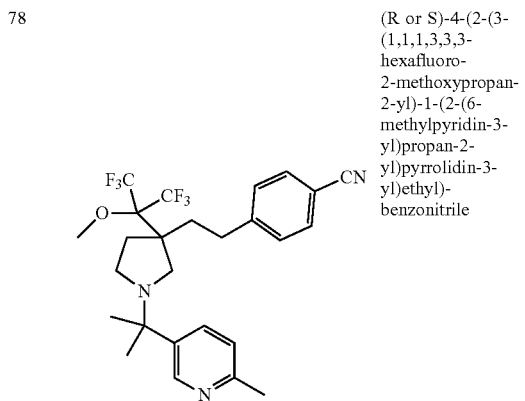 | (R or S)-4-(2-(3-(1,1,1,3,3,3-hexafluoro-2-methoxypropan-2-yl)-1-(2-(6-methylpyridin-3-yl)propan-2-yl)pyrrolidin-3-yl)ethyl)-benzonitrile |
| 79 | 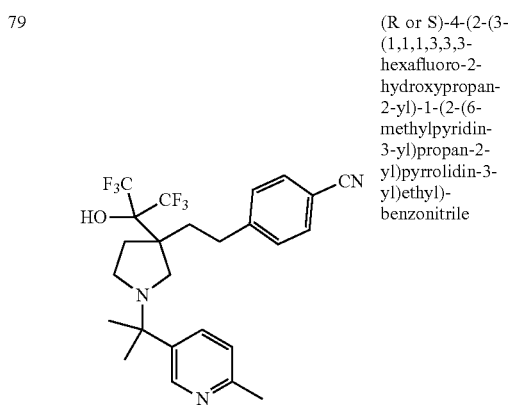 | (R or S)-4-(2-(3-(1,1,1,3,3,3-hexafluoro-2-hydroxypropan-2-yl)-1-(2-(6-methylpyridin-3-yl)propan-2-yl)pyrrolidin-3-yl)ethyl)-benzonitrile |
| 80 | 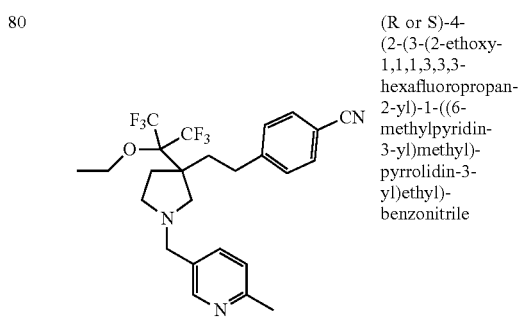 | (R or S)-4-(2-(3-(2-ethoxy-1,1,1,3,3,3-hexafluoropropan-2-yl)-1-((6-methylpyridin-3-yl)methyl)-pyrrolidin-3-yl)ethyl)-benzonitrile |
| 81 | 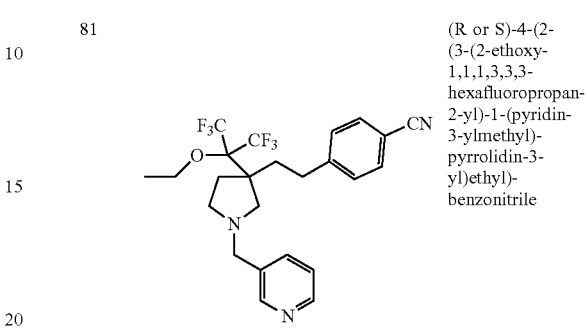 | (R or S)-4-(2-(3-(2-ethoxy-1,1,1,3,3,3-hexafluoropropan-2-yl)-1-(pyridin-3-ylmethyl)-pyrrolidin-3-yl)ethyl)-benzonitrile |
| 127 |  | (S or R)-N-((3-(4-fluorophenethyl)-1-(2-(6-methylpyridin-3-yl)propan-2-yl)pyrrolidin-3-yl)methyl)-4-methyl-benzene-sulfonamide citrate. |

2. The following compound number 6 of claim 1 or a pharmaceutically acceptable salt thereof:

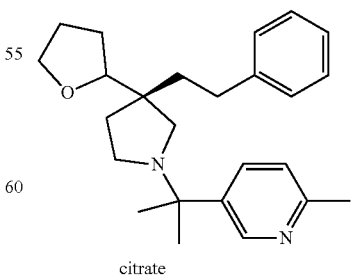

3. The following compounds of claim 1 or a pharmaceutically acceptable salt thereof:

| Compound No. | Structure | Name |
|---|---|---|
| 44 | 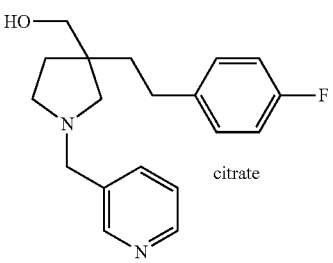 [SMILES: OCC1(CCc2ccc(F)cc2)CCN(Cc2cccnc2)C1] | (R or S)-(3-(4-fluorophenethyl)-1-(pyridin-3-ylmethyl)pyrrolidin-3-yl)methanol citrate |
| 45 | 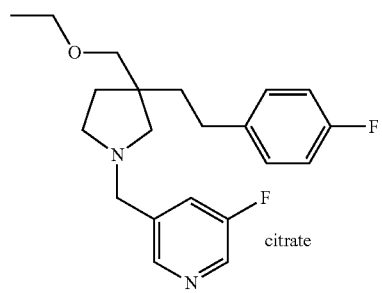 [SMILES: CCOCC1(CCc2ccc(F)cc2)CCN(Cc2cncc(F)c2)C1] | (R or S)-3-((3-(ethoxymethyl)-3-(4-fluorophenethyl)pyrrolidin-1-yl)methyl)-5-fluoropyridine citrate |
| 84 | 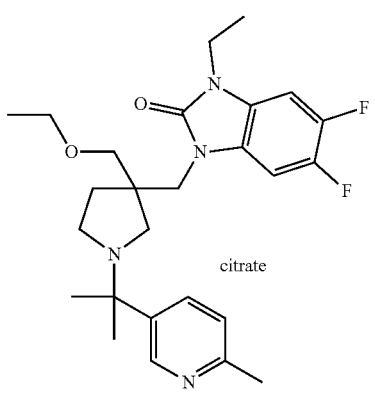 [SMILES: CCOCC1(Cn2c(=O)n(CC)c3cc(F)c(F)cc32)CCN(C(C)(C)c2ccc(C)nc2)C1] | (R or S)-1-((3-(ethoxymethyl)-1-(2-(6-methylpyridin-3-yl)propan-2-yl)pyrrolidin-3-yl)methyl)-3-ethyl-5,6-difluoro-1,3-dihydro-2H-benzo[d]imidazol-2-one citarte. |

4. The following compound number 127 of claim 1 or a pharmaceutically acceptable salt thereof, having the following structure and name:
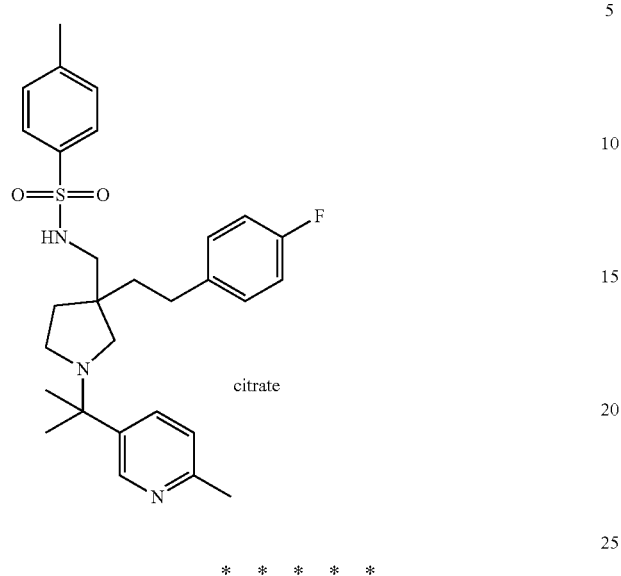
* * * * *